(12) United States Patent
Li et al.

(10) Patent No.: US 12,365,673 B2
(45) Date of Patent: *Jul. 22, 2025

(54) NITRILE DERIVATIVE THAT ACTS AS INHIBITOR OF DIPEPTIDYL PEPTIDASE 1 AND USE THEREOF

(71) Applicant: HAISCO PHARMACEUTICALS PTE. LTD., Singapore (SG)

(72) Inventors: Yao Li, Sichuan (CN); Zongjun Shi, Sichuan (CN); Guobiao Zhang, Sichuan (CN); Lei Chen, Sichuan (CN); Wenjing Wang, Sichuan (CN); Xiaobo Zhang, Sichuan (CN); Dengyu Zheng, Sichuan (CN); Bo Xu, Sichuan (CN); Xin Liu, Sichuan (CN); Yajun Wang, Sichuan (CN); Fei Ye, Sichuan (CN); Pingming Tang, Sichuan (CN); Jia Ni, Sichuan (CN); Chen Zhang, Sichuan (CN); Pangke Yan, Sichuan (CN)

(73) Assignee: Haisco Pharmaceuticals Pte. Ltd., Singapore (SG)

( * ) Notice: Subject to any disclaimer, the term of this patent is extended or adjusted under 35 U.S.C. 154(b) by 19 days.

This patent is subject to a terminal disclaimer.

(21) Appl. No.: 18/369,069

(22) Filed: Sep. 15, 2023

(65) Prior Publication Data

US 2024/0059681 A1 Feb. 22, 2024

Related U.S. Application Data

(63) Continuation of application No. 17/976,291, filed on Oct. 28, 2022, now Pat. No. 11,807,635, which is a continuation of application No. PCT/CN2021/114500, filed on Aug. 25, 2021.

(30) Foreign Application Priority Data

| Aug. 26, 2020 | (CN) | 202010871912.1 |
| Oct. 21, 2020 | (CN) | 202011129809.6 |
| Feb. 7, 2021 | (CN) | 202110167731.5 |

(51) Int. Cl.
| C07D 413/12 | (2006.01) |
| C07D 267/10 | (2006.01) |
| C07D 413/14 | (2006.01) |
| C07D 417/12 | (2006.01) |
| C07F 9/6527 | (2006.01) |

(52) U.S. Cl.
CPC ......... *C07D 413/12* (2013.01); *C07D 267/10* (2013.01); *C07D 413/14* (2013.01); *C07D 417/12* (2013.01); *C07F 9/6527* (2013.01)

(58) Field of Classification Search
CPC .. C07D 413/12; C07D 267/10; C07D 413/14; C07D 417/12
USPC .................................................. 514/211.15
See application file for complete search history.

(56) References Cited

U.S. PATENT DOCUMENTS 11,807,635 B2 * 11/2023 Li .................. C07F 9/6527
2019/0247400 A1 8/2019 Dipetrillo et al.

FOREIGN PATENT DOCUMENTS

| CN | 101945851 A | 1/2011 |
| CN | 10257 4830 A | 7/2012 |
| CN | 102596321 A | 7/2012 |
| CN | 105980367 A | 9/2016 |
| JP | 2016510784 A | 4/2016 |
| WO | WO 2015032942 A1 | 3/2015 |
| WO | WO 2015110826 A1 | 7/2015 |
| WO | WO 2016139355 A1 | 9/2016 |
| WO | WO2021092115 A1 | 5/2021 |
| WO | WO2021164735 A1 | 8/2021 |
| WO | WO2021202452 A1 | 10/2021 |

OTHER PUBLICATIONS

Doyle et al., "Discovery of Second Generation Reversible Covalent DPPI Inhibitors Leading to an Oxazepane Amidoacetonitrile Based Clinical Candidate (AZD7986)," *Journal of Medicinal Chemistry*, vol. 59, No. 20, Oct. 2, 2016 (pp. 9457-9472).

Huang, et al., "3D-QSAR, Molecular Docking and Molecular Dynamics Simulations of Oxazepane Amidoacetonitrile Derivates as Novel DPPI Inhibitors," *Journal of Molecular Structure*, vol. 1168, May 11, 2018, pp. 223-233.

International Search Report, dated Nov. 24, 2021, issued in corresponding International Application No. PCT/CN2021/114500.

(Continued)

*Primary Examiner* — Kahsay Habte

(74) *Attorney, Agent, or Firm* — Travis Young; Bozicevic, Field & Francis LLP

(57) ABSTRACT

Disclosed is a nitrile derivative compound represented by formula (I), a stereoisomer, a deuterated product, a co-crystal, a solvate or a pharmaceutically acceptable salt thereof, wherein each group is as defined in the description. The compound has dipeptidyl peptidase 1 inhibitory activity and can be used to prepare a drug for treating diseases including obstructive airway diseases, bronchiectasis, cystic fibrosis, asthma, emphysema, and chronic obstructive pulmonary diseases.

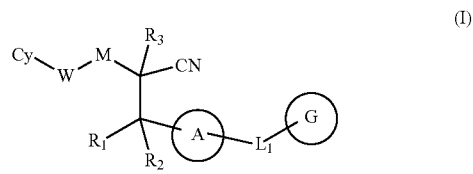

(I)

6 Claims, No Drawings

(56) References Cited

OTHER PUBLICATIONS

Kack, et al., "DPPI Inhibitors: Exploring the Role of Water in the S2 Pocket of DPPI with Substituted Pyrrolidines," *ACS Medicinal Chemistry Letters*, vol. 10, No. 8, Jul. 15, 2019, pp. 1222-1227.

* cited by examiner

NITRILE DERIVATIVE THAT ACTS AS INHIBITOR OF DIPEPTIDYL PEPTIDASE 1 AND USE THEREOF

CROSS-REFERENCE TO RELATED APPLICATIONS

This application is a continuation of U.S. patent application Ser. No. 17/976,291 filed Oct. 28, 2022, which is a continuation of International Patent Application No. PCT/CN2021/114500, filed Aug. 25, 2021, which claims the benefit of China Patent Application No. 202110167731.5, filed Feb. 7, 2021, China Patent Application No. 202011129809.6, filed Oct. 21, 2020, and China Patent Application No. 202010871912.1, filed Aug. 26, 2020, all of which are incorporated herein by reference in their entirety.

TECHNICAL FIELD

The present invention relates to a nitrile derivative as a dipeptidyl peptidase 1 inhibitor, or a stereoisomer, a deuterated product, a co-crystal, a solvate or a pharmaceutically acceptable salt thereof, and the use thereof in the preparation of a drug for treating a disease mediated by dipeptidyl peptidase 1.

BACKGROUND ART

Dipeptidyl peptidase 1 (DPP1), also known as cathepsin C, is a lysosomal cysteine protease capable of removing dipeptides from the amino terminus of a protein substrate. DPP1 was first discovered by Gutman and Fruton in 1948 (J Biol Chem, 174, 851-858). However, the cDNA of human dipeptidyl peptidase 1 was first described in 1995 (FEBS Lett, 369, 326-330). DPP1 is the only member of the papain family that functions as a tetramer, and consists of four identical subunits. Each subunit is composed of an N-terminal fragment, a heavy chain and a light chain (J Biol Chem, 270, 21626-21631).

DPP1 is highly expressed in numerous tissues such as the lung, kidney, liver, and spleen (Hoppe Seyler, Biol. Chem. 373:367-373, 1992). Consistent with its role in the activation of serine proteases in hematopoietic stem cells, DPP1 is also relatively highly expressed in neutrophils, cytotoxic lymphocytes, natural killer cells, alveolar macrophages, and mast cells. Recent data suggest that in addition to being an important enzyme in lysosomal protein degradation, DPP1 also functions as a key enzyme in granule serine protease activation in the following cells: cytotoxic T lymphocytes and natural killer cells (granzymes A and B; Proc. Nat. Acad. Sci 96:8627-8632, 1999), mast cells (chymotrypsin and plasmin; J Biol. Chem. 276:18551-18556, 2001), and neutrophils (cathepsin G, elastase, and proteinase 3; J Clin. Invest. 109:363.371, 2002). Once activated, these proteases are capable of degrading various extracellular matrix components, leading to tissue damage and chronic inflammation. DPP1 is considered to be a potent therapeutic target due to its central role in activating these proteases (J Clin Invest, 2002, 109, 363-271; J Immunol, 2004, 173, 7277-7281).

Therefore, cathepsin C inhibitors can be potentially useful in the treatment of the following diseases: neutrophil-dominated inflammatory diseases such as rheumatoid arthritis, chronic obstructive pulmonary disease (COPD), emphysema, asthma, multiple sclerosis, and cystic fibrosis (Curr. Topics Med. Chem. 10: 708-716, 2010; Expert Opin. Ther. Patents 20:497-506, 2010). In view of the role of DPP1 in the activation of some proinflammatory serine proteases, compounds inhibiting the activity of DPP1 and further inhibiting the activity of downstream serine proteases have good prospects for clinical application. At present, relevant patents have reported the synthesis of DPP1 inhibitors. WO 2004/110988 relates to certain nitrile derivatives and the use thereof as DPP1 inhibitors. WO 2009/074829 relates to peptidyl nitriles and the use thereof as DPP1 inhibitors. WO 2010/128324 relates to an alpha-aminoamide nitrile and the use thereof as a DPP1 inhibitor. WO 2012/119941 relates to peptidyl nitrile compounds and the use thereof as DPP1 inhibitors. WO 2013/041497 relates to N-[1-cyano-2-(phenyl)ethyl]-2-azabicyclo[2.2.1]heptane-3-carboxamide and the use thereof as a DPP1 inhibitor. WO 2001/096285 and WO 2003/048123 relate to beta-aminoamide nitriles having an inhibitory activity against cysteine proteases. However, there has been no DPP1 inhibitor available in the market so far, and therefore there is still an unmet clinical need for DPP1 inhibitors with high inhibitory activity and low toxicity.

SUMMARY OF THE INVENTION

The present invention first provides a compound of formula (I), (II), (III) or (IV) with high activity, high bioavailability, good pharmacokinetics, and low toxicity and side effects, or a stereoisomer, a deuterated product, a co-crystal, a solvate or a pharmaceutically acceptable salt thereof:

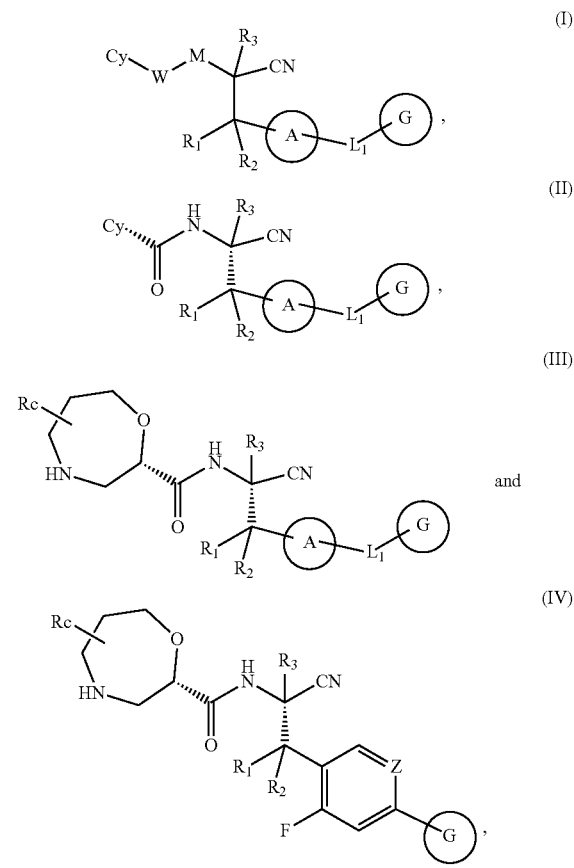

wherein ring G is a 5-12-membered carbocyclic ring, a 5-12-membered monocyclic heterocycle containing 1-3 heteroatoms selected from N, S and O, or a fused ring of formula (I-1)

(I-1)

L₁ is attached to the ring G by replacing any hydrogen atom on the ring atoms (for example, the carbon atom on the 5-12-membered carbocyclic ring, the ring carbon atom or ring heteroatom on the 5-12-membered monocyclic heterocycle, and the ring carbon atom or ring heteroatom on the fused ring of formula (I-1)), and the carbocyclic ring or monocyclic heterocycle is optionally substituted with 1-3 $R_G$ groups;
optionally, formula (I-1) has the structure (I-11)

and
optionally, formula (I-1) has the structure (I-12)

In some embodiments, ring G is a 5-9-membered monocyclic carbocyclic ring, a 5-7-membered monocyclic heterocycle containing 1-3 heteroatoms selected from N, S and O, or a fused ring of formula (I-1), optionally, formula (I-1) has the structure (I-11), and optionally, formula (I-1) has the structure (I-12).

In some embodiments, ring G is cyclopentane, cyclohexane, cycloheptane, a benzene ring, optionally substituted with 1-3 $R_G$ groups, or ring G is (I-2)

optionally, formula (I-2) has the structure (I-21)

and
optionally, formula (I-2) has the structure (I-22)

In some embodiments, (I-2)

is selected from one of the following structures:

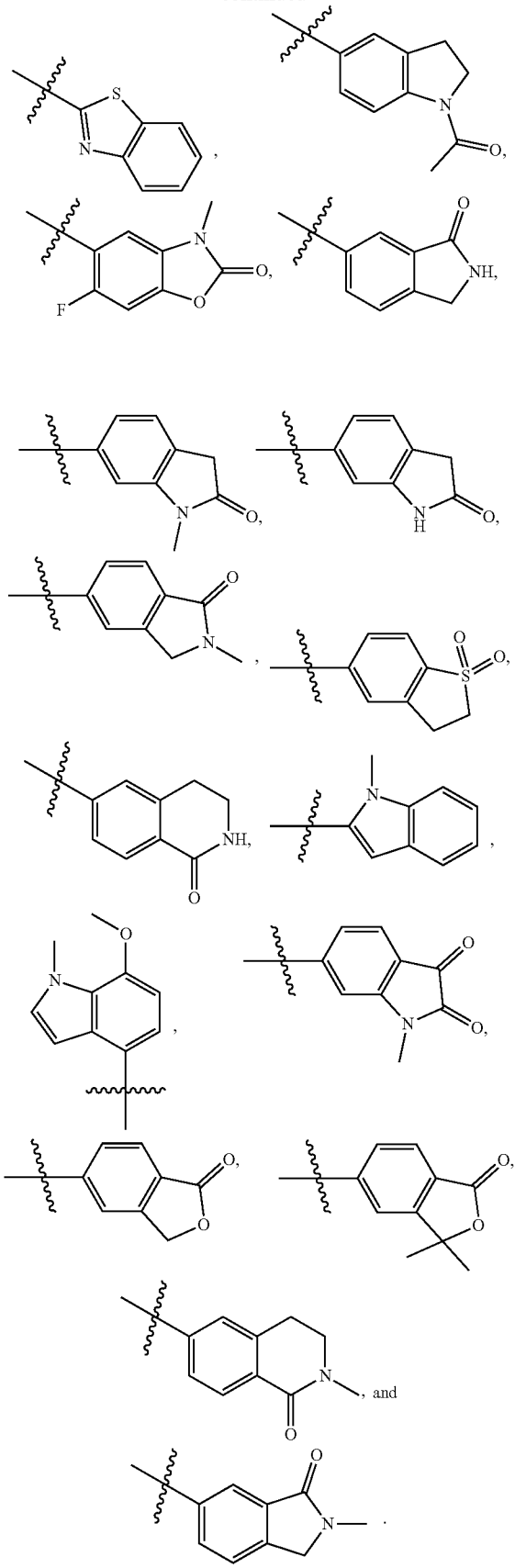

In some embodiments, ring G is a benzene ring or

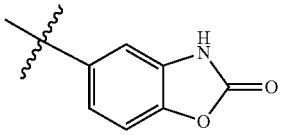 [SMILES: *c1ccc2oc(=O)[nH]c2c1]

optionally substituted with 1-2 $R_G$ groups;

each $R_G$ is independently selected from deuterium, $SF_5$, =O, halogen, cyano, hydroxyl, $NH_2$, —COOH, $C_{1-4}$ alkyl, $C_{1-4}$ alkoxy, $C_{3-6}$ cycloalkyloxy, $C_{3-6}$ cycloalkyl, $C_{2-6}$ alkenyl, $C_{2-6}$ alkynyl, —$NHC_{1-4}$ alkyl, —$N(C_{1-4}$ alkyl$)_2$, —$COC_{1-4}$ alkyl, —$COOC_{1-4}$ alkyl, —$CONH_2$, —$CONHC_{1-4}$ alkyl, —$CONHC_{3-6}$ cycloalkyl, —$CON(C_{1-4}$ alkyl$)_2$, —$NHCOC_{1-4}$ alkyl, —$NHCOC_{3-6}$ cycloalkyl, —$P(O)(C_{1-4}$ alkyl$)_2$, —$S(O)C_{1-4}$alkyl, —$S(O)_2C_{1-4}$ alkyl, —$S(O)_2C_{3-6}$ cycloalkyl, —$S(O)NH_2$, —$S(O)NHC_{1-4}$ alkyl, —$S(O)N(C_{1-4}$ alkyl$)_2$, —$S(O)_2NH_2$, and a 4-7-membered heterocycle containing 1-3 heteroatoms selected from N, S and O, and the $R_G$ is optionally further substituted with 1-3 groups selected from deuterium, $C_{1-4}$ alkyl, halo $C_{1-4}$ alkyl, hydroxy $C_{1-4}$ alkyl, —$CONH_2$, $NH_2$, $C_{1-6}$ alkoxy, hydroxyl, —COOH, halogen, and a 5-7-membered heterocycle containing 1-3 heteroatoms selected from N, S and O, and further, the 5-7-membered heterocycle is optionally substituted with 1-2 groups selected from =O, halogen, cyano, $C_{1-4}$ alkyl, and halo $C_{1-4}$ alkyl.

In some embodiments, each $R_G$ is independently selected from deuterium, $SF_5$, =O, halogen, cyano, hydroxyl, $NH_2$, $C_{1-4}$ alkyl, $C_{1-4}$ alkoxy, $C_{3-6}$ cycloalkyl, $C_{2-6}$ alkenyl, $C_{2-6}$ alkynyl, —$NHC_{1-4}$ alkyl, —$N(C_{1-4}$ alkyl$)_2$, —$COC_{1-4}$ alkyl, —$CONH_2$, —$CONHC_{1-4}$ alkyl, —$CON(C_{1-4}$ alkyl$)_2$, —$NHCOC_{1-4}$ alkyl, —$P(O)(C_{1-4}$ alkyl$)_2$, and a 4-7-membered heterocycle containing 1-3 heteroatoms selected from N, S and O, and the $R_G$ is optionally further substituted with 1-3 groups selected from deuterium, $C_{1-4}$ alkyl, halo $C_1$ alkyl, hydroxy $C_{1-4}$ alkyl, —$CONH_2$, $NH_2$, $C_{1-6}$ alkoxy, hydroxyl, halogen, and a 5-7-membered heterocycle containing 1-3 heteroatoms selected from N, S and O, and further, the 5-7-membered heterocycle is optionally substituted with 1-2 groups selected from =O, halogen, cyano, $C_{1-4}$ alkyl, and halo $C_{1-4}$ alkyl.

In some embodiments, each $R_G$ is independently selected from F, Cl, Br, I, methyl, ethyl, propyl, $SF_5$, and CN; the methyl, ethyl and propyl are optionally further substituted with 1-3 groups selected from deuterium, F, Cl, Br, and I;

and Cy is a 5-12-membered heterocycle containing 1-3 heteroatoms selected from N, S and O, and the heterocycle is optionally substituted with 1-3 groups selected from deuterium, =O, halogen, cyano, hydroxyl, $NH_2$, —COOH, $C_{1-4}$ alkyl, halo $C_{1-4}$ alkyl, hydroxy $C_{1-4}$ alkyl, $C_{1-4}$ alkoxy, $C_{3-6}$ cycloalkyloxy, $C_{1-6}$ alkoxyalkyl, halo $C_{1-4}$ alkoxy, $C_{2-6}$ alkenyl, $C_{2-6}$ alkynyl, —$NHC_{1-4}$ alkyl, —$N(C_{1-4}$ alkyl$)_2$, —$COC_{1-4}$ alkyl, —$COOC_{1-4}$ alkyl, —$CONH_2$, —$CONHC_{1-4}$ alkyl, —$CON(C_{1-4}$ alkyl$)_2$, —$NHCOC_{1-4}$ alkyl, —$S(O)C_{1-4}$ alkyl, —$S(O)_2C_{1-4}$ alkyl, —$S(O)NH_2$, —$S(O)NHC_{1-4}$ alkyl, —$S(O)N(C_{1-4}$ alkyl$)_2$, —$S(O)_2NH_2$, —$S(O)_2NHC_{1-4}$ alkyl, and —$S(O)_2N(C_{1-4}$ alkyl$)_2$.

In some specific embodiments, Cy is a 5-12-membered monocyclic heterocycle containing 1-3 heteroatoms selected from N and O, and the monocyclic heterocycle is optionally substituted with 1-3 groups selected from deuterium, =O, halogen, cyano, hydroxyl, NH$_2$, —COOH, C$_{1-4}$ alkyl, halo C$_{1-4}$ alkyl, hydroxy C$_{1-4}$ alkyl, C$_{1-4}$ alkoxy, C$_{3-6}$ cycloalkoxy, C$_{1-6}$ alkoxyalkyl, halo C$_{1-4}$ alkoxy, C$_{2-6}$ alkenyl, C$_{2-6}$ alkynyl, —NHC$_{1-4}$ alkyl, —N(C$_{1-4}$ alkyl)$_2$, —COC$_{1-4}$ alkyl, —COOC$_{1-4}$ alkyl, —CONH$_2$, —CONHC$_{1-4}$ alkyl, —CON(C$_{1-4}$ alkyl)$_2$, —NHCOC$_{1-4}$ alkyl, —S(O)C$_{1-4}$ alkyl, —S(O)$_2$C$_{1-4}$ alkyl, —S(O)NH$_2$, —S(O)NHC$_{1-4}$ alkyl, —S(O)N(C$_{1-4}$ alkyl)$_2$, —S(O)$_2$NH$_2$, —S(O)$_2$NHC$_{1-4}$ alkyl, and —S(O)$_2$N(C$_{1-4}$ alkyl)$_2$.

In some specific embodiments, Cy is a 5-8-membered monocyclic heterocycle, a 7-10-membered spirocyclic heterocycle, a 6-9-membered bridged-ring heterocycle or a 6-10-membered fused heterocycle, which contains 1-3 heteroatoms selected from N, S and O, and Cy is optionally substituted with 1-3 groups selected from =O, halogen, cyano, hydroxyl, NH$_2$, —COOH, C$_{1-4}$ alkyl, halo C$_{1-4}$ alkyl, hydroxy C$_{1-4}$ alkyl, C$_{1-4}$ alkoxy, C$_{3-6}$ cycloalkoxy, C$_{1-6}$ alkoxyalkyl, halo C$_{1-4}$ alkoxy, —NHC$_{1-4}$ alkyl, —N(C$_{1-4}$ alkyl)$_2$, —COC$_{1-4}$ alkyl, —CONH$_2$, —CONHC$_{1-4}$ alkyl, —CON(C$_{1-4}$ alkyl)$_2$, —NHCOC$_{1-4}$ alkyl, —S(O)C$_{1-4}$ alkyl, —S(O)$_2$C$_{1-4}$ alkyl, —S(O)NH$_2$, —S(O)NHC$_{1-4}$ alkyl, —S(O)N(C$_{1-4}$ alkyl)$_2$, —S(O)$_2$NH$_2$, —S(O)$_2$NHC$_{1-4}$ alkyl, and —S(O)$_2$N(C$_{1-4}$ alkyl)$_2$.

In some specific embodiments, Cy is a 5-8-membered monocyclic heterocycle containing 1-3 heteroatoms selected from N, S and O, and the monocyclic heterocycle is optionally substituted with 1-3 groups selected from =O, halogen, cyano, hydroxyl, NH$_2$, —COOH, C$_{1-4}$ alkyl, halo C$_{1-4}$ alkyl, hydroxy C$_{1-4}$ alkyl, C$_{1-4}$ alkoxy, C$_{3-6}$ cycloalkoxy, C$_{1-6}$ alkoxyalkyl, halo C$_{1-4}$ alkoxy, —NHC$_{1-4}$ alkyl, —N(C$_{1-4}$ alkyl)$_2$, —COC$_{1-4}$ alkyl, —CONH$_2$, —CONHC$_{1-4}$ alkyl, —CON(C$_{1-4}$ alkyl)$_2$, —NHCOC$_{1-4}$ alkyl, —S(O)C$_{1-4}$ alkyl, —S(O)$_2$C$_{1-4}$ alkyl, —S(O)NH$_2$, —S(O)NHC$_{1-4}$ alkyl, —S(O)N(C$_{1-4}$ alkyl)$_2$, —S(O)$_2$NH$_2$, —S(O)$_2$NHC$_{1-4}$ alkyl, and —S(O)$_2$N(C$_{1-4}$ alkyl)$_2$.

In some specific embodiments, Cy is a 5-8-membered monocyclic heterocycle containing 1-3 heteroatoms selected from N, S and O, and the monocyclic heterocycle is optionally substituted with 1-3 groups selected from =O, halogen, cyano, hydroxyl, NH$_2$, —COOH, C$_{1-4}$ alkyl, halo C$_{1-4}$ alkyl, C$_{1-4}$ alkoxy, C$_{3-6}$ cycloalkoxy, halo C$_{1-4}$ alkoxy, —NHC$_{1-4}$ alkyl, —N(C$_{1-4}$ alkyl)$_2$, —CONH$_2$, —CONHC$_{1-4}$ alkyl, —CON(C$_{1-4}$ alkyl)$_2$, —S(O)$_2$NH$_2$, —S(O)$_2$NHC$_{1-4}$ alkyl, and —S(O)$_2$N(C$_{1-4}$ alkyl)$_2$.

In some specific embodiments, Cy is

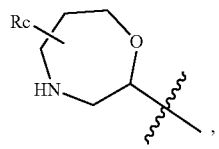

wherein Rc is H, =O, halogen, cyano, hydroxyl, NH$_2$, —COOH, C$_{1-4}$ alkyl, halo C$_{1-4}$ alkyl, hydroxy C$_{1-4}$ alkyl, C$_{1-4}$ alkoxy, C$_{1-6}$ alkoxyalkyl, or halo C$_{1-4}$ alkoxy.

In some specific embodiments, Rc is H, halogen, C$_{1-2}$ alkyl or C$_{1-2}$ alkoxy, W is C(=O), C(=S), C(=N—R$_W$), S(=O) or S(=O)$_2$, and R$_W$ is OH, CN or C$_{1-4}$ alkyl.

In some specific embodiments, W is C(=O), M is NR$_M$ or O, and R$_M$ is H, C$_{1-4}$ alkyl or C$_{3-6}$ cycloalkyl.

In some specific embodiments, M is NH; R$_1$, R$_2$, and R$_3$ are each independently selected from H, deuterium, halogen, C$_{1-4}$ alkyl, C$_{1-4}$ alkoxy, C$_{2-6}$ alkenyl, C$_{2-6}$ alkynyl, C$_{3-6}$ cycloalkyl, and a 4-7-membered heterocycle containing 1-3 heteroatoms selected from N, S and O, wherein the alkyl, alkoxy, alkenyl, alkynyl, cycloalkyl, and heterocycle are optionally substituted with 1-3 groups selected from halogen, C$_{1-4}$ alkyl, cyano, hydroxyl, NH$_2$, and —COOH; and optionally, R$_1$ and R$_2$ together with the carbon atom to which they are attached form C$_3$-6 cycloalkyl or a 4-7-membered heterocycle containing 1-3 heteroatoms selected from N, S and O, wherein the cycloalkyl or heterocycle is optionally substituted with 1-3 groups selected from =O, halogen, cyano, hydroxyl, NH$_2$, —COOH, C$_{1-4}$ alkyl, C$_{2-6}$ alkenyl, C$_{2-6}$ alkynyl, and C$_{3-6}$ cycloalkyl.

In some specific embodiments, R$_1$, R$_2$, and R$_3$ are each independently selected from H, deuterium, halogen, C$_{1-4}$ alkyl, C$_{1-4}$ alkoxy, C$_{2-6}$ alkenyl, and C$_{2-6}$ alkynyl, and the alkyl, alkoxy, alkenyl, and alkynyl are optionally substituted with 1-3 groups selected from halogen, C$_{1-4}$ alkyl, cyano, hydroxyl, NH$_2$, and COOH; and optionally, R$_1$ and R$_2$ together with the carbon atom to which they are attached form C$_{3-6}$ cycloalkyl or a 4-7-membered heterocycle containing 1-3 heteroatoms selected from N, S and O, and the cycloalkyl or heterocycle is optionally substituted with 1-3 groups selected from halogen, cyano, hydroxyl, NH$_2$, COOH, and C$_{1-4}$ alkyl.

In some specific embodiments, R$_1$, R$_2$, and R$_3$ are each independently selected from H, deuterium, halogen, C$_{1-4}$ alkyl, and C$_{1-4}$ alkoxy, and the alkyl and alkoxy are optionally substituted with 1-3 groups selected from halogen, C$_{1-4}$ alkyl, cyano, hydroxyl, NH$_2$, and COOH;

and optionally, R$_1$ and R$_2$ together with the carbon atom to which they are attached form C$_{3-6}$ cycloalkyl, and the cycloalkyl is optionally substituted with 1-3 groups selected from halogen, cyano, hydroxyl, NH$_2$, COOH, and C$_{1-4}$ alkyl.

In some specific embodiments, R$_1$, R$_2$, and R$_3$ are each independently selected from H, deuterium, F, Cl, Br, methyl, ethyl, methoxy or ethoxy, and the methyl, ethyl, methoxy or ethoxy is optionally substituted with 1-3 groups selected from F, Cl, Br, cyano, hydroxyl, and NH$_2$;

and L$_1$ is a bond, C$_{1-3}$ alkylene, —NH—, —N(C$_{1-4}$ alkyl)-, —O—, —S—, C$_{2-6}$ alkenylene, C$_{2-6}$ alkynylene, —CO—, or —CONH—, wherein the alkylene, alkenylene or alkynylene is optionally substituted with 1-3 groups selected from halogen, C$_{1-4}$ alkyl, cyano, hydroxyl, NH$_2$, and —COOH.

In some specific embodiments, L$_1$ is a bond, C$_{1-3}$ alkylene, —NH—, —O—, —S—, C$_{2-6}$ alkenylene, C$_{2-6}$ alkynylene, or —CO—, and the alkylene, alkenylene or alkynylene is optionally substituted with 1-3 groups selected from halogen, cyano, hydroxyl, and NH$_2$.

In some specific embodiments, L$_1$ is a bond, and Y$_1$ and Y$_2$ are each independently selected from CR$_4$ or N.

In some specific embodiments, Y$_1$ and Y$_2$ are CH; each R$_4$ is independently selected from H, deuterium, halogen, C$_{1-4}$ alkyl, C$_{1-4}$ alkoxy, C$_{2-6}$ alkenyl, C$_{2-6}$ alkynyl, C$_{3-6}$ cycloalkyl, cyano, hydroxyl, NH$_2$, —NHC$_{1-4}$ alkyl, —N(C$_{1-4}$ alkyl)$_2$, —COOH, —COC$_{1-4}$ alkyl, —COOC$_{1-4}$ alkyl, —CONHC$_{1-4}$ alkyl, —CON(C$_{1-4}$ alkyl)$_2$, —NHCOC$_{1-4}$ alkyl, and a 4-7-membered heterocycle containing 1-3 heteroatoms selected from N, S and O, wherein the alkyl, alkenyl, alkynyl, cycloalkyl, and heterocycle groups in the case of R$_4$ are optionally substituted with 1-3 groups selected from deuterium, halogen, cyano, hydroxyl, NH$_2$, and —COOH.

In some specific embodiments, each $R_4$ is independently selected from H, halogen, $C_{1-4}$ alkyl, $C_{1-4}$ alkoxy, $C_{2-6}$ alkenyl, $C_{2-6}$ alkynyl, $C_{3-6}$ cycloalkyl, cyano, hydroxyl, and $NH_2$, wherein the alkyl, alkenyl, alkynyl, and cycloalkyl in the case of $R_4$ are optionally substituted with 1-3 groups selected from deuterium, halogen, cyano, hydroxyl, $NH_2$ and COOH.

In some specific embodiments, $R_4$ is H;

$X_1$, $X_2$, $X_3$, and $X_4$ are each independently selected from a bond, $NR_5$, O, $CR_6R_7$, S, S(O), and $S(O)_2$, and at most one of $X_1$, $X_2$, $X_3$, and $X_4$ is a bond;

each $R_5$ is independently selected from H, $C_{1-4}$ alkyl, $—COC_{1-4}$ alkyl, $C_{2-6}$ alkenyl, $C_{2-6}$ alkynyl, and $C_{3-6}$ cycloalkyl; and the alkyl, alkenyl, alkynyl, and cycloalkyl are optionally substituted with 1-3 groups selected from deuterium, halogen, cyano, hydroxyl, $NH_2$, and COOH.

In some specific embodiments, each $R_5$ is independently selected from H, $C_{1-4}$ alkyl, $—COC_{1-4}$ alkyl and $C_{3-6}$ cycloalkyl, wherein the alkyl and cycloalkyl are optionally substituted with 1-3 groups selected from deuterium, halogen, cyano, hydroxyl, $NH_2$, and —COOH.

In some specific embodiments, $R_5$ is methyl;

$R_6$ and $R_7$ are each independently selected from H, deuterium, halogen, $C_{1-4}$ alkyl, $C_{1-4}$ alkoxy, $C_{2-6}$ alkenyl, $C_{2-6}$ alkynyl, $C_{3-6}$ cycloalkyl, cyano, hydroxyl, $NH_2$, —COOH, and a 4-7-membered heterocycle containing 1-3 heteroatoms selected from N, S and O, wherein the alkyl, alkoxy, alkenyl, alkynyl, cycloalkyl, and heterocycle are optionally substituted with 1-3 groups selected from deuterium, halogen, cyano, hydroxyl, $NH_2$, and —COOH;

optionally, $R_6$ and $R_7$ form =O;

optionally, two $R_5$ on adjacent ring atoms, two $R_6$ on adjacent ring atoms, or $R_5$ and $R_6$ on adjacent ring atoms in $X_1$, $X_2$, $X_3$, and $X_4$ together with the atoms to which they are attached form a double bond;

and optionally, $R_6$ and $R_7$ on the same carbon atom together with the carbon atom to which they are attached form a $C_{3-12}$ carbocyclic ring or a 4-7-membered heterocycle containing 1-3 heteroatoms selected from N, S and O, wherein the carbocyclic ring or heterocycle is optionally substituted with 1-3 groups selected from =O, halogen, cyano, hydroxyl, $NH_2$, —COOH, $C_{1-4}$ alkyl, $C_{2-6}$ alkenyl, $C_{2-6}$ alkynyl, and $C_{3-6}$ cycloalkyl.

In some specific embodiments, $R_6$ and $R_7$ are each independently selected from H, deuterium, halogen, $C_{1-4}$ alkyl, $C_{1-4}$ alkoxy, $C_{2-6}$ alkenyl, $C_{2-6}$ alkynyl, and $C_{3-6}$ cycloalkyl, wherein the alkyl, alkoxy, alkenyl, alkynyl, and cycloalkyl are optionally substituted with 1-3 groups selected from deuterium, halogen, cyano, hydroxyl, $NH_2$, and COOH;

optionally, $R_6$ and $R_7$ form =O;

optionally, two $R_5$ on adjacent ring atoms, two $R_6$ on adjacent ring atoms, or $R_5$ and $R_6$ on adjacent ring atoms in $X_1$, $X_2$, $X_3$, and $X_4$ together with the atoms to which they are attached form a double bond;

and optionally, $R_6$ and $R_7$ on the same carbon atom together with the carbon atom to which they are attached form $C_{3-6}$ cycloalkyl or a 4-7-membered heterocycle containing 1-3 heteroatoms selected from N, S and O, and the cycloalkyl or heterocycle is optionally substituted with 1-3 groups selected from =O, halogen, cyano, hydroxyl, $NH_2$, COOH, $C_{1-4}$ alkyl, $C_{2-6}$ alkenyl, $C_{2-6}$ alkynyl, and $C_{3-6}$ cycloalkyl.

In some specific embodiments, $R_6$ and $R_7$ are each independently selected from H, deuterium, halogen, $C_{1-4}$ alkyl, and $C_{1-4}$ alkoxy, wherein the alkyl and alkoxy are optionally substituted with 1-3 groups selected from deuterium, halogen, cyano, hydroxyl, $NH_2$, and COOH;

optionally, $R_6$ and $R_7$ form =O;

optionally, two $R_5$ on adjacent ring atoms, two $R_6$ on adjacent ring atoms, or $R_5$ and $R_6$ on adjacent ring atoms in $X_1$, $X_2$, $X_3$, and $X_4$ together with the atoms to which they are attached form a double bond;

and Z is CH or N.

The compounds of formula (I)-(III) are required to satisfy one of conditions (1)-(4):

(1) A is

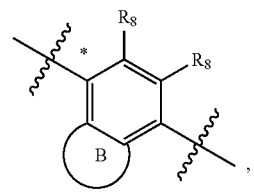

a six-membered heteroaryl or a 5-10-membered non-aromatic heterocycle, the heteroaryl and non-aromatic heterocycle contain 1-3 heteroatoms selected from N, S and O, and the A is optionally substituted with 1-3 $R_8$ groups;

* indicates the end connected to the alkyl carbon atom;

ring B is a $C_{3-12}$ carbocyclic ring or a 4-7-membered heterocycle containing 1-3 heteroatoms selected from N, S and O;

each Re is independently selected from H, =O, deuterium, halogen, $C_{1-4}$ alkyl, $C_{1-4}$ alkoxy, $—SC_{1-4}$ alkyl, $C_{2-6}$ alkenyl, $C_{2-6}$ alkynyl, $C_{3-6}$ cycloalkyl, cyano, hydroxyl, $NH_2$, $—NHC_{1-4}$ alkyl, $—N(C_{1-4}$ alkyl$)_2$, —COOH, $—COC_{1-4}$ alkyl, $—COOC_{1-4}$ alkyl, $—CONHC_{1-4}$ alkyl, $—CON(C_{1-4}$ alkyl$)_2$, $—NHCOC_{1-4}$ alkyl, and a 4-7-membered heterocycle containing 1-3 heteroatoms selected from N, S and O; the alkyl, alkoxy, alkenyl, alkynyl, cycloalkyl, and heterocycle groups in the case of Re are optionally substituted with 1-3 groups selected from deuterium, halogen, cyano, hydroxyl, $NH_2$, and —COOH;

and Cy is not substituted or unsubstituted

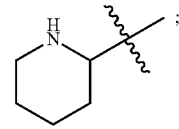 [SMILES: *C1CCCCN1]

in some specific embodiments, A is

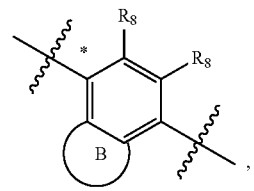

a six-membered heteroaryl or a 5-7-membered non-aromatic monocyclic heterocycle, the heteroaryl and non-aromatic monocyclic heterocycle contain 1-3 heteroatoms selected from N, S and O, and the A is optionally substituted with 1-3 Re groups;

* indicates the end connected to the alkyl carbon atom;

ring B is a $C_{4-6}$ carbocyclic ring or a 5-6-membered heterocycle containing 1-3 heteroatoms selected from N, S and O;

and each Re is independently selected from H, =O, deuterium, halogen, $C_{1-4}$ alkyl, $C_{1-4}$ alkoxy, —$SC_{1-4}$ alkyl, $C_{2-6}$ alkenyl, $C_{2-6}$ alkynyl, cyano, hydroxyl, —COOH, $NH_2$, and $C_{3-6}$ cycloalkyl, and the alkyl, alkoxy, alkenyl, alkynyl, and cycloalkyl are optionally substituted with 1-3 groups selected from deuterium, halogen, cyano, hydroxyl, $NH_2$, and —COOH;

in other specific embodiments, A is

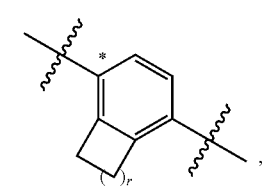,

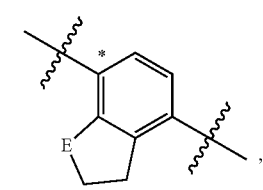,

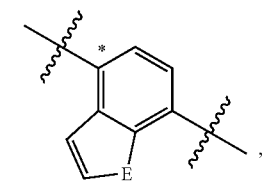,

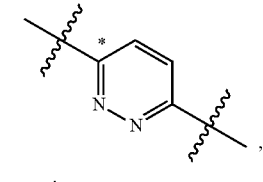,

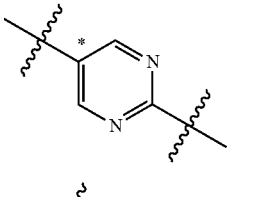 or

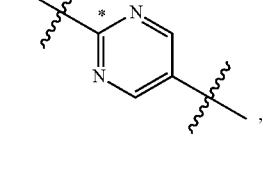, and ring A is optionally substituted with 1-3 Re groups;

each $R_8$ is independently selected from halogen, =O, cyano, hydroxyl, $NH_2$, —COOH, $C_{1-4}$ alkyl, $C_{2-6}$ alkenyl, $C_{2-6}$ alkynyl, and $C_{3-6}$ cycloalkyl;

* indicates the end connected to the alkyl carbon atom;
r is an integer of 1-3;
and E is selected from NH, S and O;

in other specific embodiments, A is

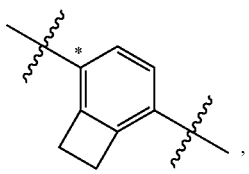,

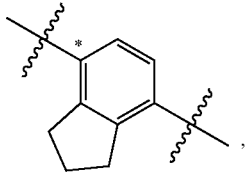,

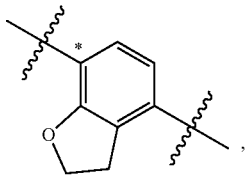,

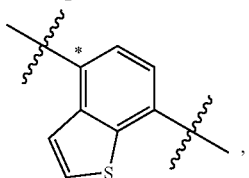,

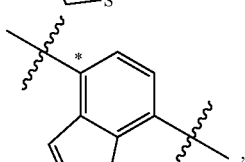,

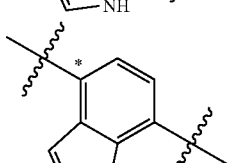,

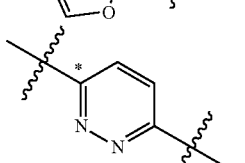,

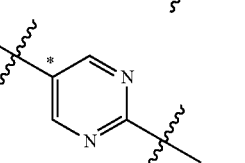 or

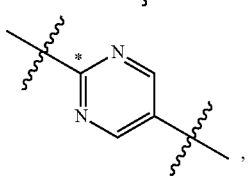, and ring A is optionally substituted with 1-3 $R_8$ groups; the substituent is located at any substitutable position on ring A, including any substitutable position on the carbon atom of the benzene ring and on the carbon atom or heteroatom of the ring fused to the benzene ring;

each $R_8$ is independently selected from halogen, =O, cyano, hydroxyl, $NH_2$, —COOH, $C_{1-4}$ alkyl, $C_{1-4}$ alkoxy, —$SC_{1-4}$ alkyl, $C_{2-6}$ alkenyl, $C_{2-6}$ alkynyl, and $C_{3-6}$ cycloalkyl; and

* indicates the end connected to the alkyl carbon atom; or (2) A is a five-membered heteroaryl containing 1-3 heteroatoms selected from N, S and O, and the A is optionally substituted with 1-3 $R_8$ groups;

each $R_8$ is independently selected from H, =O, deuterium, halogen, $C_{1-4}$ alkyl, $C_{1-4}$ alkoxy, —$SC_{1-4}$ alkyl, $C_{2-6}$ alkenyl, $C_{2-6}$ alkynyl, $C_{3-6}$ cycloalkyl, cyano, hydroxyl, $NH_2$, —$NHC_{1-4}$ alkyl, —$N(C_{1-4}$ alkyl$)_2$, —COOH, —$COC_{1-4}$ alkyl, —$COOC_{1-4}$ alkyl, —$CONHC_{1-4}$ alkyl, —$CON(C_{1-4}$ alkyl$)_2$, —$NHCOC_{1-4}$ alkyl, and a 4-7-membered heterocycle containing 1-3 heteroatoms selected from N, S and O; the alkyl, alkoxy, alkenyl, alkynyl, cycloalkyl, and heterocycle groups in the case of $R_8$ are optionally substituted with 1-3 groups selected from deuterium, halogen, cyano, hydroxyl, $NH_2$, and —COOH;

and Cy is not substituted or unsubstituted

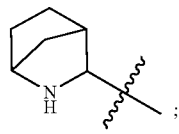 [SMILES: *C1NC2CCC1C2]
;

in some specific embodiments, A is a five-membered heteroaryl containing 1-3 heteroatoms selected from N, S and O, and the A is optionally substituted with 1-3 $R_8$ groups;

each $R_8$ is independently selected from H, =O, deuterium, halogen, $C_{1-4}$ alkyl, $C_{1-4}$ alkoxy, —$SC_{1-4}$ alkyl, $C_{2-6}$ alkenyl, $C_{2-6}$ alkynyl, cyano, hydroxyl, —COOH, $NH_2$, and $C_{3-6}$ cycloalkyl; the alkyl, alkoxy, alkenyl, alkynyl, and cycloalkyl are optionally substituted with 1-3 groups selected from deuterium, halogen, cyano, hydroxyl, $NH_2$, and —COOH;

and Cy is not substituted or unsubstituted

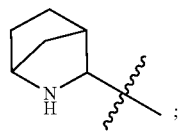
;

in some specific embodiments, A is

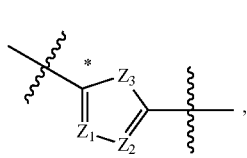
, and A is optionally substituted with 1-3 $R_8$ groups;

each $R_8$ is independently selected from halogen, cyano, hydroxyl, $NH_2$, —COOH, $C_{1-4}$ alkyl, $C_{2-6}$ alkenyl, $C_{2-6}$ alkynyl, and $C_{3-6}$ cycloalkyl;

$Z_1$ and $Z_2$ are each independently CH or N;

$Z_3$ is S, O or NH;

* indicates the end connected to the alkyl carbon atom;

in some specific embodiments, A is

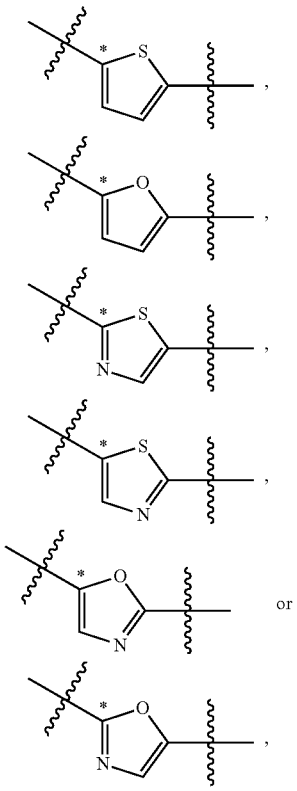

and A is optionally substituted with 1-3 groups selected from halogen, cyano, hydroxyl, $NH_2$, —COOH, $C_{1-4}$ alkyl, $C_{2-6}$ alkenyl, $C_{2-6}$ alkynyl, and $C_{3-6}$ cycloalkyl;

Cy is

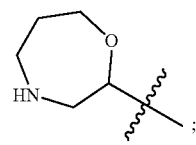
;

* indicates the end connected to the alkyl carbon atom; or (3) A is

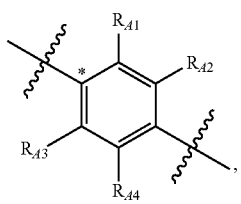
, wherein * indicates the end connected to the alkyl carbon atom;

$R_{A1}$, $R_{A2}$, $R_{A3}$, and $R_{A4}$ are each independently $R_8$, and $R_{A1}$, $R_{A2}$, $R_{A3}$, and $R_{A4}$ are not H at the same time;

each $R_8$ is independently selected from H, =O, deuterium, halogen, $C_{1-4}$ alkyl, $C_{1-4}$ alkoxy, —$SC_{1-4}$ alkyl, $C_{2-6}$ alkenyl, $C_{2-6}$ alkynyl, $C_{3-6}$ cycloalkyl, cyano, hydroxyl, $NH_2$, —$NHC_{1-4}$ alkyl, —$N(C_{1-4}$ alkyl$)_2$, —COOH, —$COC_{1-4}$ alkyl, —$COOC_{1-4}$ alkyl, —$CONHC_{1-4}$ alkyl, —$CON(C_{1-4}$ alkyl$)_2$, —$NHCOC_{1-4}$ alkyl, and a 4-7-membered heterocycle containing 1-3 heteroatoms selected from N, S and O; the alkyl, alkoxy, alkenyl, alkynyl, cycloalkyl, and heterocycle groups in the case of $R_8$ are optionally substituted with 1-3 groups selected from deuterium, halogen, cyano, hydroxyl, $NH_2$, and —COOH;

Cy is a 5-12-membered monocyclic heterocycle containing 1-3 heteroatoms selected from N, S and O, and the monocyclic heterocycle is optionally substituted with 1-3 groups selected from deuterium, =O, halogen, cyano, hydroxyl, $NH_2$, —COOH, $C_{1-4}$ alkyl, halo $C_{1-4}$ alkyl, hydroxy $C_{1-4}$ alkyl, $C_{1-4}$ alkoxy, $C_{3-6}$ cycloalkoxy, $C_{1-6}$ alkoxyalkyl, halo $C_{1-4}$ alkoxy, $C_{2-6}$ alkenyl, $C_{2-6}$alkynyl, —$NHC_{1-4}$ alkyl, —$N(C_{1-4}$ alkyl$)_2$, —$COC_{1-4}$ alkyl, —$COOC_{1-4}$ alkyl, —$CONH_2$, —$CONHC_{1-4}$ alkyl, —$CON(C_{1-4}$ alkyl$)_2$, —$NHCOC_{1-4}$ alkyl, —$S(O)C_{1-4}$ alkyl, —$S(O)_2C_{1-4}$ alkyl, —$S(O)NH_2$, —$S(O)NHC_{1-4}$ alkyl, —$S(O)N(C_{1-4}$ alkyl$)_2$, —$S(O)_2NH_2$, —$S(O)_2NHC_{1-4}$ alkyl, and —$S(O)_2N(C_{1-4}$ alkyl$)_2$;

and Cy is not substituted or unsubstituted

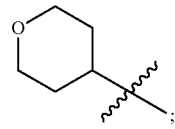 [SMILES: *C1CCOCC1]

in some specific embodiments, A is

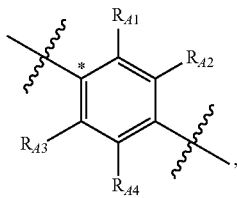

wherein * indicates the end connected to the alkyl carbon atom;

$R_{A1}$, $R_{A2}$, $R_{A3}$, and $R_{A4}$ are each independently $R_8$, and $R_{A1}$, $R_{A2}$, $R_{A3}$, and $R_{A4}$ are not H at the same time;

each $R_8$ is independently selected from H, =O, deuterium, halogen, $C_{1-4}$ alkyl, $C_{1-4}$ alkoxy, —$SC_{1-4}$ alkyl, $C_{2-6}$ alkenyl, $C_{2-6}$ alkynyl, cyano, hydroxyl, —COOH, $NH_2$, and $C_{3-6}$ cycloalkyl; the alkyl, alkoxy, alkenyl, alkynyl, and cycloalkyl are optionally substituted with 1-3 groups selected from deuterium, halogen, cyano, hydroxyl, $NH_2$, and —COOH;

and Cy is a 5-8-membered monocyclic heterocycle containing 1-3 heteroatoms selected from N, S and O, and the monocyclic heterocycle is optionally substituted with 1-3 groups selected from =O, halogen, cyano, hydroxyl, $NH_2$, —COOH, $C_{1-4}$ alkyl, halo $C_1$ alkyl, hydroxy $C_{1-4}$ alkyl, $C_{1-4}$ alkoxy, $C_{3-6}$ cycloalkoxy, $C_{1-6}$ alkoxyalkyl, halo $C_{1-4}$ alkoxy, —$NHC_{1-4}$ alkyl, —$N(C_{1-4}$ alkyl$)_2$, —$COC_{1-4}$ alkyl, —$CONH_2$, —$CONHC_{1-4}$ alkyl, —$CON(C_{1-4}$ alkyl$)_2$, —$NHCOC_{1-4}$ alkyl, —$S(O)C_{1-4}$ alkyl, —$S(O)_2C_{1-4}$ alkyl, —$S(O)NH_2$, —$S(O)NHC_{1-4}$ alkyl, —$S(O)N(C_{1-4}$ alkyl$)_2$, —$S(O)_2NH_2$, —$S(O)_2NHC_{1-4}$ alkyl, and —$S(O)_2N(C_{1-4}$ alkyl$)_2$;

in some specific embodiments, A is

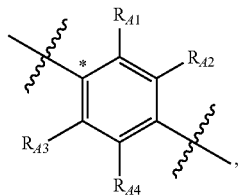

wherein * indicates the end connected to the alkyl carbon atom;

$R_{A1}$, $R_{A2}$, $R_{A3}$, and $R_{A4}$ are each independently $R_8$, and $R_{A1}$, $R_{A2}$, $R_{A3}$, and $R_{A4}$ are not H at the same time;

each $R_8$ is independently selected from H, deuterium, halogen, $C_{1-4}$ alkyl, $C_{1-4}$ alkoxy, cyano, hydroxyl, $NH_2$, and COOH, wherein the alkyl and alkoxy are optionally substituted with 1-3 groups selected from deuterium, halogen, cyano, hydroxyl, $NH_2$, and COOH;

and Cy is

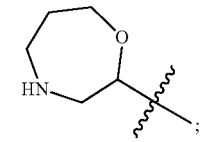

or (4) A is

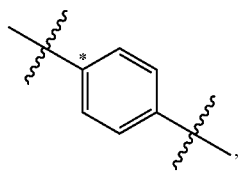 [SMILES: *c1ccc(*)cc1]

wherein * indicates the end connected to the alkyl carbon atom;

$R_1$, $R_2$, and $R_3$ are each independently selected from H, deuterium, halogen, $C_{1-4}$ alkyl, $C_{1-4}$ alkoxy, $C_{2-6}$ alkenyl, $C_{2-6}$ alkynyl, $C_{3-6}$ cycloalkyl, and a 4-7-membered heterocycle containing 1-3 heteroatoms selected from N, S and O, wherein the alkyl, alkoxy, alkenyl, alkynyl, cycloalkyl, and heterocycle are optionally substituted with 1-3 groups selected from halogen, $C_{1-4}$ alkyl, cyano, hydroxyl, $NH_2$, and —COOH, and $R_1$, $R_2$, and $R_3$ are not H at the same time;

and optionally, $R_1$ and $R_2$ together with the carbon atom to which they are attached form $C_{3-6}$ cycloalkyl or a 4-7-membered heterocycle containing 1-3 heteroatoms selected from N, S and O, wherein the cycloalkyl or heterocycle is optionally substituted with 1-3 groups selected from =O, halogen, cyano, hydroxyl, NH$_2$, —COOH, C$_{1-4}$ alkyl, C$_{2-6}$ alkenyl, C$_{2-6}$ alkynyl, and C$_{3-6}$ cycloalkyl;

in some specific embodiments, A is

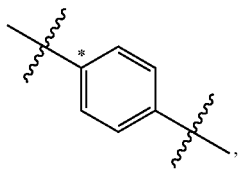 [SMILES: *c1ccc(*)cc1]

wherein * indicates the end connected to the alkyl carbon atom;

R$_1$, R$_2$, and R$_3$ are each independently selected from H, deuterium, halogen, C$_{1-4}$ alkyl, C$_{1-4}$ alkoxy, C$_{2-6}$ alkenyl, and C$_{2-6}$ alkynyl, and the alkyl, alkoxy, alkenyl, and alkynyl are optionally substituted with 1-3 groups selected from halogen, C$_{1-4}$ alkyl, cyano, hydroxyl, NH$_2$, and COOH, and R$_1$, R$_2$, and R$_3$ are not H at the same time; and optionally, R$_1$ and R$_2$ together with the carbon atom to which they are attached form C$_{3-6}$ cycloalkyl, and the cycloalkyl is optionally substituted with 1-3 groups selected from =O, halogen, cyano, hydroxyl, NH$_2$, COOH, C$_{1-4}$ alkyl, C$_{2-6}$ alkenyl, and C$_{2-6}$ alkynyl;

in some specific embodiments, A is

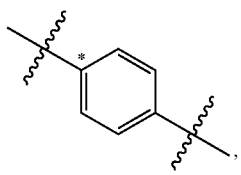 [SMILES: *c1ccc(*)cc1]

wherein * indicates the end connected to the alkyl carbon atom;

R$_1$, R$_2$, and R$_3$ are each independently selected from H, deuterium, halogen, C$_{1-4}$ alkyl, C$_{1-4}$ alkoxy, C$_{2-6}$ alkenyl, and C$_{2-6}$ alkynyl, and the alkyl, alkoxy, alkenyl, and alkynyl are optionally substituted with 1-3 groups selected from halogen, C$_{1-4}$ alkyl, cyano, hydroxyl, NH$_2$, and COOH, and R$_1$, R$_2$, and R$_3$ are not H at the same time; and optionally, R$_1$ and R$_2$ together with the carbon atom to which they are attached form C$_{3-6}$ cycloalkyl, and the cycloalkyl is optionally substituted with 1-3 groups selected from cyano, hydroxyl, NH$_2$, and COOH.

In the present invention, "〰" indicates the connecting site.

More specifically, as a first technical solution of the present invention, the present invention provides a compound of formula (I), or a stereoisomer, a deuterated product, a co-crystal, a solvate or a pharmaceutically acceptable salt thereof:

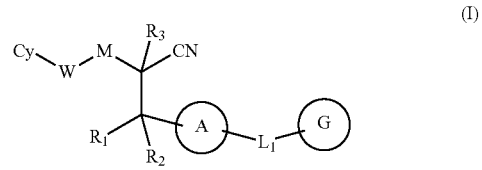

wherein ring G is a 5-12-membered carbocyclic ring, a 5-12-membered monocyclic heterocycle containing 1-3 heteroatoms selected from N, S and O, or a fused ring of formula (I-1)

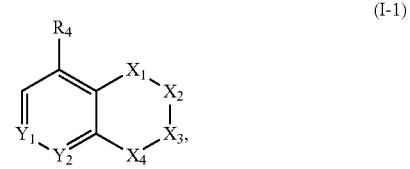

L$_1$ is attached to the ring G by replacing any hydrogen atom on the ring atoms (for example, the carbon atom on the 5-12-membered carbocyclic ring, the ring carbon atom or ring heteroatom on the 5-12-membered monocyclic heterocycle, and the ring carbon atom or ring heteroatom on the fused ring of formula (I-1)), and the carbocyclic ring or monocyclic heterocycle is optionally substituted with 1-3 R$_G$ groups;

optionally, formula (I-1) has the structure

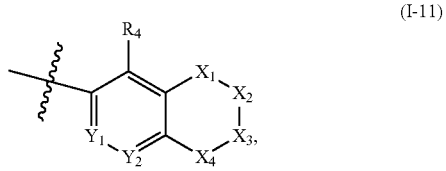

optionally, formula (I-1) has the structure

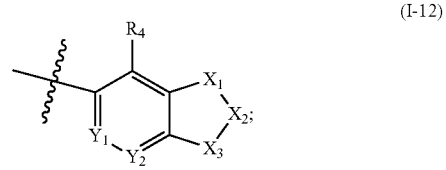

each R$_G$ is independently selected from deuterium, SF$_5$, =O, halogen, cyano, hydroxyl, NH$_2$, —COOH, C$_{1-4}$ alkyl, halo C$_{1-4}$ alkyl, C$_{1-4}$ alkoxy, C$_{3-6}$ cycloalkyloxy, C$_{3-6}$ cycloalkyl, C$_{2-6}$ alkenyl, C$_{2-6}$ alkynyl, —NHC$_{1-4}$ alkyl, —N(C$_{1-4}$ alkyl)$_2$, —COC$_{1-4}$ alkyl, —COOC$_{1-4}$ alkyl, —CONH$_2$, —CONHC$_{1-4}$ alkyl, —CONHC$_{3-6}$ cycloalkyl, —CON(C$_{1-4}$ alkyl)$_2$, —NHCOC$_{1-4}$ alkyl, —NHCOC$_3$—cycloalkyl, —P(O)(C$_{1-4}$ alkyl)$_2$, —S(O)C$_{1-4}$alkyl, —S(O)$_2$C$_{1-4}$ alkyl, —S(O)$_2$C$_{3-6}$ cycloalkyl, —S(O)NH$_2$, —S(O)NHC$_{1-4}$ alkyl, —S(O)N(C$_{1-4}$ alkyl)$_2$, —S(O)$_2$NH$_2$, and a 4-7-membered heterocycle containing 1-3 heteroatoms selected from N, S and O, and the R$_G$ is optionally further substituted with 1-3 groups selected from deuterium, C$_{1-4}$ alkyl, halo C$_{1-4}$ alkyl, hydroxy $C_{1-4}$ alkyl, —$CONH_2$, $NH_2$, $C_{1-6}$ alkoxy, hydroxyl, —COOH, halogen, and a 5-7-membered heterocycle containing 1-3 heteroatoms selected from N, S and O, and further, the 5-7-membered heterocycle is optionally substituted with 1-2 groups selected from =O, halogen, cyano, $C_{1-4}$ alkyl, and halo $C_{1-4}$ alkyl;

Cy is a 5-12-membered heterocycle containing 1-3 heteroatoms selected from N, S and O, and the heterocycle is optionally substituted with 1-3 groups selected from deuterium, =O, halogen, cyano, hydroxyl, $NH_2$, —COOH, $C_{1-4}$ alkyl, halo $C_{1-4}$ alkyl, hydroxy $C_{1-4}$ alkyl, $C_{1-4}$ alkoxy, $C_{3-6}$ cycloalkyloxy, $C_{1-6}$ alkoxyalkyl, halo $C_{1-4}$ alkoxy, $C_{2-6}$ alkenyl, $C_{2-6}$ alkynyl, —$NHC_{1-4}$ alkyl, —$N(C_{1-4}$ alkyl$)_2$, —$COC_{1-4}$ alkyl, —$COOC_{1-4}$ alkyl, —$CONH_2$, —$CONHC_{1-4}$ alkyl, —$CON(C_{1-4}$ alkyl$)_2$, —$NHCOC_{1-4}$ alkyl, —$S(O)C_{1-4}$ alkyl, —$S(O)_2C_{1-4}$ alkyl, —$S(O)NH_2$, —$S(O)NHC_{1-4}$ alkyl, —$S(O)N(C_{1-4}$ alkyl$)_2$, —$S(O)_2NH_2$, —$S(O)_2NHC_{1-4}$ alkyl, and —$S(O)_2N(C_{1-4}$ alkyl$)_2$;

W is C(=O), C(=S), C(=N—$R_W$), S(=O) or S(=O)$_2$;

M is $NR_M$ or O;

$R_W$ is OH, CN or $C_{1-4}$ alkyl;

$R_M$ is H, $C_{1-4}$ alkyl or $C_{3-6}$ cycloalkyl;

$R_1$, $R_2$, and $R_3$ are each independently selected from H, deuterium, halogen, $C_{1-4}$ alkyl, $C_{1-4}$ alkoxy, $C_{2-6}$ alkenyl, $C_{2-6}$ alkynyl, $C_{3-6}$ cycloalkyl, and a 4-7-membered heterocycle containing 1-3 heteroatoms selected from N, S and O, wherein the alkyl, alkoxy, alkenyl, alkynyl, cycloalkyl, and heterocycle are optionally substituted with 1-3 groups selected from halogen, $C_{1-4}$ alkyl, cyano, hydroxyl, $NH_2$, and —COOH;

optionally, $R_1$ and $R_2$ together with the carbon atom to which they are attached form $C_{3-6}$ cycloalkyl or a 4-7-membered heterocycle containing 1-3 heteroatoms selected from N, S and O, wherein the cycloalkyl or heterocycle is optionally substituted with 1-3 groups selected from =O, halogen, cyano, hydroxyl, $NH_2$, —COOH, $C_{1-4}$ alkyl, $C_{2-6}$ alkenyl, $C_{2-6}$ alkynyl, and $C_{3-6}$ cycloalkyl;

$L_1$ is a bond, $C_{1-3}$ alkylene, —NH—, —N($C_{1-4}$ alkyl)-, —O—, —S—, $C_{2-6}$ alkenylene, $C_{2-6}$ alkynylene, —CO—, or —CONH—, and the alkylene, alkenylene or alkynylene is optionally substituted with 1-3 groups selected from halogen, $C_{1-4}$ alkyl, cyano, hydroxyl, $NH_2$, and —COOH;

$Y_1$ and $Y_2$ are each independently selected from $CR_4$ and N;

each $R_4$ is independently selected from H, deuterium, halogen, $C_{1-4}$ alkyl, $C_{1-4}$ alkoxy, $C_{2-6}$ alkenyl, $C_{2-6}$ alkynyl, $C_{3-6}$ cycloalkyl, cyano, hydroxyl, $NH_2$, —$NHC_{1-4}$ alkyl, —$N(C_{1-4}$ alkyl$)_2$, —COOH, —$COC_{1-4}$ alkyl, —$COOC_{1-4}$ alkyl, —$CONHC_{1-4}$ alkyl, —$CON(C_{1-4}$ alkyl$)_2$, —$NHCOC_{1-4}$ alkyl, and a 4-7-membered heterocycle containing 1-3 heteroatoms selected from N, S and O, wherein the alkyl, alkenyl, alkynyl, cycloalkyl, and heterocycle groups in the case of $R_4$ are optionally substituted with 1-3 groups selected from deuterium, halogen, cyano, hydroxyl, $NH_2$, and —COOH.

$X_1$, $X_2$, $X_3$, and $X_4$ are each independently selected from a bond, $NR_5$, O, $CR_6R_7$, S, S(O), and S(O)$_2$, and at most one of $X_1$, $X_2$, $X_3$, and $X_4$ is a bond;

each $R_5$ is independently selected from H, $C_{1-4}$ alkyl, —$COC_{1-4}$ alkyl, $C_{2-6}$ alkenyl, $C_{2-6}$ alkynyl, and $C_{3-6}$ cycloalkyl, wherein the alkyl, alkenyl, alkynyl, and cycloalkyl are optionally substituted with 1-3 groups selected from deuterium, halogen, cyano, hydroxyl, $NH_2$, and COOH;

$R_6$ and $R_7$ are each independently selected from H, deuterium, halogen, $C_{1-4}$ alkyl, $C_{1-4}$ alkoxy, $C_{2-6}$ alkenyl, $C_{2-6}$ alkynyl, $C_{3-6}$ cycloalkyl, cyano, hydroxyl, $NH_2$, —COOH, and a 4-7-membered heterocycle containing 1-3 heteroatoms selected from N, S and O, wherein the alkyl, alkoxy, alkenyl, alkynyl, cycloalkyl, and heterocycle are optionally substituted with 1-3 groups selected from deuterium, halogen, cyano, hydroxyl, $NH_2$, and —COOH;

optionally, $R_6$ and $R_7$ form =O;

optionally, two $R_5$ on adjacent ring atoms, two $R_6$ on adjacent ring atoms, or $R_5$ and $R_6$ on adjacent ring atoms in $X_1$, $X_2$, $X_3$, and $X_4$ together with the atoms to which they are attached form a double bond;

optionally, $R_6$ and $R_7$ on the same carbon atom together with the carbon atom to which they are attached form a $C_{3-12}$ carbocyclic ring or a 4-7-membered heterocycle containing 1-3 heteroatoms selected from N, S and O, wherein the carbocyclic ring or heterocycle is optionally substituted with 1-3 groups selected from =O, halogen, cyano, hydroxyl, $NH_2$, —COOH, $C_{1-4}$ alkyl, $C_{2-6}$ alkenyl, $C_{2-6}$ alkynyl, and $C_{3-6}$ cycloalkyl, provided that:

(1) A is

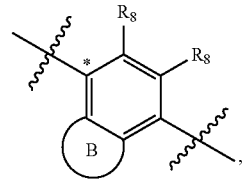

a six-membered heteroaryl or a 5-10-membered non-aromatic heterocycle, and the A is optionally substituted with 1-3 $R_8$ groups;

* indicates the end connected to the alkyl carbon atom;

ring B is a $C_{3-12}$ carbocyclic ring or a 4-7-membered heterocycle containing 1-3 heteroatoms selected from N, S and O, and the carbocyclic ring or heterocycle is optionally substituted with 1-3 groups selected from =O, halogen, cyano, hydroxyl, $NH_2$, —COOH, $C_{1-4}$ alkyl, $C_{1-4}$ alkoxy, —$SC_{1-4}$ alkyl, $C_{2-6}$ alkenyl, $C_{2-6}$ alkynyl, and $C_{3-6}$ cycloalkyl;

each $R_8$ is independently selected from H, =O, deuterium, halogen, $C_{1-4}$ alkyl, $C_{1-4}$ alkoxy, —$SC_{1-4}$ alkyl, $C_{2-6}$ alkenyl, $C_{2-6}$ alkynyl, $C_{3-6}$ cycloalkyl, cyano, hydroxyl, $NH_2$, —$NHC_{1-4}$ alkyl, —$N(C_{1-4}$ alkyl$)_2$, —COOH, —$COC_{1-4}$ alkyl, —$COOC_{1-4}$ alkyl, —$CONHC_{1-4}$ alkyl, —$CON(C_{1-4}$ alkyl$)_2$, —$NHCOC_{1-4}$ alkyl, and a 4-7-membered heterocycle containing 1-3 heteroatoms selected from N, S and O; the alkyl, alkoxy, alkenyl, alkynyl, cycloalkyl, and heterocycle groups in the case of $R_8$ are optionally substituted with 1-3 groups selected from deuterium, halogen, cyano, hydroxyl, $NH_2$, and —COOH;

and Cy is not substituted or unsubstituted

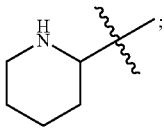 [SMILES: *C1CCCCN1]

or
(2) A is a five-membered heteroaryl containing 1-3 heteroatoms selected from N, S and O, and the A is optionally substituted with 1-3 $R_8$ groups;
each $R_8$ is independently selected from H, =O, deuterium, halogen, $C_{1-4}$ alkyl, $C_{1-4}$ alkoxy, —S$C_{1-4}$ alkyl, $C_{2-6}$ alkenyl, $C_{2-6}$ alkynyl, $C_{3-6}$ cycloalkyl, cyano, hydroxyl, $NH_2$, —NH$C_{1-4}$ alkyl, —N($C_{1-4}$ alkyl)$_2$, —COOH, —CO$C_{1-4}$ alkyl, —COO$C_{1-4}$ alkyl, —CONH$C_{1-4}$ alkyl, —CON($C_{1-4}$ alkyl)$_2$, —NHCO$C_{1-4}$ alkyl, and a 4-7-membered heterocycle containing 1-3 heteroatoms selected from N, S and O; the alkyl, alkoxy, alkenyl, alkynyl, cycloalkyl, and heterocycle groups in the case of $R_8$ are optionally substituted with 1-3 groups selected from deuterium, halogen, cyano, hydroxyl, $NH_2$, and —COOH;
and Cy is not substituted or unsubstituted

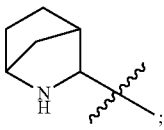 [SMILES: *C1NC2CCC1C2]

or
(3) A is

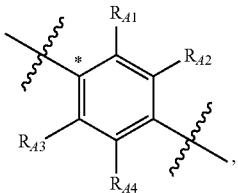

wherein * indicates the end connected to the alkyl carbon atom;
$R_{A1}$, $R_{A2}$, $R_{A3}$, and $R_{A4}$ are each independently $R_8$, and $R_{A1}$, $R_{A2}$, $R_{A3}$, and $R_{A4}$ are not H at the same time;
each $R_8$ is independently selected from H, =O, deuterium, halogen, $C_{1-4}$ alkyl, $C_{1-4}$ alkoxy, —S$C_{1-4}$ alkyl, $C_{2-6}$ alkenyl, $C_{2-6}$ alkynyl, $C_{3-6}$ cycloalkyl, cyano, hydroxyl, $NH_2$, —NH$C_{1-4}$ alkyl, —N($C_{1-4}$ alkyl)$_2$, —COOH, —CO$C_{1-4}$ alkyl, —COO$C_{1-4}$ alkyl, —CONH$C_{1-4}$ alkyl, —CON($C_{1-4}$ alkyl)$_2$, —NHCO$C_{1-4}$ alkyl, and a 4-7-membered heterocycle containing 1-3 heteroatoms selected from N, S and O; the alkyl, alkoxy, alkenyl, alkynyl, cycloalkyl, and heterocycle groups in the case of $R_8$ are optionally substituted with 1-3 groups selected from deuterium, halogen, cyano, hydroxyl, $NH_2$, and —COOH;
Cy is a 5-12-membered monocyclic heterocycle containing 1-3 heteroatoms selected from N, S and O, and the monocyclic heterocycle is optionally substituted with 1-3 groups selected from deuterium, =O, halogen, cyano, hydroxyl, $NH_2$, —COOH, $C_{1-4}$ alkyl, halo $C_{1-4}$ alkyl, hydroxy $C_{1-4}$ alkyl, $C_{1-4}$ alkoxy, $C_{3-6}$ cycloalkyloxy, $C_{1-6}$ alkoxyalkyl, halo $C_{1-4}$ alkoxy, $C_{2-6}$ alkenyl, $C_{2-6}$ alkynyl, —NH$C_{1-4}$ alkyl, —N($C_{1-4}$ alkyl)$_2$, —CO$C_{1-4}$ alkyl, —COO$C_{1-4}$ alkyl, —CONH$_2$, —CONH$C_{1-4}$ alkyl, —CON($C_{1-4}$ alkyl)$_2$, —NHCO$C_{1-4}$ alkyl, —S(O)$C_{1-4}$ alkyl, —S(O)$_2C_{1-4}$ alkyl, —S(O)NH$_2$, —S(O)NH$C_{1-4}$ alkyl, —S(O)N($C_{1-4}$ alkyl)$_2$, —S(O)$_2$NH$_2$, —S(O)$_2$NH$C_{1-4}$ alkyl, and —S(O)$_2$N($C_{1-4}$ alkyl)$_2$;
and Cy is not substituted or unsubstituted

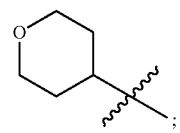

or
(4) A is

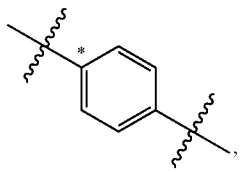 [SMILES: *c1ccc(*)cc1]

wherein * indicates the end connected to the alkyl carbon atom;
$R_1$, $R_2$, and $R_3$ are each independently selected from H, deuterium, halogen, $C_{1-4}$ alkyl, $C_{1-4}$ alkoxy, $C_{2-6}$ alkenyl, $C_{2-6}$ alkynyl, $C_{3-6}$ cycloalkyl, and a 4-7-membered heterocycle containing 1-3 heteroatoms selected from N, S and O, wherein the alkyl, alkoxy, alkenyl, alkynyl, cycloalkyl, and heterocycle are optionally substituted with 1-3 groups selected from halogen, $C_{1-4}$ alkyl, cyano, hydroxyl, $NH_2$, and —COOH, and $R_1$, $R_2$, and $R_3$ are not H at the same time; and
optionally, $R_1$ and $R_2$ together with the carbon atom to which they are attached form $C_{3-6}$ cycloalkyl or a 4-7-membered heterocycle containing 1-3 heteroatoms selected from N, S and O, wherein the cycloalkyl or heterocycle is optionally substituted with 1-3 groups selected from =O, halogen, cyano, hydroxyl, $NH_2$, —COOH, $C_{1-4}$ alkyl, $C_{2-6}$ alkenyl, $C_{2-6}$ alkynyl, and $C_{3-6}$ cycloalkyl.
As a second technical solution of the present invention, the present invention provides a compound of formula (I), or a stereoisomer, a deuterated product, a co-crystal, a solvate or a pharmaceutically acceptable salt thereof, wherein the compound has a structure of formula (II):

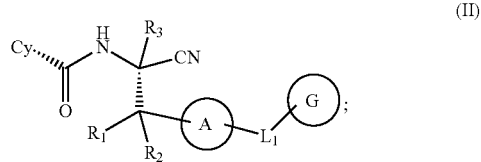

and each group is as described in the first technical solution.

As a third technical solution of the present invention, the present invention provides a compound of formula (II), or a stereoisomer, a deuterated product, a co-crystal, a solvate or a pharmaceutically acceptable salt thereof, wherein ring G is a 5-9-membered monocyclic carbocyclic ring, a 5-7-membered monocyclic heterocycle containing 1-3 heteroatoms selected from N, S and O, or a fused ring of formula (I-1)

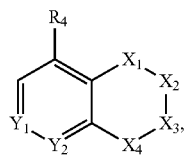

(I-1)

$L_1$ is attached to the ring G by replacing any hydrogen atom on the ring atoms, and the monocyclic carbocyclic ring or monocyclic heterocycle is optionally substituted with 1-3 $R_G$ groups;

optionally, formula (I-1) has the structure

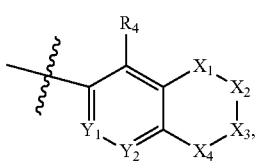

(I-11)

and optionally, formula (I-1) has the structure

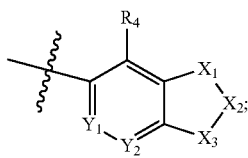

(I-12)

each $R_G$ is independently selected from deuterium, $SF_5$, =O, halogen, cyano, hydroxyl, $NH_2$, —COOH, $C_{1-4}$ alkyl, halo $C_{1-4}$ alkyl, $C_{1-4}$ alkoxy, $C_{3-6}$ cycloalkyloxy, $C_{3-6}$ cycloalkyl, $C_{2-6}$ alkenyl, $C_{2-6}$ alkynyl, —NHC$_{1-4}$ alkyl, —N(C$_{1-4}$ alkyl)$_2$, —COC$_{1-4}$ alkyl, —COOC$_{1-4}$ alkyl, —CONH$_2$, —CONHC$_{1-4}$ alkyl, —CONHC$_{3-6}$ cycloalkyl, —CON(C$_{1-4}$ alkyl)$_2$, —NHCOC$_{1-4}$ alkyl, —NHCOC$_{3-6}$ cycloalkyl, —P(O)(C$_{1-4}$ alkyl)$_2$, —S(O)C$_{1-4}$alkyl, —S(O)$_2$C$_{1-4}$ alkyl, —S(O)$_2$C$_{3-6}$ cycloalkyl, —S(O)NH$_2$, —S(O)NHC$_{1-4}$ alkyl, —S(O)N(C$_{1-4}$ alkyl)$_2$, —S(O)$_2$NH$_2$, and a 4-7-membered heterocycle containing 1-3 heteroatoms selected from N, S and O, and the $R_G$ is optionally further substituted with 1-3 groups selected from deuterium, $C_{1-4}$ alkyl, halo $C_{1-4}$ alkyl, hydroxy $C_{1-4}$ alkyl, —CONH$_2$, NH$_2$, $C_{1-6}$ alkoxy, hydroxyl, —COOH, halogen, and a 5-7-membered heterocycle containing 1-3 heteroatoms selected from N, S and O, and further, the 5-7-membered heterocycle is optionally substituted with 1-2 groups selected from =O, halogen, cyano, $C_{1-4}$ alkyl, and halo $C_{1-4}$ alkyl;

Cy is a 5-8-membered monocyclic heterocycle, a 7-10-membered spirocyclic heterocycle, a 6-9-membered bridged-ring heterocycle or a 6-10-membered fused heterocycle, which contains 1-3 heteroatoms selected from N, S and O, and Cy is optionally substituted with 1-3 groups selected from =O, halogen, cyano, hydroxyl, NH$_2$, —COOH, $C_{1-4}$ alkyl, halo $C_{1-4}$ alkyl, hydroxy $C_{1-4}$ alkyl, $C_{1-4}$ alkoxy, $C_{3-6}$ cycloalkyloxy, $C_{1-6}$ alkoxyalkyl, halo $C_{1-4}$ alkoxy, —NHC$_{1-4}$ alkyl, —N(C$_{1-4}$ alkyl)$_2$, —COC$_{1-4}$ alkyl, —CONH$_2$, —CONHC$_{1-4}$ alkyl, —CON(C$_{1-4}$ alkyl)$_2$, —NHCOC$_{1-4}$ alkyl, —S(O)C$_{1-4}$ alkyl, —S(O)$_2$C$_{1-4}$ alkyl, —S(O)NH$_2$, —S(O)NHC$_{1-4}$ alkyl, —S(O)N(C$_{1-4}$ alkyl)$_2$, —S(O)$_2$NH$_2$, —S(O)$_2$NHC$_{1-4}$ alkyl, and —S(O)$_2$N(C$_{1-4}$ alkyl)$_2$;

$R_1$, $R_2$, and $R_3$ are each independently selected from H, deuterium, halogen, $C_{1-4}$ alkyl, $C_{1-4}$ alkoxy, $C_{2-6}$ alkenyl, and $C_{2-6}$ alkynyl, and the alkyl, alkoxy, alkenyl, and alkynyl are optionally substituted with 1-3 groups selected from halogen, $C_{1-4}$ alkyl, cyano, hydroxyl, NH$_2$, and COOH;

optionally, $R_1$ and $R_2$ together with the carbon atom to which they are attached form $C_{3-6}$ cycloalkyl or a 4-7-membered heterocycle containing 1-3 heteroatoms selected from N, S and O, and the cycloalkyl or heterocycle is optionally substituted with 1-3 groups selected from halogen, cyano, hydroxyl, NH$_2$, COOH, and $C_{1-4}$ alkyl;

each $R_4$ is independently selected from H, halogen, $C_{1-4}$ alkyl, $C_{1-4}$ alkoxy, $C_{2-6}$ alkenyl, $C_{2-6}$ alkynyl, $C_{3-6}$ cycloalkyl, cyano, hydroxyl, and NH$_2$; the alkyl, alkenyl, alkynyl, and cycloalkyl in the case of $R_4$ are optionally substituted with 1-3 groups selected from deuterium, halogen, cyano, hydroxyl, NH$_2$ and COOH;

$R_6$ and $R_7$ are each independently selected from H, deuterium, halogen, $C_{1-4}$ alkyl, $C_{1-4}$ alkoxy, $C_{2-6}$ alkenyl, $C_{2-6}$ alkynyl, and $C_{3-6}$ cycloalkyl, and wherein the alkyl, alkoxy, alkenyl, alkynyl, and cycloalkyl are optionally substituted with 1-3 groups selected from deuterium, halogen, cyano, hydroxyl, NH$_2$, and COOH;

optionally, $R_6$ and $R_7$ form =O;

optionally, two $R_5$ on adjacent ring atoms, two $R_6$ on adjacent ring atoms, or $R_5$ and $R_6$ on adjacent ring atoms in $X_1$, $X_2$, $X_3$, and $X_4$ together with the atoms to which they are attached form a double bond;

and optionally, $R_6$ and $R_7$ on the same carbon atom together with the carbon atom to which they are attached form $C_{3-6}$ cycloalkyl or a 4-7-membered heterocycle containing 1-3 heteroatoms selected from N, S and O, and the cycloalkyl or heterocycle is optionally substituted with 1-3 groups selected from =O, halogen, cyano, hydroxyl, NH$_2$, COOH, $C_{1-4}$ alkyl, $C_{2-6}$ alkenyl, $C_{2-6}$ alkynyl, and $C_{3-6}$ cycloalkyl, provided that:

(1) A is

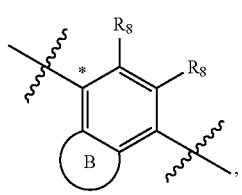

a six-membered heteroaryl or a 5-7-membered non-aromatic monocyclic heterocycle, the heteroaryl and non-aromatic monocyclic heterocycle contain 1-3 heteroatoms selected from N, S and O, and the A is optionally substituted with 1-3 $R_8$ groups;

* indicates the end connected to the alkyl carbon atom;

ring B is a $C_{4-6}$ carbocyclic ring or a 5-6-membered heterocycle containing 1-3 heteroatoms selected from N, S and O, and the carbocyclic ring or heterocycle is optionally substituted with 1-3 groups selected from =O, halogen, cyano, hydroxyl, $NH_2$, —COOH, $C_{1-4}$ alkyl, $C_{1-4}$ alkoxy, —$SC_{1-4}$ alkyl, $C_{2-6}$ alkenyl, $C_{2-6}$ alkynyl, and $C_{3-6}$ cycloalkyl;

each $R_8$ is independently selected from H, =O, deuterium, halogen, $C_{1-4}$ alkyl, $C_{1-4}$ alkoxy, —$SC_{1-4}$ alkyl, $C_{2-6}$ alkenyl, $C_{2-6}$ alkynyl, cyano, hydroxyl, —COOH, $NH_2$, and $C_{3-6}$ cycloalkyl; the alkyl, alkoxy, alkenyl, alkynyl, and cycloalkyl are optionally substituted with 1-3 groups selected from deuterium, halogen, cyano, hydroxyl, $NH_2$, and —COOH;

and Cy is not substituted or unsubstituted

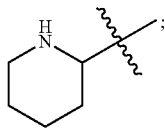

or (2) A is a five-membered heteroaryl containing 1-3 heteroatoms selected from N, S and O, and the A is optionally substituted with 1-3 $R_8$ groups;

each $R_8$ is independently selected from H, =O, deuterium, halogen, $C_{1-4}$ alkyl, $C_{1-4}$ alkoxy, —$SC_{1-4}$ alkyl, $C_{2-6}$ alkenyl, $C_{2-6}$ alkynyl, cyano, hydroxyl, —COOH, $NH_2$, and $C_{3-6}$ cycloalkyl; the alkyl, alkoxy, alkenyl, alkynyl, and cycloalkyl are optionally substituted with 1-3 groups selected from deuterium, halogen, cyano, hydroxyl, $NH_2$, and —COOH;

and Cy is not substituted or unsubstituted

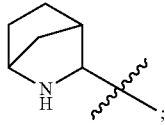

or (3) A is

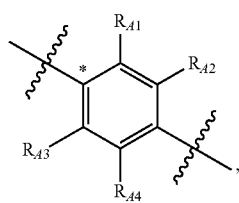

wherein * indicates the end connected to the alkyl carbon atom;

$R_{A1}$, $R_{A2}$, $R_{A3}$, and $R_{A4}$ are each independently $R_8$, and $R_{A1}$, $R_{A2}$, $R_{A3}$, and $R_{A4}$ are not H at the same time;

each $R_8$ is independently selected from H, =O, deuterium, halogen, $C_{1-4}$ alkyl, $C_{1-4}$ alkoxy, —$SC_{1-4}$ alkyl, $C_{2-6}$ alkenyl, $C_{2-6}$ alkynyl, cyano, hydroxyl, —COOH, $NH_2$, and $C_{3-6}$ cycloalkyl; the alkyl, alkoxy, alkenyl, alkynyl, and cycloalkyl are optionally substituted with 1-3 groups selected from deuterium, halogen, cyano, hydroxyl, $NH_2$, and —COOH;

Cy is a 5-8-membered monocyclic heterocycle containing 1-3 heteroatoms selected from N, S and O, and the monocyclic heterocycle is optionally substituted with 1-3 groups selected from =O, halogen, cyano, hydroxyl, $NH_2$, —COOH, $C_{1-4}$ alkyl, halo $C_{1-4}$ alkyl, hydroxy $C_{1-4}$ alkyl, $C_{1-4}$ alkoxy, $C_{3-6}$ cycloalkyloxy, $C_{1-6}$ alkoxyalkyl, halo $C_{1-4}$ alkoxy, —$NHC_{1-4}$ alkyl, —$N(C_{1-4}$ alkyl$)_2$, —$COC_{1-4}$ alkyl, —$CONH_2$, —$CONHC_{1-4}$ alkyl, —$CON(C_{1-4}$ alkyl$)_2$, —$NHCOC_{1-4}$ alkyl, —$S(O)C_{1-4}$ alkyl, —$S(O)_2C_{1-4}$ alkyl, —$S(O)NH_2$, —$S(O)NHC_{1-4}$ alkyl, —$S(O)N(C_{1-4}$ alkyl$)_2$, —$S(O)_2NH_2$, —$S(O)_2NHC_{1-4}$ alkyl, and —$S(O)_2N(C_{1-4}$ alkyl$)_2$;

and Cy is not substituted or unsubstituted

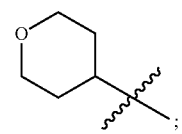

or (4) A is

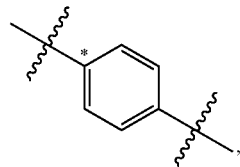 [SMILES: *c1ccc(*)cc1]

wherein * indicates the end connected to the alkyl carbon atom;

$R_1$, $R_2$, and $R_3$ are each independently selected from H, deuterium, halogen, $C_{1-4}$ alkyl, $C_{1-4}$ alkoxy, $C_{2-6}$ alkenyl, and $C_{2-6}$ alkynyl, and the alkyl, alkoxy, alkenyl, and alkynyl are optionally substituted with 1-3 groups selected from halogen, $C_{1-4}$ alkyl, cyano, hydroxyl, $NH_2$, and COOH, and $R_1$, $R_2$, and $R_3$ are not H at the same time;

optionally, $R_1$ and $R_2$ together with the carbon atom to which they are attached form $C_{3-6}$ cycloalkyl, and the cycloalkyl is optionally substituted with 1-3 groups selected from =O, halogen, cyano, hydroxyl, $NH_2$, COOH, $C_{1-4}$ alkyl, $C_{2-6}$ alkenyl, and $C_{2-6}$ alkynyl; and undefined groups are as described in the second technical solution.

As a fourth technical solution of the present invention, the present invention provides a compound of formula (I) or formula (II), or a stereoisomer, a deuterated product, a co-crystal, a solvate or a pharmaceutically acceptable salt thereof, wherein the compound further has a structure of formula (III):

(III)

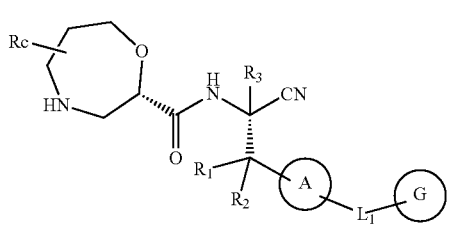

wherein Rc is H, =O, halogen, cyano, hydroxyl, NH$_2$, —COOH, C$_{1-4}$ alkyl, halo C$_{1-4}$ alkyl, hydroxy C$_{1-4}$ alkyl, C$_{1-4}$ alkoxy, C$_{1-6}$ alkoxyalkyl, or halo C$_{1-4}$ alkoxy;

R$_1$, R$_2$, and R$_3$ are each independently selected from H, deuterium, halogen, C$_{1-4}$ alkyl, and C$_{1-4}$ alkoxy, and the alkyl and alkoxy are optionally substituted with 1-3 groups selected from halogen, C$_{1-4}$ alkyl, cyano, hydroxyl, NH$_2$, and COOH;

optionally, R$_1$ and R$_2$ together with the carbon atom to which they are attached form C$_{3-6}$ cycloalkyl, and the cycloalkyl is optionally substituted with 1-3 groups selected from halogen, cyano, hydroxyl, NH$_2$, COOH, and C$_{1-4}$ alkyl;

L$_1$ is a bond, C$_{1-3}$ alkylene, —NH—, —O—, —S—, C$_{2-6}$ alkenylene, C$_{2-6}$ alkynylene, or —CO— and the alkylene, alkenylene or alkynylene is optionally substituted with 1-3 groups selected from halogen, cyano, hydroxyl, and NH$_2$;

each R$_5$ is independently selected from H, C$_{1-4}$ alkyl, and C$_{3-6}$ cycloalkyl, wherein the alkyl and cycloalkyl are optionally substituted with 1-3 groups selected from deuterium, halogen, cyano, hydroxyl, NH$_2$, and COOH;

R$_6$ and R$_7$ are each independently selected from H, deuterium, halogen, C$_{1-4}$ alkyl, and C$_{1-4}$ alkoxy, wherein the alkyl and alkoxy are optionally substituted with 1-3 groups selected from deuterium, halogen, cyano, hydroxyl, NH$_2$, and COOH;

optionally, R$_6$ and R$_7$ form =O; and optionally, two R$_5$ on adjacent ring atoms, two R$_6$ on adjacent ring atoms, or R$_5$ and R$_6$ on adjacent ring atoms in X$_1$, X$_2$, X$_3$, and X$_4$ together with the atoms to which they are attached form a double bond, provided that:

(1) A is

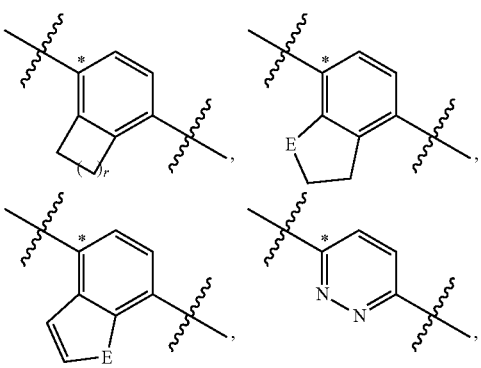

-continued

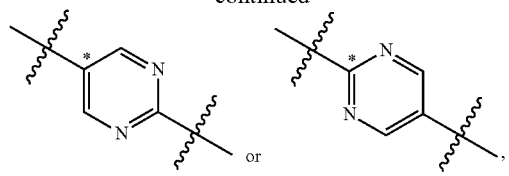

or and ring A is optionally substituted with 1-3 R$_8$ groups; the substituent is located at any substitutable position on ring A, including any substitutable position on the carbon atom of the benzene ring and on the carbon atom or heteroatom of the ring fused to the benzene ring;

each R$_8$ is independently selected from halogen, =O, cyano, hydroxyl, NH$_2$, —COOH, C$_{1-4}$ alkyl, C$_{2-6}$ alkenyl, C$_{2-6}$ alkynyl, and C$_{3-6}$ cycloalkyl;

* indicates the end connected to the alkyl carbon atom;

r is an integer of 1-3;

and E is selected from NH, S and O;

or (2) A is

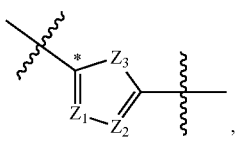

and A is optionally substituted with 1-3 R$_8$ groups;

each R$_8$ is independently selected from halogen, cyano, hydroxyl, NH$_2$, —COOH, C$_{1-4}$ alkyl, C$_{2-6}$ alkenyl, C$_{2-6}$ alkynyl, and C$_{3-6}$ cycloalkyl;

Z$_1$ and Z$_2$ are each independently CH or N;

Z$_3$ is S, O or NH;

* indicates the end connected to the alkyl carbon atom;

or (3) A is

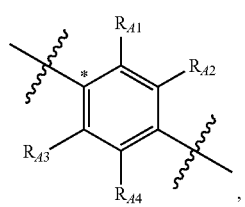

wherein * indicates the end connected to the alkyl carbon atom;

R$_{A1}$, R$_{A2}$, R$_{A3}$, and R$_{A4}$ are each independently R$_8$, and R$_{A1}$, R$_{A2}$, R$_{A3}$, and R$_{A4}$ are not H at the same time;

and each R$_8$ is independently selected from H, deuterium, halogen, C$_{1-4}$ alkyl, C$_{1-4}$ alkoxy, cyano, hydroxyl, NH$_2$, and COOH, wherein the alkyl and alkoxy are optionally substituted with 1-3 groups selected from deuterium, halogen, cyano, hydroxyl, NH$_2$, and COOH;

or (4) A is

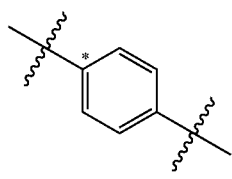
, wherein * indicates the end connected to the alkyl carbon atom;

$R_1$, $R_2$, and $R_3$ are each independently selected from H, deuterium, halogen, $C_{1-4}$ alkyl, $C_{1-4}$ alkoxy, $C_{2-6}$ alkenyl, and $C_{2-6}$ alkynyl, and the alkyl, alkoxy, alkenyl, and alkynyl are optionally substituted with 1-3 groups selected from halogen, $C_{1-4}$ alkyl, cyano, hydroxyl, $NH_2$, and COOH, and $R_1$, $R_2$, and $R_3$ are not H at the same time;

optionally, $R_1$ and $R_2$ together with the carbon atom to which they are attached form $C_{3-6}$ cycloalkyl, and the cycloalkyl is optionally substituted with 1-3 groups selected from halogen, cyano, hydroxyl, $NH_2$, and COOH; and undefined groups are as described in the third technical solution.

As a fifth technical solution of the present invention, the present invention provides a compound of formula (III), or a stereoisomer, a deuterated product, a co-crystal, a solvate or a pharmaceutically acceptable salt thereof, wherein ring G is cyclopentane, cyclohexane, cycloheptane, a benzene ring,

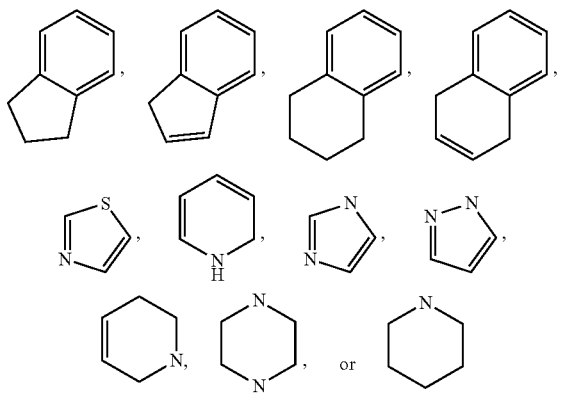

optionally substituted with 1-3 $R_G$ groups, or ring G is

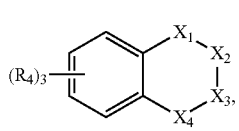

(I-2)

optionally, formula (I-2) has the structure

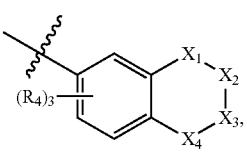

(I-21)

and optionally, formula (I-2) has the structure

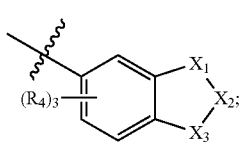

(I-22)

$L_1$ is attached to the ring G by replacing any hydrogen atom on the ring atoms, each $R_G$ is independently selected from deuterium, $SF_5$, =O, halogen, cyano, hydroxyl, $NH_2$, $C_{1-4}$ alkyl, $C_{1-4}$ alkoxy, $C_{3-6}$ cycloalkyl, $C_{2-6}$ alkenyl, $C_{2-6}$ alkynyl, $-NHC_{1-4}$ alkyl, $-N(C_{1-4}$ alkyl$)_2$, $-COC_{1-4}$ alkyl, $-CONH_2$, $-CONHC_{1-4}$ alkyl, $-CON(C_{1-4}$ alkyl$)_2$, $-NHCOC_{1-4}$ alkyl, $-P(O)(C_{1-4}$ alkyl$)_2$, and a 4-7-membered heterocycle containing 1-3 heteroatoms selected from N, S and O, and the $R_G$ is optionally further substituted with 1-3 groups selected from deuterium, $C_{1-4}$ alkyl, halo $C_{1-4}$ alkyl, hydroxy $C_{1-4}$ alkyl, $-CONH_2$, $NH_2$, $C_{1-6}$ alkoxy, hydroxyl, halogen, and a 5-7-membered heterocycle containing 1-3 heteroatoms selected from N, S and O, and further, the 5-7-membered heterocycle is optionally substituted with 1-2 groups selected from =O, halogen, cyano, $C_{1-4}$ alkyl, and halo $C_{1-4}$ alkyl, provided that:

(1) A is

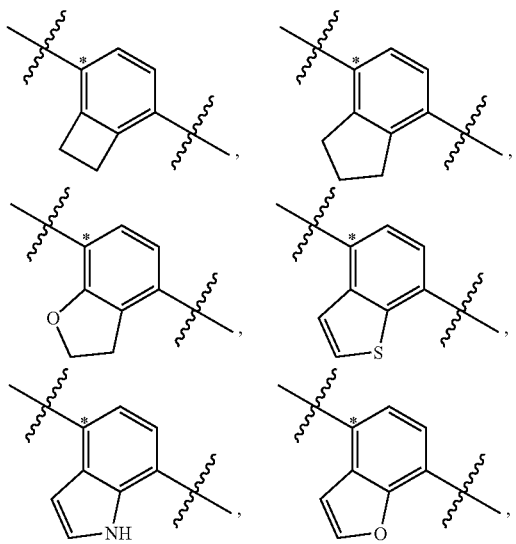

-continued

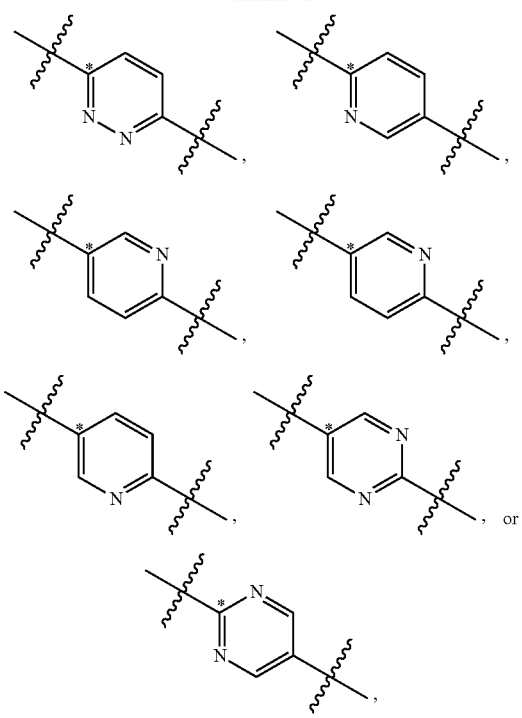

and ring A is optionally substituted with 1-3 $R_8$ groups; the substituent is located at any substitutable position on ring A, including any substitutable position on the carbon atom of the benzene ring and on the carbon atom or heteroatom of the ring fused to the benzene ring;

each $R_8$ is independently selected from =O, halogen, cyano, hydroxyl, $NH_2$, —COOH, $C_{1-4}$ alkyl, $C_{2-6}$ alkenyl, $C_{2-6}$ alkynyl, and $C_{3-6}$ cycloalkyl; and

* indicates the end connected to the alkyl carbon atom; or (2) A is

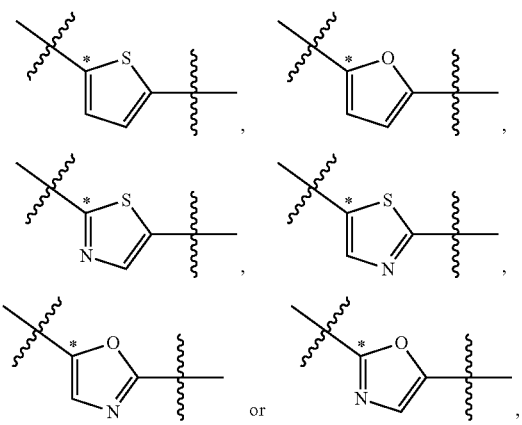

and A is optionally substituted with 1-3 groups selected from halogen, cyano, hydroxyl, $NH_2$, —COOH, $C_{1-4}$ alkyl, $C_{2-6}$ alkenyl, $C_{2-6}$ alkynyl, and $C_{3-6}$ cycloalkyl; and

* indicates the end connected to the alkyl carbon atom;

or (3) A is

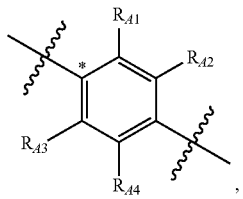

wherein * indicates the end connected to the alkyl carbon atom;

$R_{A1}$, $R_{A2}$, $R_{A3}$, and $R_{A4}$ are each independently $R_8$, and $R_{A1}$, $R_{A2}$, $R_{A3}$, and $R_{A4}$ are not H at the same time;

and each $R_8$ is independently selected from H, deuterium, halogen, $C_{1-4}$ alkyl, $C_{1-4}$ alkoxy, cyano, hydroxyl, $NH_2$, and COOH, wherein the alkyl and alkoxy are optionally substituted with 1-3 groups selected from deuterium, halogen, cyano, hydroxyl, $NH_2$, and COOH;

or (4) A is

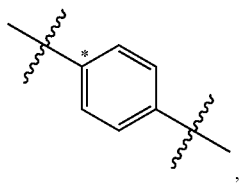 [SMILES: *c1ccc(*)cc1]

wherein * indicates the end connected to the alkyl carbon atom;

$R_1$, $R_2$, and $R_3$ are each independently selected from H, deuterium, halogen, $C_{1-4}$ alkyl, $C_{1-4}$ alkoxy, $C_{2-6}$ alkenyl, and $C_{2-6}$ alkynyl, and the alkyl, alkoxy, alkenyl, and alkynyl are optionally substituted with 1-3 groups selected from halogen, $C_{1-4}$ alkyl, cyano, hydroxyl, $NH_2$, and COOH, and $R_1$, $R_2$, and $R_3$ are not H at the same time;

optionally, $R_1$ and $R_2$ together with the carbon atom to which they are attached form $C_{3-6}$ cycloalkyl, and the cycloalkyl is optionally substituted with 1-3 groups selected from halogen, cyano, hydroxyl, $NH_2$, and COOH; and undefined groups are as described in the fourth technical solution.

As a sixth technical solution of the present invention, the present invention provides a compound of formula (III), or a stereoisomer, a deuterated product, a co-crystal, a solvate or a pharmaceutically acceptable salt thereof, wherein (I-2)

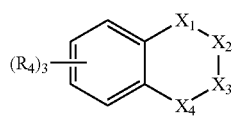

is selected from one of the following structures:

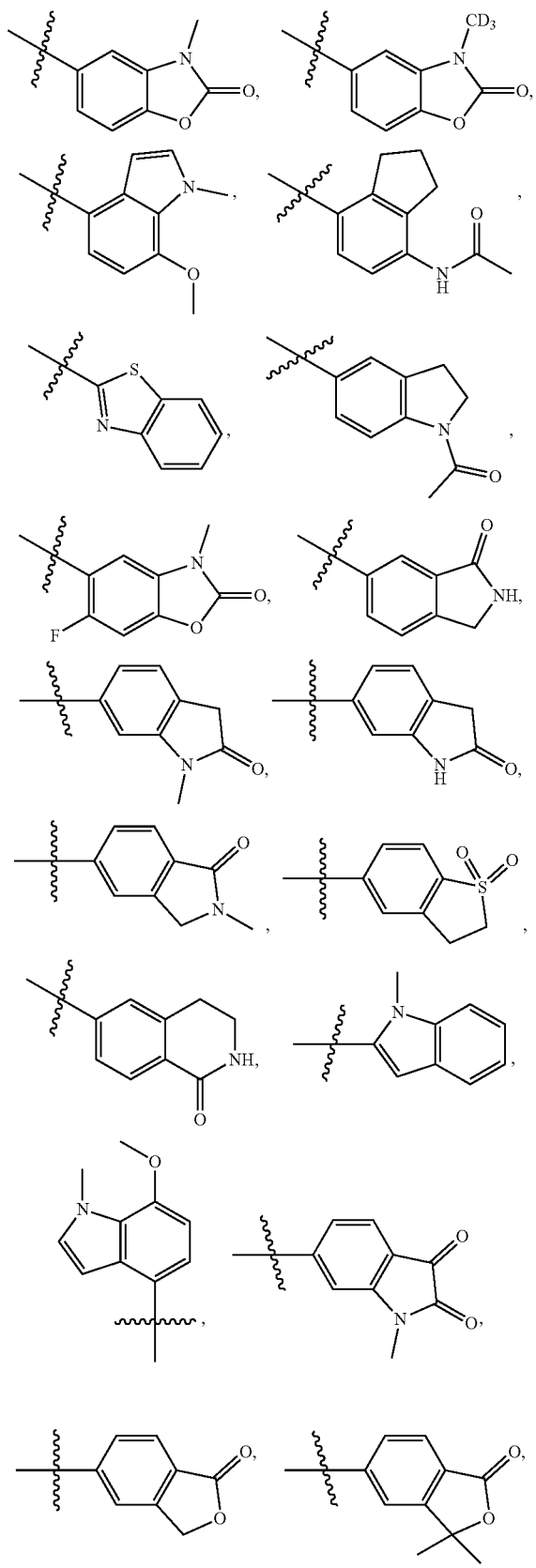

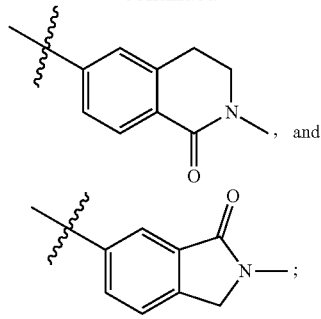

and undefined groups are as described in the fifth technical solution.

As a seventh technical solution of the present invention, the present invention provides a compound of formula (I), or a stereoisomer, a deuterated product, a co-crystal, a solvate or a pharmaceutically acceptable salt thereof, wherein the compound has a structure of formula (IV):

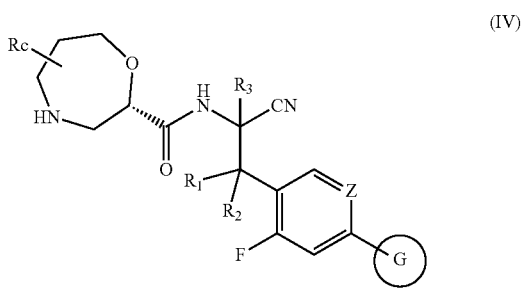

(IV)

wherein Rc is H, halogen, $C_{1-2}$ alkyl or $C_{1-2}$ alkoxy;

$R_1$, $R_2$, and $R_3$ are each independently selected from H, deuterium, F, Cl, Br, methyl, ethyl, methoxy or ethoxy, and the methyl, ethyl, methoxy or ethoxy is optionally substituted with 1-3 groups selected from F, Cl, Br, cyano, hydroxyl, and $NH_2$;

Z is CH or N;

ring G is a benzene ring or

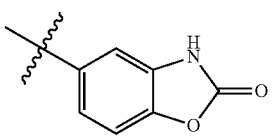 [SMILES: *c1ccc2oc(=O)[nH]c2c1]

optionally substituted with 1-2 $R_G$ groups; and each $R_G$ is independently selected from F, Cl, Br, I, methyl, ethyl, propyl, $SF_5$ and CN, wherein the methyl, ethyl or propyl is optionally further substituted with 1-3 groups selected from deuterium, F, Cl, Br, and I.

As an eighth technical solution of the present invention, the present invention provides a compound of formula (I), or a stereoisomer, a deuterated product, a co-crystal, a solvate or a pharmaceutically acceptable salt thereof, wherein the compound is selected from one of the following structures:

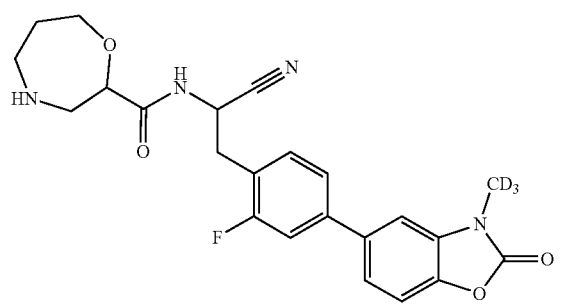
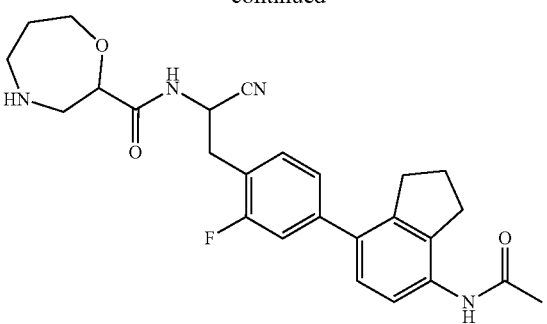
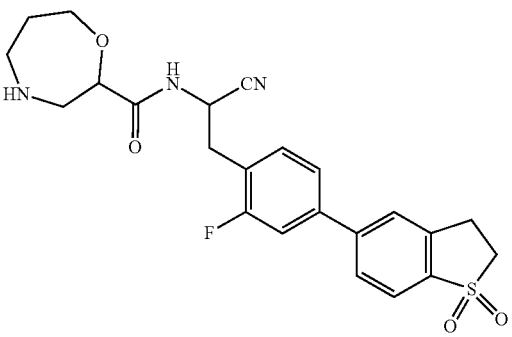
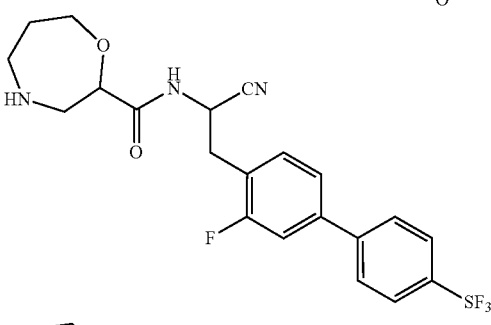
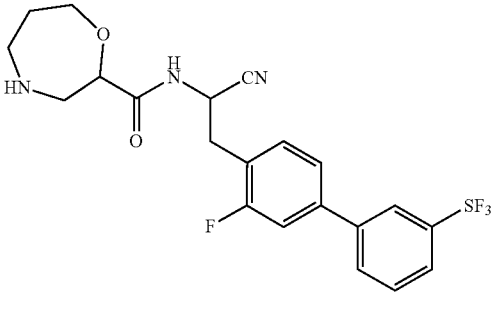
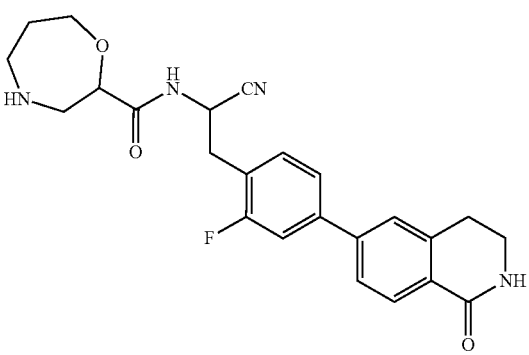

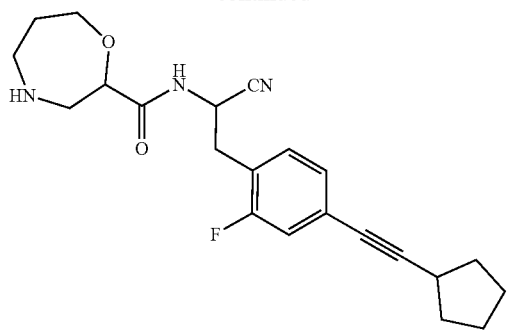
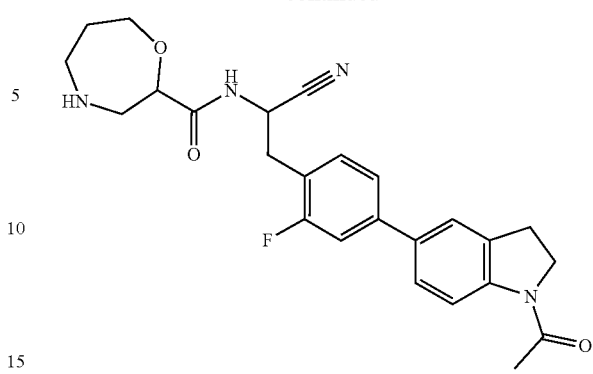
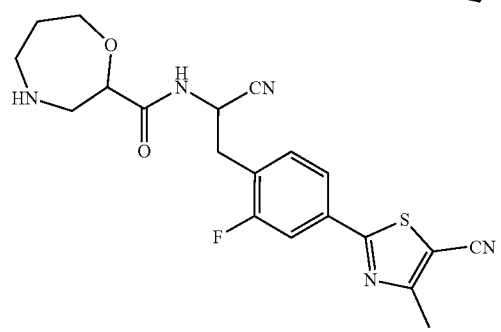
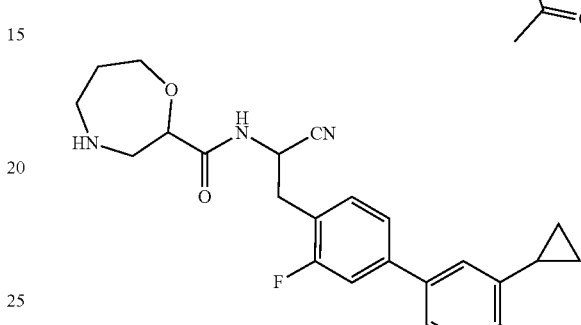
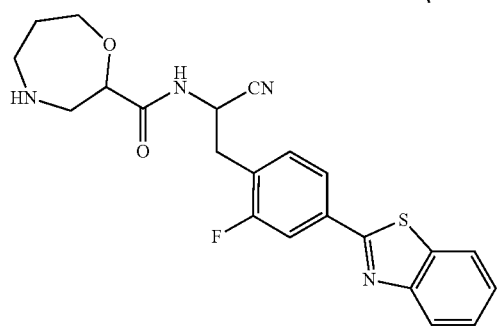
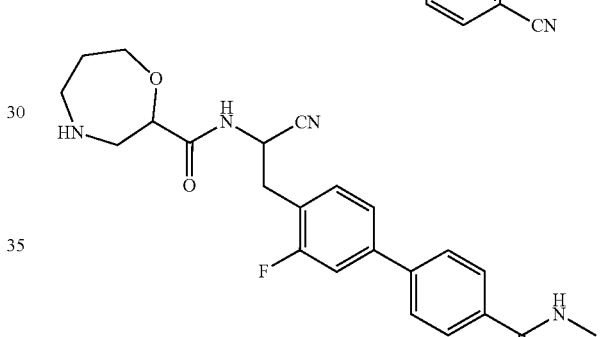
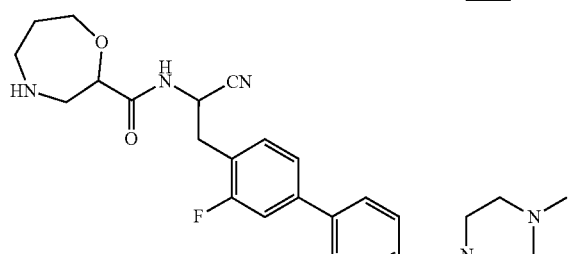
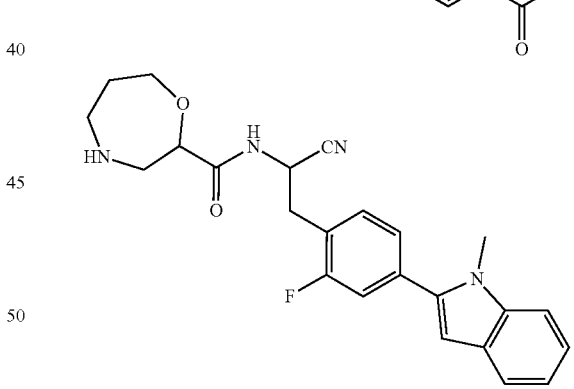
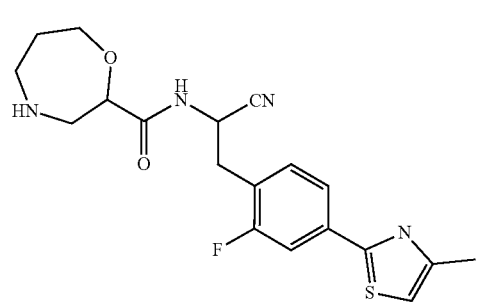
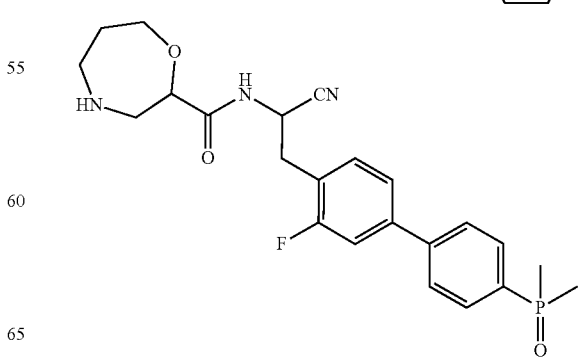

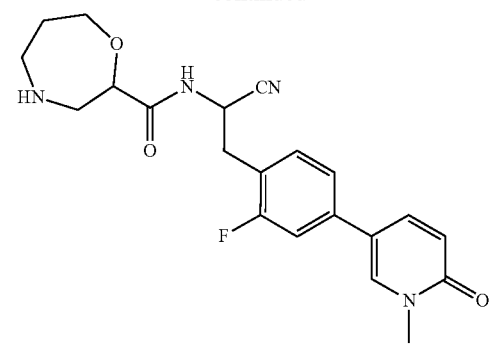
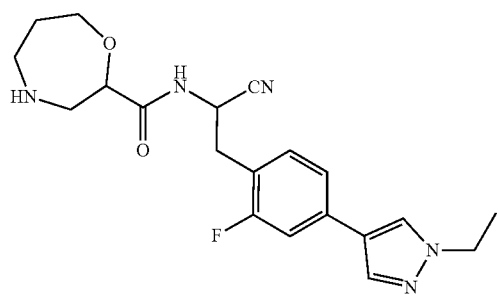
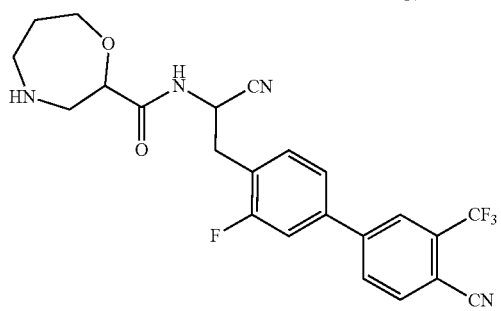
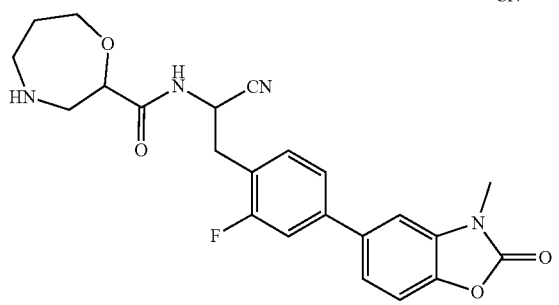
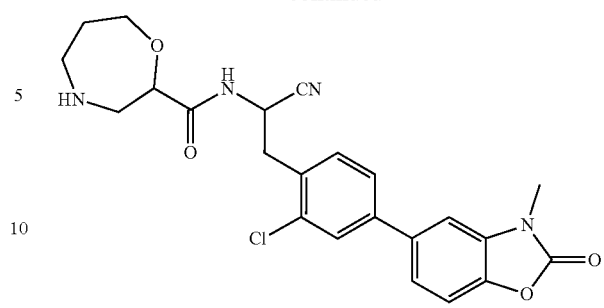
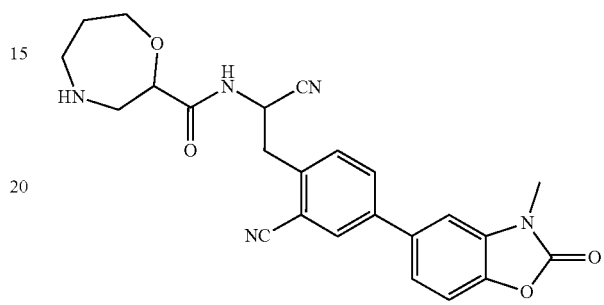
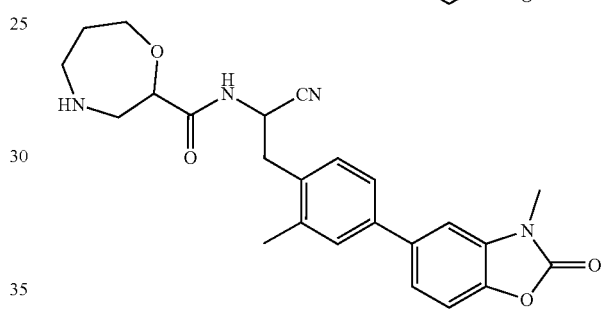
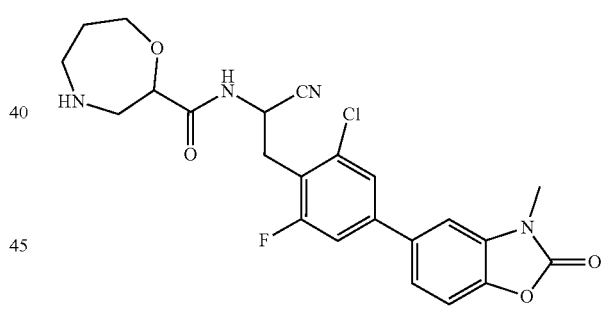
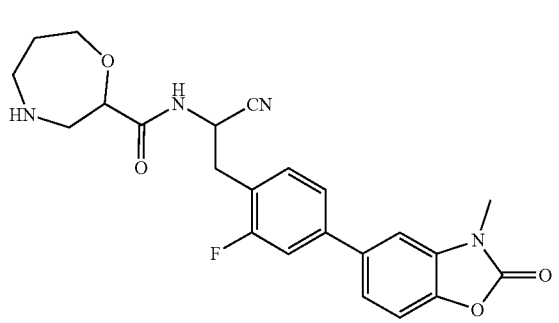
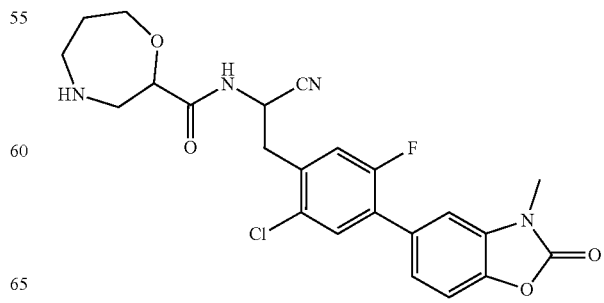

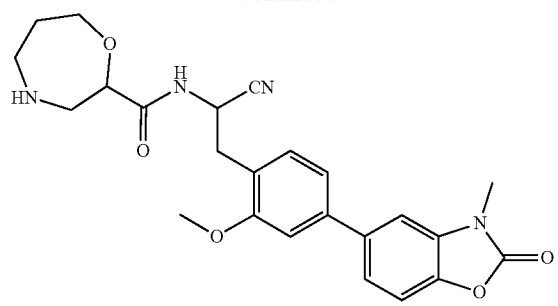
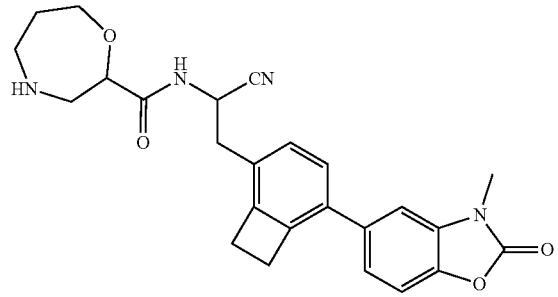
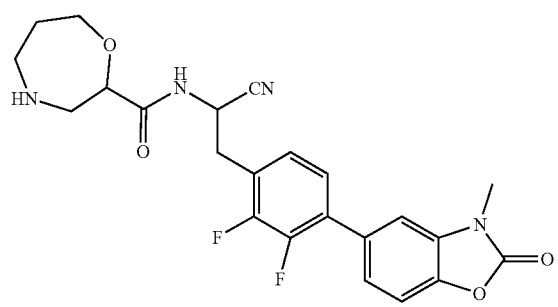
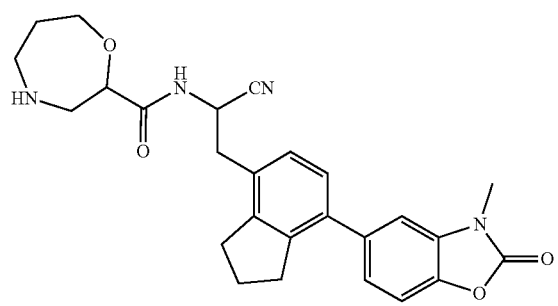
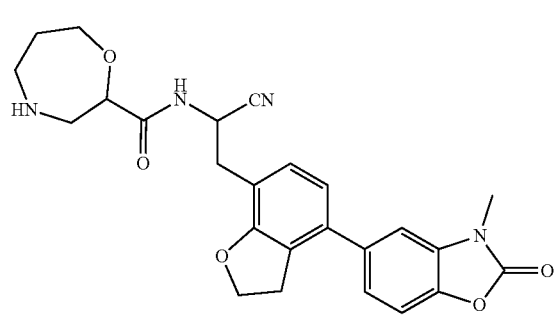
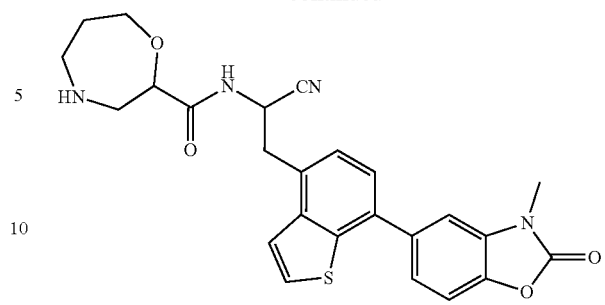
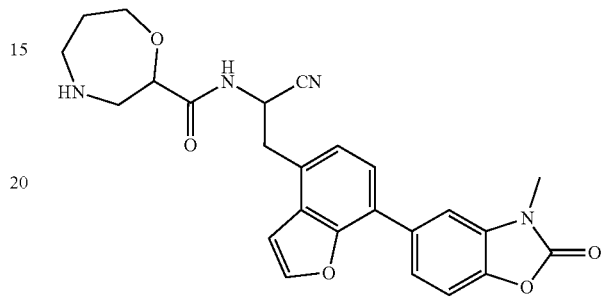
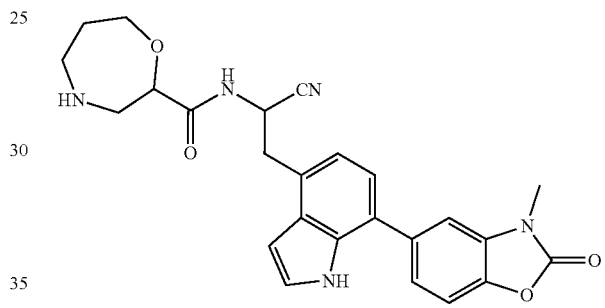
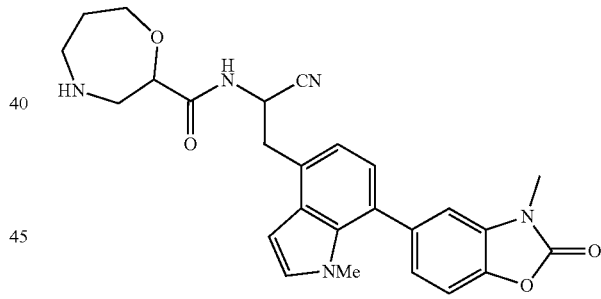
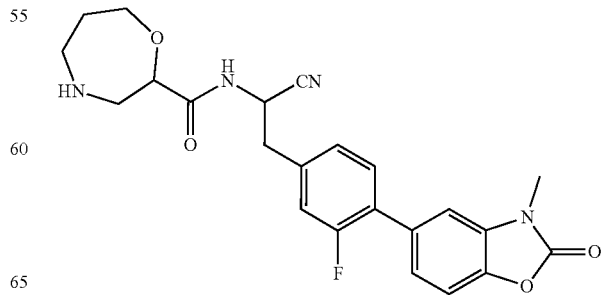

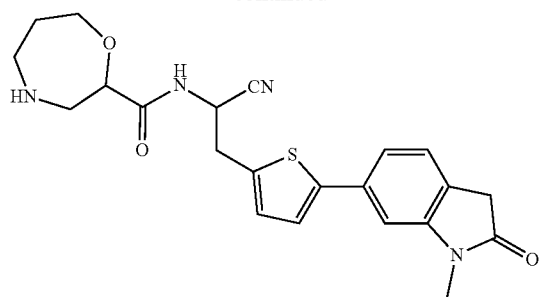
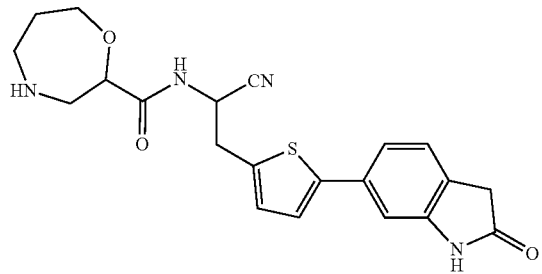
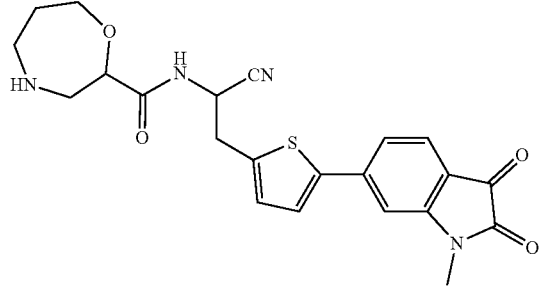
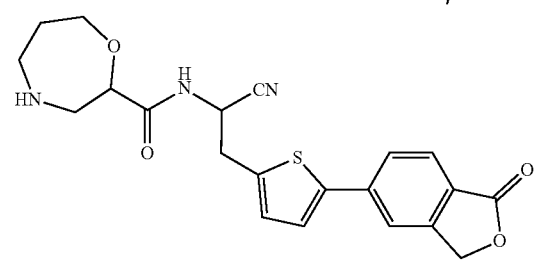
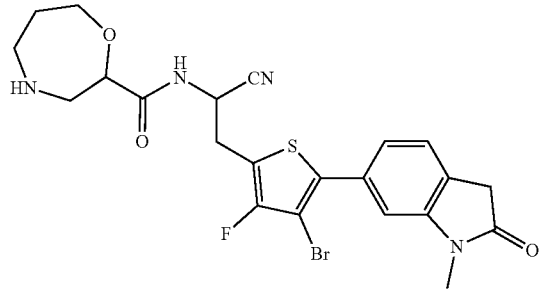
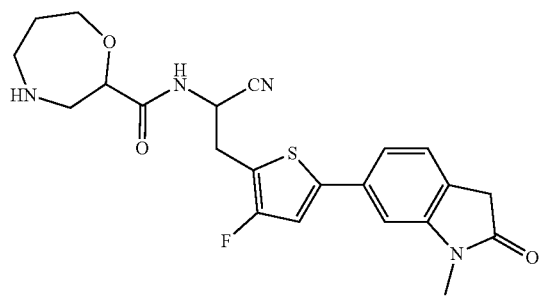
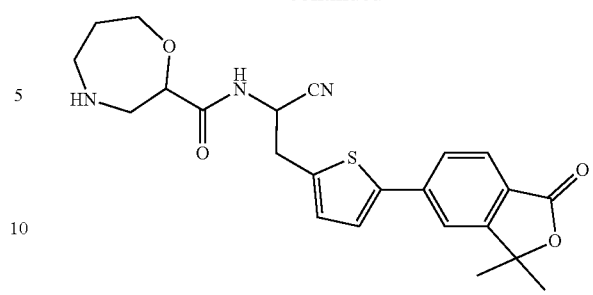
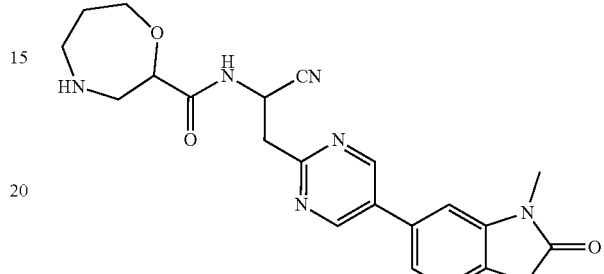
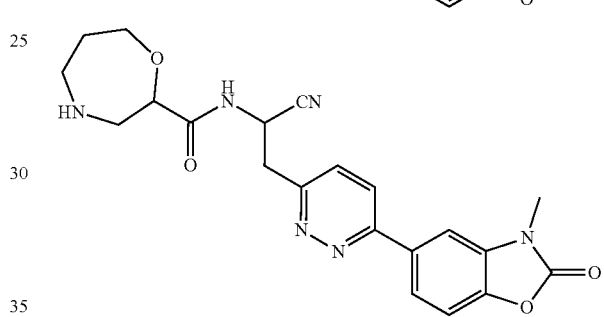
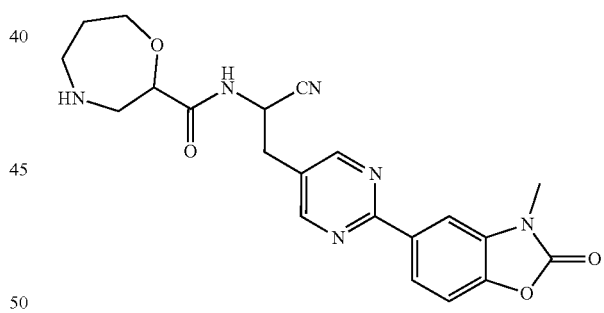
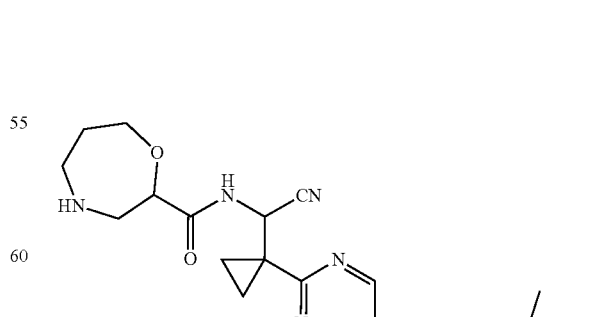
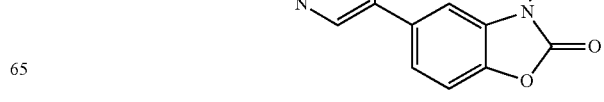

-continued
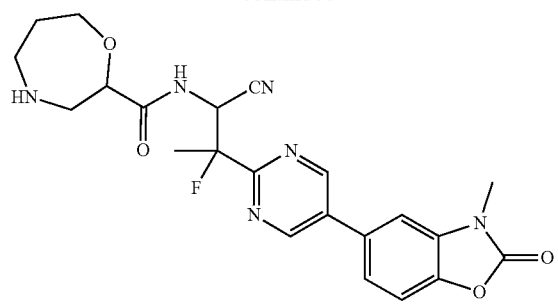
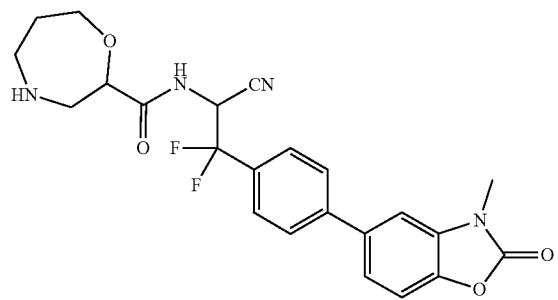
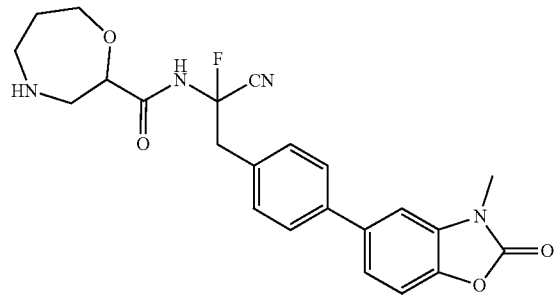
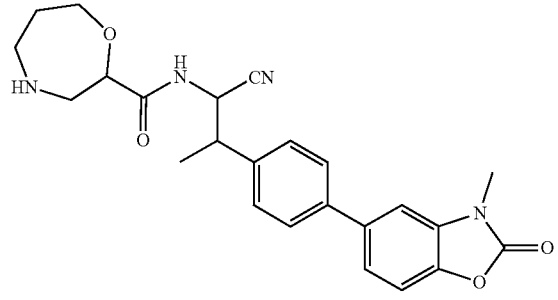
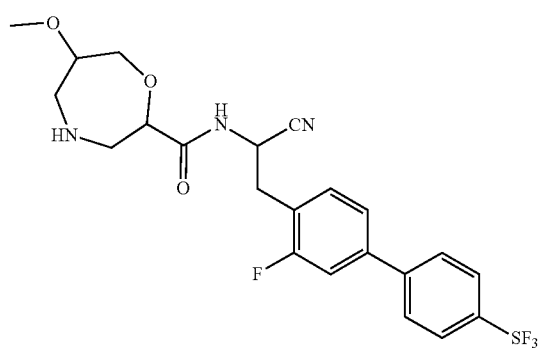
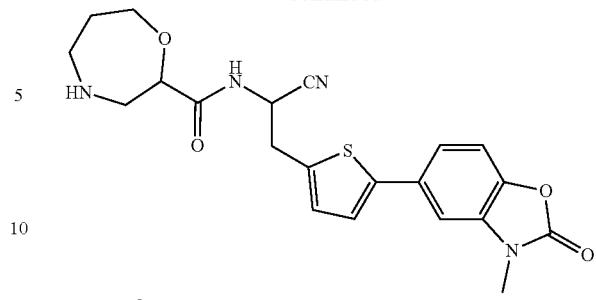
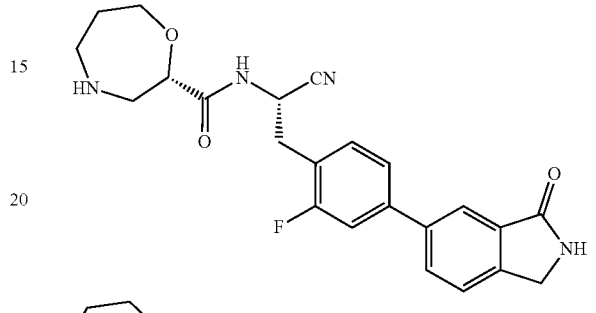
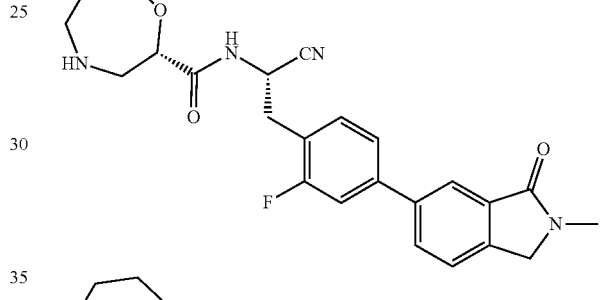
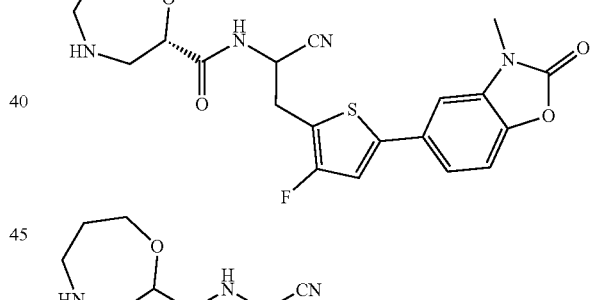
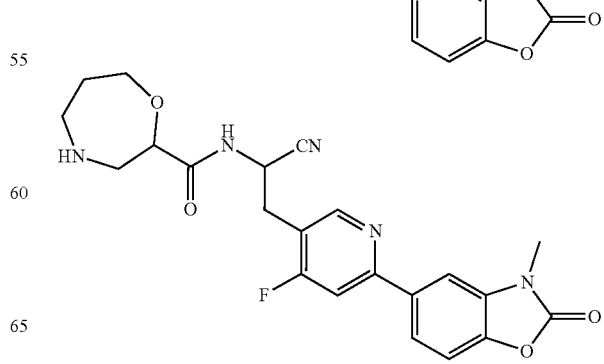

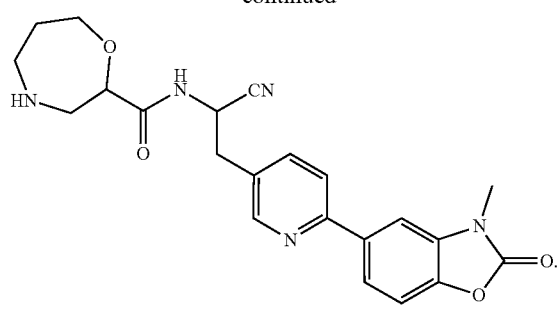
As a ninth technical solution of the present invention, the present invention provides a compound of formula (I), or a stereoisomer, a deuterated product, a co-crystal, a solvate or a pharmaceutically acceptable salt thereof, wherein the compound is selected from one of the following structures:
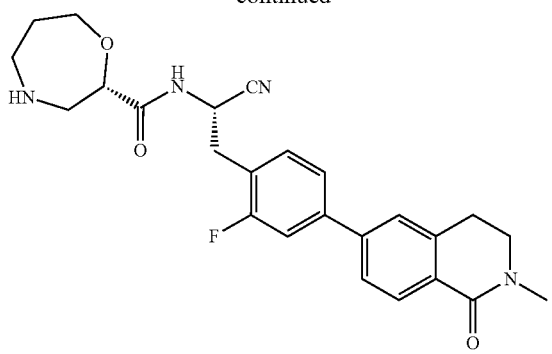
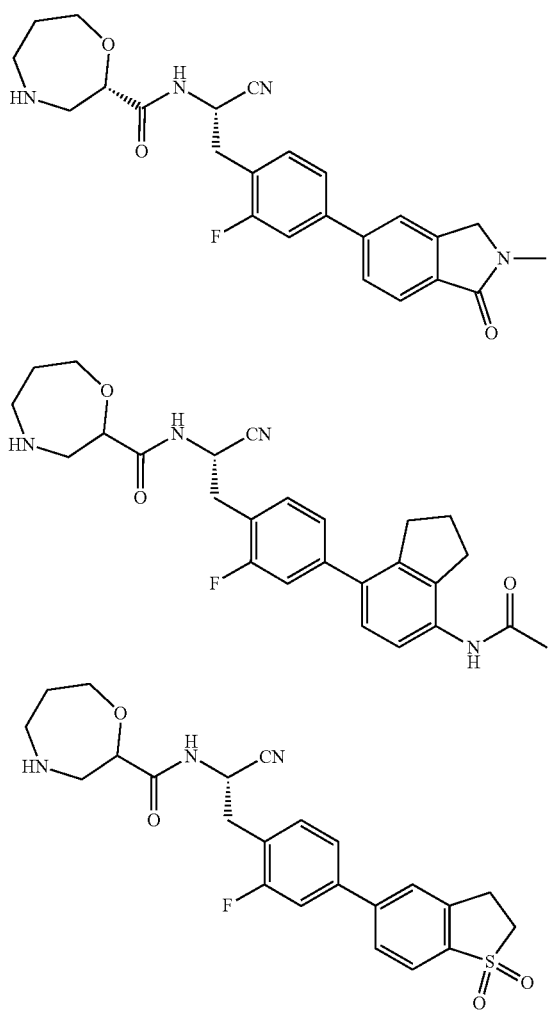

49
-continued
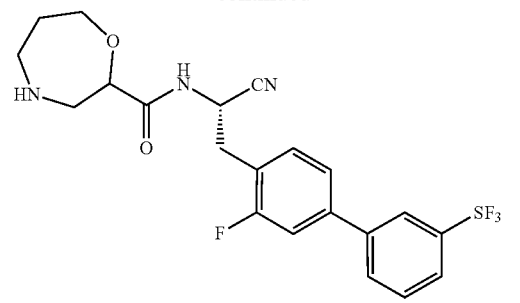
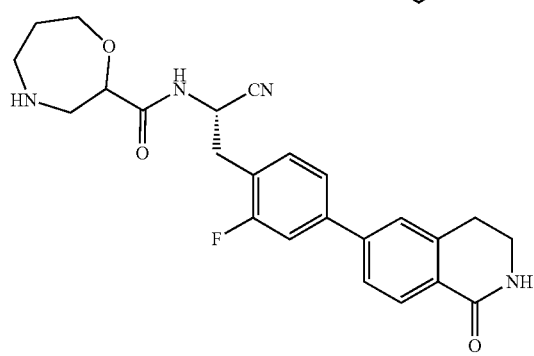
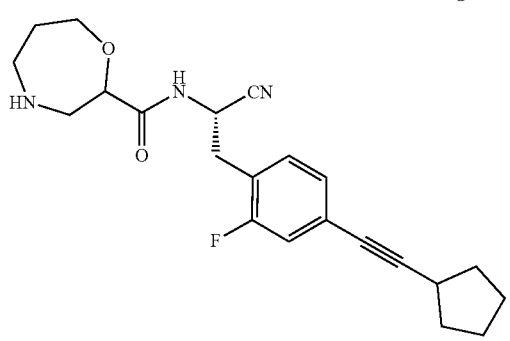
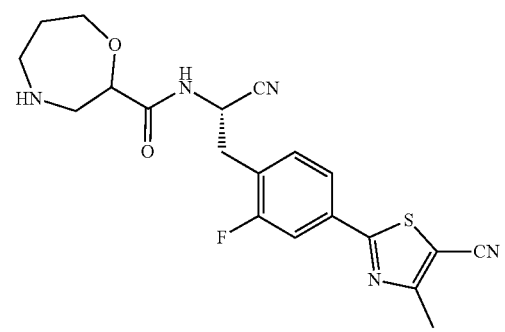
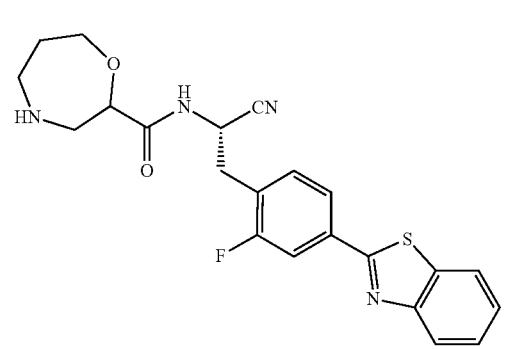
50
-continued
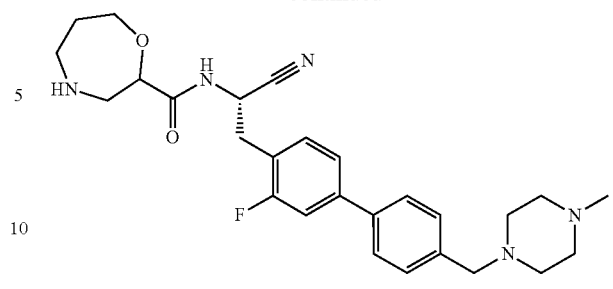
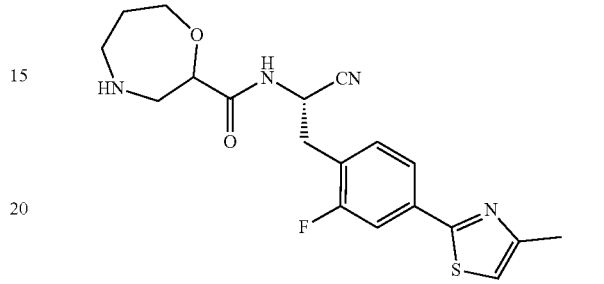
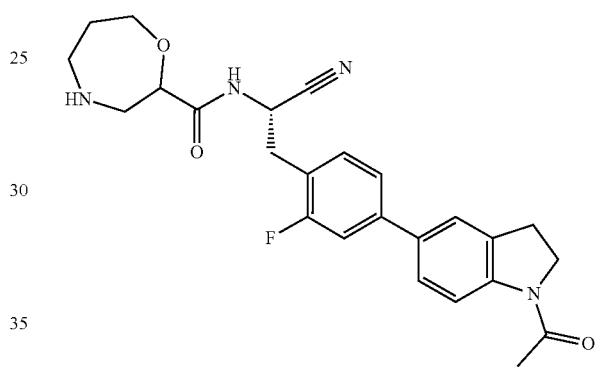
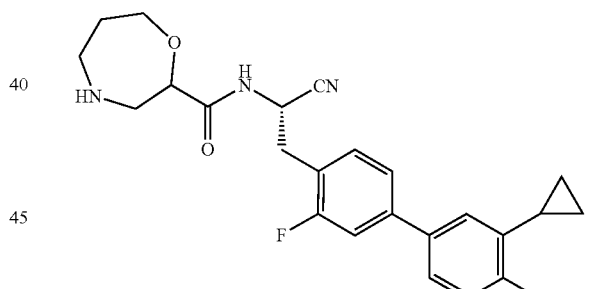
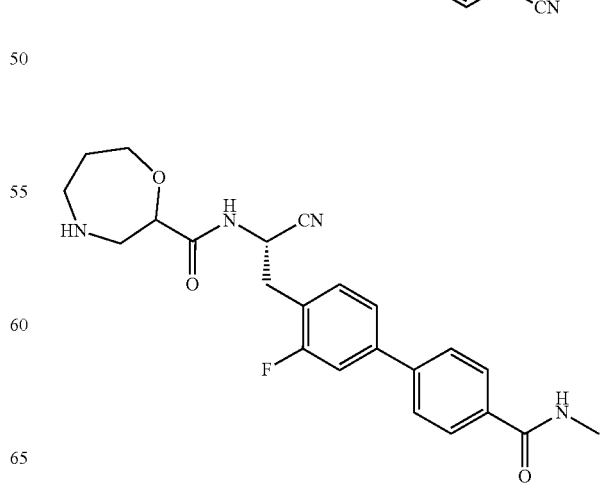

51
-continued
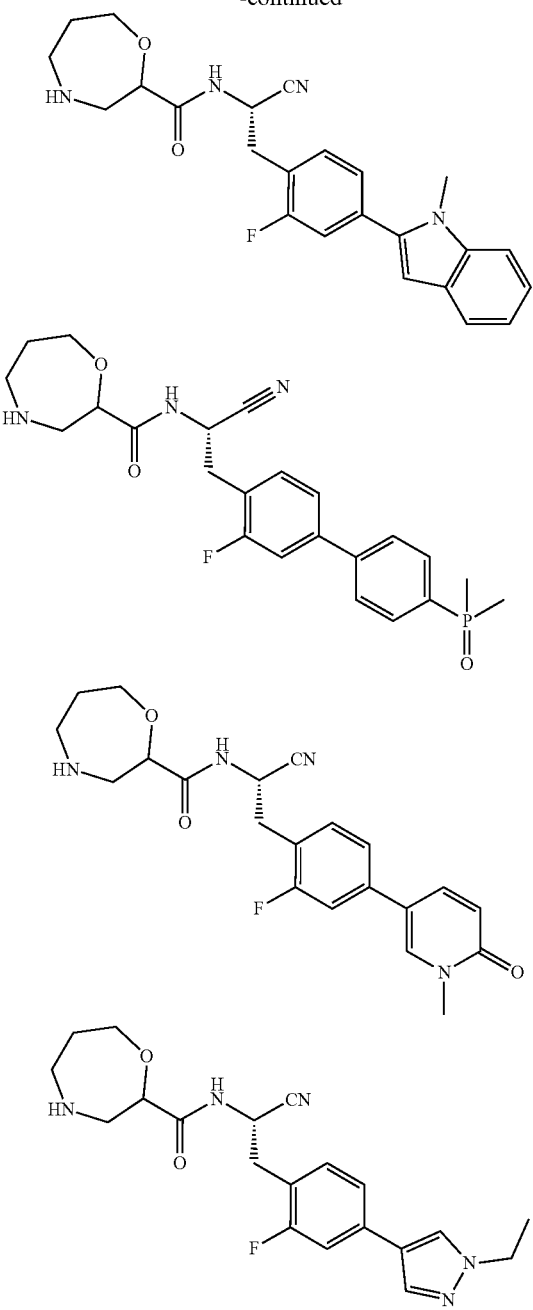
52
-continued
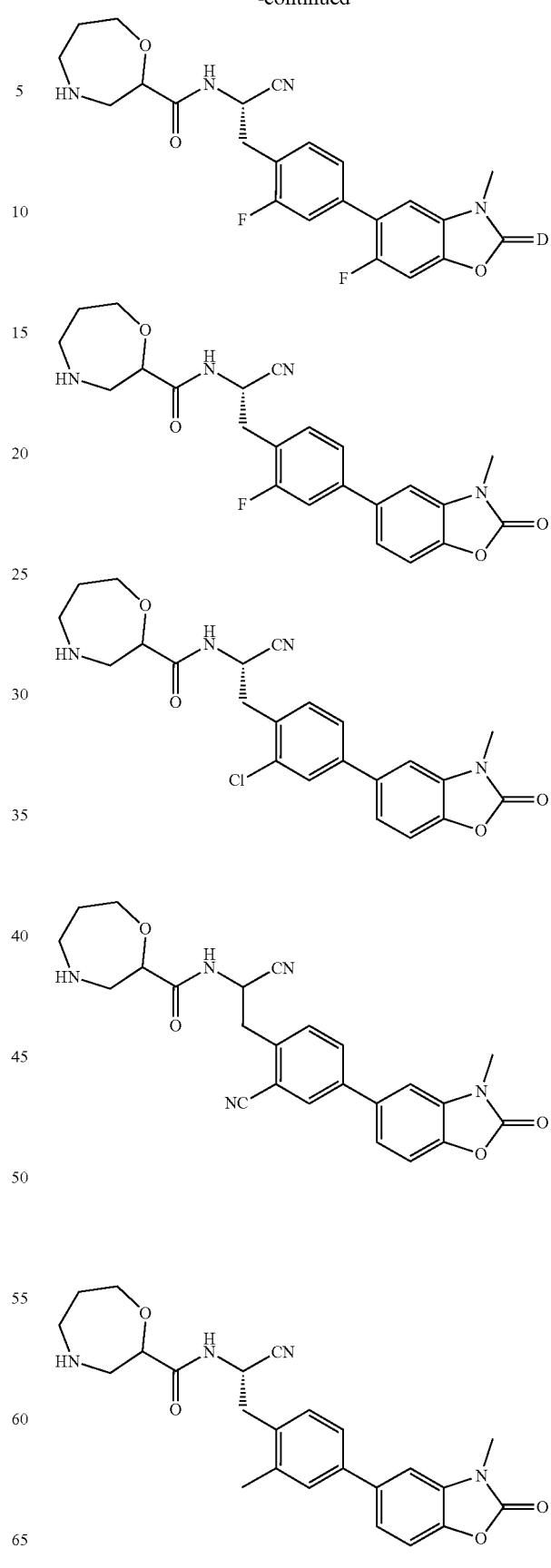

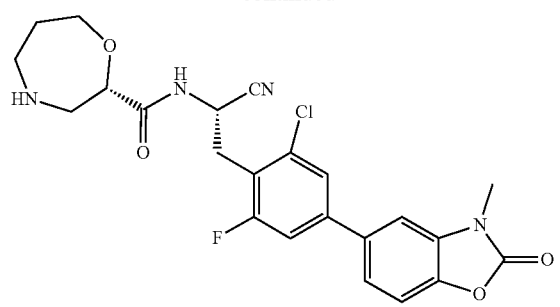
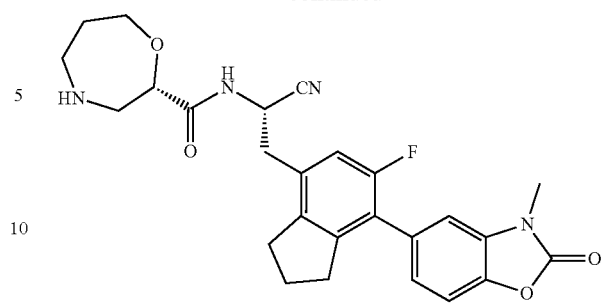
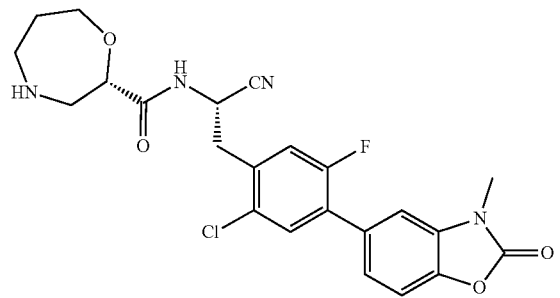
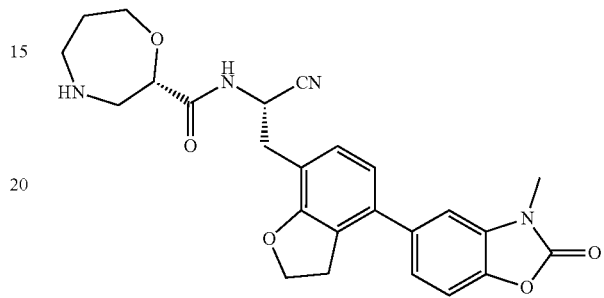
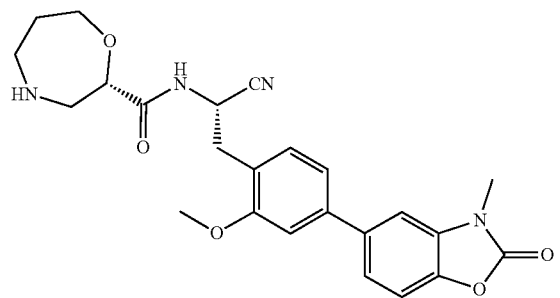
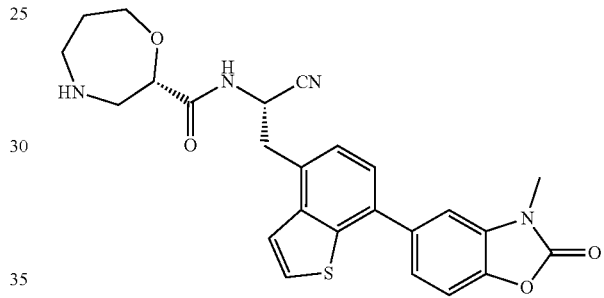
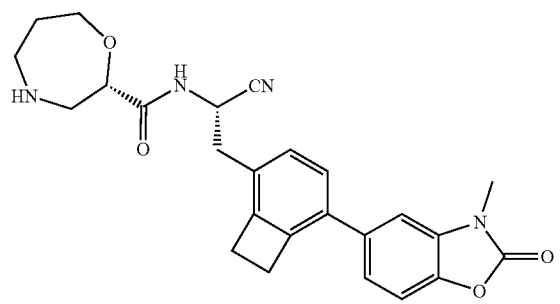
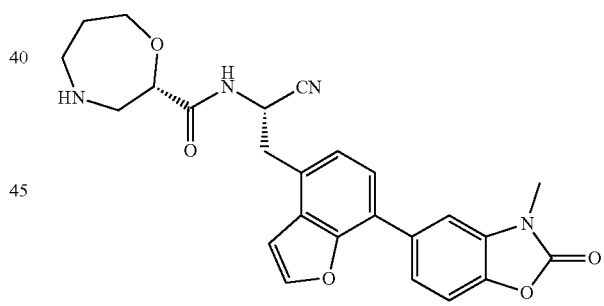
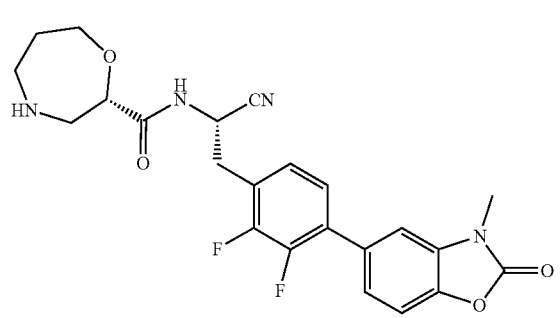
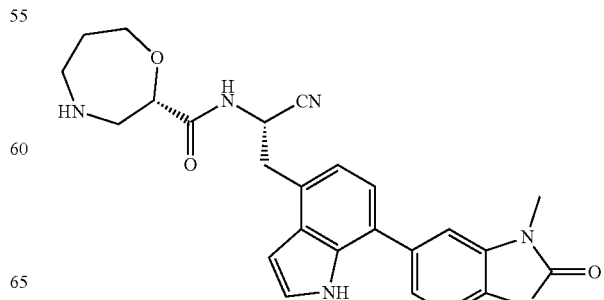

55
-continued
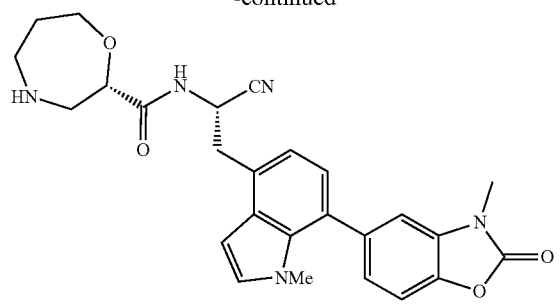
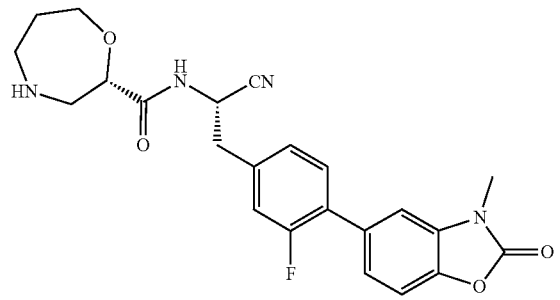
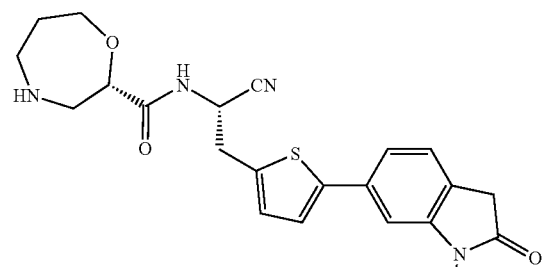
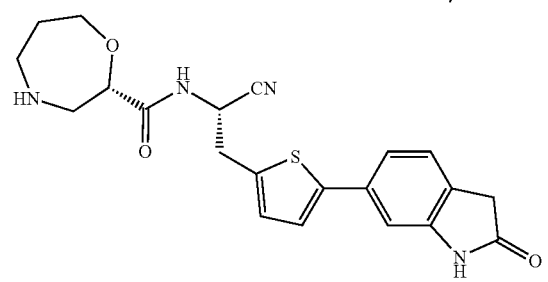
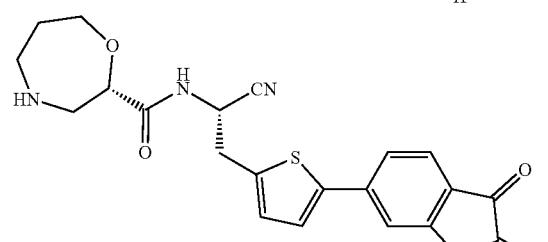
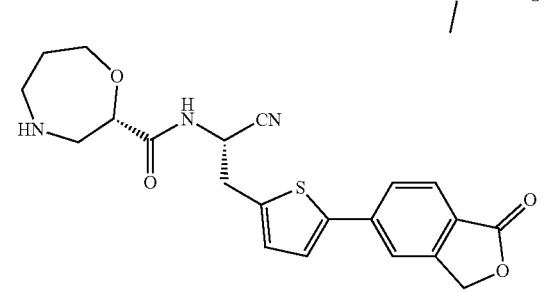
56
-continued
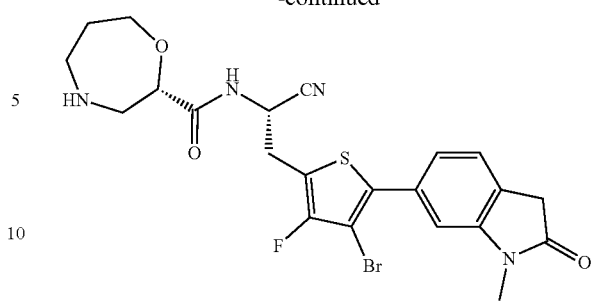
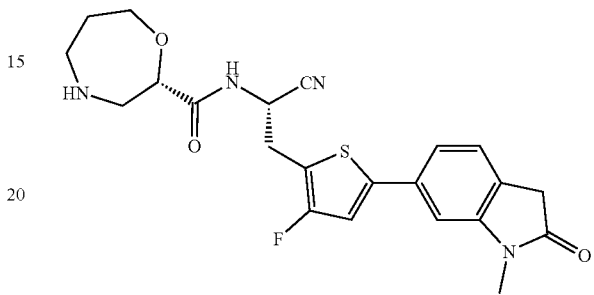
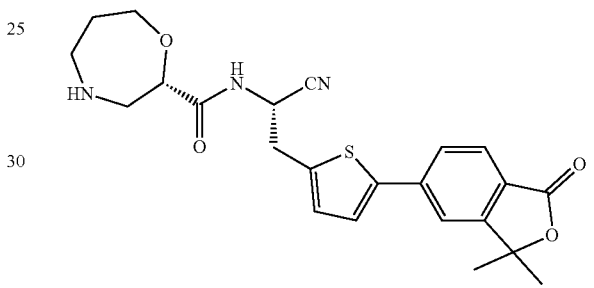
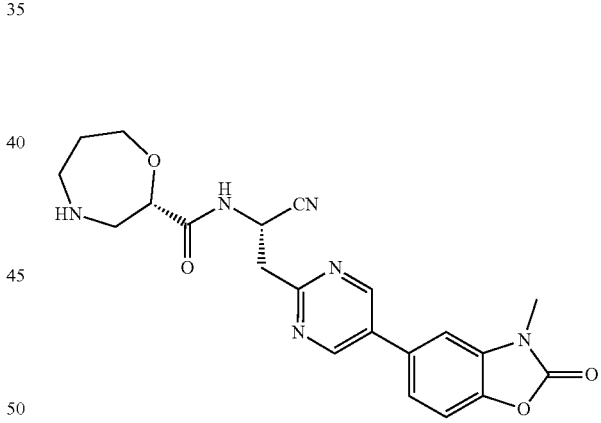
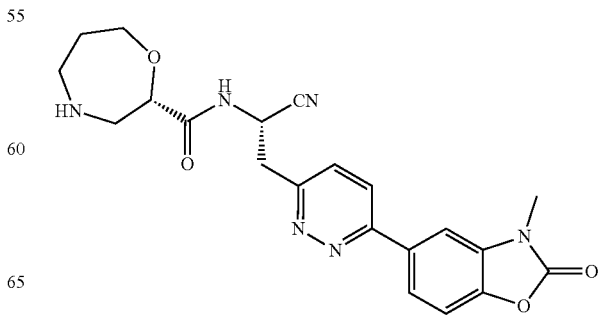

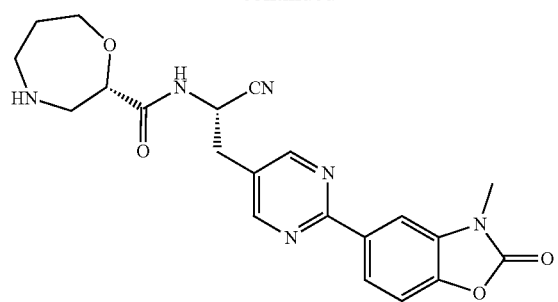
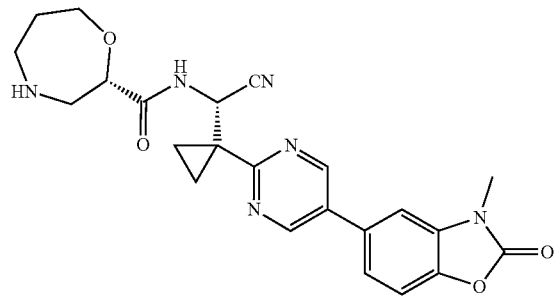
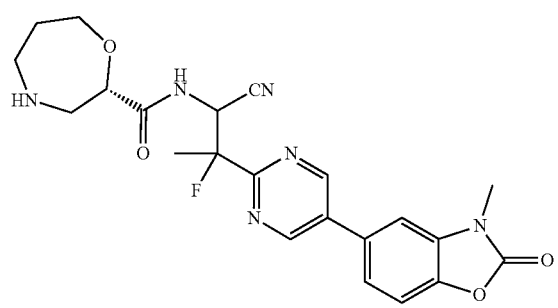
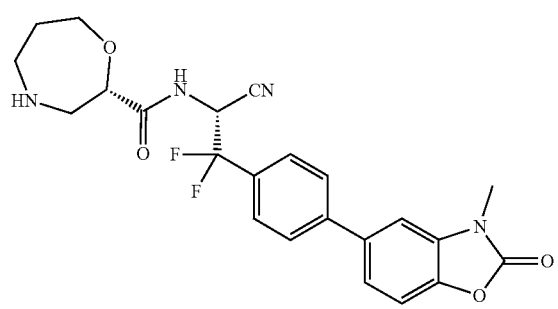
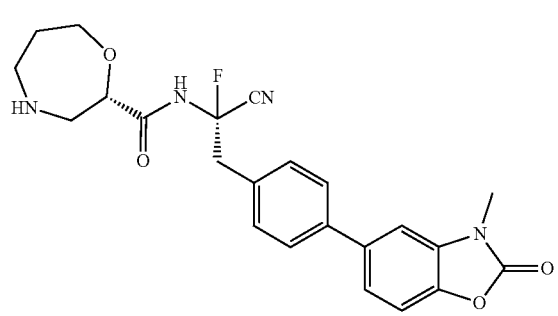
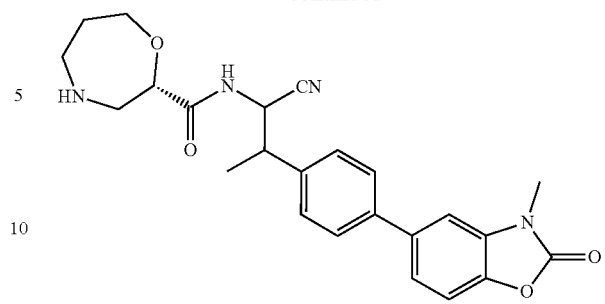
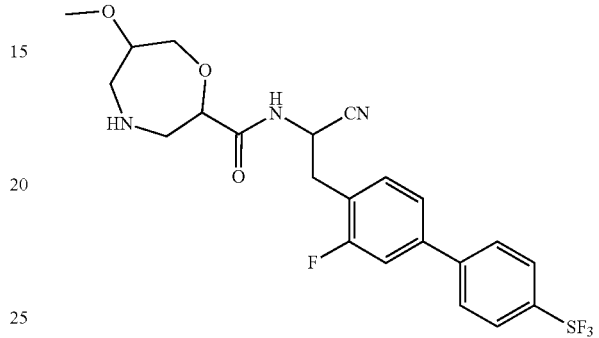
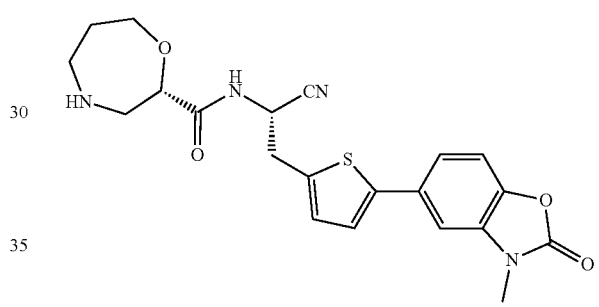
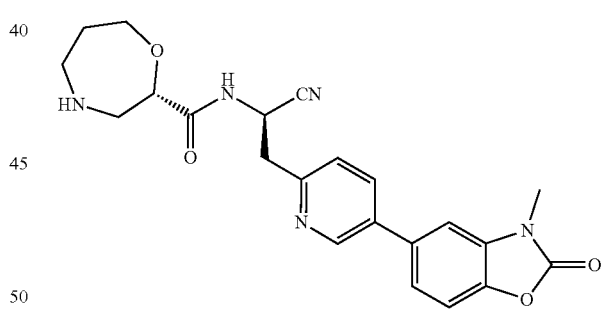
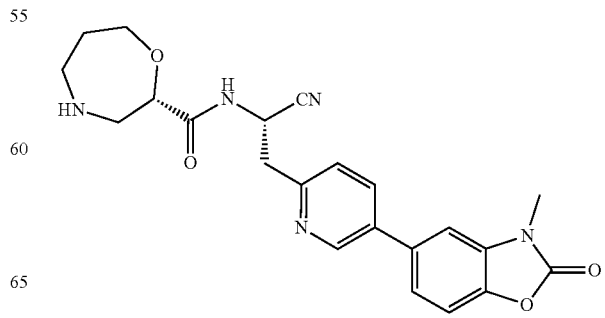

-continued

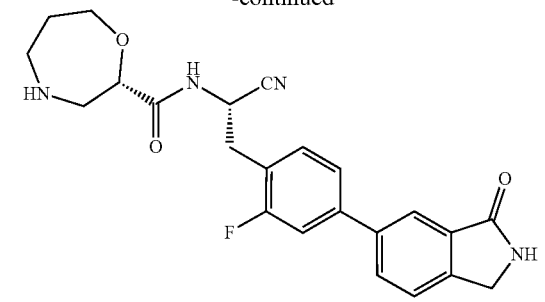
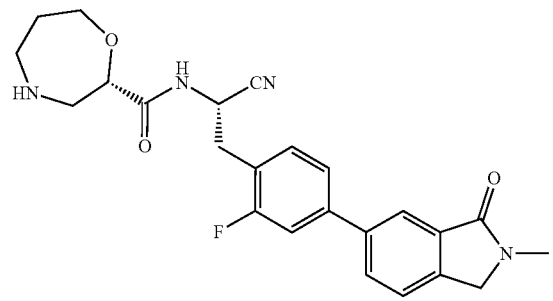
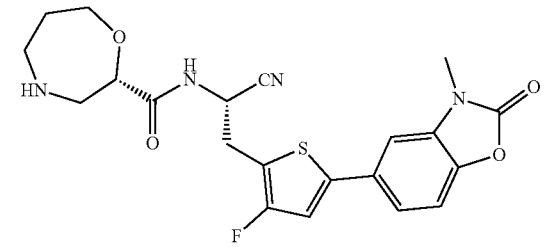
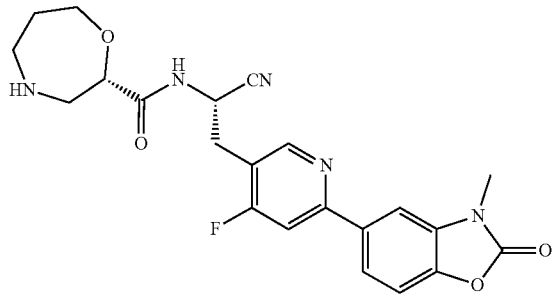
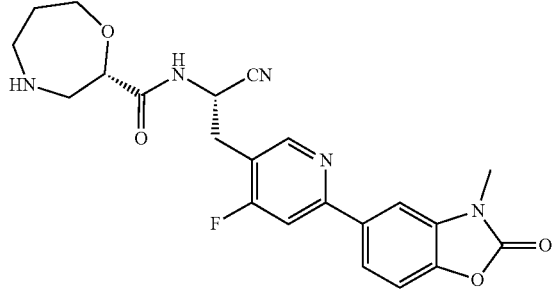
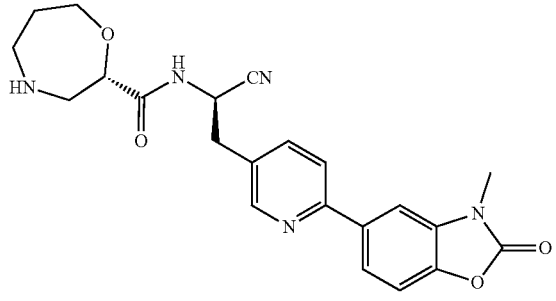

-continued

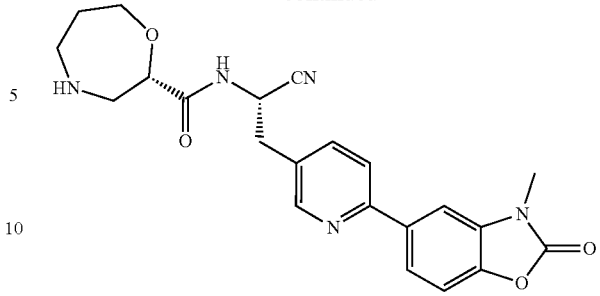
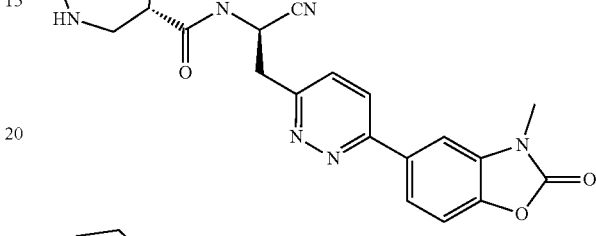
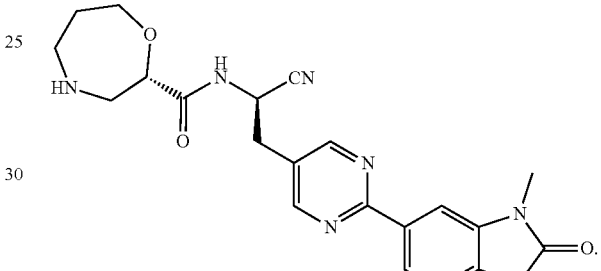

As a tenth technical solution of the present invention, the present invention also provides a pharmaceutical composition comprising the compound, or the stereoisomer, deuterated product, co-crystal, solvate or pharmaceutically acceptable salt thereof according to any one of the first to ninth technical solutions, and a pharmaceutically acceptable carrier and/or excipient.

The present invention also further provides the use of the compound, or the stereoisomer, deuterated product, co-crystal, solvate or pharmaceutically acceptable salt thereof according to any one of the first to ninth technical solutions, or the composition according to the tenth technical solution in the preparation of a drug for treating a disease mediated by dipeptidyl peptidase 1.

Still further, the disease mediated by dipeptidyl peptidase 1 is selected from obstructive airway diseases, bronchiectasis, cystic fibrosis, asthma, emphysema, chronic obstructive pulmonary diseases and other diseases.

Synthetic Route

Those skilled in the art would have been able to prepare the compounds of the present invention according to known organic synthesis techniques, and the starting materials used therein are commercially available chemicals and (or) compounds described in chemical documents. "Commercially available chemicals" are obtained from regular commercial sources, and suppliers include: Titan Technology Co., Ltd., Energy Chemical Co., Ltd., Shanghai Demo Co., Ltd., Chengdu Kelong Chemical Co., Ltd., Accela Chem Bio Co., Ltd., Pharma Block Sciences (Nanjing), Inc., WuXi Apptec Co., Ltd., J&K Scientific Co., Ltd., etc.

References and monographs in the art introduce in detail the synthesis of reactants that can be used to prepare the compounds described herein, or provide articles describing the preparation method for reference. The references and monographs include: "Synthetic Organic Chemistry", John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992; Fuhrhop, J. and Penzlin G. "Organic Synthesis: Concepts, Methods, Starting Materials", Second, Revised and Enlarged Edition (1994) John Wiley & Sons ISBN: 3-527-29074-5; Hoffman, R. V. "Organic Chemistry, An Intermediate Text" (1996) Oxford University Press, ISBN 0-19-509618-5; Larock, R. C. "Comprehensive Organic Transformations: A Guide to Functional Group Preparations" 2nd Edition (1999) Wiley-VCH, ISBN: 0-471-19031-4; March, J. "Advanced Organic Chemistry: Reactions, Mechanisms, and Structure" 4th Edition (1992) John Wiley & Sons, ISBN: 0-471-60180-2; Otera, J. (editor) "Modem Carbonyl Chemistry" (2000) Wiley-VCH, ISBN: 3-527-29871-1; Patai, S. "Patai's 1992 Guide to the Chemistry of Functional Groups" (1992) Interscience ISBN: 0-471-93022-9; Solomons, T. W. G. "Organic Chemistry" 7th Edition (2000) John Wiley & Sons, ISBN: 0-471-19095-0; Stowell, J. C., "Intermediate Organic Chemistry" 2nd Edition (1993) Wiley-Interscience, ISBN: 0-471-57456-2; "Industrial Organic Chemicals: Starting Materials and Intermediates: An Ullmann's Encyclopedia" (1999) John Wiley & Sons, ISBN: 3-527-29645-X, in 8 volumes; "Organic Reactions" (1942-2000) John Wiley & Sons, in over 55 volumes; and "Chemistry of Functional Groups", John Wiley & Sons, in 73 volumes.

Specific and similar reactants can be selectively identified by the indexes of known chemicals prepared by the Chemical Abstracts Service of the American Chemical Society, wherein the indexes are available in most public libraries or university libraries and online. Chemicals that are known but not commercially available in the catalog are optionally prepared by custom chemical synthesis plants, wherein many of standard chemical supply plants (for example, those listed above) provide custom synthesis services. Reference document for the preparation and selection of the pharmaceutically acceptable salts of the compounds described herein is P. H. Stahl & C. G. Wermuth "Handbook of Pharmaceutical Salts", Verlag Helvetica Chimica Acta, Zurich, 2002.

Term

Unless otherwise specified, the terms of the present invention have the following meanings.

The carbon, hydrogen, oxygen, sulfur, nitrogen or halogen involved in the groups and compounds of the present invention all comprises their isotopes, and the carbon, hydrogen, oxygen, sulfur, nitrogen or halogen involved in the groups and compounds of the present invention is optionally further substituted with one or more of their corresponding isotopes, wherein the isotopes of carbon comprise $^{12}C$, $^{13}C$ and $^{14}C$, the isotopes of hydrogen comprise protium (H), deuterium (D, also known as heavy hydrogen), and tritium (T, also known as superheavy hydrogen), the isotopes of oxygen comprise $^{16}O$, $^{17}O$ and $^{18}O$, the isotopes of sulfur comprise $^{32}S$, $^{33}S$, $^{34}S$ and $^{36}S$, the isotopes of nitrogen comprise $^{14}N$ and $^{15}N$, the isotope of fluorine comprises $^{19}F$, the isotopes of chlorine comprise $^{35}Cl$ and $^{37}Cl$, and the isotopes of bromine comprise $^{79}Br$ and $^{81}Br$.

The term "halogen" herein refers to F, Cl, Br, I, or isotopes thereof.

The term "halo" or "substituted with halogen" refers to being substituted with one or more groups selected from F, Cl, Br, I, or isotopes thereof, wherein the upper limit of the number of halogen substituents is equal to the sum of the number of hydrogens that can be substituted in the group to be substituted. Without particular limitation, the number of halogen substituents is any integer between 1 and the upper limit, and when the number of halogen substituents is greater than 1, the group to be substituted can be substituted with the same or different halogen. Generally, the circumstances of being substituted with 1-5 halogen, 1-3 halogen, 1-2 halogen, and 1 halogen are included.

The term "deuterium" refers to the isotope deuterium of hydrogen (H).

The term "deuterated" refers to the case where a hydrogen atom on alkyl, cycloalkyl, alkylene, aryl, heteroaryl, alkenyl, alkynyl and other groups is substituted with at least one isotope deuterium, wherein the upper limit of the number of deuterium substituents is equal to the sum of the number of hydrogens that can be substituted in the group to be substituted. Without particular limitation, the number of deuterium substituents is any integer between 1 and the upper limit, preferably 1-20 deuterium atoms, more preferably 1-10 deuterium atoms, more preferably 1-6 deuterium atoms, further preferably 1-3 deuterium atoms.

Group "$C_{x-y}$" refers to a group comprising x to y carbon atoms, for example, "$C_{1-6}$ alkyl" refers to alkyl comprising 1-6 carbon atoms.

The term "alkyl" refers to a monovalent straight or branched saturated aliphatic hydrocarbon group. Unless otherwise specified, the alkyl refers to alkyl containing 1 to 20 carbon atoms, preferably alkyl containing 1 to 8 carbon atoms, more preferably alkyl containing 1 to 6 carbon atoms, and further preferably alkyl containing 1 to 4 carbon atoms. Non-limiting examples of alkyl include methyl, ethyl, n-propyl, isopropyl, n-butyl, sec-butyl, neobutyl, tert-butyl, n-pentyl, isoamyl, neopentyl, n-hexyl and various branched isomers thereof.

The term "alkylene" refers to a bivalent straight or branched saturated alkyl. Examples of alkylene include, but are not limited to, methylene, ethylidene, etc.

The term "haloalkyl" refers to an alkyl group in which one or more hydrogens are substituted with one or more halogen atoms (e.g., fluorine, chlorine, bromine, iodine, or isotopes thereof), wherein the upper limit of the number of halogen substituents is equal to the sum of the number of hydrogens that can be substituted in the alkyl group. Without particular limitation, the number of halogen substituents is any integer between 1 and the upper limit. Generally, the alkyl group is substituted with 1-5 halogen, 1-3 halogen, 1-2 halogen or 1 halogen; when the number of halogen substituents is greater than 1, the group to be substituted can be substituted with the same or different halogen; and specific examples include, but are not limited to, —$CF_3$, —$CH_2Cl$, —$CH_2CF_3$, —$CCl_2$, $CF_3$, etc.

The term "alkoxy" or "alkyloxy" refers to —O-alkyl, such as —O—$C_{1-8}$ alkyl, —O—$C_{1-4}$ alkyl, —O—$C_{1-4}$ alkyl or —O—$C_{1-2}$ alkyl. Non-limiting and specific examples of alkoxy or alkyloxy include methoxy, ethoxy, n-propoxy, isopropoxy, n-butoxy, sec-butoxy, tert-butoxy, n-pentoxy, n-hexyloxy, cyclopropoxy, cyclobutoxy, etc. The alkoxy may be optionally substituted with a substituent.

The term "haloalkoxy" refers to —O-haloalkyl, such as —O-halo $C_{1-8}$ alkyl, —O-halo $C_{1-6}$ alkyl, —O-halo $C_{1-4}$ alkyl or —O-halo $C_{1-2}$ alkyl; and the upper limit of the number of halogen substituents is equal to the sum of the number of hydrogens that can be substituted in the group to be substituted. Without particular limitation, the number of halogen substituents is any integer between 1 and the upper limit, preferably 1-5 halogen, 1-3 halogen, 1-2 halogen, and 1 halogen; when the number of halogen substituents is greater than 1, the group to be substituted can be substituted with the same or different halogen; and non-limiting examples of haloalkoxy include monofluoromethoxy, difluoromethoxy, trifluoromethoxy, difluoroethyloxy, etc.

The term "alkylamino" or "alkamino" refers to amino substituted with one or two alkyl, and is also written as —N-(alkyl)$_2$ or —NH-alkyl, wherein the latter is also known as monoalkylamino. Non-limiting examples of alkylamino or alkamino include dimethylamino, monomethylamino, diethylamino, monoethylamino, etc.

The term "alkenyl" refers to a straight or branched hydrocarbon group comprising at least one carbon-carbon double bond (C=C) and generally comprises 2 to 18 carbon atoms, such as 2 to 8 carbon atoms, further such as 2 to 6 carbon atoms, and more further such as 2 to 4 carbon atoms. Examples of alkenyl include, but are not limited to vinyl, allyl, 1-propenyl, 2-propenyl, 1-butenyl, 2-butenyl, 3-butenyl, 1-pentenyl, 2-pentenyl, 3-pentenyl, 4-pentenyl, 1-methyl-1-butenyl, 2-methyl-1-butenyl, 2-methyl-3-butenyl, 1-hexenyl, 2-hexenyl, 3-hexenyl, 4-hexenyl, 5-hexenyl, 1-methyl-1-pentenyl, 2-methyl-1-pentenyl, 1-heptenyl, 2-heptenyl, 3-heptenyl, 4-heptenyl, 1-octenyl, 3-octenyl, 1-nonenyl, 3-nonenyl, 1-decenyl, 4-decenyl, 1,3-butadiene, 1,3-pentadiene, 1,4-pentadiene, 1,4-hexadiene, etc.; and the alkenyl may further be optionally substituted with a substituent.

The term "alkenylene" refers to a straight or branched divalent unsaturated hydrocarbon group containing at least one carbon-carbon double bond (C=C). Unless otherwise specified, an alkenylene contains 2-6 carbon atoms, preferably 2-4 carbon atoms, and non-limiting examples of alkenylene include ethenylene. The alkenylene may be optionally substituted with a substituent.

The term "alkynyl" refers to a straight or branched hydrocarbon group containing at least one carbon-carbon triple bond (C≡C) and generally comprises 2 to 18 carbon atoms; further, alkynyl comprises 2 to 8 carbon atoms; further, alkynyl comprises 2 to 6 carbon atoms, and more further, alkynyl comprises 2 to 4 carbon atoms. Examples of alkynyl include, but are not limited to ethynyl, 1-propynyl, 2-propynyl, butynyl, 2-butynyl, 3-butynyl, 1-methyl-2-propynyl, 4-pentynyl, 3-pentynyl, 1-methyl-2-butynyl, 2-hexynyl, 3-hexynyl, 2-heptynyl, 3-heptynyl, 4-heptynyl, 3-octynyl, 3-nonynyl, 4-decynyl, etc.; and the alkynyl may be optionally substituted with a substituent.

The term "alkynylene" refers to a straight or branched, divalent unsaturated hydrocarbon group containing a carbon-carbon triple bond (C≡C) and generally comprises 2-6 carbon atoms, and further comprises 2-4 carbon atoms. Non-limiting examples of alkynylene include ethynylene, propynylene, and butynylene, and the alkynylene may be optionally substituted with a substituent. The term "cycloalkyl" refers to a saturated or partially unsaturated, non-aromatic carbocyclic hydrocarbon group containing no ring heteroatoms. The cycloalkyl may be monocyclic, bicyclic or polycyclic, the bicyclic or polycyclic cycloalkyl may be in the form of a fused ring, a spiro ring, a bridged ring or a combination thereof, and may comprise one or more aromatic rings, but the ring system is non-aromatic as a whole, and the connecting site may be on an aromatic ring or a non-aromatic ring. Generally, the cycloalkyl contains 3 to 20 carbon atoms; further, the cycloalkyl contains 3-8 carbon atoms; and still further, the cycloalkyl contains 3-6 carbon atoms; when the cycloalkyl is monocyclic cycloalkyl, the cycloalkyl contains 3-15 carbon atoms, or 3-10 carbon atoms, or 3-8 carbon atoms, or 3-6 carbon atoms; when the cycloalkyl is bicyclic or polycyclic cycloalkyl, the cycloalkyl contains 5-12 carbon atoms, or 5-11 carbon atoms, or 6-10 carbon atoms; and non-limiting examples of cycloalkyl include cyclopropyl, cyclobutyl, cyclopentyl, cyclohexyl, cycloheptyl, butenyl, cyclopentenyl cyclohexenyl,

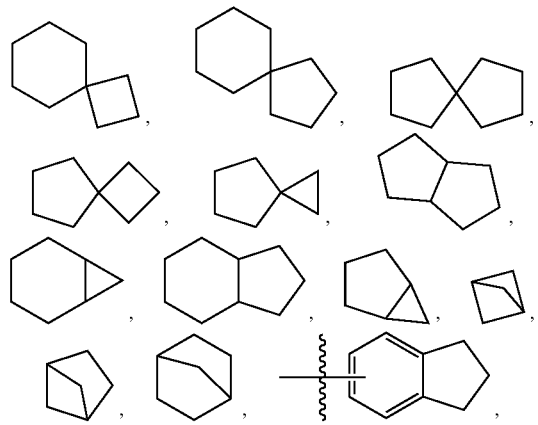

etc., and cycloalkyl may be optionally substituted with a substituent. The term "cycloalkylene" refers to a divalent saturated, substituted or unsubstituted cycloalkyl. Non-limiting examples include

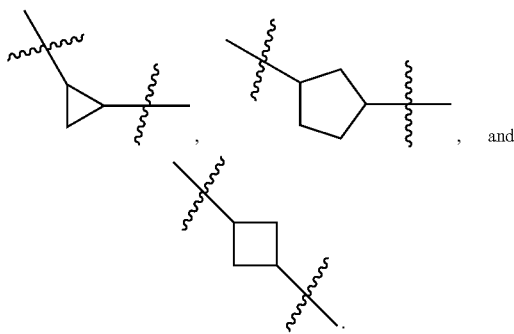

The term "carbocyclic ring" or "carbocyclyl" refers to a substituted or unsubstituted, saturated or unsaturated, and aromatic or non-aromatic carbocyclic group, includes a monocyclic carbocyclic ring, a bicyclic bridged ring, a bicyclic fused ring, a bicyclic spiro ring, a polycyclic ring containing at least three rings, etc. and generally contains 3 to 14 carbon atoms, preferably 3-12 carbon atoms, and more preferably 6-8 carbon atoms or 3-6 carbon atoms. In non-limiting examples, a monocyclic carbocyclic ring includes cyclopropyl, cyclobutyl, cyclo ent 1, cyclohex 1, cycloheptyl or phenyl, etc.; a bicyclic bridged ring includes

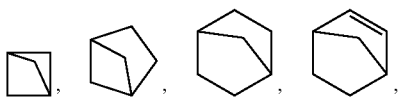

etc.; a bicyclic fused ring includes

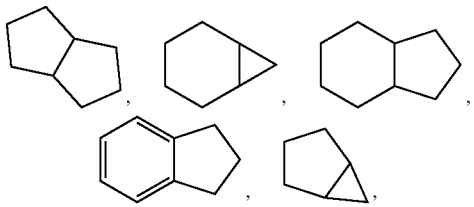

etc.; a bicyclic spiro ring includes

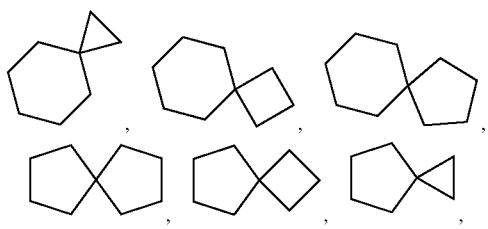

etc.; and a tricyclic ring includes

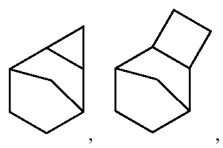

etc.

The term "heterocycle" or "heterocyclyl" refers to a substituted or unsubstituted, saturated or unsaturated aromatic ring or non-aromatic ring, and when not particularly limited, contains 1 to 5 heteroatoms selected from N, O or S, preferably 1 to 4 heteroatoms, more preferably 1 to 3 heteroatoms, including a monocyclic heterocycle, a bicyclic bridged heterocycle, a bicyclic fused heterocycle, a bicyclic spiro heterocycle, a polycyclic heterocycle containing at least three rings, etc., preferably a 3- to 15-membered heterocycle, more preferably a 4-14-membered heterocycle, more preferably a 4-10-membered heterocycle and a 5-12-membered heterocycle, and further preferably a 5-8-membered heterocycle and a 5-6-membered heterocycle. The heterocycle is preferably a saturated heterocycle, such as a 5-12-membered saturated heterocycle, further preferably a 5-8-membered saturated heterocycle, a 7-membered saturated heterocycle or a 5-6-membered saturated heterocycle. The ring atoms N and S of the heterocyclyl may be oxidized to various oxidation states. Heterocyclyl can be connected to a heteroatom or a carbon atom, and non-limiting examples of heterocyclyl include epoxyethyl, azacyclopropyl, oxetanyl, azetidinyl, 1,3-dioxolanyl, 1,4-dioxolanyl, 1,3-dioxanyl, piperazinyl, azacycloheptyl, pyridyl, furyl, thienyl, pyranyl, N-alkylpyrrolyl, pyrimidinyl, pyrazinyl, pyrazolyl, pyridazinyl, imidazoly, piperidyl, piperadinyl, morpholinyl, thiomorpholinyl, 1,3-dithianyl, dihydrofuryl, dihydropyranyl, dithiolanyl, tetrahydrofuryl, tetrahydropyrrolyl, tetrahydroimidazolyl, oxazolyl, dihydrooxazolyl, tetrahydrooxazolyl, tetrahydrothiazolyl, tetrahydropyranyl, benzoimidazolyl, benzopyridyl, pyrrolopyridinyl, benzodihydrofuryl, azabicyclo[3.2.1]octyl, azabicyclo[5.2.0]nonanyl, oxatricyclo[5.3.1.1]dodecyl, azaadamantyl, oxaspiro[3.3]heptyl,

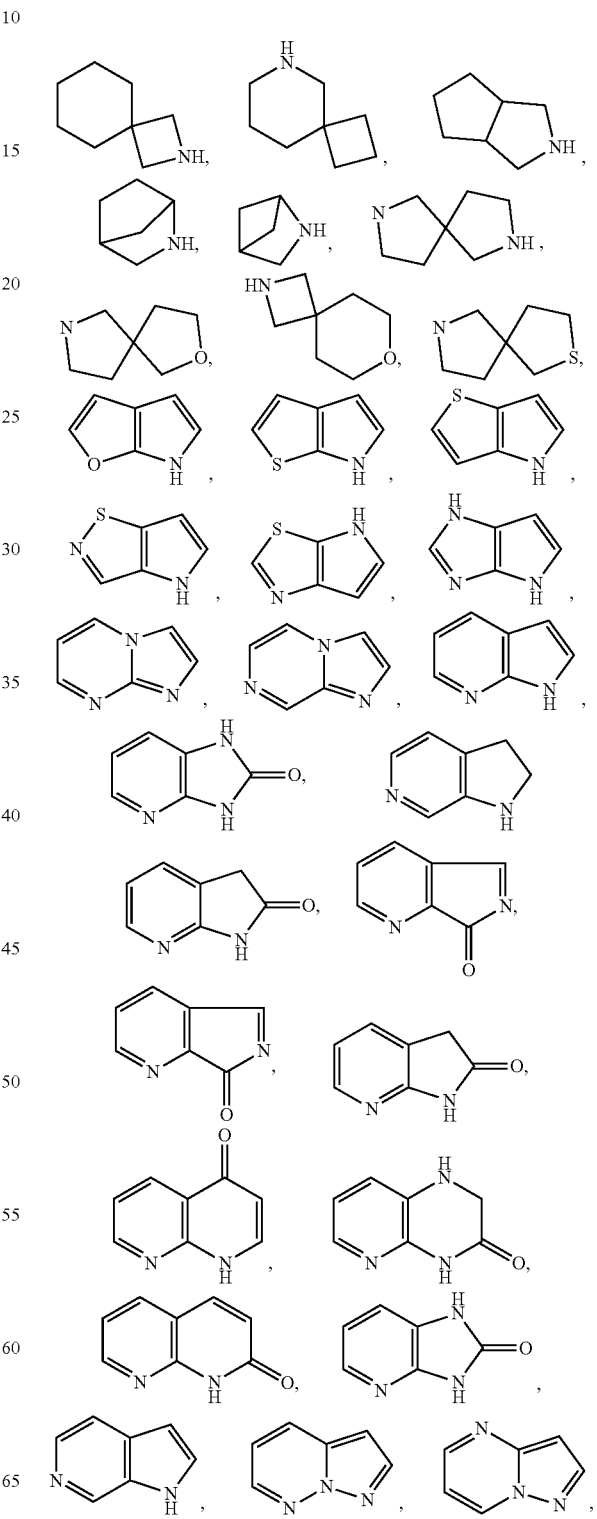

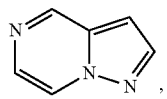 , 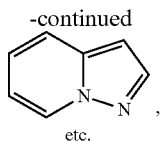 , 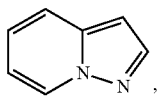 ,
etc.

The term "heterocyclene" refers to a substituted or unsubstituted, saturated or unsaturated, aromatic or non-aromatic, divalent heterocyclic group. Non-limiting examples of heterocyclene include

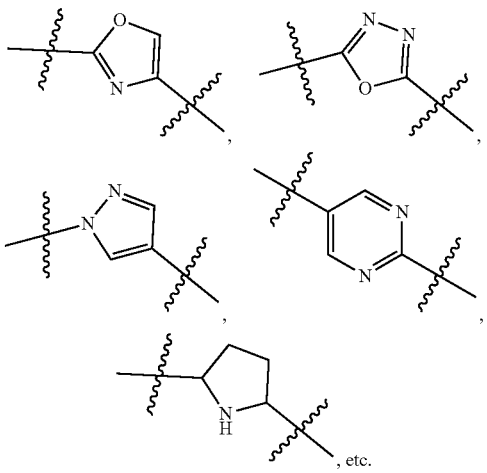

, etc.

The term "aryl" refers to an aromatic group, including 5- and 6-membered monocyclic aromatic groups that may contain 0 to 4 heteroatoms (N, S and O), and a polycyclic system having at least one aromatic ring. The concept of aryl includes aromatic carbocyclic rings and heteroaromatic rings, such as phenyl, pyrrole, furan, thiophene, thiazole, isothiazole, imidazole, triazole, tetrazole, pyrazole, oxazole, isoxazole, pyridine, pyrazine, pyridazine, pyrimidine, etc. Polycyclic (tricyclic or bicyclic) aryl includes such as naphthalene, benzoxazole, benzodioxazole, benzothiazole, benzoimidazole, benzothiophene, methylenedioxybenzene, quinoline, isoquinoline, naphthyridine, indole, benzofuran, purine, deazapurine, or indolizine. Those aryl groups that have heteroatoms in the ring structure may also be referred to as "aromatic heterocycle", "heteroaryl" or "heteroaromatic ring".

The term "spiro ring" refers to a polycyclic group sharing one carbon atom (referred to as a spiro atom) between rings, which may contain 0 or at least 1 double bond or triple bond, and may contain 0 to 5 heteroatoms selected from N, O, S, P, Si and an oxidation state thereof. Generally, a spiro ring is a 6- to 14-membered ring, or a 6- to 12-membered ring, or a 6- to 10-membered ring. Generally, a spiro ring is a spiro ring formed by a three-membered ring and a three-membered ring, a three-membered ring and a four-membered ring, a three-membered ring and a five-membered ring, a three-membered ring and a six-membered ring, a four-membered ring and a four-membered ring, a four-membered ring and a five-membered ring, a four-membered ring and a six-membered ring, a five-membered ring and a five-membered ring or a five-membered ring and a six-membered ring. Non-limiting examples of spiro ring include:

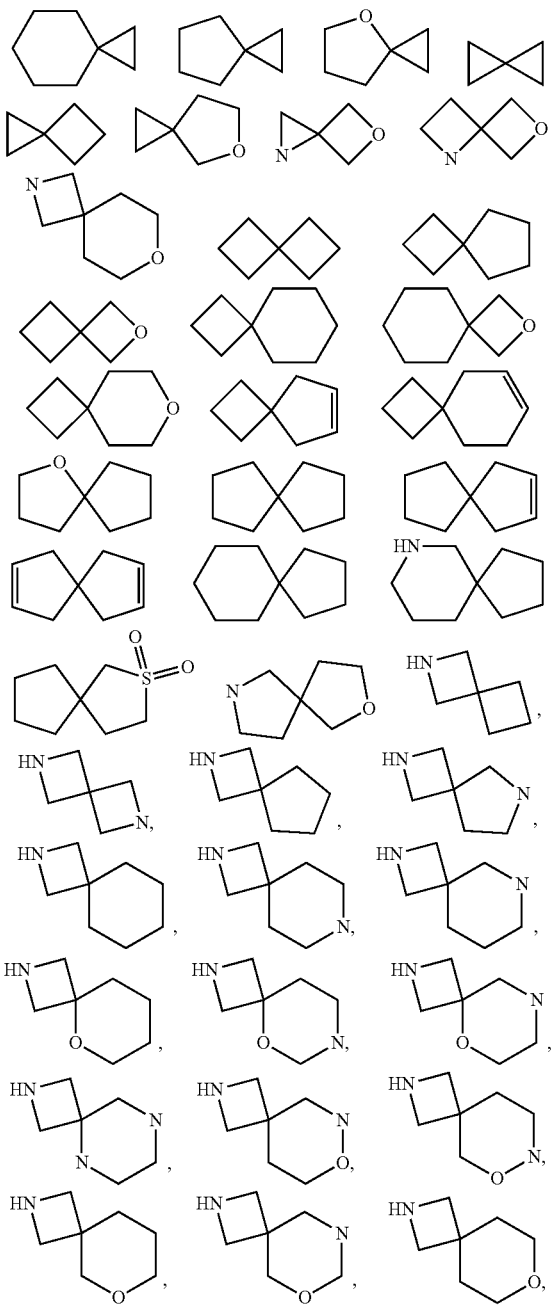

and the spiro ring may be optionally substituted with a substituent.

The term "fused ring" refers to a polycyclic group in which the rings share two adjacent ring atoms and one chemical bond, and may contain one or more double or triple bonds and a fused ring may contain 0 to 5 heteroatoms selected from N, S, O, P, Si and an oxidation state thereof. Generally, a fused ring is a 5- to 20-membered ring, or a 5- to 14-membered ring, or a 5- to 12-membered ring or a 5- to 10-membered ring. Generally, a fused ring is in the form of a three-membered ring fused a four-membered ring (indicating a fused ring formed by a three-membered ring and a four-membered ring, and either the three-membered ring or the four-membered ring may be possibly used as the basic ring according to the IUPAC nomenclature; similarly hereinafter), a three-membered ring fused a five-membered ring, a three-membered ring fused a six-membered ring, a four-membered ring fused a four-membered ring, a four-membered ring fused a five-membered ring, a four-membered ring fused a six-membered ring, a five-membered ring fused a five-membered ring, a five-membered ring fused a six-membered ring, and a six-membered ring fused a six-membered ring. Non-limiting examples of fused ring include purine, quinoline, isoquinoline, benzopyran, benzofuran, benzothiophene, and

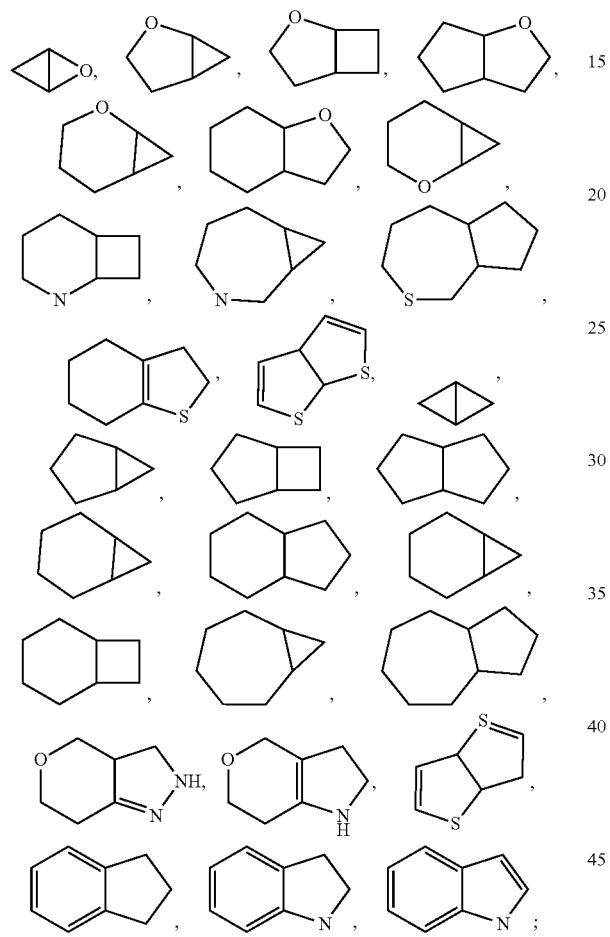

and the fused ring may be optionally substituted with a substituent.

The term "bridged ring" refers to a ring system in which two non-adjacent ring atoms are shared between two rings and a bridged ring may contain 1 or more double or triple bonds. The bridged ring may contain 0 to 5 heteroatoms selected from N, S, O, P, Si and an oxidation state thereof. Generally, the bridged ring has 5 to 20, 5 to 14, 5 to 12, or 5 to 10 ring atoms. Non-limiting examples of bridged ring include adamantane,

-continued

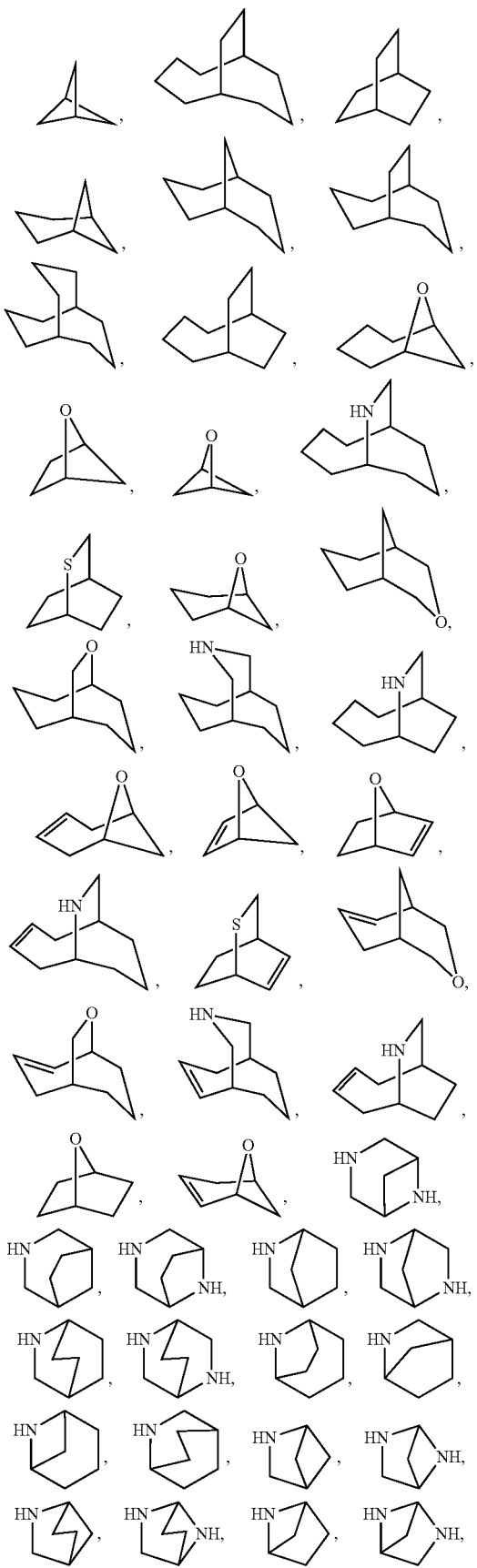

-continued

Unless otherwise specified, the term "substitute" or "substituent" refers to any substitution at a position allowed by chemical theory, and the number of substituents conforms to the rules of chemical bonding. Exemplary substituents include, but are not limited to: $C_{1-6}$ alkyl, $C_{2-6}$ alkenyl, $C_{2-6}$ alkynyl, $C_{3-8}$ heteroalkyl, $C_{5-12}$ aryl, 5-12-membered heteroaryl, hydroxyl, $C_{1-6}$ alkoxy, $C_{1-12}$ aryloxy, thiol, $C_{1-6}$ alkylthio, cyano, halogen, $C_{1-6}$ alkylthiocarbonyl, $C_{1-6}$ alkylcarbamoyl, N-carbamoyl, nitro, silyl, sulfinyl, sulfonyl, sulfoxide, halo $C_{1-6}$ alkyl, halo $C_{1-6}$ alkoxy, amino, phosphonic acid, —$CO_2(C_{1-4}$ alkyl), —$OC(=O)(C_{1-4}$ alkyl), —$OCO_2(C_{1-4}$ alkyl), —$C(=O)NH_2$, —$C(=O)N(C_{1-4}$ alkyl)$_2$, —$OC(=O)NH(C_{1-6}$ alkyl), —$NHC(=O)(C_{1-6}$ alkyl), —$N(C_{1-6}$ alkyl)$C(=O)(C_{1-6}$ alkyl), —$NHCO_2(C_{1-4}$ alkyl), —$NHC(=O)N(C_{1-4}$ alkyl)$_2$, —$HC(=O)NH(C_{1-4}$ alkyl), —$NHC(=O)NH_2$, —$NHSO_2(C_{1-6}$ alkyl), —$SO_2N(C_{1-6}$ alkyl)$_2$, —$SO_2NH(C_{1-4}$ alkyl), —$SO_2NH_2$, —$SO_2C_{1-4}$ alkyl, etc.

The term "optional" or "optionally" refers to that the event or circumstance subsequently described may but not necessarily occur, and the description includes the occasions where the events or circumstances occur or do not occur. For example, "alkyl optionally substituted with F" means that an alkyl may but not necessarily be substituted by F, and the description includes the case where the alkyl is substituted with F and the case where the alkyl is not substituted with F.

When the substituent is optionally further substituted, a group that cannot form according to common chemical knowledge is not included.

If a given group is selected from atoms or groups such as H or deuterium and the group is optionally further substituted, the case where H or deuterium atom is further substituted is not included.

The term "pharmaceutically acceptable salt" refers to a salt of the compound of the present invention, which salt maintains the biological effectiveness and characteristics of a free acid or a free base and is obtained by reacting the free acid with a non-toxic inorganic base or organic base, or reacting the free base with a non-toxic inorganic acid or organic acid.

The term "pharmaceutical composition" represents a mixture of one or more compounds described herein or the stereoisomers, solvates, pharmaceutically acceptable salts or co-crystals thereof and other components comprising physiologically/pharmaceutically acceptable carriers and/or excipients.

The term "carrier" refers to: a system that does not cause significant irritation to the organism and does not eliminate the biological activity and characteristics of the administered compound, and can change the way the drug enters the human body and the distribution of the drug in the body, control the release rate of the drug and delivery the drug to targeted organs. Non-limiting examples of the carrier include microcapsule, microsphere, nanoparticle, liposome, etc.

The term "excipient" refers to: a substance that is not a therapeutic agent per se, but used as a diluent, adjuvant, adhesive and/or vehicle for addition to a pharmaceutical composition, thereby improving the disposal or storage properties thereof, or allowing to or promoting the formation of a compound or a pharmaceutical composition into a unit dosage form for administration. As is known to those skilled in the art, a pharmaceutically acceptable excipient can provide various functions and can be described as a wetting agent, a buffer, a suspending agent, a lubricant, an emulsifier, a disintegrating agent, an absorbent, a preservative, a surfactant, a colorant, a flavoring agent and a sweetening agent. Examples of pharmaceutically acceptable excipients include, but are not limited to: (1) sugars, such as lactose, glucose and sucrose; (2) starch, such as corn starch and potato starch; (3) cellulose and its derivatives, such as sodium carboxymethyl cellulose, ethyl cellulose, cellulose acetate, hydroxypropyl methylcellulose, hydroxypropyl cellulose, microcrystalline cellulose and croscarmellose (such as croscarmellose sodium); (4) tragacanth powder; (5) malt; (6) gelatin; (7) talc; (8) excipients, such as cocoa butter or suppository wax; (9) oils, such as peanut oil, cottonseed oil, safflower oil, sesame oil, olive oil, corn oil and soybean oil; (10) diols, such as propylene glycol; (11) polyols, such as glycerol, sorbitol, mannitol and polyethylene glycol; (12) esters, such as ethyl oleate and ethyl laurate; (13) agar; (14) buffers, such as magnesium hydroxide and aluminum hydroxide; (15) alginic acid; (16) pyrogen-free water; (17) isotonic saline; (18) Ringer's solution; (19) ethanol; (20) pH buffered solution; (21) polyester, polycarbonate and/or polyanhydride; and (22) other non-toxic compatible substances used in a pharmaceutical preparation.

The term "stereoisomer" refers to an isomer produced as a result of different spatial arrangement of atoms in molecules, including cis-trans isomers, enantiomers and conformational isomers.

The term "solvate" refers to a substance formed by the compound of the present invention or the salt thereof and a stoichiometric or non-stoichiometric solvent bound by intermolecular non-covalent forces. When the solvent is water, the solvate is a hydrate.

The term "co-crystal" refers to a crystal formed by the combination of active pharmaceutical ingredient (API) and co-crystal former (CCF) under the action of hydrogen bonds or other non-covalent bonds. The pure state of API and CCF are both solid at room temperature, and there is a fixed stoichiometric ratio between various components. The co-crystal is a multi-component crystal, which includes both a binary co-crystal formed between two neutral solids and a multi-element co-crystal formed between a neutral solid and a salt or solvate.

DETAILED DESCRIPTION OF EMBODIMENTS

The content of the present invention is described in detail with the following examples. If a specific condition is not indicated in the examples, a conventional condition is used in an experimental method. The listed examples are intended to better illustrate the content of the present invention, but should not be construed as limiting the content of the present invention. According to the above-mentioned content of the invention, those skilled in the art can make unsubstantial modifications and adjustments to the embodiments, which still fall within the protection scope of the present invention.

Detection Method

The structures of the compounds are determined by nuclear magnetic resonance (NMR) or (and) mass spectrometry (MS). The NMR shift (δ) is given in the unit of 10-6 (ppm). NMR is determined with Bruker Avance III 400 and Bruker Avance 300; the solvent for determination is deuterated dimethyl sulfoxide (DMSO-d6), deuterated chloroform (CDCl3) and deuterated methanol (CD3OD); and the internal standard is tetramethylsilane (TMS);

MS is measured with (Agilent 6120B (ESI) and Agilent 6120B (APCI));

HPLC is determined with Agilent 1260DAD high pressure liquid chromatograph (Zorbax SB-C18 100×4.6 mm, 3.5 μM);

Yantai Huanghai HSGF254 or Qingdao GF254 silica gel plate is used as a thin layer chromatography silica plate, and the silica gel plate for the thin layer chromatography (TLC) is of the specification of 0.15 mm-0.20 mm, and the specification when separating and purifying a product by thin layer chromatography is 0.4 mm-0.5 mm.

For the column chromatography, Yantai Huanghai silica gel of 200-300 mesh silica gel is generally used as a carrier.

Description of Abbreviations

Burgess reagent: (Methoxycarbonylsulfamoyl)triethylammonium hydroxide, inner salt
Pd(dppf)Cl$_2$: [1,1'-bis(diphenylphosphino)ferrocene]dichloropalladium (II)
X-Phos: 2-dicyclohexylphosphino-2,4,6-triisopropylbiphenyl
DMF: N,N'-dimethylformamide
HATU: 2-(7-azobenzotriazole)-N,N,N',N'-tetramethyluronium hexafluorophosphate
DIPEA: N,N-diisopropylethylamine
LDA: Lithium diisopropylamide
PE: Petroleum ether
EA: Ethyl acetate
THF: Tetrahydrofuran
MeOH: Methanol
DCM: Dichloromethane
TMSOTf: Trimethylsilyl trifluoromethanesulfonate Intermediates INT-1: tert-butyl (S)-(1-cyano-2-(4-(4,4,5,5-tetramethyl-1,3,2-dioxaborolan-2-yl)phenyl)ethyl)carbamate

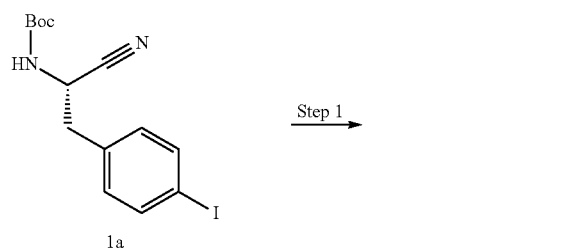

Compound 1a (4.50 g, 12.1 mmol, prepared with reference to WO 2013041497) was dissolved in 1,4-dioxane (45 ml), and pinacolborane (3.12 g, 24.2 mmol), triethylamine (3.67 g, 36.3 mmol), and Pd(dppf)Cl$_2$ (877 mg, 1.2 mmol) were added. Upon completion of the addition, the mixture was reacted under microwave at 100° C. for 1 hour. After completion of the reaction, the reaction solution was filtered and the filtrate was concentrated. The obtained residue was separated and purified by silica gel column chromatography (eluent: PE:EA (v/v)=1:0-10:1) to give INT-1 as a white solid (2.1 g, yield: 46.7%). LCMS m/z=373.2 [M+1]$^+$.

$^1$H NMR (400 MHz, CDCl$_3$) δ 7.81 (d, 2H), 7.29 (d, 2H), 4.81 (s, 1H), 4.72 (s, 1H), 3.15-3.03 (m, 2H), 1.44 (s, 9H), 1.34 (s, 12H).

INT-2: tert-butyl (S)-(1-cyano-2-(2-fluoro-4-(4,4,5,5-tetramethyl-1,3,2-dioxaborolan-2-yl)phenyl)ethyl)carbamate

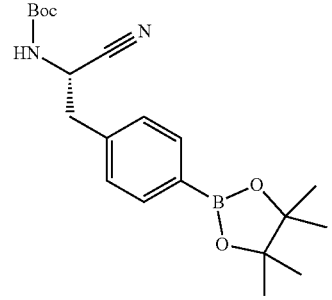

Compound 2a (2.0 g, 5.8 mmol, prepared with reference to WO 2016016242) was dissolved in ethylene glycol dimethyl ether (40 ml), and bis(pinacolato)diboron (2.23 g, 8.7 mmol), potassium acetate (1.70 g, 17.4 mmol), and Pd(dppf)Cl$_2$ (423.1 mg, 0.58 mmol) were added. Upon completion of the addition, the mixture was warmed to 90° C. and reacted for 3 hours. After completion of the reaction, the reaction solution was filtered and the filtrate was concentrated. The obtained residue was separated and purified by silica gel column chromatography (eluent: PE:EA (v/v)=1:0-10:1) to give INT-2 as a white solid (2.1 g, yield: 92.1%). LCMS m/z=335.2 [M+1−56]$^+$.

$^1$H NMR (400 MHz, CDCl$_3$) δ 7.56 (d, 1H), 7.50 (d, 1H), 7.29 (d, 1H), 4.99 (d, 1H), 4.82 (s, 1H), 3.18-3.16 (m, 2H), 1.42 (s, 9H), 1.34 (s, 12H).

Example 1: (S)—N—((S)-1-cyano-2-(2-fluoro-4-(3-methyl-2-oxo-2,3-dihydrobenzo[d]oxazol-5-yl)phenyl)ethyl)-1,4-oxazepane-2-carboxamide (Compound 1)

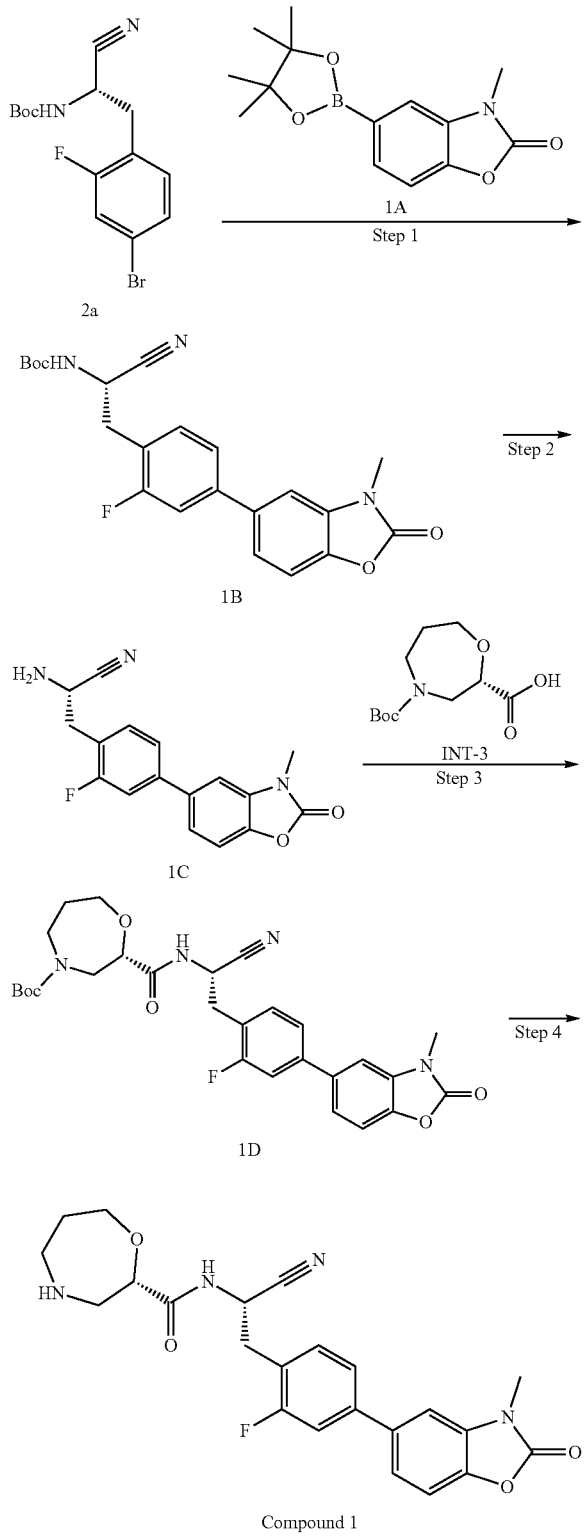

Step 1: (S)-tert-butyl (1-cyano-2-(2-fluoro-4-(3-methyl-2-oxo-2,3-dihydrobenzo[d]oxazol-5-yl)phenyl)ethyl)carbamate (1B)

1A (0.29 g, 0.85 mmol, synthesized with reference to WO 2016016242 A1) was dissolved in 1,4-dioxane (10 mL) and water (0.4 mL), and intermediate 2a (0.35 g, 1.27 mmol), potassium carbonate (0.24 g, 1.70 mmol), and [1,1'-bis(diphenylphosphino)ferrocene]palladium dichloride dichloromethane complex (70 mg, 0.09 mmol) were added. Upon completion of the addition, the mixture was reacted at 90° C. for 3 h. The reaction solution was cooled to room temperature and saturated aqueous sodium chloride solution (20 mL) was added. The resulting mixture was extracted with ethyl acetate (20 mL×3). The organic phases were combined, dried over anhydrous sodium sulfate, filtered and concentrated, and the residue was separated and purified by silica gel column chromatography (PE:EA (v/v)=4:1) to obtain the title compound 1B (white solid, 0.34 g, 99.0%). LC-MS (ESI): m/z=412.1 [M+H]$^+$.

Step 2: (S)-2-amino-3-(2-fluoro-4-(3-methyl-2-oxo-2,3-dihydrobenzo[d]oxazol-5-yl)phenyl)propanenitrile (1C)

1B (0.34 g, 0.83 mmol) was dissolved in formic acid (5 mL) and upon completion of the addition, the mixture was reacted at room temperature overnight. The reaction solution was concentrated to dryness and ethyl acetate (25 mL) was added. Then saturated aqueous sodium bicarbonate solution was added dropwise to adjust the pH to about 8. The organic layer was separated and the remaining aqueous layer was extracted with ethyl acetate (25 mL×3). The organic phases were combined, dried over anhydrous sodium sulfate, filtered and concentrated to obtain a crude product of the title compound 1C (pale yellow solid, 0.21 g, 69.5%). LC-MS (ESI): m/z=312.1 [M+H]$^+$.

Step 3: (S)-tert-butyl 2-(((S)-1-cyano-2-(2-fluoro-4-(3-methyl-2-oxo-2,3-dihydrobenzo[d]oxazol-5-yl)phenyl)ethyl)carbamoyl)-1,4-oxazepane-4-carboxylate (1D)

1C (0.21 g, 0.60 mmol) was dissolved in DMF (10 mL), and DIPEA (0.23 g, 1.80 mmol), HATU (0.34 g, 0.90 mmol), and INT-3 (0.22 g, 0.90 mmol, prepared with reference to WO 2015110826) were added. Upon completion of the addition, the mixture was reacted at room temperature overnight. The reaction was quenched by adding saturated aqueous ammonium chloride solution dropwise, and saturated aqueous sodium chloride solution (30 mL) was added. The resulting mixture was extracted with ethyl acetate (25 mL), and the organic phase was washed with saturated aqueous sodium chloride solution (25 mL×3), dried over anhydrous sodium sulfate, filtered and concentrated to obtain the title compound 1D (pale yellow solid, 0.32 g, 99.0%), which was directly used in the next reaction. LC-MS (ESI): m/z=483.1 [M−57+H]$^+$.

Step 4: (S)—N—((S)-1-cyano-2-(2-fluoro-4-(3-methyl-2-oxo-2,3-dihydrobenzo[d]oxazol-5-yl)phenyl)ethyl)-1,4-oxazepane-2-carboxamide (Compound 1)

1D (0.32 g, 0.59 mmol) was dissolved in formic acid (2.5 mL) and upon completion of the addition, the mixture was reacted at 50° C. for 10 min. The reaction solution was concentrated to dryness and ethyl acetate (20 mL) was added. Then saturated aqueous sodium bicarbonate solution was added dropwise to adjust the pH to about 8. The organic layer was separated and the remaining aqueous layer was extracted with ethyl acetate (25 mL×3). The organic phases were combined, dried over anhydrous sodium sulfate, filtered and concentrated, and the residue was separated and purified by silica gel column chromatography (dichloromethane:methanol (v/v)=20:1) to obtain the title compound 1 (0.15 g, 58.0%). LC-MS (ESI): m/z=439.1 [M+H]⁺.

¹H NMR (400 MHz, CDCl₃) δ 7.43-7.22 (m, 5H), 7.12 (d, 1H), 5.19 (dd, 1H), 4.18-4.04 (m, 1H), 4.05-3.95 (m, 1H), 3.78 (m, 1H), 3.46 (s, 3H), 3.41-3.17 (m, 3H), 3.03-2.87 (m, 3H), 1.88 (m, 2H).

Example 2: N—((S)-1-cyano-2-(2-methoxy-4-(3-methyl-2-oxo-2,3-dihydrobenzo[d]oxazol-5-yl)phenyl)ethyl)-1,4-oxazepane-2-carboxamide (Compound 2)

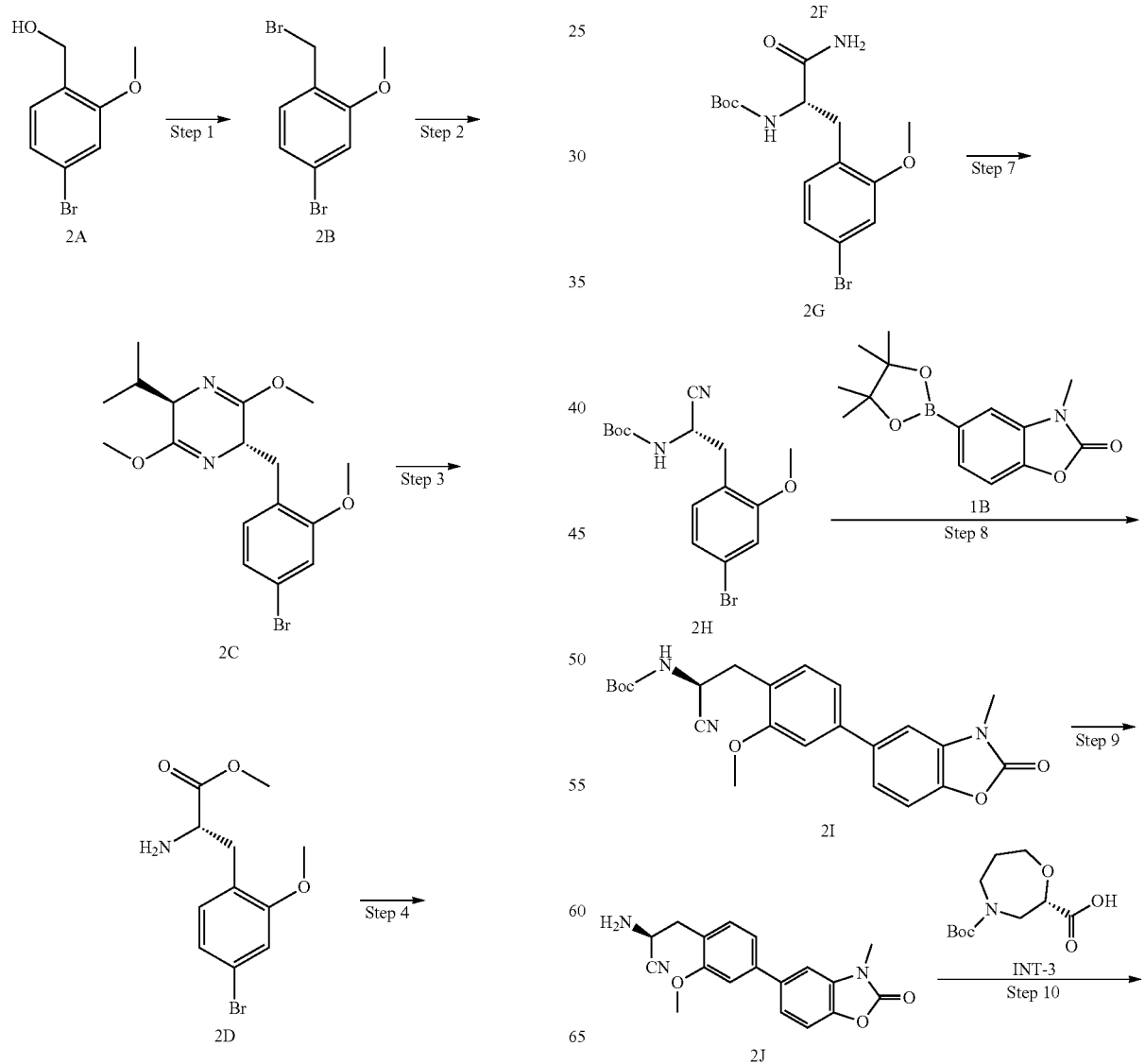

-continued

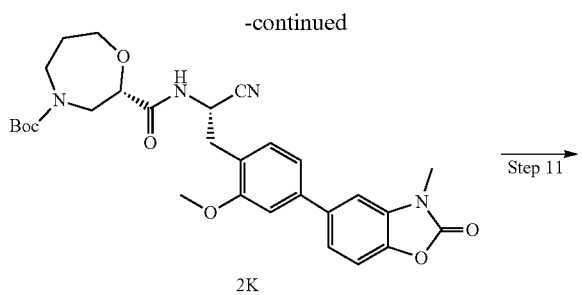

2K

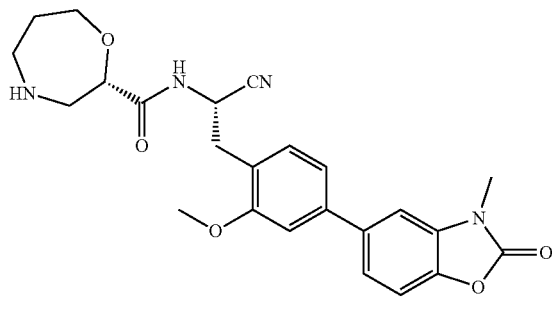

Compound 2

Step 1: 4-bromo-1-(bromomethyl)-2-methoxybenzene (2B)

(2A) (4 g, 18.43 mmol) was dissolved in DCM (60 mL) and CBr$_4$ (9.09 g, 27.64 mmol) was added. Then PPh$_3$ (7.24 g, 27.64 mmol) was slowly added and the mixture was reacted at room temperature for 1 hour. PE/EA (v/v=5:1, 12 mL) was added to the reaction solution. The resulting mixture was stirred and filtered off with suction, and the filtrate was concentrated. The residue was separated and purified by silica gel column chromatography (PE:EA (v/v)=30:1-20:1) to obtain the title compound (2B) as a white solid (3.9 g, yield: 76%).

Step 2: (2S,5R)-2-(4-bromo-2-methoxybenzyl)-5-isopropyl-3,6-dimethoxy-2,5-dihydropyrazine (2C)

(R)-2-isopropyl-3,6-dimethoxy-2,5-dihydropyrazine (1 g, 5.43 mmol) was dissolved in THF (20 mL). The mixture was subjected to nitrogen replacement and cooled to −78° C., and n-butyllithium (6.5 mmol, 2.5 M in toluene, 2.6 mL) was added. The resulting mixture was reacted for 1 h and subsequently a solution of 2B (1.67 g, 5.97 mmol) in THF (8 mL) was added. The reaction at −78° C. was allowed to continue for 2 hours. The reaction was quenched with saturated NH$_4$Cl solution, and the system was extracted with EA (10 mL×3). The organic phases were combined, washed with saturated brine (10 mL), dried over anhydrous sodium sulfate, and concentrated. The crude product was passed through a silica gel column (EA/PE (v/v)=0%-6%) to obtain the title compound (2C) as a colorless oil (1.82 g, yield: 87%). LCMS m/z=383.3 [M+1]$^+$

Step 3: methyl (S)-2-amino-3-(4-bromo-2-methoxyphenyl)propanoate (2D)

2C (1.82 g, 4.75 mmol) was dissolved in acetonitrile (15 mL), and 1 M HCl (5 mL) was added. The mixture was reacted at room temperature overnight and the system was subjected to rotary evaporation. Saturated aqueous sodium bicarbonate solution was added to neutralize the system to a weakly basic pH, EA (15 mL×3) was added for extraction, and liquid-liquid separation was carried out. The organic phases were combined, washed with saturated brine (10 mL), dried over anhydrous sodium sulfate and concentrated, and the residue was separated and purified by silica gel column chromatography (DCM:MeOH (v/v)=20:1-10:1) to obtain 2D (1.34 g, yield: 97%). LCMS m/z=288.1 [M+1]$^+$

Step 4: methyl (S)-3-(4-bromo-2-methoxyphenyl)-2-((tert-butoxycarbonyl)amino)propanoate (2E)

2D (1.34 g, 4.69 mmol) was dissolved in DCM (20 mL), and triethylamine (1.3 mL) and di-tert-butyl dicarbonate (1.23 g, 5.63 mmol) were added. The mixture was reacted at room temperature for 3 h. Water was added to the system for extraction and liquid-liquid separation was carried out. The organic phases were combined, washed with saturated brine (10 mL), dried over anhydrous sodium sulfate and concentrated, and the residue was separated and purified by silica gel column chromatography (DCM:MeOH (v/v)=20:1-10:1) to obtain 2E as a colorless oil (0.7 g, yield: 31%). LCMS m/z=288.1 [M−boc+1]$^+$

Step 5: (S)-3-(4-bromo-2-methoxyphenyl)-2-((tert-butoxycarbonyl)amino)propanoic acid (2F)

2E (0.7 g, 1.87 mmol) was dissolved in methanol (10 mL) and water (6 mL), and then NaOH (1.50 g, 3.74 mmol) was added. The mixture was reacted at room temperature for 2 hours and methanol was removed by rotary evaporation. Dilute hydrochloric acid was added to adjust the solution to a weakly acidic pH. EA (10 mL×3) was added for extraction and liquid-liquid separation was carried out. The organic phase was subjected to rotary evaporation to obtain the crude product (2F) (0.65 g). LCMS m/z=274.2 [M−boc+1]$^+$

Step 6: tert-butyl (S)-(1-amino-3-(4-bromo-2-methoxyphenyl)-1-oxopropan-2-yl)carbamate (2G)

2F (0.65 g, 1.73 mmol), NH$_4$Cl (0.74 g), and HATU (0.66 g, 1.73 mmol) were dissolved in DMF (15 mL), and then DIPEA (1.15 mL) was added. The mixture was reacted at room temperature overnight. Water and EA were added for extraction and liquid-liquid separation was carried out, and the organic phase was dried over anhydrous Na$_2$SO$_4$ and concentrated to obtain the crude product (2G) (0.62 g). LCMS m/z=273.1 [M−boc+1]$^+$

Step 7: tert-butyl (S)-(2-(4-bromo-2-methoxyphenyl)-1-cyanoethyl)carbamate (2H)

2G (0.62 g, 1.66 mmol) was dissolved in DCM (10 mL) and then Burgess reagent (0.79 g, 3.32 mmol) was added. The mixture was reacted at room temperature overnight. The system was concentrated and subjected to rotary evaporation and the crude product was separated and purified by silica gel column chromatography (EA/PE (v/v)=0%-25%) to obtain 2H (0.5 g, yield: 85%). LCMS m/z=355.1 [M+1]$^+$

Step 8: tert-butyl (S)-(1-cyano-2-(2-methoxy-4-(3-methyl-2-oxo-2,3-dihydrobenzo[d]oxazol-5-yl)phenyl)ethyl)carbamate (2I)

2H (0.5 g, 1.41 mmol), 1B (0.11 g, 1.41 mmol), [1,1'-bis (diphenylphosphino)ferrocene]palladium dichloride dichloromethane complex (115 mg, 0.14 mmol), and potassium carbonate (390 mg, 2.82 mmol) were dissolved in 1,4- dioxane (20 mL), the system was under the protection of nitrogen replacement, and the mixture was reacted at 90° C. for 3 hours. The reaction solution was concentrated and subjected to rotary evaporation, then dissolved in DCM and filtered off with suction through celite, and the filtrate was subjected to rotary evaporation. The crude product was separated by silica gel column chromatography (EA/PE (v/v)=0%-40%) to obtain 2I as a pale yellow solid (550 mg, yield: 92%). LCMS m/z=424.2 [M+1]$^+$

Step 9: (S)-2-amino-3-(2-methoxy-4-(3-methyl-2-oxo-2,3-dihydrobenzo[d]oxazol-5-yl)phenyl)propanenitrile (2J)

2I (135 mg, 0.32 mmol) was dissolved in formic acid (8 mL) and the mixture was stirred at room temperature overnight. The system was diluted with DCM and saturated sodium bicarbonate solution was added to adjust the system to a weakly basic pH. Liquid-liquid separation was carried out using DCM and water, and the organic phase was dried, concentrated, and subjected to rotary evaporation to obtain the crude product (2J) (90 mg), which was directly used in the next reaction. LCMS m/z=324.1 [M+1]$^+$

Step 10: tert-butyl (S)-2-(((S)-1-cyano-2-(2-methoxy-4-(3-methyl-2-oxo-2,3-dihydrobenzo[d]oxazol-5-yl)phenyl)ethyl)carbamoyl)-1,4-oxazepane-4-carboxylate (2K)

2J (90 mg, 0.28 mmol) and INT-3 (82 mg, 0.34 mmol) were dissolved in DMF (5 mL), and then HATU (0.12 g, 0.31 mmol) and DIPEA (0.2 mL) were added. The mixture was reacted at room temperature overnight. Water and EA were added to the reaction system for extraction and liquid-liquid separation, and the organic phase was dried and concentrated to obtain the crude product as a pale yellow oil, which was purified by chromatography (MeOH/DCM (v/v)=0-10%) to obtain 2K (90 mg). LCMS m/z=549.1 [M+1]$^+$

Step 11: (S)—N—((S)-1-cyano-2-(2-methoxy-4-(3-methyl-2-oxo-2,3-dihydrobenzo[d]oxazol-5-yl)phenyl)ethyl)-1,4-oxazepane-2-carboxamide (Compound 2)

2K (90 mg, 0.16 mmol) was dissolved in formic acid (5 mL) and the mixture was reacted at room temperature for 4 hours. The system was diluted with DCM and saturated sodium bicarbonate solution was added to adjust the system to a weakly basic pH. Liquid-liquid separation was carried out using DCM and water, and the organic phase was dried, concentrated, and subjected to rotary evaporation to obtain a residue, which was separated and purified by silica gel column chromatography (DCM:MeOH (v/v)=50:1 to 5:1) to obtain the title compound 2 (13 mg, yield: 18%). LC-MS m/z=451.2 [M+1]$^+$ $^1$H NMR (400 MHz, CDCl$_3$) δ 7.49 (d, 1H), 7.32-7.28 (m, 2H), 7.14-7.12 (m, 2H), 7.05 (d, 1H), 5.13-5.06 (m, 1H), 4.18-4.14 (m, 1H), 4.07-4.01 (m, 1H), 3.96 (s, 3H), 3.82-3.76 (m, 1H), 3.46 (s, 3H), 3.44-3.41 (m, 1H), 3.27-3.16 (m, 3H), 3.07-2.97 (m, 3H), 2.93-2.87 (q, 1H), 1.98-1.94 (q, 2H).

Example 3: (S)—N—((S)-1-cyano-2-(3-fluoro-4-(3-methyl-2-oxo-2,3-dihydrobenzo[d]oxazol-5-yl)phenyl)ethyl)-1,4-oxazepane-2-carboxamide (Compound 3)

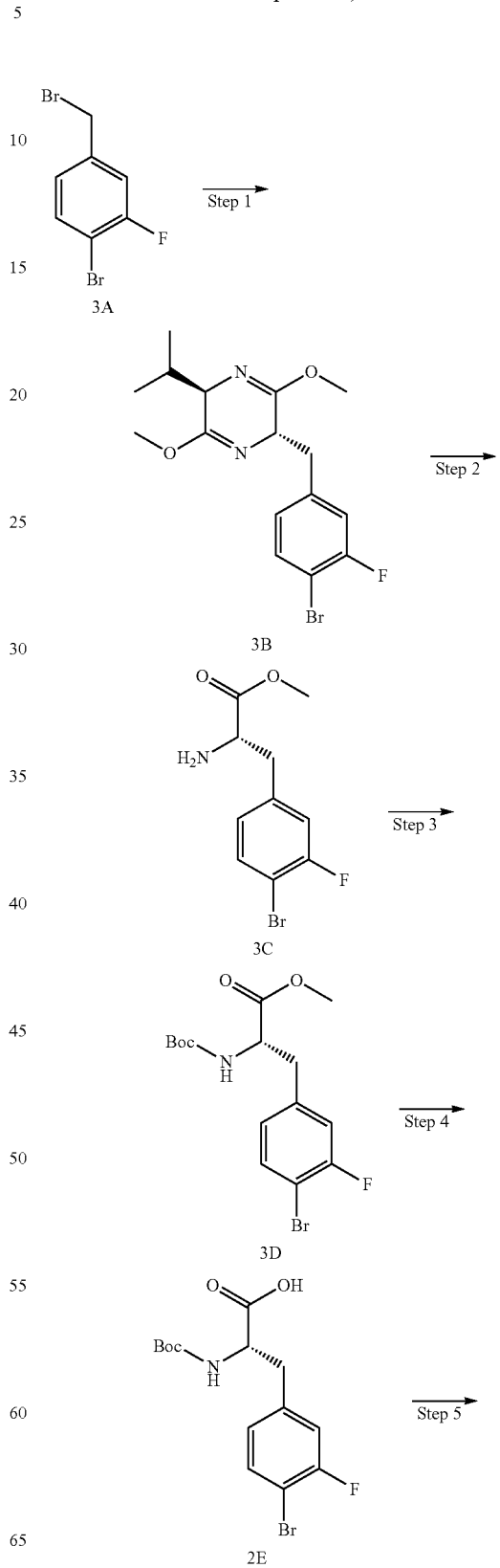

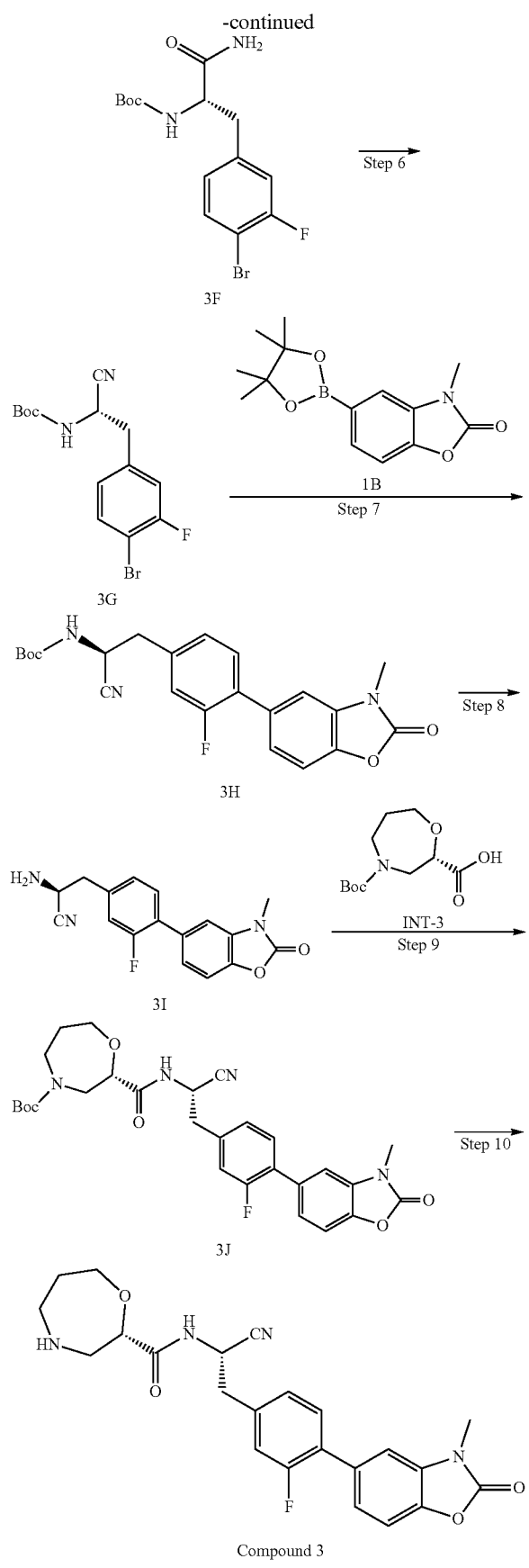
Compound 3 was prepared from compound 3A with reference to the preparation method of compound 2. LC-MS m/z=439.2 [M+1]+
$^1$H NMR (400 MHz, CDCl$_3$) δ 7.43 (t, 1H), 7.31-7.27 (m, 2H), 7.21-7.17 (m, 2H), 7.14 (d, 1H), 5.21-5.15 (m, 1H), 4.30-4.27 (m, 1H), 4.08-4.02 (m, 1H), 3.84-3.77 (m, 1H), 3.53-3.49 (m, 1H), 3.44 (s, 3H), 3.23-3.04 (m, 5H), 2.04-2.00 (m, 3H), 1.26-1.22 (m, 1H).
$^{19}$F NMR (376 MHz, CDCl$_3$) δ −117.13.
Example 4: (S)—N—((S)-1-cyano-2-(5-(1-methyl-2-oxoindolin-6-yl)thiophen-2-yl)ethyl)-1,4-oxazepane-2-carboxamide (Compound 4)
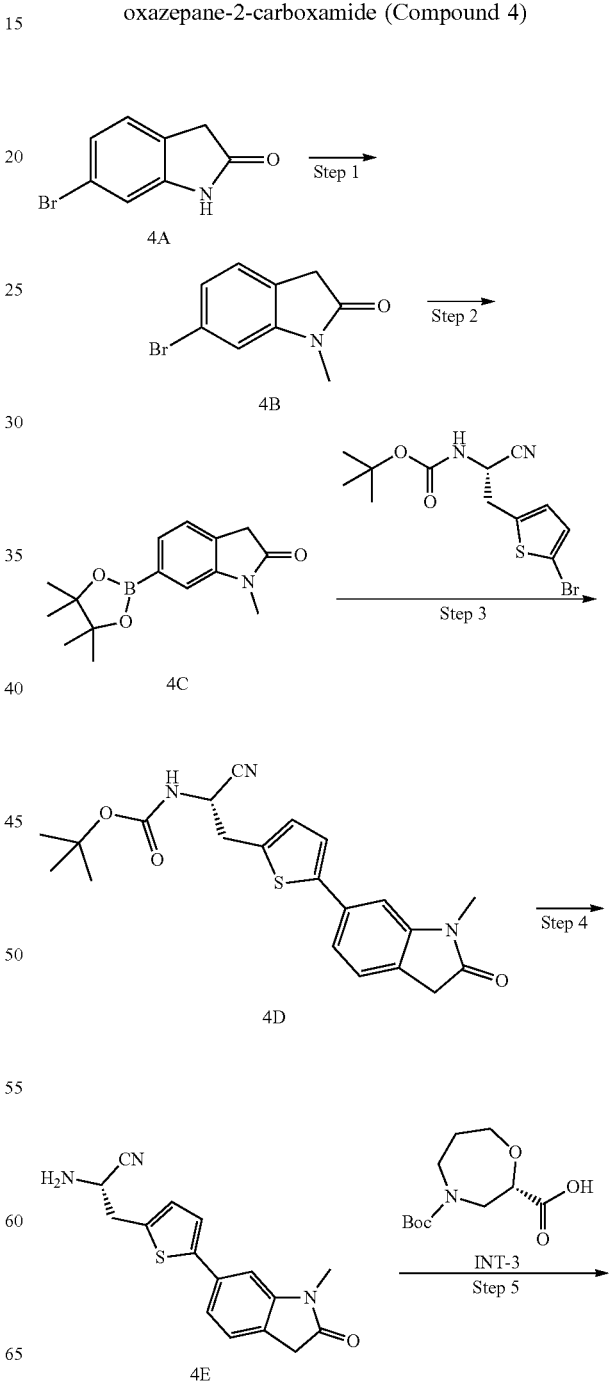

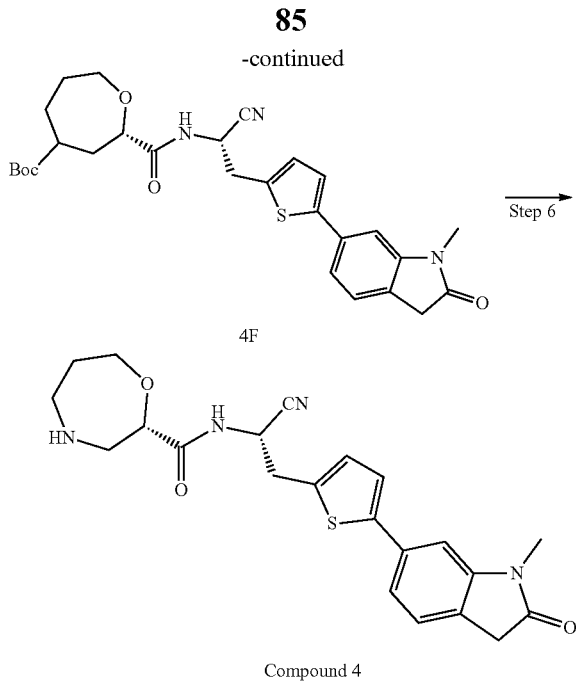

Compound 4

Step 1: 6-bromo-1-methylindolin-2-one (4B)

4A (5 g, 23.5 mmol) was dissolved in 200 mL of acetonitrile and then potassium carbonate (23 g, 94.32 mmol) and iodomethane (2.96 mL, 47.16 mmol) were added. The mixture was heated to 70° C. and stirred overnight. The reaction solution was concentrated and extracted with DCM and water, the organic phase was dried and concentrated, and the residue was separated by column chromatography (PE:EA=2:1 (v/v)) to obtain a brown solid 4B (1.8 g, 34%). LC-MS (ESI): m/z=226.1 [M+H]$^+$.

Step 2: 1-methyl-6-(4,4,5,5-tetramethyl-1,3,2-dioxaborolan-2-yl)indolin-2-one (4C)

Compound 4B (1 g, 4.42 mmol), palladium acetate (200 mg, 0.88 mmol), potassium acetate (0.87 g, 8.84 mmol), 2-(dicyclohexylphosphino)-2,4,6-triisopropyl biphenyl (1.2 g, 2.65 mmol), and bis(pinacolato)diboron (1.35 g, 5.3 mmol) were mixed and dissolved in 50 mL of 1,4-dioxane, and the mixture was heated to 95° C. under N$_2$ protection and reacted for 3 hours. After the completion of the reaction detected by LCMS, the reaction solution was concentrated and separated by column chromatography (PE:EA (v/v)=1:1) to obtain a pale yellow solid 4C (880 mg, 73%). LC-MS (ESI): m/z=274.2 [M+H]$^+$.

Step 3: tert-butyl-(S)-(1-cyano-2-(5-(1-methyl-2-oxoindolin-6-yl)thiophen-2-yl)ethyl)carbamate (4D)

Tert-butyl N-[(1S)-2-(5-bromothiophen-2-yl)-1-cyanoethyl]carbamate (480 mg, 1.45 mmol), 4C (475 mg, 1.74 mmol), potassium carbonate (400 mg, 2.9 mmol), and [1,1'-bis(diphenylphosphino)ferrocene]palladium dichloride dichloromethane complex (21 mg, 0.29 mmol) were mixed and dissolved in 5 mL of 1,4-dioxane and 0.1 mL of water, and the mixture was heated to 120° C. under microwave and reacted for 1 hour. After the completion of the reaction detected by LCMS, the reaction solution was concentrated and separated by column chromatography (PE:EA (v/v)=1:1) to obtain a pale yellow solid 4D (175 mg, 33%). LC-MS (ESI): m/z=398.2 [M+H]$^+$.

Step 4: (S)-2-amino-3-(5-(1-methyl-2-oxoindolin-6-yl)thiophen-2-yl)propanenitrile (4E)

Formic acid (3 mL) was added to compound 4D (175 mg, 0.44 mmol) and the mixture was stirred at room temperature for 3 hours. After the completion of the reaction detected by LCMS, saturated sodium carbonate solution was added to the reaction solution to adjust the pH to 10. The resulting mixture was extracted with DCM and the organic phase was dried and concentrated to obtain the product 4E (119 mg, 91%). LC-MS (ESI): m/z=298.1 [M+H]$^+$.

Step 5: tert-butyl-(S)-2-(((S)-1-cyano-2-(5-(1-methyl-2-oxoindolin-6-yl)thiophen-2-yl)ethyl)carbamoyl)-1,4-oxazepane-4-carboxylate (4F)

Compound 4E (119 mg, 0.4 mmol), INT-3 (98 mg, 0.4 mmol), HATU (180 mg, 0.48 mmol), and DIEA (0.13 mL, 0.8 mmol) were mixed and dissolved in DMF, and the mixture was stirred at room temperature overnight. After the completion of the reaction detected by LCMS, water and EA were added for extraction, the organic phase was dried and concentrated, and the residue was separated by column chromatography (PE:EA (v/v)=1:1) to obtain a yellow solid 4F (165 mg, 78%). LC-MS (ESI): m/z=525.2 [M+H]$^+$.

Step 6: (S)—N—((S)-1-cyano-2-(5-(1-methyl-2-oxoindolin-6-yl)thiophen-2-yl)ethyl)-1,4-oxazepane-2-carboxamide (Compound 4)

Compound 4F (145 mg, 0.28 mmol) was dissolved in 3 mL of a formic acid solution and the mixture was reacted at room temperature for 3 hours. After the completion of the reaction detected by LCMS, the reaction solution was poured into saturated sodium carbonate solution to adjust the pH to 10. The resulting mixture was extracted with EA, the organic phase was dried and concentrated, and the residue was separated and purified by silica gel column chromatography (methanol:dichloromethane (v/v)=1:100-1:10) to obtain compound 4 (45 mg, 38%). LC-MS (ESI): m/z=425.2 [M+H]$^+$.

$^1$H NMR (400 MHz, DMSO-d$_6$): 8.67-8.69 (m, 1H), 7.40-7.41 (d, 1H), 7.18-7.28 (m, 3H), 6.99-7.00 (m, 1H), 4.94-5.03 (m, 1H), 4.01-4.04 (m, 1H), 3.71-3.77 (m, 1H), 3.55 (s, 2H), 3.33-3.46 (m, 3H), 3.16 (s, 3H), 3.07-3.12 (m, 1H), 2.61-2.81 (m, 4H), 1.69-1.78 (m, 2H).

Example 5: (S)—N—((S)-1-cyano-2-(5-(3-methyl-2-oxo-2,3-dihydrobenzo[d]oxazol-5-yl)thiophen-2-yl)ethyl)-1,4-oxazepane-2-carboxamide (Compound 5)

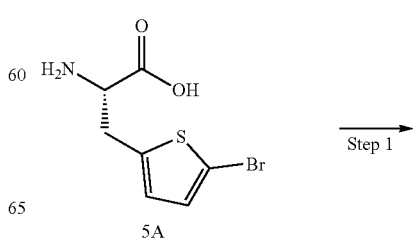

5A

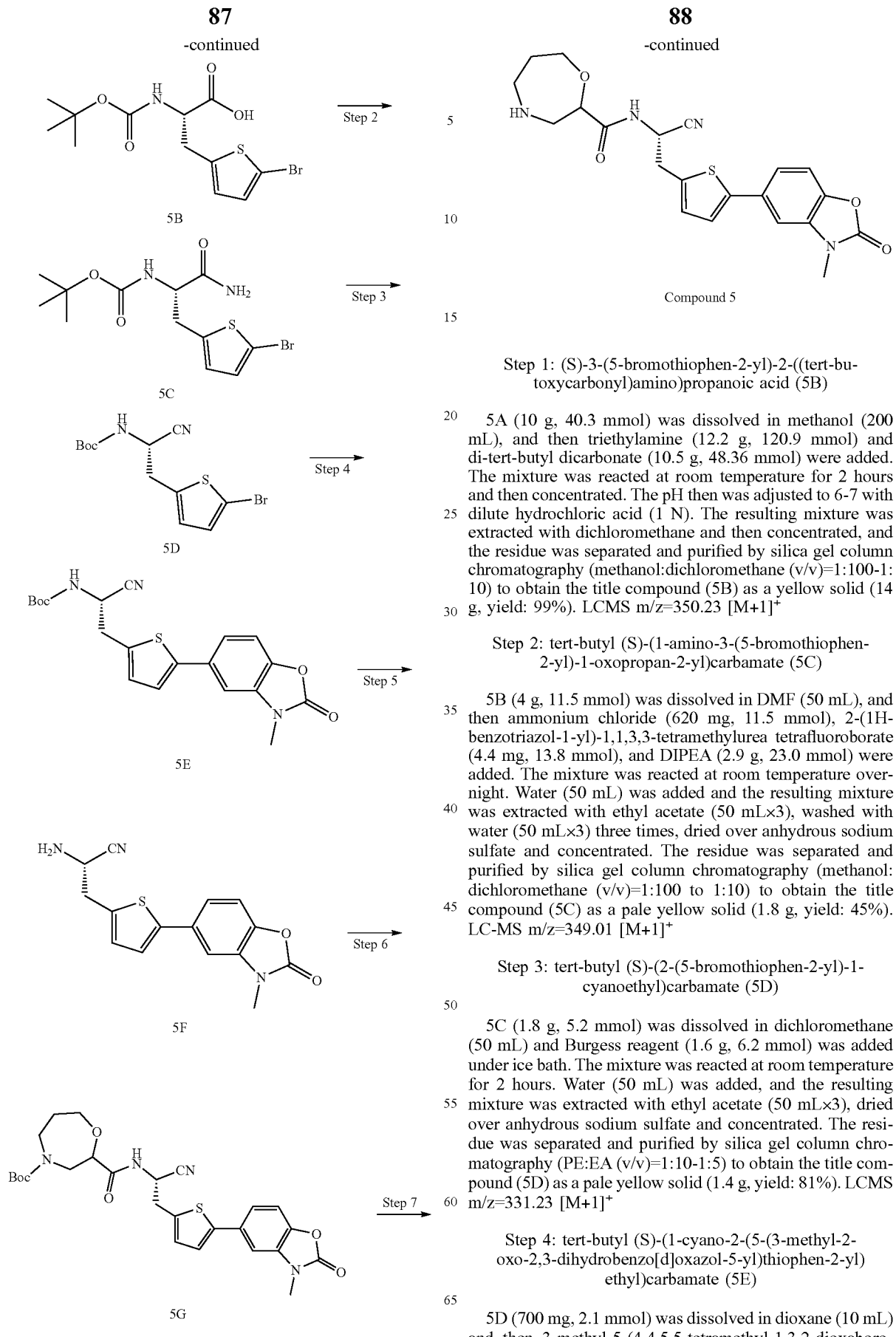

Step 1: (S)-3-(5-bromothiophen-2-yl)-2-((tert-butoxycarbonyl)amino)propanoic acid (5B)

5A (10 g, 40.3 mmol) was dissolved in methanol (200 mL), and then triethylamine (12.2 g, 120.9 mmol) and di-tert-butyl dicarbonate (10.5 g, 48.36 mmol) were added. The mixture was reacted at room temperature for 2 hours and then concentrated. The pH then was adjusted to 6-7 with dilute hydrochloric acid (1 N). The resulting mixture was extracted with dichloromethane and then concentrated, and the residue was separated and purified by silica gel column chromatography (methanol:dichloromethane (v/v)=1:100-1:10) to obtain the title compound (5B) as a yellow solid (14 g, yield: 99%). LCMS m/z=350.23 [M+1]$^+$ Step 2: tert-butyl (S)-(1-amino-3-(5-bromothiophen-2-yl)-1-oxopropan-2-yl)carbamate (5C)

5B (4 g, 11.5 mmol) was dissolved in DMF (50 mL), and then ammonium chloride (620 mg, 11.5 mmol), 2-(1H-benzotriazol-1-yl)-1,1,3,3-tetramethylurea tetrafluoroborate (4.4 mg, 13.8 mmol), and DIPEA (2.9 g, 23.0 mmol) were added. The mixture was reacted at room temperature overnight. Water (50 mL) was added and the resulting mixture was extracted with ethyl acetate (50 mL×3), washed with water (50 mL×3) three times, dried over anhydrous sodium sulfate and concentrated. The residue was separated and purified by silica gel column chromatography (methanol:dichloromethane (v/v)=1:100 to 1:10) to obtain the title compound (5C) as a pale yellow solid (1.8 g, yield: 45%). LC-MS m/z=349.01 [M+1]$^+$ Step 3: tert-butyl (S)-(2-(5-bromothiophen-2-yl)-1-cyanoethyl)carbamate (5D)

5C (1.8 g, 5.2 mmol) was dissolved in dichloromethane (50 mL) and Burgess reagent (1.6 g, 6.2 mmol) was added under ice bath. The mixture was reacted at room temperature for 2 hours. Water (50 mL) was added, and the resulting mixture was extracted with ethyl acetate (50 mL×3), dried over anhydrous sodium sulfate and concentrated. The residue was separated and purified by silica gel column chromatography (PE:EA (v/v)=1:10-1:5) to obtain the title compound (5D) as a pale yellow solid (1.4 g, yield: 81%). LCMS m/z=331.23 [M+1]$^+$ Step 4: tert-butyl (S)-(1-cyano-2-(5-(3-methyl-2-oxo-2,3-dihydrobenzo[d]oxazol-5-yl)thiophen-2-yl)ethyl)carbamate (5E)

5D (700 mg, 2.1 mmol) was dissolved in dioxane (10 mL) and then 3-methyl-5-(4,4,5,5-tetramethyl-1,3,2-dioxaborolan-2-yl)benzo[d]oxazole-2(3H) (825 mg, 3.0 mmol), potassium carbonate (869 mg, 6.3 mmol), [1,1'-bis(diphenylphosphino)ferrocene]palladium dichloride (70 mg), and water (2 mL) were added. The mixture was reacted at 100° C. under microwave and nitrogen protection for 12 hours and then concentrated, and the residue was separated and purified by silica gel column chromatography (PE:EA (v/v)=1:5-1:1) to obtain the title compound (5E) as a yellow solid (290 mg, yield: 34%). LCMS m/z=400.13 [M+1]+

Step 5: (S)-2-amino-3-(5-(3-methyl-2-oxo-2,3-dihydrobenzo[d]oxazol-5-yl)thiophen-2-yl)propanenitrile (5F)

5E (290 mg, 0.73 mmol) was dissolved in formic acid (5 mL) and the mixture was reacted at room temperature for 3 hours, adjusted to pH=7-8 with saturated aqueous sodium carbonate solution, and then extracted with dichloromethane (50 mL×3). The organic phases were combined, washed with saturated aqueous sodium chloride solution (50 mL), dried over anhydrous sodium sulfate, and concentrated, and the residue was separated and purified by silica gel column chromatography (methanol:dichloromethane (v/v)=1:100-1:10) to obtain the title compound (5F) as a yellow solid (150 mg, yield: 69%). LCMS m/z=300.07 [M+1]+

Step 6: tert-butyl (S)-2-(((S)-1-cyano-2-(5-(3-methyl-2-oxo-2,3-dihydrobenzo[d]oxazol-5-yl)thiophen-2-yl)ethyl)carbamoyl)-1,4-oxazepane-4-carboxylate (5G)

5F (90 mg, 0.30 mmol) was dissolved in DMF (10 mL), and HATU (152 mg, 0.4 mmol), DIEA (116 mg, 0.9 mmol), and (S)-4-(tert-butoxycarbonyl)-1,4-oxaheptane-2-carboxylic acid (73 mg, 0.30 mmol) were successively added. The mixture was reacted at room temperature for 12 hours. Water (30 mL) was added, and the resulting mixture was extracted with ethyl acetate (30 mL×3). The organic phases were combined, washed with water (30 mL×2) and then saturated brine (30 mL×1), dried over anhydrous sodium sulfate, and concentrated, and the residue was separated and purified by silica gel column chromatography (methanol:dichloromethane (v/v)=1:100-1:10) to obtain the title compound (5G) as a yellow solid (100 mg, yield: 64%). LCMS m/z=527.19 [M+1]+

Step 7: (S)—N—((S)-1-cyano-2-(5-(3-methyl-2-oxo-2,3-dihydrobenzo[d]oxazol-5-yl)thiophen-2-yl)ethyl)-1,4-oxazepane-2-carboxamide (Compound 5)

5G (100 mg, 0.19 mmol) was dissolved in formic acid (2 mL), and the mixture was reacted at room temperature for 3 hours, adjusted to pH=7-8 with saturated aqueous sodium carbonate solution, and then extracted with dichloromethane (30 mL×3). The organic phases were combined, washed with saturated aqueous sodium chloride solution (50 mL), dried over anhydrous sodium sulfate, and concentrated, and the residue was separated and purified by silica gel column chromatography (methanol:dichloromethane (v/v)=1:100-1:10) to obtain the title compound 5 (25 mg, yield: 31%). LCMS M/Z (ESI): m/z=427.14 [M+1]+

$^1$H NMR (400 MHz, DMSO-d$_6$) δ 8.72 (d, 1H), 7.52-7.44 (m, 1H), 7.40-7.29 (m, 3H), 7.01 (d, 1H), 5.04-4.88 (m, 1H), 4.11-3.98 (m, 1H), 3.98-3.84 (m, 1H), 3.81-3.68 (m, 1H), 3.47-3.38 (m, 2H), 3.38 (s, 3H), 3.36-3.32 (m, 1H), 3.24-3.12 (m, 1H), 2.94-2.62 (m, 3H), 1.90-1.69 (m, 2H).

Example 6: (S)—N—((S)-2-(4-(7-acetamido-2,3-dihydro-1H-inden-4-yl)-2-fluorophenyl)-1-cyanoethyl)-1,4-oxazepane-2-carboxamide (Compound 6)

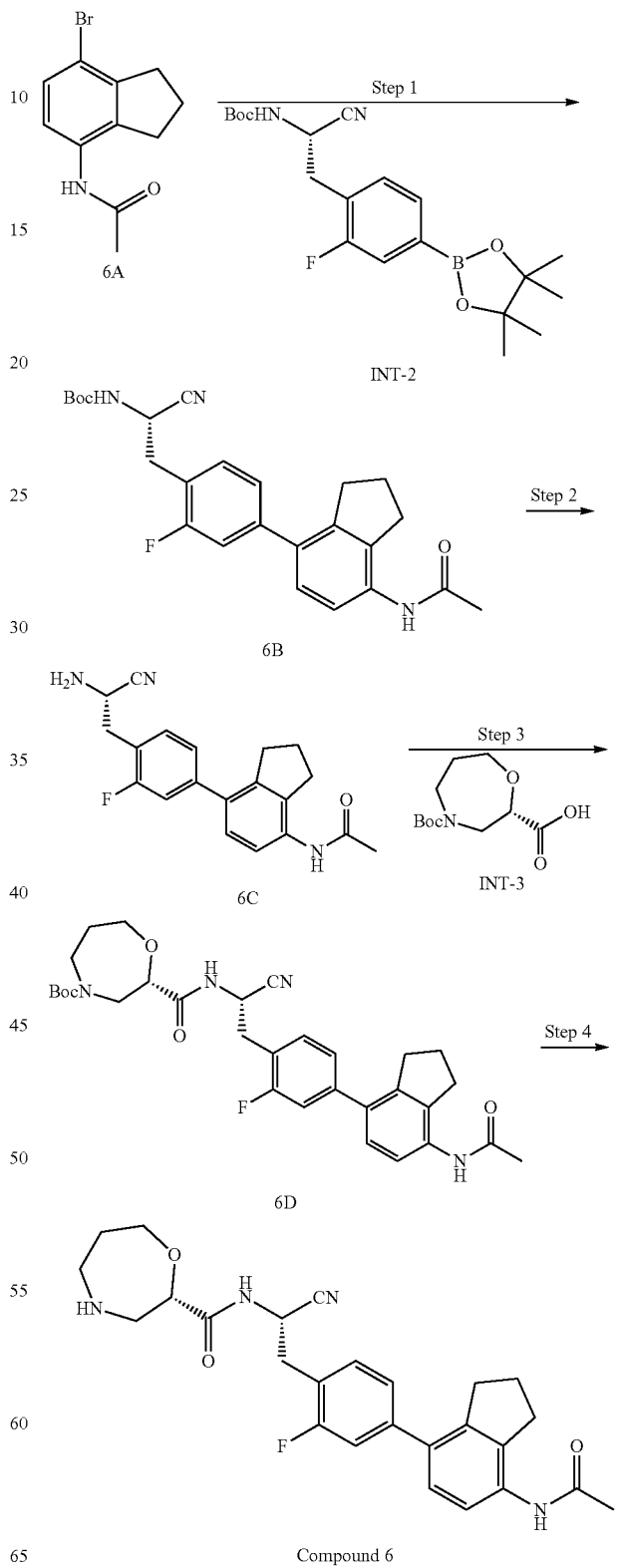

Step 1: tert-butyl (S)-(2-(4-(7-acetamido-2,3-di-hydro-1H-inden-4-yl)-2-fluorophenyl)-1-cyanoethyl)carbamate (6B)

6A (254.0 mg, 1.00 mmol, prepared with reference to *Journal of Medicinal Chemistry*, 2015, 58, 878-887), INT-2 (470.0 mg, 1.20 mmol), Pd(dppf)Cl$_2$ (160.0 mg, 0.20 mmol), and potassium carbonate (280.0 mg, 2.00 mmol) were added to a single-necked flask, and then 1,4-dioxane (10 mL) and water (0.4 mL) were added. The mixture was subjected to nitrogen replacement 3 times and then reacted at 95° C. for 4 hours. The reaction solution was cooled to room temperature and then concentrated, and the residue was separated and purified by silica gel column chromatography (PE:EA (v/v)=2:1) to obtain the title compound 6B as a white solid (360.0 mg, 82.3%). LC-MS (ESI): m/z=381.1 [M−57+H]$^+$.

Step 2: (S)—N-(7-(4-(2-amino-2-cyanoethyl)-3-fluorophenyl)-2,3-dihydro-1H-inden-4-yl)acetamide (6C)

6B (360.0 mg, 0.82 mmol) was dissolved in formic acid (5 mL) and the mixture was reacted at 35° C. for 4 h. The reaction system was adjusted to a basic pH with saturated potassium carbonate solution, extracted with ethyl acetate (30 mL×2), dried over anhydrous sodium sulfate, filtered and concentrated to obtain the title compound 6C as a pale yellow oil (270.0 mg, 97.6%), which was directly used in the next reaction. LC-MS (ESI): m/z=338.2 [M+H]$^+$.

Step 3: tert-butyl (S)-2-(((S)-2-(4-(7-acetamido-2,3-dihydro-1H-inden-4-yl)-2-fluorophenyl)-1-cyanoethyl)carbamoyl)-1,4-oxazepane-4-carboxylate (6D)

6C (270 mg, 0.80 mmol) was dissolved in DMF (5 mL) and then INT-3 (235.2 mg, 0.96 mmol), HATU (364.8 mg, 0.96 mmol), and DIPEA (309.6 mg, 2.40 mmol) were added. Upon completion of the addition, the mixture was reacted at room temperature overnight. Water (20 mL) was added to the system. The resulting mixture was extracted with ethyl acetate (30 mL×2), dried over anhydrous sodium sulfate, filtered, and concentrated, and the residue was separated and purified by silica gel column chromatography (PE:EA (v/v)=2:1) to obtain the title compound 6D as a white solid (370.0 mg, 82.0%). LC-MS (ESI): m/z=563.3 [M−H]$^−$

Step 4: (S)—N—((S)-2-(4-(7-acetamido-2,3-dihydro-1H-inden-4-yl)-2-fluorophenyl)-1-cyanoethyl)-1,4-oxazepane-2-carboxamide (Compound 6)

6D (370 mg, 0.66 mmol) was dissolved in formic acid (5 mL) and the mixture was reacted at 35° C. for 4 h. The reaction system was adjusted to a basic pH with saturated potassium carbonate solution, extracted with ethyl acetate (30 mL×2), dried over anhydrous sodium sulfate, filtered and concentrated, and the residue was separated and purified by silica gel column chromatography (dichloromethane:methanol (v/v)=30:1) to obtain the title compound 6 (90.0 mg, 30.0%).

$^1$H NMR (400 MHz, CDCl$_3$) δ 7.85 (d, 1H), 7.34 (t, 1H), 7.19-7.13 (m, 3H), 6.98 (s, 1H), 5.21-5.15 (m, 1H), 4.09 (q, 1H), 4.03-3.97 (m, 1H), 3.79-3.73 (m, 1H), 3.29 (dd, 1H), 3.24-3.17 (m, 2H), 2.99 (t, 2H), 2.96-2.85 (m, 5H), 2.22 (s, 3H), 2.15-2.07 (m, 2H), 1.87-1.80 (m, 2H), 1.61-1.50 (m, 2H). LC-MS (ESI): m/z=465.2 [M+H]$^+$.

Example 7: (S)—N—((S)-1-cyano-2-(4-(1,1-dioxido-2,3-dihydrobenzo[b]thiophen-5-yl)-2-fluorophenyl)ethyl)-1,4-oxazepane-2-carboxamide (Compound 7)

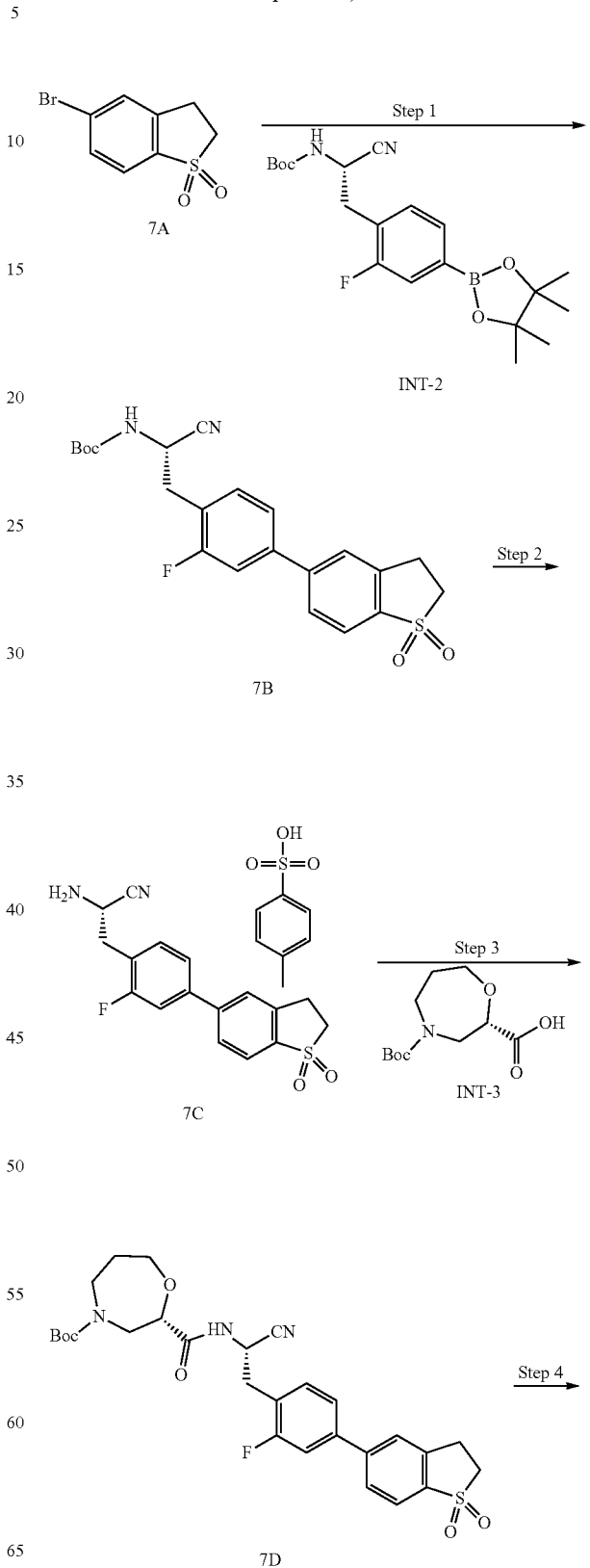

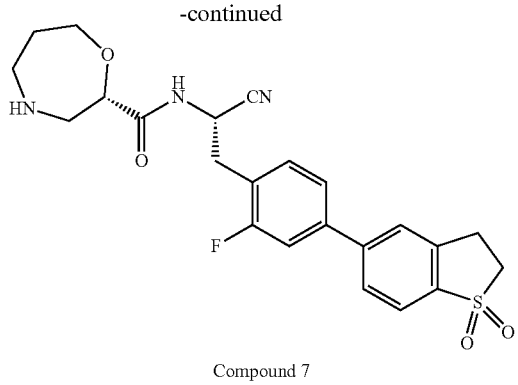

Compound 7

Step 1: tert-butyl (S)-(1-cyano-2-(4-(1,1-dioxido-2,3-dihydrobenzo[b]thiophen-5-yl)-2-fluorophenyl)ethyl)carbamate (7B)

7A (0.200 g, 0.81 mmol, prepared with reference to EP 3342765), INT-2 (0.316 g, 0.81 mmol), [1,1'-bis(diphenylphosphino)ferrocene]palladium dichloride dichloromethane complex (0.066 g, 0.081 mmol), and potassium carbonate (0.33 g, 2.43 mmol) were dissolved in 1,4-dioxane (10 mL), water (2 mL) was added, and then the mixture was subjected to nitrogen replacement 3 times and reacted at 90° C. under nitrogen atmosphere for 4 hours. The reaction solution was concentrated to dryness and dissolved with dichloromethane, and the mixture was filtered and concentrated. The residue was separated and purified by silica gel column chromatography (PE:EA (v/v)=5:1) to obtain the title compound 7B as a white solid (0.25 g, 71.8%). LC-MS (ESI): m/z=431.1 [M+H]$^+$.

Step 2: (S)-2-amino-3-(4-(1,1-dioxido-2,3-dihydrobenzo[b]thiophen-5-yl)-2-fluorophenyl)propanenitrile 4-methylbenzenesulfonate (7C)

7B (0.25 g, 0.58 mmol) was dissolved in acetonitrile (5 mL) and then p-toluenesulfonic acid (0.331 g, 1.74 mmol) was added. Upon completion of the addition, the mixture was reacted at room temperature for 16 h and then filtered. The filter cake was rinsed once with acetonitrile (2 mL) and subjected to rotary evaporation to obtain the title compound 7C as a white solid (0.240 g, 82.2%), which was directly used in the next reaction.

Step 3: tert-butyl (S)-2-(((S)-1-cyano-2-(4-(1,1-dioxido-2,3-dihydrobenzo[b]thiophen-5-yl)-2-fluoro phenyl)ethyl)carbamoyl)-1,4-oxazepane-4-carboxylate (7D)

INT-3 (0.161 g, 0.66 mmol) was dissolved in dichloromethane (10 mL), and then triethylamine (0.17 g, 1.32 mmol) and N,N,N',N'-tetramethyl-O-(7-azabenzotriazol-1-yl)uronium hexafluorophosphate (0.25 g, 0.66 mmol) were added. Upon completion of the addition, the mixture was reacted at room temperature for 1 hour under stirring, and then 7C (0.24 g, 0.477 mmol) was added. The resulting mixture was reacted at room temperature overnight. After the reaction was completed, the reaction solution was concentrated to obtain the crude product 7D, which was directly used in the next reaction. LC-MS (ESI): m/z=556.3 [M−H]$^-$.

Step 4: (S)—N—((S)-1-cyano-2-(4-(1,1-dioxido-2,3-dihydrobenzo[b]thiophen-5-yl)-2-fluorophenyl)ethyl)-1,4-oxazepane-2-carboxamide (Compound 7)

Crude product 7D was dissolved in acetonitrile (10 mL), and p-toluenesulfonic acid (0.331 g, 1.74 mmol) was added. Upon completion of the addition, the mixture was reacted at room temperature for 16 h and then concentrated to dryness. Ethyl acetate (25 mL) was added and saturated aqueous sodium bicarbonate solution was added dropwise to adjust the pH to about 8. The organic layer was separated and the remaining aqueous layer was extracted with ethyl acetate (25 mL×2). The combined organic phase was dried over anhydrous sodium sulfate, filtered and concentrated, and the residue was separated and purified by silica gel column chromatography (dichloromethane:methanol (v/v)=20:1) to obtain the title compound 7 (110 mg, two-step yield: 50.5%).

$^1$H NMR (400 MHz, CDCl$_3$) δ 7.82 (d, 1H), 7.65 (d, 1H), 7.54 (s, 1H), 7.42 (d, 1H), 7.38 (s, 1H), 7.32 (d, 1H), 7.25-7.19 (m, 1H), 5.22-5.11 (m, 1H), 4.14-4.10 (m, 1H), 4.09-4.00 (m, 1H), 3.82-3.76 (m, 1H), 3.58-3.52 (m, 2H), 3.50-3.42 (m, 2H), 3.41-3.32 (m, 1H), 3.24 (t, 2H), 3.00-2.93 (m, 2H), 1.90 (d, 2H), 1.60-1.51 (m, 1H), 1.39 (dd, 1H). LC-MS (ESI): m/z=458.1 [M+H]$^+$.

Example 8: (S)—N—((S)-1-cyano-2-(3-fluoro-4'-(pentafluoro-16-sulfanyl)-[1,1'-biphenyl]-4-yl)ethyl)-1,4-oxazepane-2-carboxamide (Compound 8)

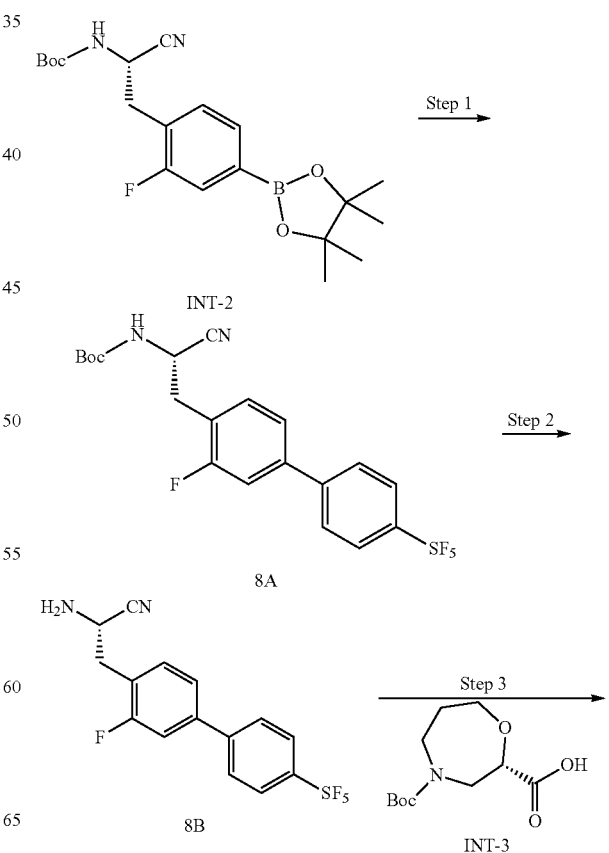

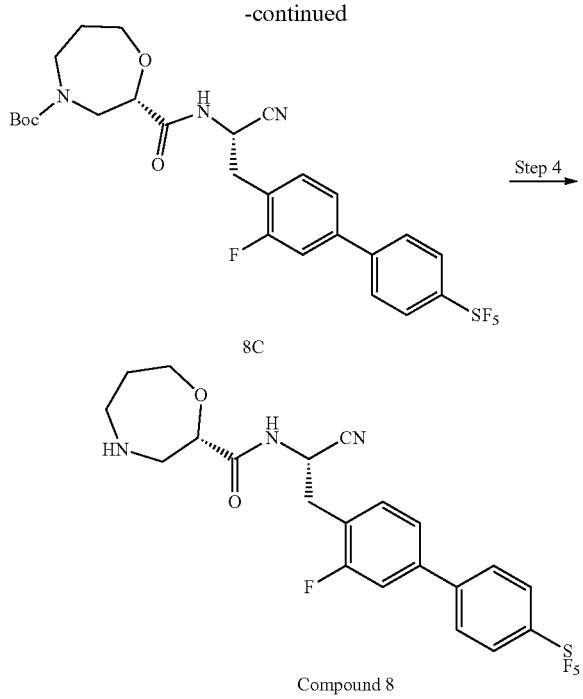

8C

Compound 8

Step 1: tert-butyl (S)-(1-cyano-2-(3-fluoro-4'-(pentafluoro-16-sulfanyl)-[1,1'-biphenyl]-4-yl)ethyl)carbamate (8A)

INT-2 (0.69 g, 1.77 mmol) was dissolved in dioxane (30 mL) and then (4-bromophenyl)sulfur pentafluoride (0.5 g, 1.77 mmol), potassium carbonate (0.24 mg, 1.77 mmol), [1,1'-bis(diphenylphosphino)ferrocene]palladium dichloride (260 mg, 0.35 mmol) and water (6 mL) were added. The mixture was reacted at 100° C. under nitrogen protection for 4 hours and concentrated, and the residue was separated and purified by silica gel column chromatography (PE:EA (v/v)=1:10-1:5) to obtain the title compound 8A (600 mg, yield: 80%). LCMS m/z=467.11 [M+1]$^+$ Step 2: (S)-2-amino-3-(3-fluoro-4'-(pentafluoro-16-sulfanyl)-[1,1'-biphenyl]-4-yl)propanenitrile (8B)

8A (0.6 g, 1.29 mmol) was dissolved in acetonitrile (20 mL) and p-toluenesulfonic acid (0.67 g, 3.87 mmol) was added. The mixture was reacted at 30° C. for 2 hours. Water (30 mL) was added and the resulting mixture was adjusted to pH=7-8 with saturated aqueous sodium carbonate solution, extracted with dichloromethane (50 mL×3), then washed with saturated brine (50 mL×1), dried over anhydrous sodium sulfate and concentrated to obtain the title compound 8B (0.4 g, yield: 84%). LCMS m/z=367.32 [M+1]$^+$ Step 3: tert-butyl (S)-2-(((S)-1-cyano-2-(3-fluoro-4'-(pentafluoro-16-sulfanyl)-[1,1'-biphenyl]-4-yl)ethyl)carbamoyl)-1,4-oxazepane-4-carboxylate (8C)

8B (200 mg, 0.55 mmol) was dissolved in DMF (10 mL) and then HATU (250 mg, 0.66 mmol), DIPEA (260 mg, 2.02 mmol), and INT-3 (130 mg, 0.55 mmol) were successively added. The mixture was reacted at room temperature for 12 hours. Water (30 mL) was added and the resulting mixture was extracted with ethyl acetate (30 mL×3). The organic phases were combined, washed with water (30 mL×2) and saturated brine (30 mL×1), dried over anhydrous sodium sulfate, and concentrated, and the residue was separated and purified by silica gel column chromatography (ethyl acetate: dichloromethane (v/v)=1:10-1:5) to obtain the title compound 8C (250 mg, yield: 76%). LCMS m/z=594.18 [M+1]$^+$ Step 4: (S)—N—((S)-1-cyano-2-(3-fluoro-4'-(pentafluoro-16-sulfanyl)-[1,1'-biphenyl]-4-yl)ethyl)-1,4-oxazepane-2-carboxamide (Compound 8)

8C (250 mg, 0.42 mmol) was dissolved in acetonitrile (20 mL), and p-toluenesulfonic acid (220 mg, 1.26 mmol) was added. The mixture was reacted at 30° C. for 3 hours, then adjusted to pH=7-8 with saturated aqueous sodium carbonate solution and extracted with dichloromethane (40 mL×3). The organic phases were combined, washed with saturated aqueous sodium chloride solution (50 mL), dried over anhydrous sodium sulfate and concentrated, and the residue was separated and purified by silica gel column chromatography (dichloromethane:methanol (v/v)=0.01:1-0.1:1) to obtain the title compound 8 (80 mg, 38%).

$^1$H NMR (400 MHz, DMSO-d$_6$) δ 8.70 (d, 1H), 8.12-7.87 (m, 4H), 7.67-7.57 (m, 2H), 7.54-7.47 (m, 1H), 5.15-4.85 (m, 1H), 4.03-3.97 (m, 1H), 3.90-3.80 (m, 1H), 3.76-3.69 (m, 1H), 3.35-3.28 (m, 2H), 3.26-3.19 (m, 1H), 3.12-3.01 (m, 1H), 2.88-2.72 (m, 1H), 2.67-2.52 (m, 2H), 1.81-1.62 (m, 2H). LCMS m/z (ESI): m/z=494.13 [M+1]$^+$

Example 9: (S)—N—((S)-1-cyano-2-(3-fluoro-3'-(pentafluoro-16-sulfanyl)-[1,1'-biphenyl]-4-yl)ethyl)-1,4-oxazepane-2-carboxamide (Compound 9)

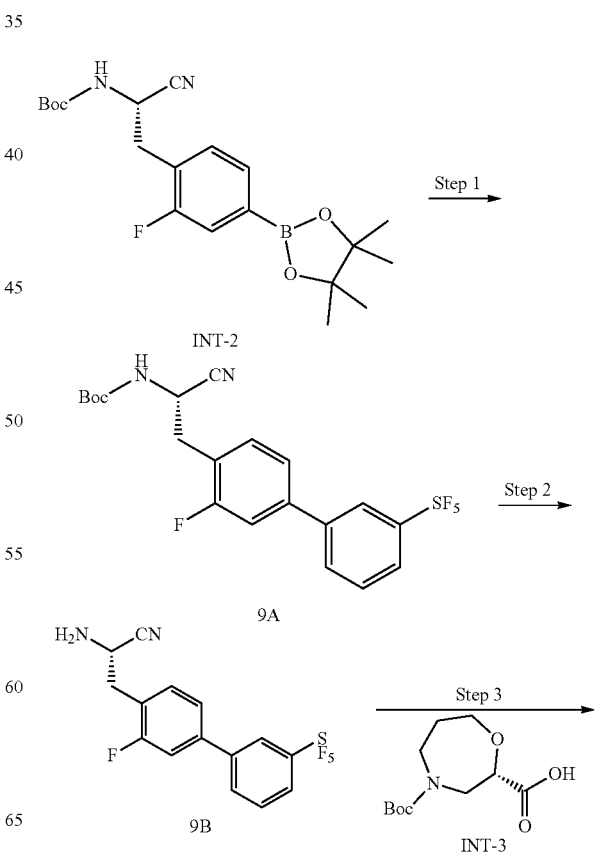

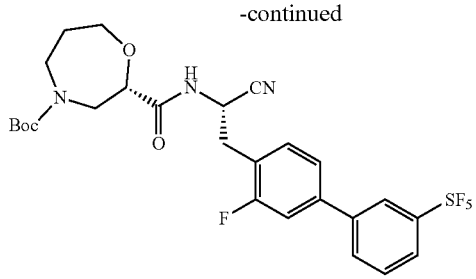

9C

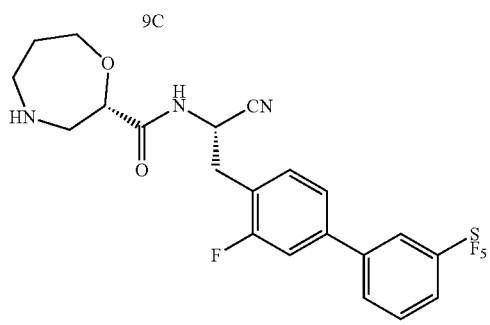

Compound 9

Step 1: tert-butyl (S)-(1-cyano-2-(3-fluoro-3'-(pentafluoro-16-sulfanyl)-[1,1'-biphenyl]-4-yl)ethyl)carbamate (9A)

INT-2 (0.69 g, 1.77 mmol) was dissolved in dioxane (30 mL), and then (3-bromophenyl)sulfur pentafluoride (0.5 g, 1.77 mmol), potassium carbonate (0.24 mg, 1.77 mmol), [1,1'-bis(diphenylphosphino)ferrocene]palladium dichloride (260 mg, 0.35 mmol), and water (6 mL) were added. The mixture was reacted at 100° C. under nitrogen protection for 4 hours and concentrated, and the residue was separated and purified by silica gel column chromatography (PE:EA (v/v)=1:10-1:5) to obtain the title compound 9A (600 mg, yield: 80%). LCMS m/z=467.11 [M+1]$^+$ Step 2: (S)-2-amino-3-(3-fluoro-4'-(pentafluoro-16-sulfanyl)-[1,1'-biphenyl]-4-yl)propanenitrile (9B)

9A (0.6 g, 1.29 mmol) was dissolved in acetonitrile (20 mL) and p-toluenesulfonic acid (0.67 g, 3.87 mmol) was added. The mixture was reacted at 30° C. for 2 hours. Water (30 mL) was added and the resulting mixture was adjusted to pH=7-8 with saturated aqueous sodium carbonate solution, extracted with dichloromethane (50 mL×3), then washed with saturated brine (50 mL×1), dried over anhydrous sodium sulfate and concentrated to obtain the title compound 9B (0.4 g, yield: 84%). LCMS m/z=367.32 [M+1]$^+$ Step 3: tert-butyl (S)-2-(((S)-1-cyano-2-(3-fluoro-3'-(pentafluoro-16-sulfanyl)-[1,1'-biphenyl]-4-yl)ethyl)carbamoyl)-1,4-oxazepane-4-carboxylate (9C)

9B (200 mg, 0.55 mmol) was dissolved in DMF (10 mL) and then HATU (250 mg, 0.66 mmol), DIEA (260 mg, 2.02 mmol), and INT-3 (130 mg, 0.55 mmol) were successively added. The mixture was reacted at room temperature for 12 hours. Water (30 mL) was added and the resulting mixture was extracted with ethyl acetate (30 mL×3). The organic phases were combined, washed with water (30 mL×2) and saturated brine (30 mL×1), dried over anhydrous sodium sulfate, and concentrated, and the residue was separated and purified by silica gel column chromatography (ethyl acetate:dichloromethane (v/v)=1:10-1:5) to obtain the title compound 9C (250 mg, yield: 76%). LCMS m/z=594.18 [M+1]$^+$ Step 4: (S)—N—((S)-1-cyano-2-(3-fluoro-3'-(pentafluoro-16-sulfanyl)-[1,1'-biphenyl]-4-yl)ethyl)-1,4-oxazepane-2-carboxamide (Compound 9)

9C (250 mg, 0.42 mmol) was dissolved in acetonitrile (20 mL), and p-toluenesulfonic acid (220 mg, 1.26 mmol) was added. The mixture was reacted at 30° C. for 3 hours, then adjusted to pH=7-8 with saturated aqueous sodium carbonate solution and extracted with dichloromethane (40 mL×3). The organic phases were combined, washed with saturated aqueous sodium chloride solution (50 mL), dried over anhydrous sodium sulfate and concentrated, and the residue was separated and purified by silica gel column chromatography (dichloromethane:methanol (v/v)=0.01:1-0.1:1) to obtain the title compound 9 (78 mg, 37%).

$^1$H NMR (400 MHz, DMSO-d$_6$) δ 8.69 (d, 1H), 8.12 (s, 1H), 8.01 (d, 1H), 7.93 (d, 1H), 7.76-7.44 (m, 4H), 5.21-4.95 (m, 1H), 4.05-3.97 (m, 1H), 3.91-3.80 (m, 1H), 3.77-3.63 (m, 1H), 3.32 (d, 2H), 3.26-3.18 (m, 1H), 3.10-3.00 (m, 1H), 2.83-2.73 (m, 1H), 2.66-2.54 (m, 2H), 1.81-1.61 (m, 2H). LCMS m/z (ESI): m/z=494.13 [M+1]$^+$

Example 10: (S)—N—((S)-1-cyano-2-(2-fluoro-4-(1-oxo-1,2,3,4-tetrahydroisoquinolin-6-yl)phenyl)ethyl)-1,4-oxazepane-2-carboxamide (Compound 10)

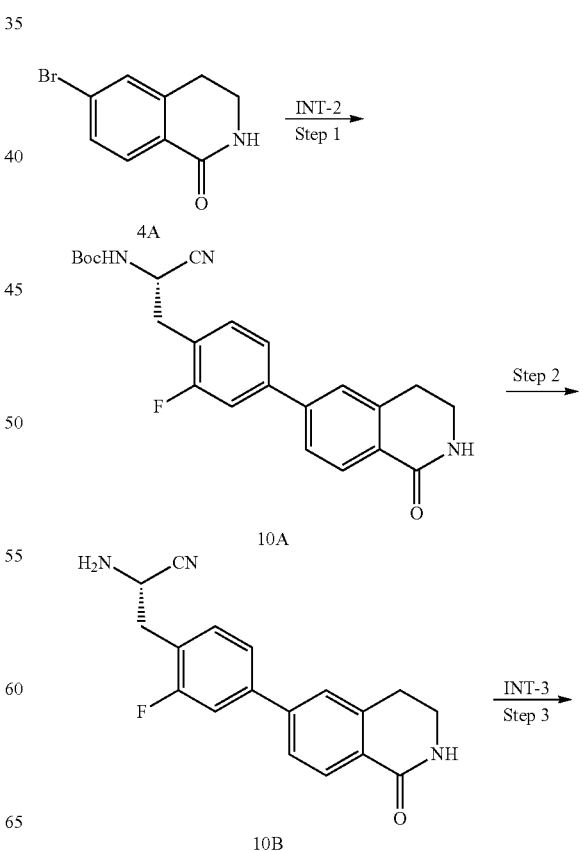

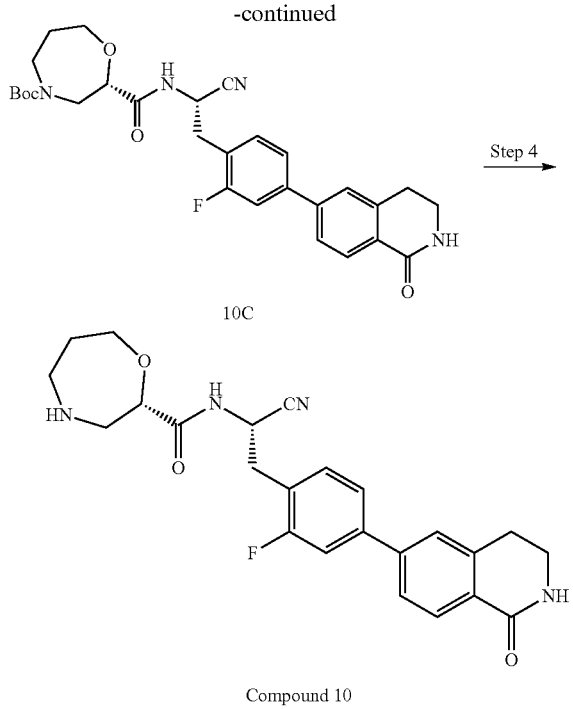

Compound 10

Step 1: tert-butyl (S)-(1-cyano-2-(2-fluoro-4-(1-oxo-1,2,3,4-tetrahydroisoquinolin-6-yl)phenyl)ethyl) carbamate (10A)

4A (0.27 g, 1.2 mmol), INT-2 (0.36 g, 0.92 mmol), [1,1'-bis(diphenylphosphino)ferrocene]palladium dichloride (71 mg, 0.1 mmol), and potassium carbonate (0.28 g, 2.0 mmol) were successively added to 1,4-dioxane (15 mL) and water (3 mL), and the system was subjected to nitrogen replacement three times and reacted at 100° C. for 2 hours. After the reaction was completed, the reaction solution was cooled to room temperature, water (50 mL) was added, and the resulting aqueous phase was extracted with ethyl acetate (50 mL×2). The combined organic phase was washed with saturated aqueous sodium chloride solution (100 mL), dried over anhydrous sodium sulfate, and filtered. The filtrate was concentrated under reduced pressure. The residue was separated by silica gel column chromatography (PE:EA=3:1-1:1) to obtain 10A as a brown solid (0.32 g, yield: 84%). LCMS m/z=410.2[M+1]⁺.

Step 2: (S)-2-amino-3-(2-fluoro-4-(1-oxo-1,2,3,4-tetrahydroisoquinolin-6-yl)phenyl)propanenitrile (10B)

10A (0.32 g, 0.78 mmol) was dissolved in formic acid (5.0 mL) and upon completion of the addition, the mixture was reacted at 50° C. for 10 minutes. The reaction solution was concentrated to dryness. Ethyl acetate (60 mL) was added and then saturated aqueous sodium bicarbonate solution was added dropwise to adjust the pH to about 8. The organic layer was separated and the aqueous phase was extracted with ethyl acetate (60 mL×2). The combined organic phase was dried over anhydrous sodium sulfate, filtered and concentrated to obtain the title compound 10B (0.24 g, yield: 100%). LCMS m/z=310.2[M+1]⁺.

Step 3: tert-butyl (S)-2-(((S)-1-cyano-2-(2-fluoro-4-(1-oxo-1,2,3,4-tetrahydroisoquinolin-6-yl)phenyl)ethyl)carbamoyl)-1,4-oxazepane-4-carboxylate (10C)

10B (0.24 g, 0.78 mmol) was dissolved in DMF (10 mL) and then INT-3 (0.25 g, 1.0 mmol), diisopropylethylamine (0.19 g, 1.5 mmol), and N,N,N',N'-tetramethyl-O-(7-azabenzotriazol-1-yl)uronium hexafluorophosphate (0.38 g, 1 mmol) were added. Upon completion of the addition, the mixture was reacted at room temperature for 1 hour. Saturated aqueous sodium chloride solution (30 mL) was added and the resulting mixture was extracted with ethyl acetate (60 mL×2). The organic phase was washed with saturated aqueous sodium chloride solution (60 mL), dried over anhydrous sodium sulfate, filtered and concentrated, and the residue was separated by silica gel column chromatography (PE:EA=2:1-1:2) to obtain the title compound 10C as a pale yellow solid (0.25 g, yield: 60%).

Step 4: (S)—N—((S)-1-cyano-2-(2-fluoro-4-(1-oxo-1,2,3,4-tetrahydroisoquinolin-6-yl)phenyl)ethyl)-1,4-oxazepane-2-carboxamide (Compound 10)

10C (0.25 g, 0.47 mmol) was dissolved in formic acid (5.0 mL) and the mixture was reacted at 50° C. for 10 minutes. The reaction solution was concentrated under reduced pressure and ethyl acetate (60 mL) was added. Then saturated aqueous sodium bicarbonate solution was added dropwise to adjust the pH to about 8. The organic layer was separated and the remaining aqueous layer was extracted with ethyl acetate (60 mL×5). The combined organic phase was dried over anhydrous sodium sulfate, filtered and concentrated, and the residue was separated and purified by silica gel column chromatography (dichloromethane:methanol (v/v)=4:1) to obtain compound 10 (0.12 g, yield: 59%).

¹H NMR (400 MHz, DMSO-d₆) δ 8.78 (d, 1H), 7.96-7.87 (m, 2H), 7.70-7.64 (m, 2H), 7.63-7.53 (m, 2H), 7.47 (t, 1H), 5.11-5.01 (m, 1H), 4.13-4.06 (m, 1H), 3.92-3.82 (m, 1H), 3.78-3.70 (m, 1H), 3.43-3.31 (m, 2H), 3.26-3.10 (m, 2H), 2.97 (t, 2H), 2.94-2.84 (m, 1H), 2.79-2.61 (m, 2H), 2.04-1.92 (m, 1H), 1.82-1.73 (m, 2H). LC-MS m/z=437.2 [M+1]⁺

Example 11: (S)—N—((S)-1-cyano-2-(4-(cyclopentylethynyl)-2-fluorophenyl)ethyl)-1,4-oxazepane-2-carboxamide (Compound 11)

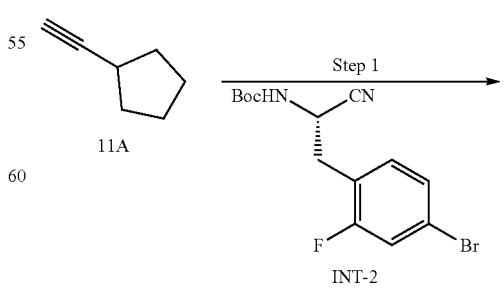

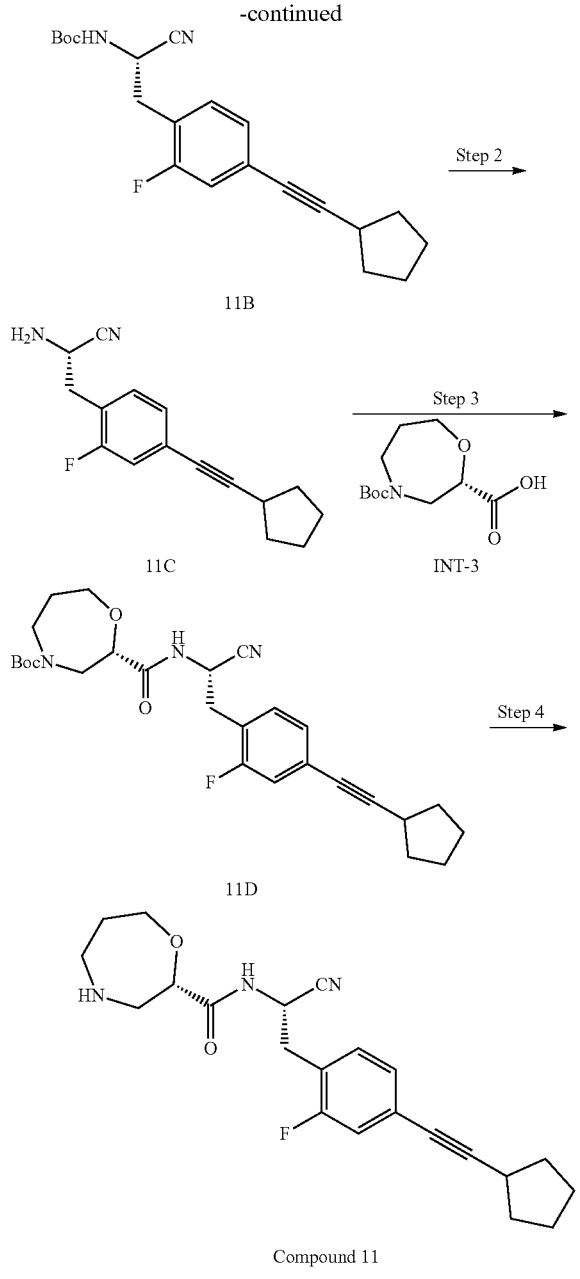

Step 2: (S)-2-amino-3-(4-(cyclopentylethynyl)-2-fluorophenyl)propanenitrile (11C)

11B (172 mg, 0.48 mmol) was dissolved in formic acid (5 mL) and the mixture was reacted at 35° C. for 4 h. The reaction system was adjusted to a basic pH with saturated potassium carbonate solution, extracted with ethyl acetate (30 mL×2), dried over anhydrous sodium sulfate, filtered and concentrated to obtain the title compound 11C as a pale yellow oil (130 mg, 100.0%), which was directly used in the next reaction. LC-MS (ESI): m/z=257.1 [M+H]$^+$.

Step 3: tert-butyl (S)-2-(((S)-1-cyano-2-(4-(cyclopentylethynyl)-2-fluorophenyl)ethyl)carbamoyl)-1,4-oxazepane-4-carboxylate (11D)

11C (130 mg, 0.51 mmol) was dissolved in DMF (5 mL) and then INT-3 (150 mg, 0.61 mmol), HATU (230 mg, 0.61 mmol), and DIPEA (200 mg, 1.53 mmol) were added. Upon completion of the addition, the mixture was reacted at room temperature overnight. Water (20 mL) was added to the system. The resulting mixture was extracted with ethyl acetate (30 mL×2), dried over anhydrous sodium sulfate, filtered, and concentrated, and the residue was separated and purified by silica gel column chromatography (PE:EA (v/v)=2:1) to obtain the title compound 11D as a white solid (190.0 mg, 77.0%). LC-MS (ESI): m/z=428.3 [M−57+H]$^+$.

Step 4: (S)—N—((S)-1-cyano-2-(4-(cyclopentylethynyl)-2-fluorophenyl)ethyl)-1,4-oxazepane-2-carboxamide (Compound 11)

11D (190 mg, 0.39 mmol) was dissolved in formic acid (5 mL) and the mixture was reacted at 35° C. for 4 h. The reaction system was adjusted to a basic pH with saturated potassium carbonate solution, extracted with ethyl acetate (30 mL×2), dried over anhydrous sodium sulfate, filtered and concentrated, and the residue was separated and purified by silica gel column chromatography (dichloromethane:methanol (v/v)=30:1) to obtain compound 11 (50.0 mg, 33.0%).

$^1$H NMR (400 MHz, CDCl$_3$) δ 7.20-7.17 (m, 2H), 7.07 (dd, 1H), 7.02 (dd, 1H), 5.08-5.02 (m, 1H), 4.09 (q, 1H), 3.94-3.89 (m, 1H), 3.71-3.64 (m, 1H), 3.22 (dd, 1H), 3.13-3.03 (m, 2H), 2.87-2.80 (m, 3H), 2.78-2.70 (m, 1H), 2.02-1.88 (m, 3H), 1.82-1.67 (m, 4H), 1.66-1.50 (m, 4H). LC-MS (ESI): m/z=384.2 [M+H]$^+$.

Example 12: (S)—N—((S)-1-cyano-2-(4-(5-cyano-4-methylthiazol-2-yl)-2-fluorophenyl)ethyl)-1,4-oxazepane-2-carboxamide (Compound 12)

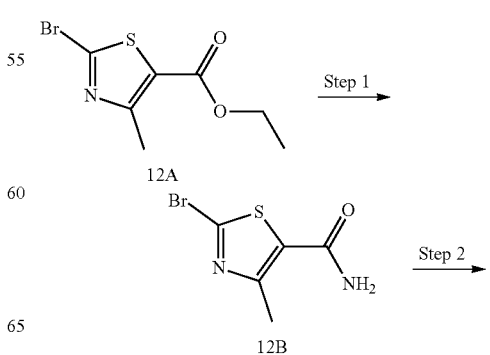

Step 1: tert-butyl (S)-(1-cyano-2-(4-(cyclopentylethynyl)-2-fluorophenyl)ethyl)carbamate (11B)

11A (66 mg, 0.70 mmol), INT-2 (200 mg, 0.58 mmol), Pd(dppf)Cl$_2$ (115.0 mg, 0.14 mmol), and potassium carbonate (193.2 mg, 1.4 mmol) were added to a single-necked flask, and then 1,4-dioxane (10 mL) and water (0.4 mL) were added. The mixture was subjected to nitrogen replacement 3 times and then reacted at 95° C. for 4 hours. The reaction solution was cooled to room temperature and then concentrated, and the residue was separated and purified by silica gel column chromatography (PE:EA (v/v)=3:1) to obtain the title compound 11B as a white solid (172.0 mg, 83.5%). LC-MS (ESI): m/z=300.1 [M−57+H]$^+$.

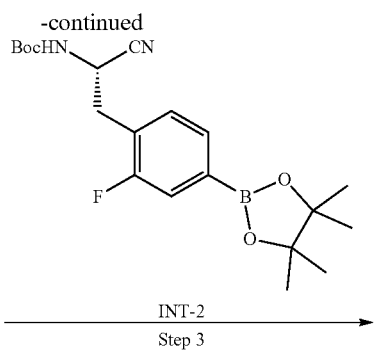
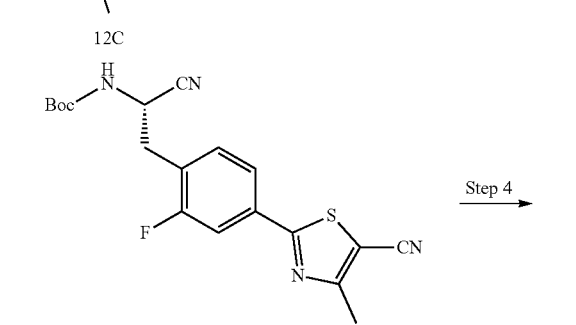
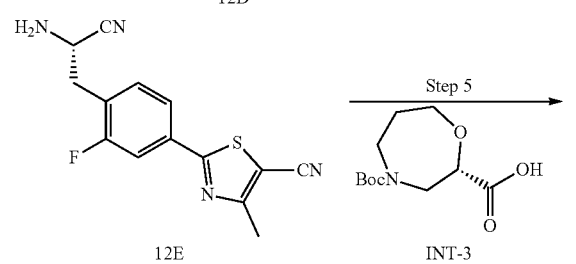
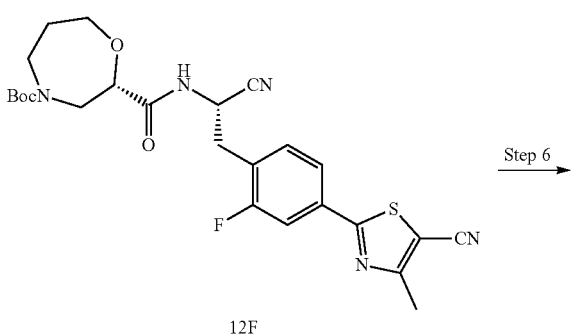
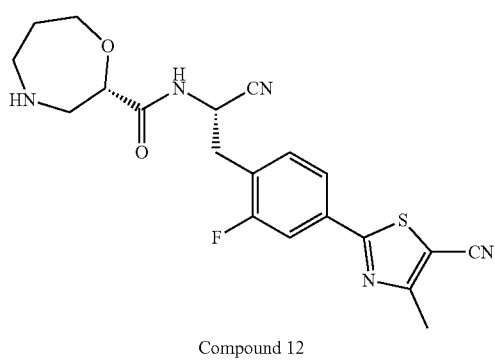

Step 1: 2-bromo-4-methylthiazole-5-carboxamide (12B)

12A (1.20 g, 4.8 mmol) was dissolved in 30% ammonia water (30 mL) and the mixture was reacted at 35° C. for 24 h. The reaction solution was cooled to room temperature and extracted with ethyl acetate (30 mL×3). The combined organic phase was dried over anhydrous sodium sulfate, filtered, and concentrated to obtain the title compound 12B as a yellow solid (0.80 g, 75.4%). LC-MS (ESI): m/z=221.0 [M+H]$^+$.

Step 2: 2-bromo-4-methylthiazole-5-carbonitrile (12C)

12B (0.55 g, 2.49 mmol) was dissolved in dichloromethane (25 mL) and then Burgess reagent (1.19 g, 4.98 mmol) was added. Upon completion of the addition, the mixture was reacted at room temperature overnight. After concentration, the residue was separated and purified by silica gel column chromatography (PE:EA (v/v)=5:1) to obtain the title compound 12C as a white solid (0.40 g, 80.1%). LC-MS (ESI): m/z=203.0 [M+H]$^+$.

Step 3: (S)-(1-cyano-2-(4-(5-cyano-4-methylthiazol-2-yl)-2-fluorophenyl)ethyl) tert-butyl carbamate (12D)

12C (199 mg, 0.98 mmol), INT-2 (458.9 mg, 1.18 mmol), Pd(dppf)Cl$_2$ (160.5 mg, 0.20 mmol), and potassium carbonate (270.9 mg, 1.96 mmol) were added to a single-necked flask, and then 1,4-dioxane (10 mL) and water (0.4 mL) were added. The mixture was subjected to nitrogen replacement 3 times and then reacted at 95° C. for 4 hours. The reaction solution was cooled to room temperature and then concentrated, and the residue was separated and purified by silica gel column chromatography (PE:EA (v/v)=3:1) to obtain the title compound 12D as a yellow solid (172.0 mg, 45.5%). LC-MS (ESI): m/z=331.0 [M−57+H]$^+$.

Step 4: (S)-2-(4-(2-amino-2-cyanoethyl)-3-fluorophenyl)-4-methylthiazole-5-carbonitrile (12E)

12D (172 mg, 0.45 mmol) was dissolved in formic acid (5 mL) and the mixture was reacted at 35° C. for 4 h. The reaction system was adjusted to a basic pH with saturated potassium carbonate solution, extracted with ethyl acetate (30 mL×2), dried over anhydrous sodium sulfate, filtered and concentrated to obtain the title compound 12E as a pale yellow oil (120 mg, 96.0%), which was directly used in the next reaction. LC-MS (ESI): m/z=287.1 [M+H]$^+$.

Step 5: tert-butyl (S)-2-(((S)-1-cyano-2-(4-(5-cyano-4-methylthiazol-2-yl)-2-fluorophenyl)ethyl)carbamoyl)-1,4-oxazepane-4-carboxylate (12F)

12E (120 mg, 0.42 mmol) was dissolved in DMF (5 mL) and then INT-3 (120 mg, 0.50 mmol), HATU (190 mg, 0.50 mmol), and DIPEA (160 mg, 1.26 mmol) were added. Upon completion of the addition, the mixture was reacted at room temperature overnight. Water (20 mL) was added to the system. The resulting mixture was extracted with ethyl acetate (30 mL×2), dried over anhydrous sodium sulfate, filtered, and concentrated, and the residue was separated and purified by silica gel column chromatography (PE:EA (v/v)=2:1) to obtain the title compound 12F as a yellow solid (160.0 mg, 74.2%). LC-MS (ESI): m/z=458.1 [M−57+H]⁺.

Step 6: (S)—N—((S)-1-cyano-2-(4-(5-cyano-4-methylthiazol-2-yl)-2-fluorophenyl)ethyl)-1,4-oxazepane-2-carboxamide (Compound 12)

12F (160 mg, 0.31 mmol) was dissolved in formic acid (5 mL) and the mixture was reacted at 35° C. for 4 h. The reaction system was adjusted to a basic pH with saturated potassium carbonate solution, extracted with ethyl acetate (30 mL×2), dried over anhydrous sodium sulfate, filtered and concentrated, and the residue was separated and purified by silica gel column chromatography (dichloromethane:methanol (v/v)=30:1) to obtain the title compound 12 (50.0 mg, 39.0%).

¹H NMR (400 MHz, CDCl₃) δ 7.72 (dd, 1H), 7.69 (dd, 1H), 7.44 (t, 1H), 5.22-5.16 (m, 1H), 4.09 (q, 1H), 4.05-3.99 (m, 1H), 3.80-3.73 (m, 1H), 3.30 (dd, 1H), 3.26-3.23 (m, 2H), 2.97-2.90 (m, 3H), 2.67 (s, 3H), 1.19-1.82 (m, 4H). LC-MS (ESI): m/z=414.2 [M+H]⁺.

Example 13: (S)—N—((S)-2-(4-(benzo[d]thiazol-2-yl)-2-fluorophenyl)-1-cyanoethyl)-1,4-oxazepane-2-carboxamide (Compound 13)

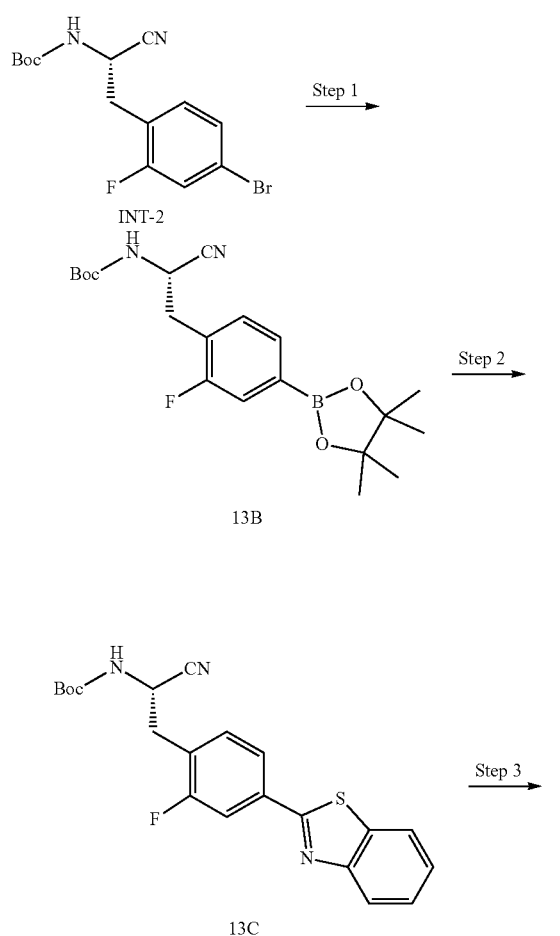

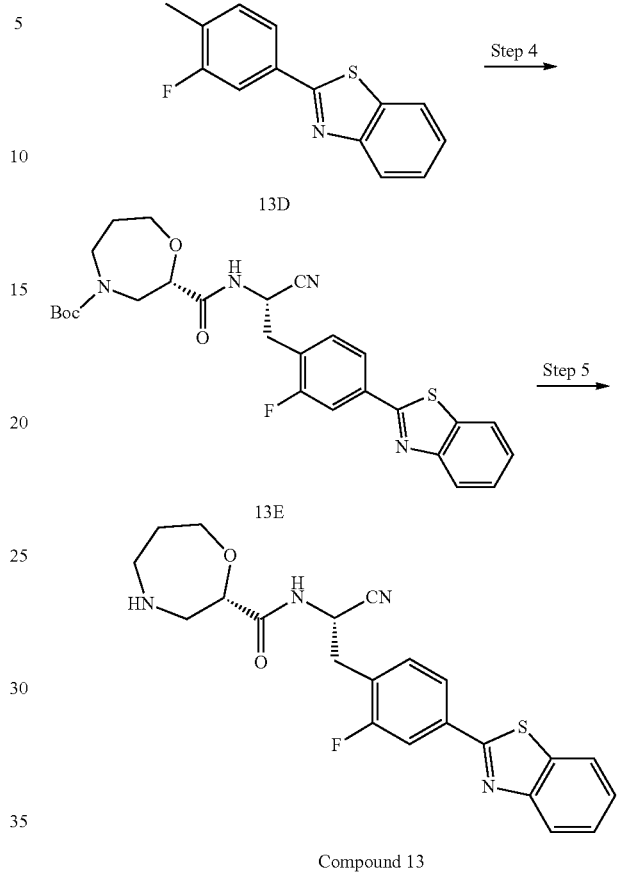

Compound 13

Step 1: tert-butyl (S)-(1-cyano-2-(2-fluoro-4-(4,4,5,5-tetramethyl-1,3,2-dioxaborolan-2-yl)phenyl)ethyl)carbamate (13B)

INT-2 (5.00 g, 14.57 mmol) was dissolved in 1,4-dioxane (100 mL) and then bis(pinacolato)diboron (4.81 g, 18.94 mmol), potassium acetate (4.29 g, 43.71 mmol), and [1,1'-bis(diphenylphosphino)ferrocene]palladium dichloride dichloromethane complex (2.39 g, 2.91 mmol) were added. Upon completion of the addition, the mixture was heated to 100° C. and reacted for 2 h under nitrogen protection. The reaction solution was cooled to room temperature, filtered and concentrated, and the residue was separated and purified by silica gel column chromatography (PE:EA (v/v)=6:1) to obtain the title compound 13B as a colorless liquid (5.00 g, 87.93%). LC-MS (ESI): m/z=391.2 [M+H]⁺.

Step 2: tert-butyl (S)-(2-(4-(benzo[d]thiazol-2-yl)-2-fluorophenyl)-1-cyanoethyl)carbamate (13C)

13B (0.40 g, 1.02 mmol) was dissolved in 1,4-dioxane (10 mL) and water (0.4 mL), and then 2-bromobenzothiazole (0.26 g, 1.22 mmol), [1,1'-bis(diphenylphosphino)ferrocene]palladium dichloride dichloromethane complex (0.17 g, 0.20 mmol), and potassium carbonate (0.28 g, 2.04 mmol) were added. Upon completion of the addition, the mixture was heated to 90° C. and reacted for 2 h under nitrogen protection. Then the reaction solution was reacted at room temperature overnight. The resulting reaction mixture was concentrated to dryness and saturated aqueous ammonium chloride solution (50 mL) was added. The resulting mixture was extracted with ethyl acetate (20 mL×3). The combined organic phase was dried over anhydrous sodium sulfate, filtered and concentrated, and the residue was separated and purified by silica gel column chromatography (PE:EA (v/v)=4:1) to obtain the title compound 13C as a pale yellow liquid (0.24 g, 59.20%). LC-MS (ESI): m/z=398.1 [M+H]+.

Step 3: (S)-2-amino-3-(4-(benzo[d]thiazol-2-yl)-2-fluorophenyl)propanenitrile (13D)

13C (0.32 g, 0.81 mmol) was dissolved in formic acid (5 mL) and upon completion of the addition, the mixture was reacted at 30° C. for 3 h. Saturated aqueous sodium bicarbonate solution was added dropwise to adjust the pH to about 8, and the resulting mixture was extracted with ethyl acetate (25 mL×3). The combined organic phase was dried over anhydrous sodium sulfate, filtered and concentrated to obtain the title compound 13D as a colorless liquid (0.24 g, 99.65%), which was directly used in the next reaction. LC-MS (ESI): m/z=298.1 [M+H]+.

Step 4: tert-butyl (S)-2-(((S)-2-(4-(benzo[d]thiazol-2-yl)-2-fluorophenyl)-1-cyanoethyl)carbamoyl)-1,4-oxazepane-4-carboxylate (13E)

13D (0.24 g, 0.81 mmol) was dissolved in dichloromethane (10 mL) and then INT-1 (0.26 g, 1.05 mmol), diisopropylethylamine (0.31 g, 2.43 mmol), and N,N,N',N'-tetramethyl-O-(7-azabenzotriazol-1-yl)uronium hexafluorophosphate (0.46 g, 1.22 mmol) were added. Upon completion of the addition, the mixture was reacted at room temperature overnight. Saturated aqueous sodium chloride solution (30 mL) was added and then the resulting mixture was extracted with ethyl acetate (25 mL). The organic phase was washed with saturated aqueous sodium chloride solution (25 mL×3), dried over anhydrous sodium sulfate, filtered and concentrated, and the residue was separated and purified by silica gel column chromatography (PE:EA (v/v)=4:1) to obtain the title compound 13E as a pale yellow solid (0.25 g, 58.83%). LC-MS (ESI): m/z=469.2 [M−57+H]+.

Step 5: (S)—N—((S)-2-(4-(benzo[d]thiazol-2-yl)-2-fluorophenyl)-1-cyanoethyl)-1,4-oxazepane-2-carboxamide (Compound 13)

13E (0.32 g, 0.59 mmol) was dissolved in formic acid (2.0 mL) and upon completion of the addition, the mixture was reacted at 35° C. for 4 h. The reaction solution was concentrated to dryness and ethyl acetate (25 mL) was added. Then saturated aqueous sodium bicarbonate solution was added dropwise to adjust the pH to about 8. The organic layer was separated and the remaining aqueous layer was extracted with ethyl acetate (25 mL×3). The combined organic phase was dried over anhydrous sodium sulfate, filtered and concentrated, and the residue was separated and purified by silica gel column chromatography (dichloromethane:methanol (v/v)=20:1) to obtain the title compound 13 (30 mg, 14.72%).

1H NMR (400 MHz, CDCl3) δ 8.08 (d, 1H), 7.94-7.78 (m, 3H), 7.47 (m, 3H), 5.21 (dd, 1H), 4.15-3.92 (m, 2H), 3.76 (m, 1H), 3.38-3.19 (m, 3H), 2.95 (dt, 3H), 1.87 (d, 2H). LC-MS (ESI): m/z=425.1 [M+H]+.

Example 14: (S)—N—((S)-1-cyano-2-(3-fluoro-4'-((4-methylpiperazin-1-yl)methyl)-[1,1'-biphenyl]-4-yl)ethyl)-1,4-oxazepane-2-carboxamide (Compound 14)

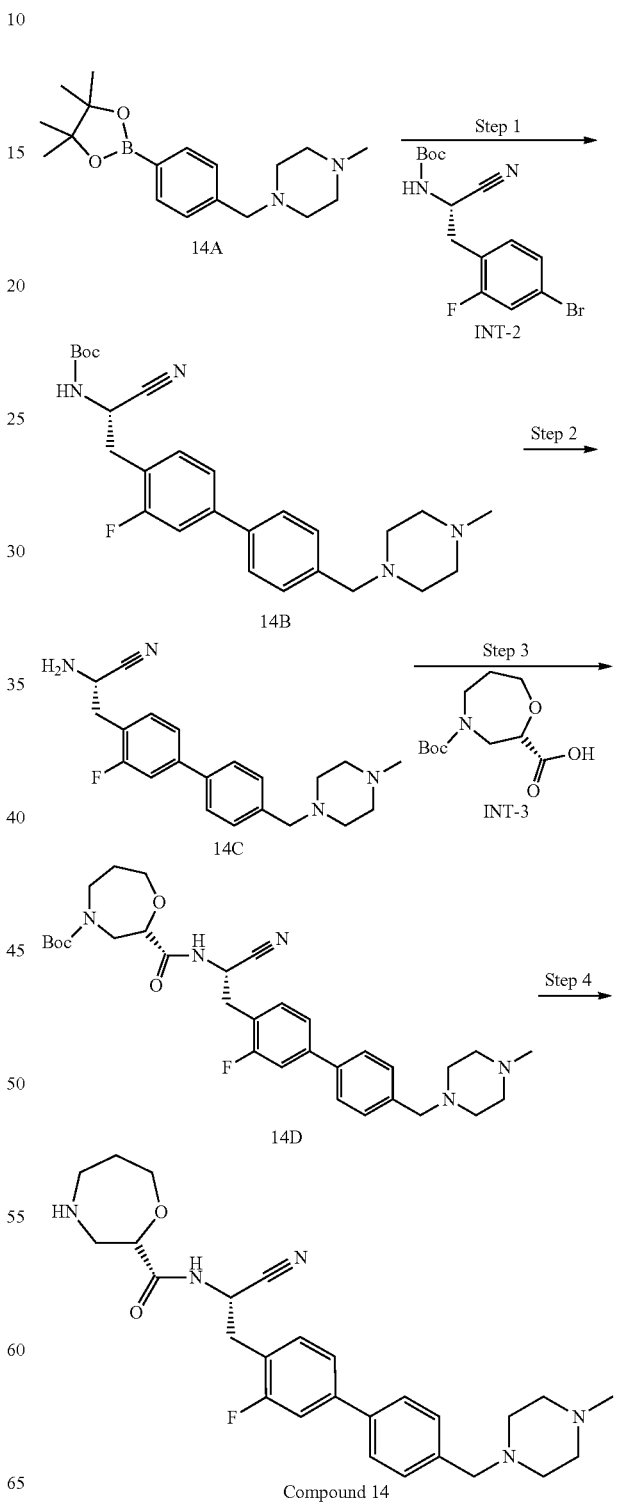

Compound 14

Step 1: tert-butyl-(S)-(1-cyano-2-(3-fluoro-4'-((4-methylpiperazin-1-yl)methyl)-[1,1'-biphenyl]-4-yl)ethyl)carbamate (14B)

14A (2.54 g, 8.04 mmol), INT-2 (2.3 g, 6.70 mmol), potassium carbonate (1.85 g, 13.4 mmol), and [1,1'-bis(diphenylphosphino)ferrocene]palladium dichloride (0.98 g, 1.34 mmol) were dissolved in 1,4-dioxane (100 ml) and water (10 ml). The system was subjected to nitrogen replacement three times, warmed to 95° C., refluxed for 3 h, and filtered, the filter cake was washed with ethyl acetate (100 ml), and the filtrate was dried over anhydrous sodium sulfate and concentrated. The obtained residue was separated and purified by silica gel column chromatography (methanol:dichloromethane (v/v)=0%-15%) to obtain the title compound 14B as a dark brown solid (3.00 g, 99.0%). LC-MS (ESI): m/z=453.3 [M+H]$^+$.

Step 2: (S)-2-amino-3-(3-fluoro-4'-((4-methylpiperazin-1-yl)methyl)-[1,1'-biphenyl]-4-yl)propanenitrile (14C)

14B (3.26 g, 7.2 mmol) was dissolved in formic acid (40 ml) and the mixture was stirred at room temperature overnight. Water (40 ml) and dichloromethane (80 ml) were added. The resulting mixture was adjusted to a basic pH with sodium bicarbonate, the organic phase was separated, and the aqueous phase was further extracted with dichloromethane (80 ml×2). The organic phases were combined, dried over anhydrous sodium sulfate and concentrated, and the obtained residue was separated and purified by silica gel column chromatography (methanol:dichloromethane (v/v)=0%-10%) to obtain the title compound 14C as a dark brown oil (2.32 g, 91.3%). LC-MS (ESI): m/z=353.3 [M+H]$^+$.

Step 3: tert-butyl-(S)-2-(((S)-1-cyano-2-(3-fluoro-4'-((4-methylpiperazin-1-yl)methyl)-[1,1'-biphenyl]-4-yl)ethyl)carbamoyl)-1,4-oxazepane-4-carboxylate (14D)

14C (500 mg, 1.42 mmol), INT-3 (348 mg, 1.42 mmol), N,N,N',N'-tetramethyl-O-(7-azabenzotriazol-1-yl)uronium hexafluorophosphate (648 mg, 1.70 mmol), and DIPEA (366 mg, 2.84 mmol) were dissolved in dichloromethane (15 ml) and the mixture was stirred at room temperature for 4 h. The reaction solution was washed with saturated sodium bicarbonate solution (10 ml×3), the organic phase was separated, dried over anhydrous sodium sulfate, and concentrated, and the obtained residue was separated and purified by silica gel column chromatography (methanol:dichloromethane (v/v)=0%-10%) to obtain the title compound 14D as a yellow solid (400 mg, 48.6%). LC-MS (ESI): m/z=580.3 [M+H]$^+$.

Step 4: (S)—N—((S)-1-cyano-2-(3-fluoro-4'-((4-methylpiperazin-1-yl)methyl)-[1,1'-biphenyl]-4-yl)ethyl)-1,4-oxazepane-2-carboxamide (Compound 14)

14D (400 mg, 0.69 mmol) and 2,6-dimethylpyridine (74 mg, 0.69 mmol) were dissolved in dichloromethane (20 ml) and the mixture was stirred under an ice-water bath. Tert-butyldimethylsilyl trifluoromethanesulfonate (550 mg, 2.07 mmol) was added dropwise to the reaction flask. Upon completion of the dropwise addition, the ice-water bath was removed, and the mixture was stirred and reacted at room temperature for 2 h. The reaction solution was washed with saturated sodium bicarbonate solution (20 ml×2), the organic phase was separated, dried over anhydrous sodium sulfate, and concentrated, and the obtained residue was separated and purified by silica gel column chromatography (methanol:dichloromethane (v/v)=0%-15%) to obtain the title compound 14 (57 mg, 17.2%). LC-MS (ESI): m/z=480.3 [M+H]$^+$.

$^1$H NMR (400 MHz, DMSO-d$_6$) δ 8.69 (d, 1H), 7.64 (d, 2H), 7.54-7.46 (m, 2H), 7.43 (t, 1H), 7.37 (d, 2H), 5.04 (dd, 1H), 4.01 (dd, 1H), 3.90-3.82 (m, 1H), 3.73 (ddd, 1H), 3.48 (s, 2H), 3.19 (dd, 1H), 3.06 (dd, 1H), 2.83-2.74 (m, 1H), 2.68-2.61 (m, 1H), 2.58 (dd, 1H), 2.35 (d, 8H), 2.15 (s, 3H), 1.74 (ddd, 2H).

Example 15: (S)—N—((S)-1-cyano-2-(2-fluoro-4-(4-methylthiazol-2-yl)phenyl)ethyl)-1,4-oxazepane-2-carboxamide (Compound 15)

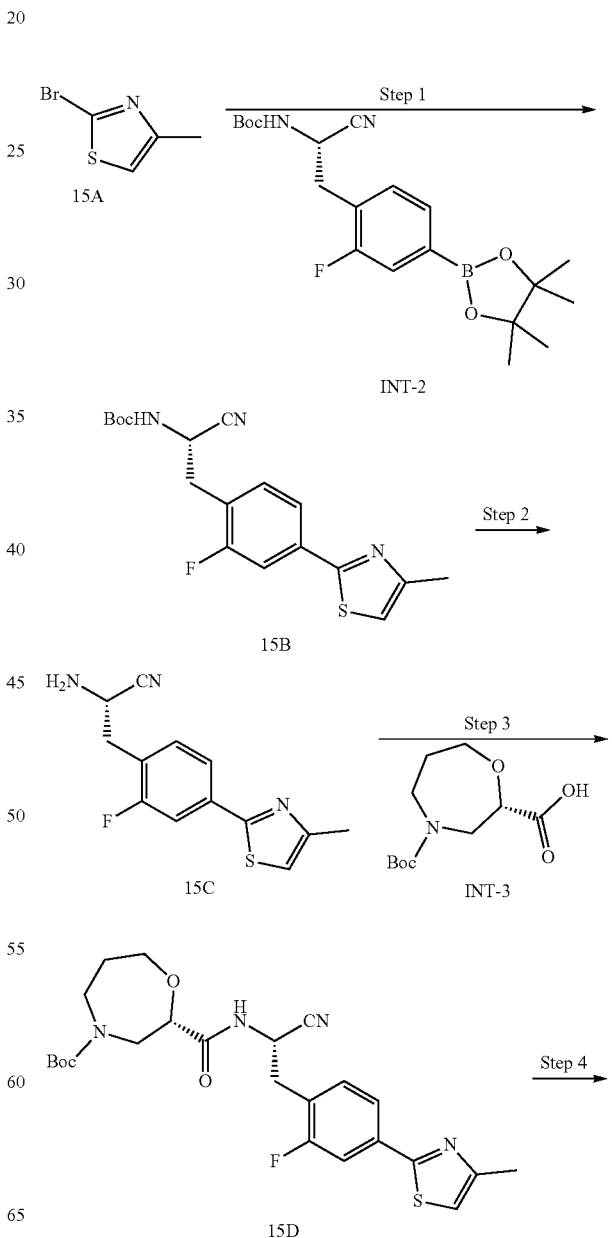

-continued

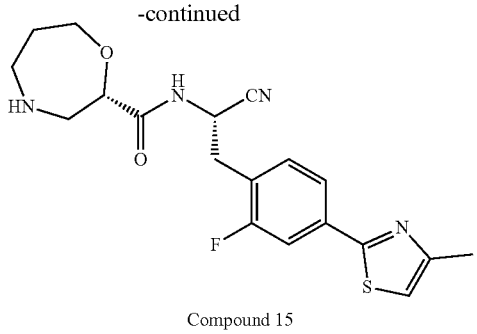

Compound 15

Step 1: tert-butyl (S)-(1-cyano-2-(2-fluoro-4-(4-methylthiazol-2-yl)phenyl)ethyl)carbamate (15B)

15A (0.23 g, 1.28 mmol), INT-2 (0.50 g, 1.28 mmol), [1,1'-(diphenylphosphino)ferrocene]palladium dichloride (94 mg, 0.13 mmol), and potassium carbonate (0.53 g, 3.84 mmol) were dissolved in a mixed solvent of dioxane (27 mL) and water (3 mL), and the mixture was reacted at 90° C. under nitrogen protection for 5 h. The reaction solution was cooled to room temperature and 50 mL of water was added. The resulting mixture was extracted with ethyl acetate (20 mL×3). The organic layers were combined, successively washed with saturated sodium bicarbonate (20 mL) and saturated brine (20 mL), dried over anhydrous sodium sulfate, and concentrated, and the residue was separated and purified by silica gel column chromatography (PE:EA (v/v)=2:1) to obtain the title compound 15B (0.25 g, 53%). LC-MS (ESI): m/z=362.1 [M+H]$^+$.

Step 2: (S)-2-amino-3-(2-fluoro-4-(4-methylthiazol-2-yl)phenyl)propanenitrile (15C)

15B (0.25 mg, 0.68 mmol) was dissolved in anhydrous formic acid (4 mL) and the mixture was reacted at 50° C. for 20 min. The reaction solution was cooled to room temperature and concentrated to remove most of the solvent. Saturated sodium bicarbonate solution (20 mL) was added to the residue and the resulting mixture was extracted with ethyl acetate (10 mL×3). The organic layers were combined, dried over anhydrous sodium sulfate, and concentrated, and the residue was separated and purified by silica gel column chromatography (dichloromethane:methanol (v/v)=97:3) to obtain the title compound 15C (0.17 g, 96%). LC-MS (ESI): m/z=262.2 [M+H]$^+$.

Step 3: tert-butyl (S)-2-(((S)-1-cyano-2-(2-fluoro-4-(4-methylthiazol-2-yl)phenyl)ethyl) carbamoyl)-1,4-oxazepane-4-carboxylate (15D)

INT-3 (0.18 g, 0.73 mmol) was dissolved in DMF (5 mL) and then HATU (0.42 g, 1.09 mmol) and DIPEA (0.28 g, 2.19 mmol) were added under nitrogen protection. After the mixture was stirred at room temperature for 20 min, 15C (0.19 g, 0.73 mmol) was added. The resulting mixture was reacted at room temperature for 1 h. To the reaction solution, 30 mL of water was added. The resulting mixture was extracted with ethyl acetate (15 mL×5). The organic layers were combined, dried over anhydrous sodium sulfate and concentrated. The residue was separated and purified by silica gel column chromatography (dichloromethane/methanol (v/v)=97:3) to obtain the title compound 15D (0.26 g, 73%). LC-MS (ESI): m/z=489.1 [M+H]$^+$.

Step 4: (S)—N—((S)-1-cyano-2-(2-fluoro-4-(4-methylthiazol-2-yl)phenyl)ethyl)-1,4-oxazepane-2-carboxamide (Compound 15)

15D (0.26 g, 0.53 mmol) was dissolved in formic acid (4.0 mL) and upon completion of the addition, the mixture was reacted at 50° C. for 30 min. The reaction solution was concentrated to dryness and ethyl acetate (25 mL) was added. Then saturated aqueous sodium bicarbonate solution was added dropwise to adjust the pH to about 8. The organic layer was separated and the remaining aqueous layer was extracted with ethyl acetate (25 mL×2). The combined organic phase was dried over anhydrous sodium sulfate, filtered and concentrated, and the residue was separated and purified by silica gel column chromatography (PE:EA (v/v)=1:2) to obtain the title compound 15 (80 mg, 39%).

$^1$H NMR (400 MHz, DMSO-d$_6$) δ 8.97 (d, J=8.4 Hz, 1H), 7.74-7.66 (m, 2H), 7.48 (t, J=7.8 Hz, 1H), 7.39 (s, 1H), 5.05 (m, 1H), 4.31 (d, J=9.4 Hz, 1H), 3.90 (m, 1H), 3.76 (m, 1H), 3.36-3.32 (m, 1H), 3.21 (m, 1H), 3.15-3.07 (m, 1H), 2.97 (m, 1H), 2.82 (dd, J=14.0, 9.4 Hz, 1H), 2.43 (s, 3H), 1.92 (p, J=5.6 Hz, 2H), 1.29-1.21 (m, 1H). LC-MS (ESI): m/z=389.1 [M+H]$^+$.

Example 16: (S)—N—((S)-2-(4-(1-acetylindolin-5-yl)-2-fluorophenyl)-1-cyanoethyl)-1,4-oxazepane-2-carboxamide (Compound 16)

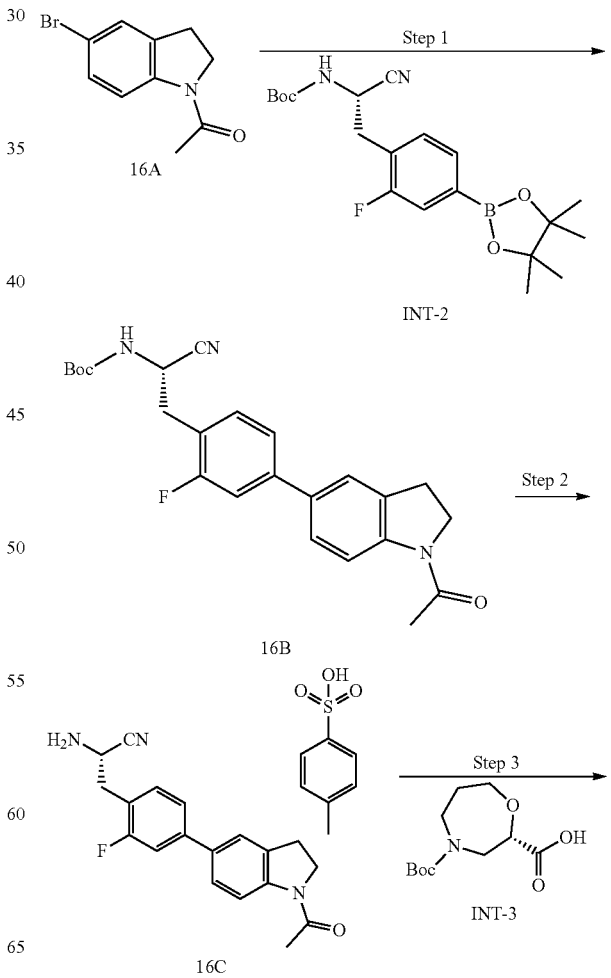

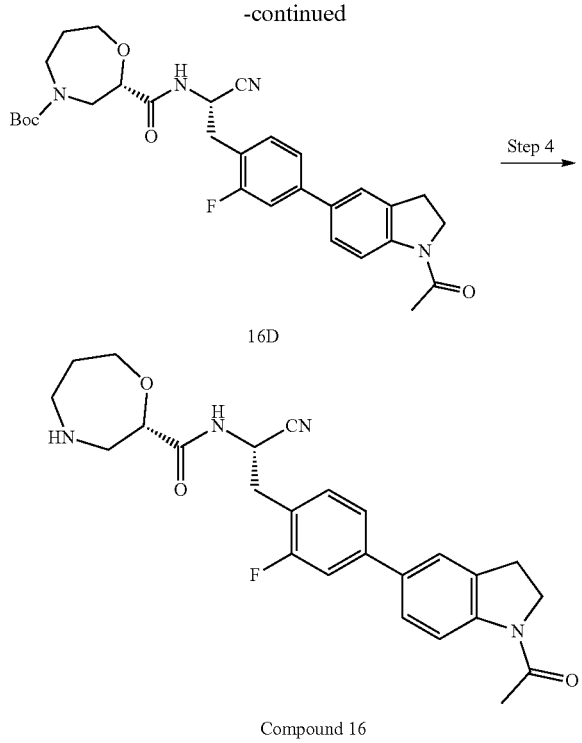

16D

Compound 16

Step 1: tert-butyl (S)-(2-(4-(1-acetylindolin-5-yl)-2-fluorophenyl)-1-cyanoethyl)carbamate (16B)

16A (0.200 g, 0.83 mmol), INT-2 (0.323 g, 0.83 mmol), [1,1'-bis(diphenylphosphino)ferrocene]palladium dichloride dichloromethane complex (0.067 g, 0.083 mmol), and potassium carbonate (0.343 g, 2.49 mmol) were dissolved in 1,4-dioxane (10 mL), water (2 mL) was added, and then the mixture was subjected to nitrogen replacement 3 times and reacted at 90° C. under nitrogen atmosphere for 4 hours. The reaction solution was concentrated to dryness and dissolved with dichloromethane, and the mixture was filtered and concentrated. The residue was separated and purified by silica gel column chromatography (PE:EA (v/v)=5:1) to obtain the title compound 16B as a white solid (0.100 g, 28.4%). LC-MS (ESI): m/z=424.1 [M+H]$^+$.

Step 2: (S)-3-(4-(1-acetylindolin-5-yl)-2-fluorophenyl)-2-aminopropanenitrile 4-methylbenzenesulfonate (16C)

16B (0.100 g, 0.24 mmol) was dissolved in acetonitrile (2 mL) and then p-toluenesulfonic acid monohydrate (0.134 g, 0.71 mmol) was added. Upon completion of the addition, the mixture was reacted at room temperature for 16 h and then filtered. The filter cake was rinsed once with acetonitrile (1 mL) and subjected to rotary evaporation to obtain the title compound 16C as a white solid (0.100 g, 85.5%), which was directly used in the next reaction.

Step 3: tert-butyl (S)-2-(((S)-2-(4-(1-acetylindolin-5-yl)-2-fluorophenyl)-1-cyanoethyl)carbamoyl)-1,4-oxazepane-4-carboxylate (16D)

INT-3 (0.074 g, 0.303 mmol) was dissolved in dichloromethane (5 mL), and then triethylamine (0.061 g, 0.606 mmol) and N,N,N',N'-tetramethyl-O-(7-azabenzotriazol-1-yl)uronium hexafluorophosphate (0.115 g, 0.303 mmol) were added. Upon completion of the addition, the mixture was reacted at room temperature for 1 hour under stirring, and then 16C (0.100 g, 0.202 mmol) was added. The resulting mixture was reacted at room temperature overnight. After the reaction was completed, the reaction solution was concentrated to obtain the crude product 16D, which was directly used in the next reaction. LC-MS (ESI): m/z=549.2 [M−H]$^−$.

Step 4: (S)—N—((S)-2-(4-(1-acetylindolin-5-yl)-2-fluorophenyl)-1-cyanoethyl)-1,4-oxazepane-2-carboxamide (Compound 16)

Crude product 16D was dissolved in acetonitrile (10 mL), and p-toluenesulfonic acid monohydrate (0.134 g, 0.71 mmol) was added. Upon completion of the addition, the mixture was reacted at room temperature for 16 h and then concentrated to dryness. Ethyl acetate (25 mL) was added and saturated aqueous sodium bicarbonate solution was added dropwise to adjust the pH to about 8. The organic layer was separated and the remaining aqueous layer was extracted with ethyl acetate (25 mL×2). The combined organic phase was dried over anhydrous sodium sulfate, filtered and concentrated, and the residue was separated and purified by silica gel column chromatography (dichloromethane:methanol (v/v)=20:1) to obtain the title compound 16 (27 mg, two-step yield: 29.7%).

$^1$H NMR (400 MHz, CD$_3$OD) δ 8.15 (d, 1H), 7.51 (s, 1H), 7.47-7.28 (m, 4H), 5.14 (dd, 1H), 4.23-4.09 (m, 3H), 4.05-3.96 (m, 1H), 3.82-3.74 (m, 1H), 3.34 (s, 1H), 3.30-3.17 (m, 5H), 3.05-2.95 (m, 1H), 2.93-2.82 (m, 1H), 2.72 (dd, 1H), 2.25 (s, 3H), 1.97-1.83 (m, 2H). LC-MS (ESI): m/z=451.2 [M+H]$^+$.

Example 17: (S)—N—((S)-1-cyano-2-(4'-cyano-3'-cyclopropyl-3-fluoro-[1,1'-biphenyl]-4-yl)ethyl)-1,4-oxazepane-2-carboxamide (Compound 17)

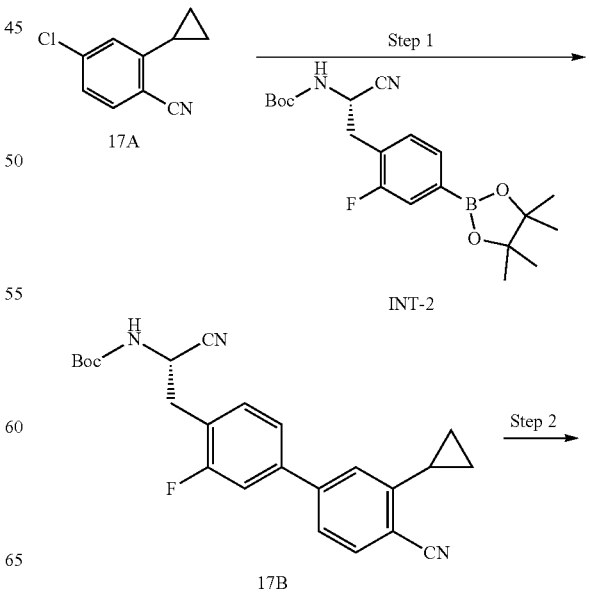

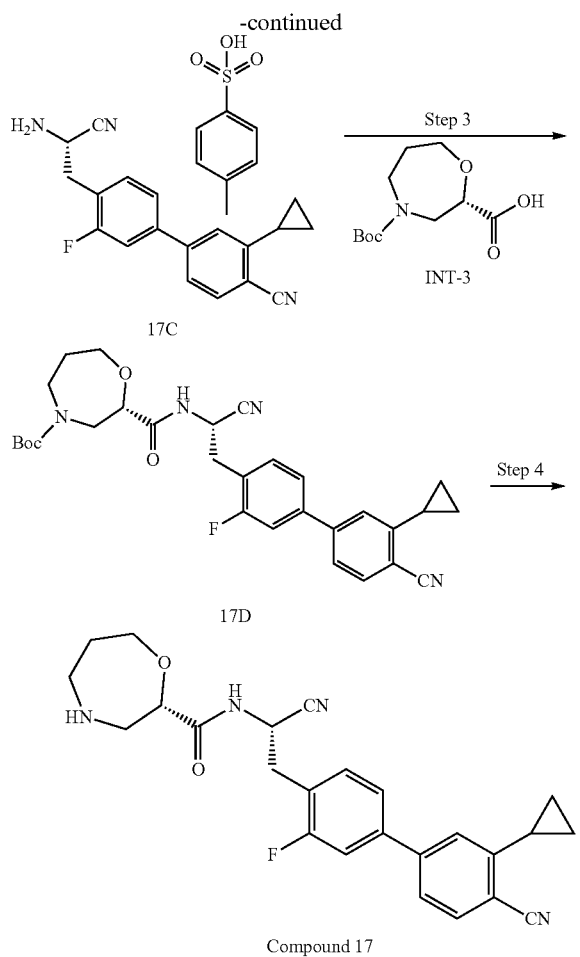

Step 1: tert-butyl (S)-(1-cyano-2-(4'-cyano-3'-cyclo-propyl-3-fluoro-[1,1'-biphenyl]-4-yl)ethyl)carbamate (17B)

17A (0.300 g, 1.67 mmol), INT-2 (0.646 g, 1.67 mmol), [1,1'-bis(diphenylphosphino)ferrocene]palladium dichloride dichloromethane complex (0.134 g, 0.167 mmol), and potassium carbonate (0.686 g, 4.98 mmol) were dissolved in 1,4-dioxane (15 mL), water (3 mL) was added, and then the mixture was subjected to nitrogen replacement 3 times and reacted at 100° C. under nitrogen atmosphere for 16 hours. The reaction solution was concentrated to dryness and dissolved with dichloromethane, and the mixture was filtered and concentrated. The residue was separated and purified by silica gel column chromatography (PE:EA (v/v)=5:1) to obtain the title compound 17B as a white solid (0.380 g, 55.4%). LC-MS (ESI): m/z=406.1 [M+H]$^+$.

Step 2: (S)-4'-(2-amino-2-cyanoethyl)-3-cyclopropyl-3'-fluoro-[1,1'-biphenyl]-4-carbonitrile 4-methyl benzenesulfonate (17C)

17B (0.380 g, 0.94 mmol) was dissolved in acetonitrile (5 mL) and then p-toluenesulfonic acid monohydrate (534 g, 2.81 mmol) was added. Upon completion of the addition, the mixture was reacted at room temperature for 16 h and then filtered. The filter cake was rinsed once with acetonitrile (2 mL) and subjected to rotary evaporation to obtain the title compound 17C as a white solid (0.360 g, 80.5%), which was directly used in the next reaction.

Step 3: tert-butyl (S)-2-(((S)-1-cyano-2-(4'-cyano-3'-cyclopropyl-3-fluoro-[1,1'-biphenyl]-4-yl)ethyl) carbamoyl)-1,4-oxazepane-4-carboxylate (17D)

INT-3 (0.123 g, 0.503 mmol) was dissolved in dichloromethane (5 mL), and then triethylamine (0.101 g, 1.00 mmol) and N,N,N',N'-tetramethyl-O-(7-azabenzotriazol-1-yl)uronium hexafluorophosphate (0.193 g, 0.503 mmol) were added. Upon completion of the addition, the mixture was stirred at room temperature for 1 hour, and then 17C (0.160 g, 0.335 mmol) was added. The resulting mixture was reacted at room temperature overnight. After the reaction was completed, the reaction solution was concentrated to obtain the crude product 17D, which was directly used in the next reaction. LC-MS (ESI): m/z=531.2 [M–H]$^-$.

Step 4: (S)—N—((S)-1-cyano-2-(4'-cyano-3'-cyclopropyl-3-fluoro-[1,1'-biphenyl]-4-yl)ethyl)-1,4-oxazepane-2-carboxamide (Compound 17)

Crude product 17D was dissolved in acetonitrile (10 mL), and p-toluenesulfonic acid monohydrate (0.190 g, 1.00 mmol) was added. Upon completion of the addition, the mixture was reacted at room temperature for 16 h and then concentrated to dryness. Ethyl acetate (25 mL) was added and saturated aqueous sodium bicarbonate solution was added dropwise to adjust the pH to about 8. The organic layer was separated and the remaining aqueous layer was extracted with ethyl acetate (25 mL×2). The combined organic phase was dried over anhydrous sodium sulfate, filtered and concentrated, and the residue was separated and purified by silica gel column chromatography (dichloromethane:methanol (v/v)=20:1) to obtain the title compound 17 (60 mg, two-step yield: 41.4%).

$^1$H NMR (400 MHz, CDCl$_3$) δ 7.66 (d, 1H), 7.44-7.37 (m, 2H), 7.33 (dd, 1H), 7.28 (d, 2H), 7.10 (s, 1H), 5.15 (dt, 1H), 4.22 (dt, 1H), 4.12-3.99 (m, 1H), 3.85-3.73 (m, 1H), 3.57-3.41 (m, 1H), 3.30-3.17 (m, 2H), 3.13-2.97 (m, 3H), 2.34 (ddd, 1H), 2.07-1.94 (m, 2H), 1.24-1.15 (m, 2H), 0.92-0.83 (m, 2H). LC-MS (ESI): m/z=433.2 [M+H]$^+$.

Example 18: (S)—N—((S)-1-cyano-2-(3-fluoro-4'-(methylcarbamoyl)-[1,1'-biphenyl]-4-yl)ethyl)-1,4-oxazepane-2-carboxamide (Compound 18)

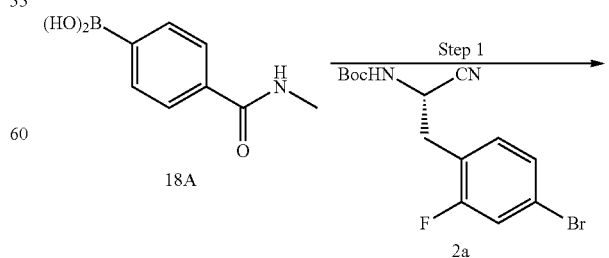

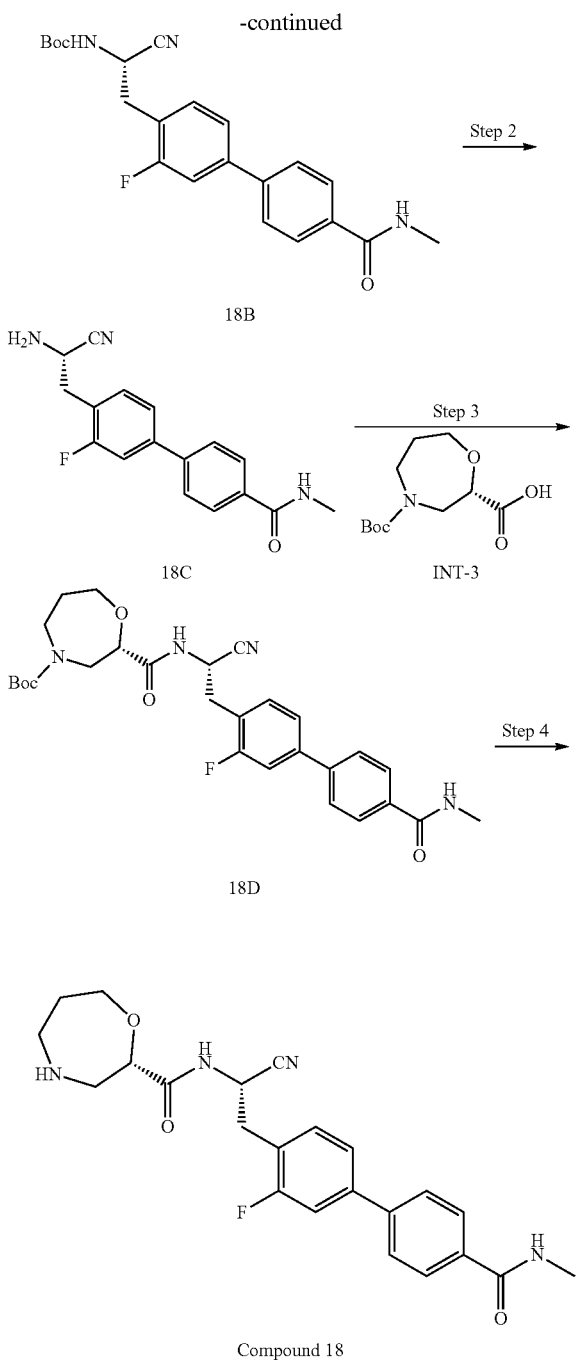

Step 1: tert-butyl (S)-(1-cyano-2-(3-fluoro-4'-(methylcarbamoyl)-[1,1'-biphenyl]-4-yl)ethyl) carbamate (18B)

18A (0.50 g, 1.46 mmol), 2a (0.26 g, 1.46 mmol), [1,1'-(diphenylphosphino)ferrocene]palladium dichloride (0.11 mg, 0.15 mmol), and potassium carbonate (0.61 g, 4.38 mmol) were dissolved in a mixed solvent of dioxane (27 mL) and water (3 mL), and the mixture was reacted at 90° C. under nitrogen protection for 5 h. The reaction solution was cooled to room temperature and 50 mL of water was added. The resulting mixture was extracted with ethyl acetate (20 mL×3). The organic layers were combined, successively washed with saturated sodium bicarbonate (20 mL) and saturated brine (20 mL), dried over anhydrous sodium sulfate, and concentrated, and the residue was separated and purified by silica gel column chromatography (PE:EA (v/v)=2:1) to obtain the title compound 18B (0.34 g, 59%). LC-MS (ESI): m/z=398.2 [M+H]$^+$.

Step 2: (S)-4'-(2-amino-2-cyanoethyl)-3'-fluoro-N-methyl-[1,1'-biphenyl]-4-carboxamide (18C)

18B (0.34 mg, 0.86 mmol) was dissolved in anhydrous formic acid (4 mL) and the mixture was reacted at 50° C. for 20 min. The reaction solution was cooled to room temperature and concentrated to remove most of the solvent. Saturated sodium bicarbonate solution (20 mL) was added to the residue and the resulting mixture was extracted with ethyl acetate (10 mL×3). The organic layers were combined, dried over anhydrous sodium sulfate, and concentrated, and the residue was separated and purified by silica gel column chromatography (dichloromethane:methanol (v/v)=97:3) to obtain the title compound 18C (0.22 g, 87%). LC-MS (ESI): m/z=298.1 [M+H]$^+$.

Step 3: tert-butyl (S)-2-(((S)-1-cyano-2-(3-fluoro-4'-(methylcarbamoyl)-[1,1'-biphenyl]-4-yl)ethyl)carbamoyl)-1,4-oxazepane-4-carboxylate (18D)

INT-3 (0.23 g, 0.76 mmol) was dissolved in DMF (5 mL) and then HATU (0.43 g, 1.14 mmol) and DIPEA (0.29 g, 2.28 mmol) were added under nitrogen protection. After the mixture was stirred at room temperature for 20 min, 18C (0.23 g, 0.76 mmol) was added. The resulting mixture was reacted at room temperature for 1 h. To the reaction solution, 30 mL of water was added. The resulting mixture was extracted with ethyl acetate (15 mL×5). The organic layers were combined, dried over anhydrous sodium sulfate and concentrated. The residue was separated and purified by silica gel column chromatography (dichloromethane/methanol (v/v)=97:3) to obtain the title compound 18D (0.31 g, 77%). LC-MS (ESI): m/z=469.2 [M−56+H]$^+$.

Step 4: (S)—N—((S)-1-cyano-2-(3-fluoro-4'-(methylcarbamoyl)-[1,1'-biphenyl]-4-yl)ethyl)-1,4-oxazepane-2-carboxamide (Compound 18)

18D (0.31 g, 0.59 mmol) was dissolved in formic acid (4.0 mL) and upon completion of the addition, the mixture was reacted at 50° C. for 30 min. The reaction solution was concentrated to dryness and ethyl acetate (25 mL) was added. Then saturated aqueous sodium bicarbonate solution was added dropwise to adjust the pH to about 8. The organic layer was separated and the remaining aqueous layer was extracted with ethyl acetate (25 mL×2). The combined organic phase was dried over anhydrous sodium sulfate, filtered and concentrated, and the residue was separated and purified by silica gel column chromatography (PE:EA (v/v)=1:2) to obtain the title compound 18 (50 mg, 20%).

$^1$H NMR (400 MHz, DMSO-d$_6$) δ 8.98 (d, 1H), 8.49 (d, 1H), 7.93 (d, 2H), 7.81 (d, 2H), 7.64-7.57 (m, 2H), 7.47 (t, 1H), 5.06 (m, 1H), 4.35-4.29 (m, 1H), 3.91 (m, 1H), 3.77 (m, 1H), 3.38 (m, 1H), 3.18 (m, 1H), 2.98 (m, 2H), 2.87 (m, 1H), 2.80 (d, 3H), 1.92 (m, 2H), 1.23 (m, 1H). LC-MS (ESI): m/z=425.2 [M+H]$^+$.

Example 19: (S)—N—((S)-1-cyano-2-(2-fluoro-4-(1-methyl-1H-indol-2-yl)phenyl)ethyl)-1,4-oxazepane-2-carboxamide (Compound 19)

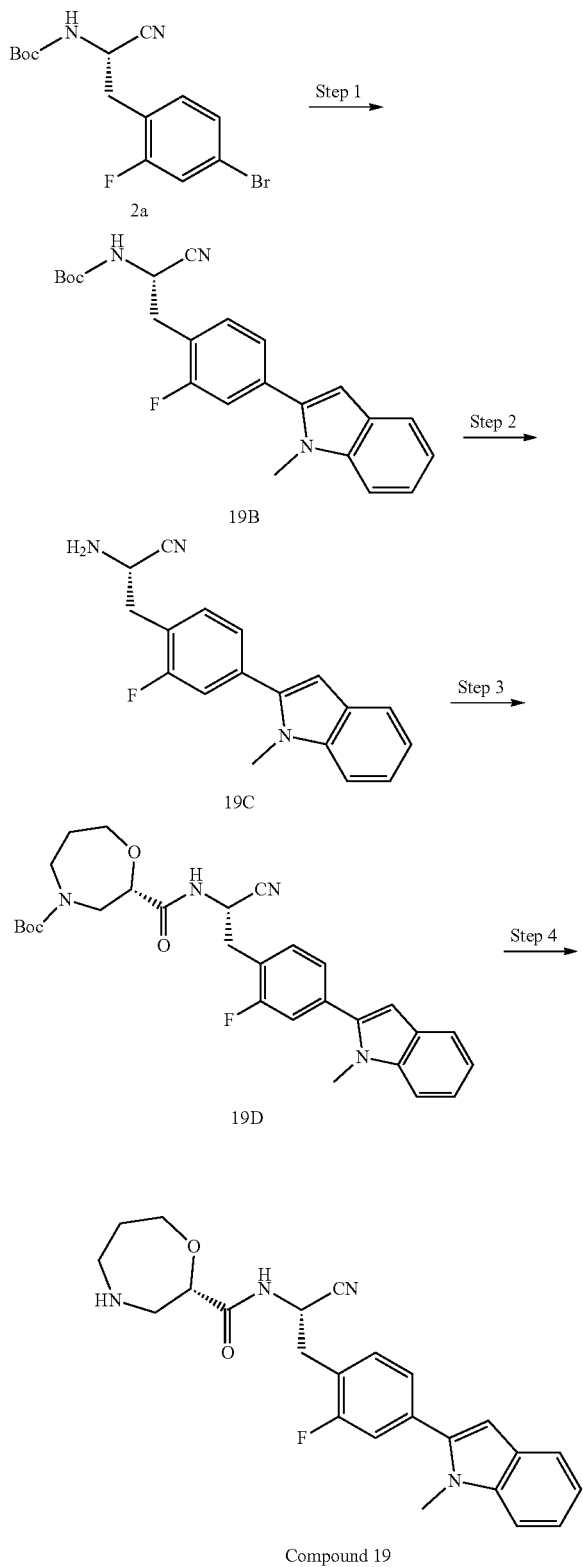

Step 1: tert-butyl (S)-(1-cyano-2-(2-fluoro-4-(1-methyl-1H-indol-2-yl) phenyl)ethyl)carbamate (19B)

2a (0.40 g, 1.17 mmol) was dissolved in 1,4-dioxane (10 mL) and water (0.4 mL), and then 1-methyl-2-indoleboronic acid pinacol ester (0.39 g, 1.52 mmol), [1,1'-bis(diphenylphosphino)ferrocene]palladium dichloride dichloromethane complex (0.19 g, 0.23 mmol), and potassium carbonate (0.32 g, 2.34 mmol) were added. Upon completion of the addition, the mixture was heated to 90° C. and reacted for 2 h under nitrogen protection. Then the reaction solution was reacted at room temperature overnight. The resulting reaction mixture was concentrated to dryness and saturated aqueous ammonium chloride solution (50 mL) was added. The resulting mixture was extracted with ethyl acetate (20 mL×3). The combined organic phase was dried over anhydrous sodium sulfate, filtered and concentrated, and the residue was separated and purified by silica gel column chromatography (PE:EA (v/v)=10:1, 4:1) to obtain the title compound 19B as a white solid (0.25 g, 54.31%). LC-MS (ESI): m/z=394.2 [M+H]$^+$.

Step 2: (S)-2-amino-3-(2-fluoro-4-(1-methyl-1H-indol-2-yl)phenyl)propanenitrile (19C)

19B (0.37 g, 0.94 mmol) was dissolved in acetonitrile (30 mL) and p-toluenesulfonic acid monohydrate (0.54 g, 2.82 mmol) was added. Upon completion of the addition, the mixture was reacted at room temperature for 4 h. The reaction solution was concentrated to dryness and ethyl acetate (25 mL) was added. Then saturated aqueous sodium bicarbonate solution was added dropwise to adjust the pH to about 8. The organic layer was separated and the remaining aqueous layer was extracted with ethyl acetate (25 mL×3). The combined organic phase was dried over anhydrous sodium sulfate, filtered and concentrated, and the residue was separated and purified by silica gel column chromatography (PE:EA (v/v)=1:1) to obtain the title compound 19C as a pale yellow solid (0.25 g, 90.67%). LC-MS (ESI): m/z=294.3 [M+H]$^+$.

Step 3: tert-butyl (S)-2-(((S)-1-cyano-2-(2-fluoro-4-(1-methyl-1H-indol-2-yl)phenyl)ethyl)carbamoyl)-1,4-oxazepane-4-carboxylate (19D)

19C (0.25 g, 0.85 mmol) was dissolved in dichloromethane (10 mL) and then INT-3 (0.21 g, 0.85 mmol), diisopropylethylamine (0.55 g, 4.25 mmol), and N,N,N',N'-tetramethyl-O-(7-azabenzotriazol-1-yl)uronium hexafluorophosphate (0.32 g, 0.85 mmol) were added. Upon completion of the addition, the mixture was reacted at room temperature overnight. Saturated aqueous sodium chloride solution (30 mL) was added and then the resulting mixture was extracted with ethyl acetate (25 mL). The organic phase was washed with saturated aqueous sodium chloride solution (25 mL×3), dried over anhydrous sodium sulfate, filtered and concentrated, and the residue was separated and purified by silica gel column chromatography (PE:EA (v/v)=2:1) to obtain the title compound 19D as a white solid (0.40 g, 90.39%). LC-MS (ESI): m/z=485.1 [M−57+H]$^+$.

Step 4: (S)—N—((S)-1-cyano-2-(2-fluoro-4-(1-methyl-1H-indol-2-yl)phenyl)ethyl)-1,4-oxazepane-2-carboxamide (Compound 19)

19D (0.40 g, 0.77 mmol) was dissolved in acetonitrile (30 mL) and p-toluenesulfonic acid monohydrate (0.44 g, 2.31 mmol) was added. Upon completion of the addition, the mixture was reacted at room temperature for 4 h. The reaction solution was concentrated to dryness and ethyl acetate (25 mL) was added. Then saturated aqueous sodium bicarbonate solution was added dropwise to adjust the pH to about 8. The organic layer was separated and the remaining aqueous layer was extracted with ethyl acetate (25 mL×3). The combined organic phase was dried over anhydrous sodium sulfate, filtered and concentrated, and the residue was separated and purified by silica gel column chromatography (dichloromethane:methanol (v/v)=20:1) to obtain the title compound 19 as a pale yellow solid (0.15 g, 46.33%).

$^1$H NMR (400 MHz, CDCl$_3$) δ 7.64 (d, 1H), 7.46-7.03 (m, 6H), 6.59 (s, 1H), 5.25-5.09 (m, 1H), 4.15 (dd, 1H), 4.07-3.90 (m, 1H), 3.82-3.61 (m, 4H), 3.37 (dd, 1H), 3.25 (t, 2H), 3.12-2.86 (m, 3H), 1.93-1.75 (m, 2H). LC-MS (ESI): m/z=421.2 [M+H]$^+$.

Example 20: (S)—N—((S)-1-cyano-2-(4'-(dimethylphosphoryl)-3-fluoro-[1,1'-biphenyl]-4-yl)ethyl)-1,4-oxazepane-2-carboxamide (Compound 20)

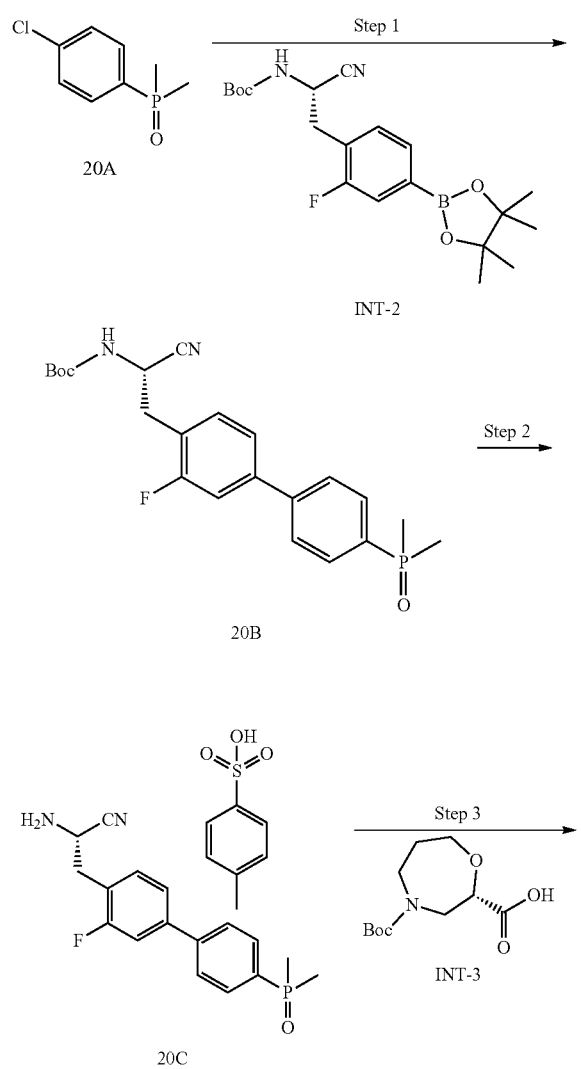

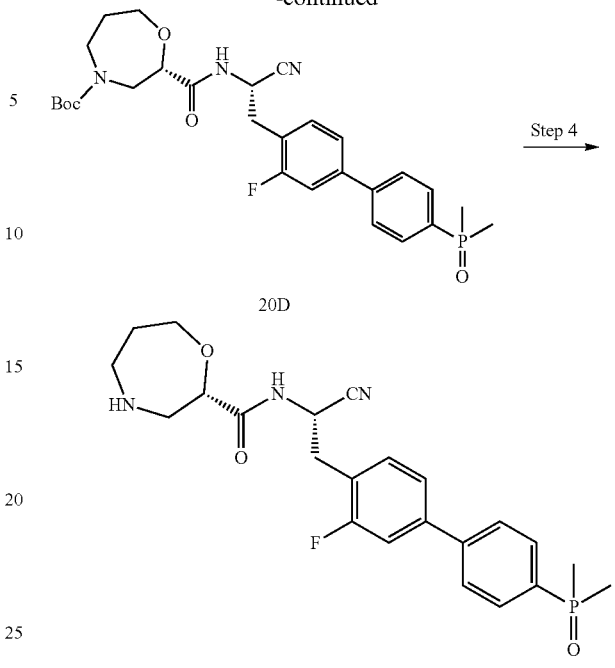

Compound 20

Step 1: tert-butyl (S)-(1-cyano-2-(4'-(dimethylphosphoryl)-3-fluoro-[1,1'-biphenyl]-4-yl)ethyl)carbamate (20B)

20A (0.200 g, 1.29 mmol), INT-2 (0.502 g, 1.29 mmol), [1,1'-bis(diphenylphosphino)ferrocene]palladium dichloride dichloromethane complex (0.105 g, 0.129 mmol), and potassium carbonate (0.534 g, 3.87 mmol) were dissolved in 1,4-dioxane (15 mL), water (3 mL) was added, and then the mixture was subjected to nitrogen replacement 3 times and reacted at 90° C. under nitrogen atmosphere for 4 hours. The reaction solution was concentrated to dryness and dissolved with dichloromethane, and the mixture was filtered and concentrated. The residue was separated and purified by silica gel column chromatography (PE:EA (v/v)=5:1) to obtain the title compound 20B as a white solid (0.420 g, 78.5%). LC-MS (ESI): m/z=417.2 [M+H]$^+$.

Step 2: (S)-2-amino-3-(4'-(dimethylphosphoryl)-3-fluoro-[1,1'-biphenyl]-4-yl)propanenitrile 4-methyl benzenesulfonate (20C)

20B (0.420 g, 1.01 mmol) was dissolved in acetonitrile (8 mL) and then p-toluenesulfonic acid monohydrate (0.575 g, 3.03 mmol) was added. Upon completion of the addition, the mixture was reacted at room temperature for 16 h and then filtered. The filter cake was rinsed once with acetonitrile (2 mL) and subjected to rotary evaporation to obtain the title compound 20C as a white solid (0.500 g, 99.9%), which was directly used in the next reaction.

Step 3: tert-butyl (S)-2-(((S)-1-cyano-2-(4'-(dimethylphosphoryl)-3-fluoro-[1,1'-biphenyl]-4-yl)ethyl)carbamoyl)-1,4-oxazepane-4-carboxylate (20D)

INT-3 (0.148 g, 0.605 mmol) was dissolved in dichloromethane (10 mL), and then triethylamine (0.124 g, 1.23 mmol) and N,N,N',N'-tetramethyl-O-(7-azabenzotriazol-1-yl)uronium hexafluorophosphate (0.230 g, 0.605 mmol) were added. Upon completion of the addition, the mixture was reacted at room temperature for 1 hour under stirring, and then 20C (0.200 g, 0.41 mmol) was added. The resulting mixture was reacted at room temperature overnight. After the reaction was completed, the reaction solution was concentrated to obtain the crude product 20D, which was directly used in the next reaction. LC-MS (ESI): m/z=542.2 [M−H]⁻.

Step 4: (S)—N—((S)-1-cyano-2-(4'-(dimethylphosphoryl)-3-fluoro-[1,1'-biphenyl]-4-yl)ethyl)-1,4-oxazepane-2-carboxamide (Compound 20)

Crude product 20D was dissolved in acetonitrile (10 mL), and p-toluenesulfonic acid monohydrate (0.234 g, 1.23 mmol) was added. Upon completion of the addition, the mixture was reacted at room temperature for 16 h and then concentrated to dryness. Ethyl acetate (25 mL) was added and saturated aqueous sodium bicarbonate solution was added dropwise to adjust the pH to about 8. The organic layer was separated and the remaining aqueous layer was extracted with ethyl acetate (25 mL×2). The combined organic phase was dried over anhydrous sodium sulfate, filtered and concentrated, and the residue was separated and purified by silica gel column chromatography (dichloromethane:methanol (v/v)=20:1) to obtain the title compound 20 (60 mg, two-step yield: 33.1%).

$^1$H NMR (400 MHz, CDCl$_3$) δ 7.83 (d, 1H), 7.81 (d, 1H), 7.69 (dd, 2H), 7.41 (d, 2H), 7.38-7.30 (m, 2H), 5.18 (dd, 1H), 4.20 (dd, 1H), 4.09-3.98 (m, 1H), 3.84-3.74 (m, 1H), 3.41 (dd, 1H), 3.31-3.17 (m, 2H), 3.06-2.91 (m, 3H), 1.96 (s, 1H), 1.78 (d, 6H), 1.38 (dd, 1H), 1.22 (dd, 1H). LC-MS (ESI): m/z=444.3 [M+H]⁺.

Example 21: (S)—N—((S)-1-cyano-2-(2-fluoro-4-(1-methyl-6-oxo-1,6-dihydropyridin-3-yl)phenyl)ethyl)-1,4-oxazepane-2-carboxamide (Compound 21)

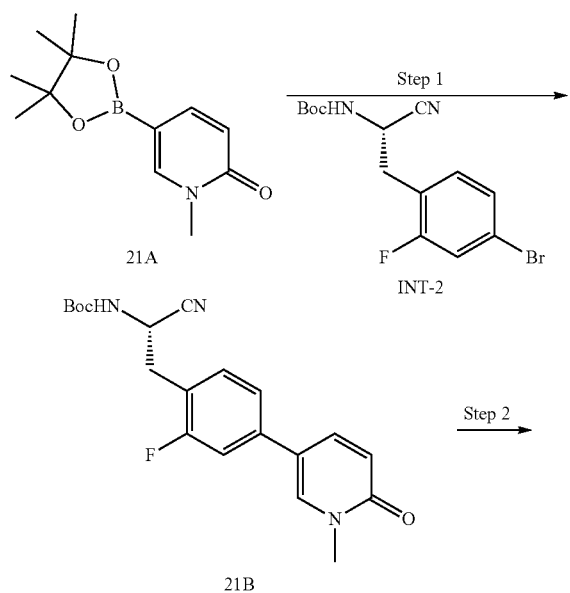

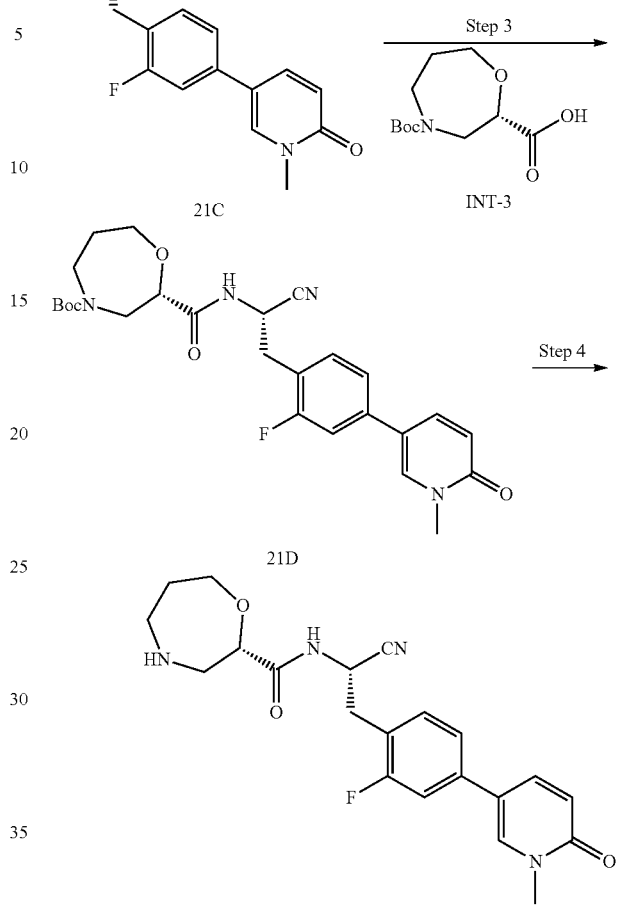

Compound 21

Step 1: tert-butyl (S)-(1-cyano-2-(2-fluoro-4-(1-methyl-6-oxo-1,6-dihydropyridin-3-yl)phenyl)ethyl)carbamate (21B)

The reactant 21A (0.47 g, 2.0 mmol) and INT-2 (0.69 g, 2.0 mmol) were dissolved in 1,4-dioxane (50 ml) and then potassium carbonate (0.83 g, 6.0 mmol) and Pd(dppf)Cl$_2$ (0.15 g, 0.2 mmol) were added. The mixture was under the protection of nitrogen replacement and reacted at 100° C. TLC and LC-MS showed that there was still a small amount of starting materials. The reaction solution was concentrated and subjected to rotary evaporation, then dissolved in DCM and filtered off with suction through celite, and the filtrate was subjected to rotary evaporation and passed through a column (EA/PE=0%-40%) to obtain the title compound 21B as a pale yellow solid (0.50 g, 67.3%). LC-MS (ESI): m/z=372.3 [M+H]⁺.

Step 2: (S)-2-amino-3-(2-fluoro-4-(1-methyl-6-oxo-1,6-dihydropyridin-3-yl)phenyl)propanenitrile (21C)

21B (0.5 g 1.35 mmol) was dissolved in anhydrous formic acid (10 ml). After the mixture was reacted at 50° C. for 0.5 h, TLC detection showed complete reaction of the substrate. Formic acid was removed by rotary evaporation at a low temperature, and saturated sodium bicarbonate solution was added to adjust the pH to 8-10. The resulting mixture was extracted with DCM (20 ml×2), dried over anhydrous sodium sulfate, subjected to rotary evaporation and passed through a column (DCM:CH$_3$OH=10:1) to obtain the title compound 21C as a pale yellow liquid (0.35 g, 95.6%). LC-MS (ESI): m/z=272.3 [M+H]$^+$.

Step 3: tert-butyl(S)-2-(((S)-1-cyano-2-(2-fluoro-4-(1-methyl-6-oxo-1,6-dihydropyridin-3-yl)phenyl)ethyl)carbamoyl)-1,4-oxazepane-4-carboxylate (21D)

INT-3 (0.32 g, 1.29 mmol), HATU (0.59 g, 1.55 mmol), and DIPEA (0.5 ml) were dissolved in dichloromethane (30 ml) at room temperature. After the mixture was stirred at room temperature for 10 min, 21C (0.35 g, 1.29 mmol) was added and the resulting mixture was stirred at room temperature for 1 h. TLC detection showed that the reaction was completed. Water (10 ml) was added to quench the reaction, and the reaction solution was extracted with dichloromethane (15 ml×2). The organic phases were combined, dried over anhydrous sodium sulfate and concentrated under reduced pressure, and the residue was purified by column chromatography (PE:EA=1:1) to obtain the title compound 21D (0.4 g, 62%). LC-MS (ESI): m/z=443.1 [M−56+H]$^+$.

Step 4: (S)—N—((S)-1-cyano-2-(2-fluoro-4-(1-methyl-6-oxo-1,6-dihydropyridin-3-yl)phenyl)ethyl)-1,4-oxazepane-2-carboxamide (Compound 21)

21D (0.4 g 0.8 mmol) was dissolved in anhydrous formic acid (10 ml). After the mixture was stirred at 50° C. for 0.5 h, TLC detection showed complete reaction of the substrate. Formic acid was removed by rotary evaporation at a low temperature, and saturated sodium bicarbonate solution was added to adjust the pH to 8-10. The resulting mixture was extracted with dichloromethane (20 ml×2), dried over anhydrous sodium sulfate, subjected to rotary evaporation and passed through a column (DCM:CH$_3$OH=10:1) to obtain compound 21 (0.2 g, 62.7%). LC-MS (ESI): m/z=399.1 [M+H]$^+$.

$^1$H NMR (400 MHz, DMSO-d$_6$) δ 8.71-8.69 (m, 1H), 8.22 (s, 1H), 7.87-7.84 (m, 1H), 7.48-7.37 (m, 3H), 6.48-6.46 (m, 1H), 5.03-4.99 (m, 1H), 4.05-4.02 (m, 1H), 3.90-3.84 (m, 1H), 3.76-3.70 (m, 1H), 3.50 (s, 3H), 3.25-3.09 (m, 4H), 2.86-2.80 (m, 1H), 2.70-2.58 (m, 2H), 1.80-1.71 (m, 2H).

Example 22: (S)—N—((S)-1-cyano-2-(4-(1-ethyl-1H-pyrazol-4-yl)-2-fluorophenyl)ethyl)-1,4-oxazepane-2-carboxamide (Compound 22)

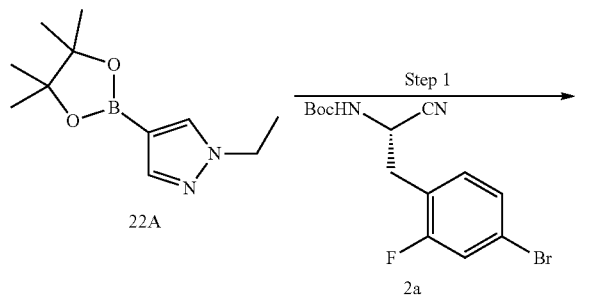

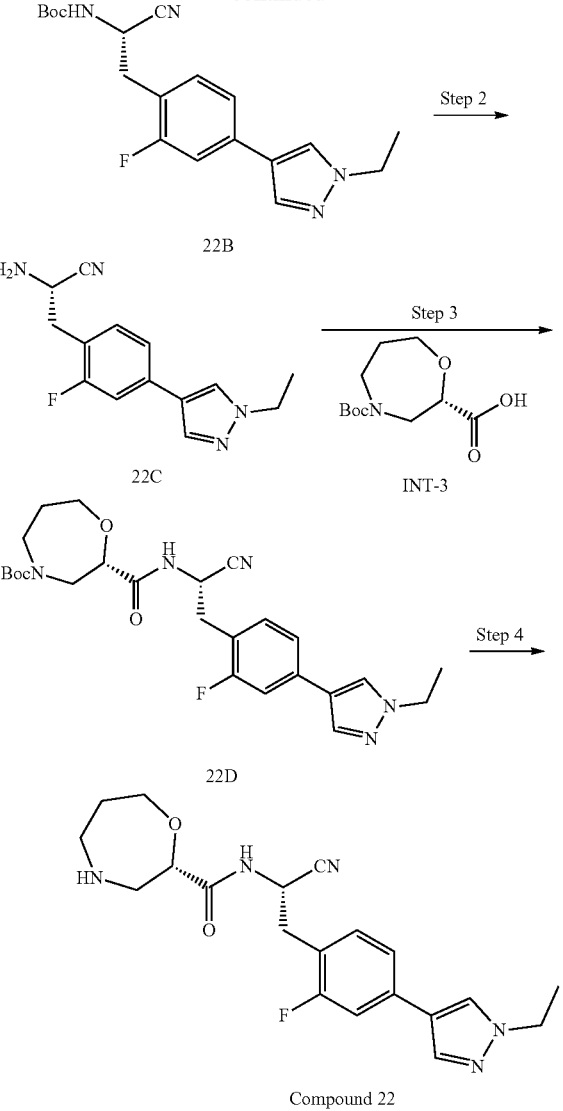

Step 1: (S)-tert-butyl (1-cyano-2-(4-(1-ethyl-1H-pyrazol-4-yl)-2-fluorophenyl)ethyl)carbamate (22B)

2a (0.32 g, 1.46 mmol) was dissolved in DMF (10 mL), and intermediate 1 (0.5 g, 1.46 mmol), potassium carbonate (0.61 g, 4.38 mmol), and 1,1'-bisdiphenylphosphino ferrocene palladium dichloride (0.11 g, 0.15 mmol) were added. Upon completion of the addition, the mixture was reacted at 100° C. for 3 hours. The reaction solution was cooled to room temperature and saturated aqueous sodium chloride solution (20 mL) was added. The resulting mixture was extracted with dichloromethane (20 mL×3). The combined organic phase was dried over anhydrous sodium sulfate, filtered and concentrated, and the residue was separated and purified by silica gel column chromatography (PE:EA (v/v) =2:1) to obtain the title compound 22B as a colorless liquid (0.44 g, 84.1%). LC-MS (ESI): m/z=359.1 [M+H]$^+$.

Step 2: (S)-2-amino-3-(4-(1-ethyl-1H-pyrazol-4-yl)-2-fluorophenyl)propanenitrile (22C)

22B (0.40 g, 1.12 mmol) was dissolved in formic acid (10 mL) and upon completion of the addition, the mixture was reacted at 50° C. for 2 h. The reaction solution was concentrated to dryness and ethyl acetate (25 mL) was added. Saturated aqueous sodium bicarbonate solution was added dropwise to adjust the pH to about 8, and the organic layer was separated. The remaining aqueous layer was extracted with ethyl acetate (25 mL×2). The combined organic phase was dried over anhydrous sodium sulfate, filtered and concentrated to obtain the title compound 22C as a colorless liquid (0.29 g, 100%), which was directly used in the next reaction.

Step 3: (S)-tert-butyl 2-(((S)-1-cyano-2-(4-(1-ethyl-1H-pyrazol-4-yl)-2-fluorophenyl)ethyl)carbamoyl)-1,4-oxazepane-4-carboxylate (22D)

22C (0.30 g, 1.16 mmol) was dissolved in DMF (10 mL) and then INT-3 (0.28 g, 1.16 mmol), diisopropylethylamine (0.45 g, 3.48 mmol), and N,N,N',N'-tetramethyl-O-(7-azabenzotriazol-1-yl)uronium hexafluorophosphate (0.66 g, 1.74 mmol) were added. Upon completion of the addition, the mixture was reacted at room temperature overnight. Saturated aqueous sodium chloride solution (30 mL) was added. The resulting mixture was extracted with ethyl acetate (25 mL), and the organic phase was washed with saturated aqueous sodium chloride solution (25 mL×3), dried over anhydrous sodium sulfate, filtered and concentrated to obtain the title compound 22D as a pale yellow solid (0.30 g, 53.3%), which was directly used in the next reaction. LC-MS (ESI): m/z=430.1 [M−57+H]$^+$.

Step 4: (S)—N—((S)-1-cyano-2-(4-(1-ethyl-1H-pyrazol-4-yl)-2-fluorophenyl)ethyl)-1,4-oxazepane-2-carboxamide (Compound 22)

22D (0.15 g, 0.31 mmol) was dissolved in formic acid (2.0 mL) and upon completion of the addition, the mixture was reacted at 35° C. for 4 h. The reaction solution was concentrated to dryness and ethyl acetate (25 mL) was added. Then saturated aqueous sodium bicarbonate solution was added dropwise to adjust the pH to about 8. The organic layer was separated and the remaining aqueous layer was extracted with ethyl acetate (25 mL×2). The combined organic phase was dried over anhydrous sodium sulfate, filtered and concentrated, and the residue was separated and purified by silica gel column chromatography (PE:EA (v/v)=1:2) to obtain the title compound 22 (80 mg, 66.9%).

$^1$H NMR (400 MHz, CDCl$_3$) δ 9.43 (s, 1H), 9.10-9.08 (m, 1H), 8.27 (s, 1H), 7.92 (s, 1H), 7.44-7.31 (m, 3H), 5.03-4.96 (m, 1H), 4.51-4.48 (m, 1H), 4.17-4.11 (m, 2H), 3.96-3.90 (m, 1H), 5.82-4.76 (m, 1H), 3.47-3.43 (m, 1H), 3.29-3.21 (m, 2H), 3.16-3.07 (m, 2H), 2.98-2.92 (m, 1H), 2.12-1.96 (m, 2H), 1.42-1.38 (m, 3H). LC-MS (ESI): m/z=386.1 [M+H]$^+$.

Example 23: (S)—N—((S)-1-cyano-2-(2-fluoro-4-(3-(methyl-d3)-2-oxo-2,3-dihydrobenzo[d]oxazol-5-yl)phenyl) ethyl)-1,4-oxazepane-2-carboxamide (Compound 23)

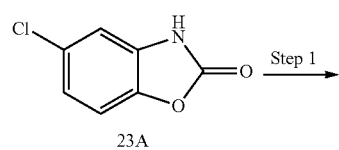

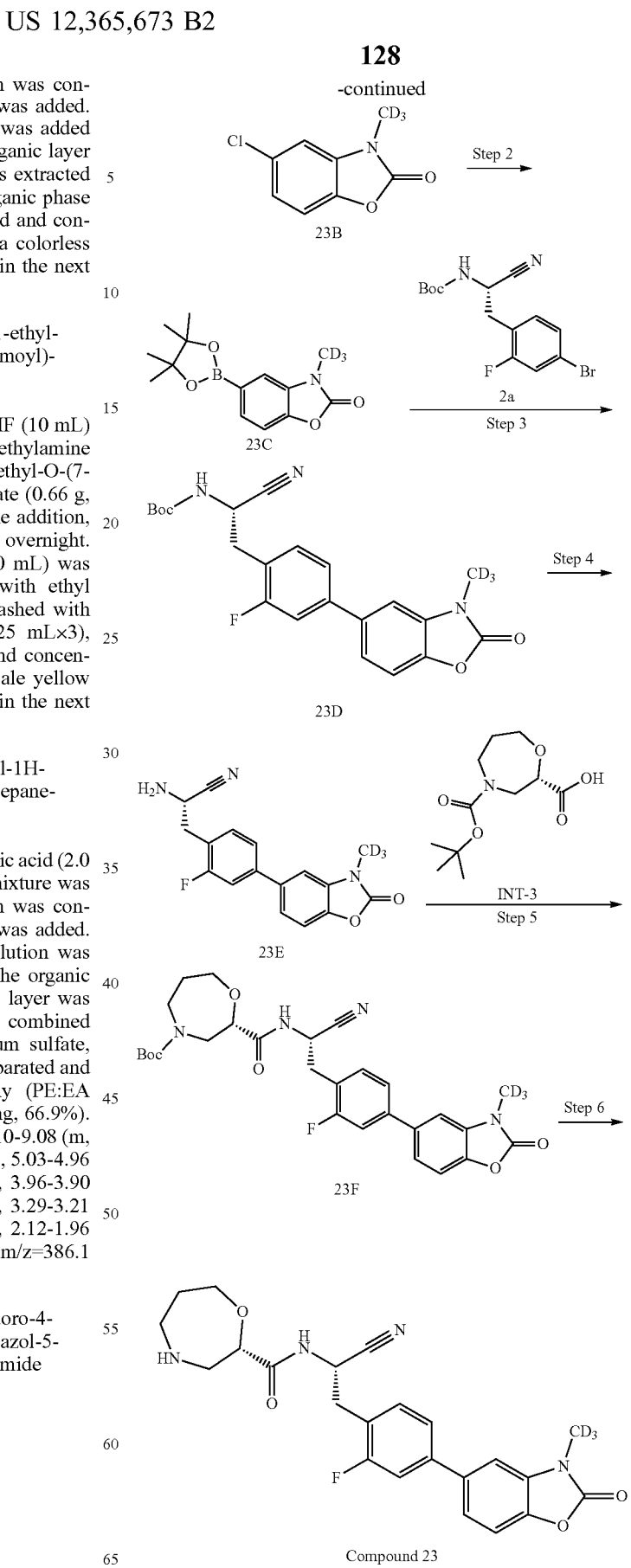

Step 1: 5-chloro-3-(methyl-d3)benzo[d]oxazol-2(3H)-one (23B)

23A (5 g, 29.49 mmol) was dissolved in DMF (25 mL), and then cesium carbonate (10.57 g, 32.44 mmol) and deuterated iodomethane (4.28 g, 29.52 mmol) were added. The mixture was reacted at 25° C. for 4 hours. After completion of the reaction, the reaction solution was poured into water (60 mL) and filtered, and the filter cake was collected, dissolved with dichloromethane, and washed with saturated brine. The organic phase was collected, dried over anhydrous sodium sulfate, and filtered, and the filtrate was concentrated to obtain compound 23B as a brown solid (5.4 g, yield: 98.1%). LCMS m/z=187.0 [M+1]$^+$

Step 2: 3-(methyl-d3)-5-(4,4,5,5-tetramethyl-1,3,2-dioxaborolan-2-yl)benzo[d]oxazol-2(3H)-one (23C)

Compound 23B (5.4 g, 28.94 mmol) was dissolved in 1,4-dioxane (54 ml) and then pinacolborane (12.49 g, 49.20 mmol), potassium acetate (8.52 g, 86.82 mmol), palladium acetate (652 mg, 2.89 mmol), and X-Phos (2.73 g, 5.79 mmol) were added. Upon completion of the addition, the mixture was warmed to 100° C. and reacted for 3 hours. After completion of the reaction, the reaction solution was filtered and the filtrate was concentrated. The obtained residue was separated and purified by silica gel column chromatography (eluent: PE:EA (v/v)=1:0-10:1) to give 23C as a white solid (7.2 g, yield: 89.8%). LC-MS m/z=279.2 [M+1]$^+$

Step 3: tert-butyl (S)-(1-cyano-2-(2-fluoro-4-(3-(methyl-d3)-2-oxo-2,3-dihydrobenzo[d]oxazol-5-yl)phenyl) ethyl)carbamate (23D)

Compound 23C (2.0 g, 7.19 mmol) was dissolved in a mixed solvent of 1,4-dioxane (20 ml) and water (4 ml), and then 2a (2.47 mg, 7.19 mmol) was added. Subsequently, potassium carbonate (2.98 g, 21.57 mmol), palladium acetate (161 mg, 0.72 mmol), and X-Phos (686 mg, 1.44 mmol) were successively added. Upon completion of the addition, the mixture was subjected to nitrogen replacement 3 times, warmed to 100° C., and reacted for 5 hours. After completion of the reaction, the reaction solution was directly concentrated, and the obtained residue was separated and purified by silica gel column chromatography (eluent: PE:EA (v/v)=1:0-5:1) to obtain compound 23D as a white solid (2.57 g, 86.2%). LCMS m/z=415.3 [M+1]$^+$

Step 4: (S)-2-amino-3-(2-fluoro-4-(3-(methyl-d3)-2-oxo-2,3-dihydrobenzo[d]oxazol-5-yl)phenyl) propanenitrile (23E)

Compound 23D (1 g, 2.41 mmol) was dissolved in anhydrous formic acid (10 ml) and the mixture was stirred at 25° C. for 5 hours. After completion of the reaction, the reaction solution was slowly poured into saturated sodium bicarbonate solution (100 ml) to a pH of 7-8. Then the resulting mixture was extracted with dichloromethane (50 mL×3). The organic phases were combined, washed with saturated brine (30 ml), dried over anhydrous sodium sulfate, and filtered, and the filtrate was concentrated to obtain compound 23E as a pale yellow solid (710 mg, 93.5%). LCMS m/z=315.2 [M+1]$^+$

Step 5: tert-butyl (S)-2-(((S)-1-cyano-2-(2-fluoro-4-(3-(methyl-d3)-2-oxo-2,3-dihydrobenzo[d]oxazol-5-yl)phenyl)ethyl)carbamoyl)-1,4-oxazepane-4-carboxylate (23F)

Under nitrogen protection, compound 23E (656 mg, 2.07 mmol) was dissolved in DMF (7 ml), and then INT-3 (510 mg, 2.07 mmol), diisopropylethylamine (1.34 g, 10.35 mmol), and 2-(7-azabenzotriazole)-N,N,N',N'-tetramethyluronium hexafluorophosphate (1.18 g, 3.10 mmol) were added. Upon completion of the addition, the mixture was warmed to 25° C. and reacted for 3 hours. After completion of the reaction, the reaction solution was poured into water (20 ml) and then extracted with ethyl acetate (50 mL×3). The organic phases were combined, washed with saturated brine (40 mL×3), dried over anhydrous sodium sulfate, and filtered, the filtrate was concentrated, and the obtained residue was separated and purified by silica gel column chromatography (eluent: PE:EA (v/v)=1:0-1:1) to obtain compound 23F as a yellow solid (837 mg, 74.7%). LCMS m/z=486.3 [M−tBu+1]$^+$

Step 6: (S)—N—((S)-1-cyano-2-(2-fluoro-4-(3-(methyl-d3)-2-oxo-2,3-dihydrobenzo[d]oxazol-5-yl) phenyl) ethyl)-1,4-oxazepane-2-carboxamide (Compound 23)

Compound 23F (837 mg, 1.55 mmol) was dissolved in anhydrous formic acid (3 ml) and the mixture was stirred at 25° C. for 3 hours. After completion of the reaction, the reaction solution was slowly poured into saturated sodium bicarbonate solution (30 ml) to a pH of 7-8. Then the resulting mixture was extracted with dichloromethane (50 mL×3). The organic phases were combined, washed with saturated brine (30 ml), dried over anhydrous sodium sulfate, and filtered, the filtrate was concentrated, and the residue was separated and purified by a preparative liquid chromatography column (conditions for preparative liquid chromatography: C18 reverse-phase preparative column, mobile phase: deionized water containing 0.1% trifluoroacetic acid (A) and acetonitrile containing 0.1% trifluoroacetic acid (B), gradient elution, mobile phase B content=5%-50%, elution time: 15 min, flow rate: 12 mL/min, and column temperature: 30° C.; and retention time: 3.7 min) to obtain compound 23 (300 mg, yield: 43.8%)

$^1$H NMR (400 MHz, DMSO-d$_6$) δ 8.76 (d, 1H), 7.65 (d, J=1.8, 1H), 7.62-7.50 (m, 2H), 7.49-7.42 (m, 2H), 7.38 (m, 1H), 5.05 (m, 1H), 4.13 (m, 1H), 3.99-3.82 (m, 1H), 3.74 (m, 1H), 3.65-3.52 (m, 1H), 3.30 (m, 2H), 3.16 (m, 2H), 3.00-2.80 (m, 1H), 2.74-2.58 (m, 1H), 1.88-1.68 (m, 2H). LCMS m/z=442.1 [M+1]$^+$

Example 24: (S)—N—((S)-1-cyano-2-(2-fluoro-4-(2-methyl-1-oxo-1,2,3,4-tetrahydroisoquinolin-6-yl) phenyl)ethyl)-1,4-oxazepane-2-carboxamide (Compound 24)

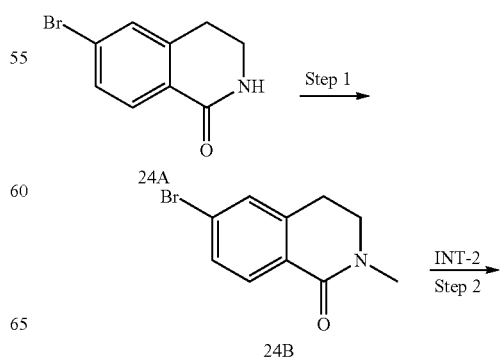

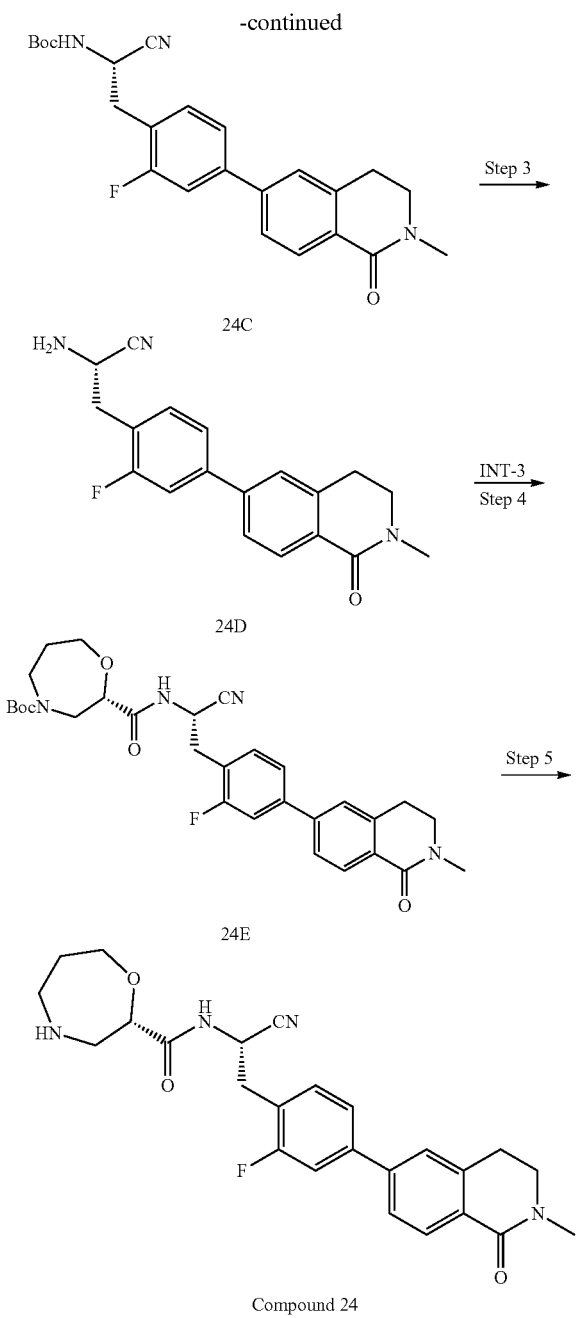

filtered, the filtrate was concentrated under reduced pressure, and the residue was separated by silica gel column chromatography (PE:EA=6:1) to obtain the target compound, i.e., 6-bromo-2-methyl-3,4-dihydroisoquinolin-1(2H)-one (24B) as a yellow solid (0.48 g, yield: 79%).

Step 2: tert-butyl (S)-(1-cyano-2-(2-fluoro-4-(2-methyl-1-oxo-1,2,3,4-tetrahydroisoquinolin-6-yl)phenyl)ethyl)carbamate (24C)

24B (0.29 g, 1.2 mmol), INT-2 (0.39 g, 1.0 mmol), [1,1'-bis(diphenylphosphino)ferrocene]palladium dichloride (71 mg, 0.1 mmol), and potassium carbonate (0.28 g, 2.0 mmol) were successively added to 1,4-dioxane (15 mL) and water (3 mL), and the system was subjected to nitrogen replacement three times and reacted at 100° C. for 2 hours. After the reaction was completed, the reaction solution was cooled to room temperature, water (50 mL) was added, and the resulting aqueous phase was extracted with ethyl acetate (50 mL×2). The combined organic phase was washed with saturated aqueous sodium chloride solution (100 mL), dried over anhydrous sodium sulfate, and filtered. The filtrate was concentrated under reduced pressure. The residue was separated by silica gel column chromatography (PE:EA=3:1-2:1) to obtain 24C as a brown solid (0.35 g, yield: 83%). LCMS m/z=424.2[M+1]$^+$.

Step 3: (S)-2-amino-3-(2-fluoro-4-(2-methyl-1-oxo-1,2,3,4-tetrahydroisoquinolin-6-yl)phenyl)propane nitrile (24D)

24C (0.35 g, 0.83 mmol) was dissolved in formic acid (6.0 mL) and upon completion of the addition, the mixture was reacted at 50° C. for 10 minutes. The reaction solution was concentrated to dryness. Ethyl acetate (60 mL) was added and then saturated aqueous sodium bicarbonate solution was added dropwise to adjust the pH to about 8. The organic layer was separated and the aqueous phase was extracted with ethyl acetate (60 mL×2). The combined organic phase was dried over anhydrous sodium sulfate, filtered and concentrated to obtain the title compound 24D (0.24 g, yield: 89%).

Step 4: tert-butyl (S)-2-(((S)-1-cyano-2-(2-fluoro-4-(2-methyl-1-oxo-1,2,3,4-tetrahydroisoquinolin-6-yl)phenyl)ethyl)carbamoyl)-1,4-oxazepane-4-carboxylate (24E)

24D (0.24 g, 0.74 mmol) was dissolved in DMF (10 mL) and then INT-3 (0.25 g, 1.0 mmol), diisopropylethylamine (0.19 g, 1.5 mmol), and N,N,N',N'-tetramethyl-O-(7-azabenzotriazol-1-yl)uronium hexafluorophosphate (0.38 g, 1 mmol) were added. Upon completion of the addition, the mixture was reacted at room temperature for 1 hour. Water (30 mL) was added and the resulting mixture was extracted with ethyl acetate (60 mL×2). The organic phase was washed with saturated aqueous sodium chloride solution (60 mL), dried over anhydrous sodium sulfate, filtered and concentrated, and the residue was separated by silica gel column chromatography (PE:EA=2:1-1:2) to obtain the title compound 24E as a pale yellow solid (0.28 g, yield: 69%).

Step 5: (S)—N—((S)-1-cyano-2-(2-fluoro-4-(2-methyl-1-oxo-1,2,3,4-tetrahydroisoquinolin-6-yl)phenyl) ethyl)-1,4-oxazepane-2-carboxamide (Compound 24)

24E (0.28 g, 0.51 mmol) was dissolved in formic acid (6.0 mL) and the mixture was reacted at 50° C. for 10 minutes.

Step 1: 6-bromo-2-methyl-3,4-dihydroisoquinolin-1(2H)-one (24B)

24A (0.57 g, 2.5 mmol) was dissolved in dry N.N-dimethylformamide (20 mL) and the mixture was cooled to 0° C. under nitrogen protection. Sodium hydride (0.12 g, 3.0 mmol, 60% wt) was added in portions. After the addition, the resulting mixture was reacted under such conditions for 20 minutes and then iodomethane (0.51 g, 3.6 mmol) was added dropwise to the system. After the addition, the mixture was reacted at room temperature for 30 minutes. Water (100 mL) was added to quench the reaction and the resulting mixture was extracted with ethyl acetate (100 mL×2). The organic phases were combined, washed with saturated brine (100 mL×1), dried over anhydrous sodium sulfate, and The reaction solution was concentrated under reduced pressure and ethyl acetate (60 mL) was added. Then saturated aqueous sodium bicarbonate solution was added dropwise to adjust the pH to about 8. The organic layer was separated and the remaining aqueous layer was extracted with ethyl acetate (60 mL×5). The combined organic phase was dried over anhydrous sodium sulfate, filtered and concentrated, and the residue was separated and purified by silica gel column chromatography (dichloromethane:methanol (v/v)=10:1) to obtain compound 24 (0.18 g, yield: 78%).

$^1$H NMR (400 MHz, DMSO-$d_6$) δ 8.82 (d, 1H), 7.93 (d, 1H), 7.71-7.63 (m, 2H), 7.63-7.53 (m, 2H), 7.47 (t, 1H), 5.11-5.01 (m, 1H), 4.15 (dd, 1H), 3.94-3.84 (m, 1H), 3.80-3.70 (m, 1H), 3.58 (t, 2H), 3.37-3.16 (m, 4H), 3.08-3.01 (m, 4H), 3.00-2.90 (m, 1H), 2.89-2.65 (m, 2H), 1.88-1.74 (m, 2H). LC-MS (ESI): m/z=451.3 [M+H]$^+$.

Example 25: (S)—N—((S)-1-cyano-2-(2-fluoro-4-(2-methyl-1-oxoisoindolin-5-yl)phenyl)ethyl)-1,4-oxazepane-2-carboxamide (Compound 25)

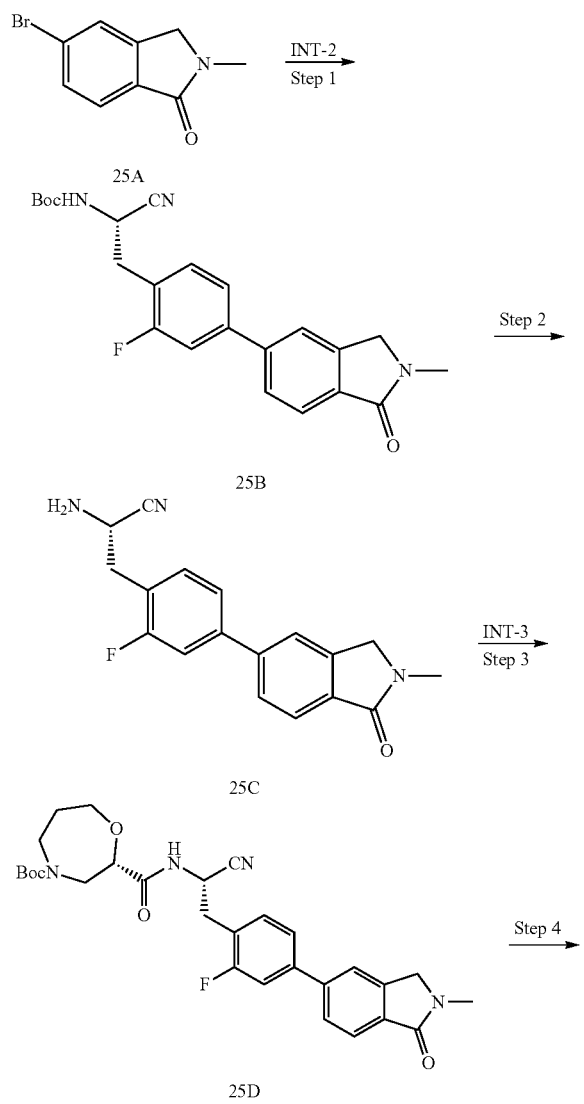

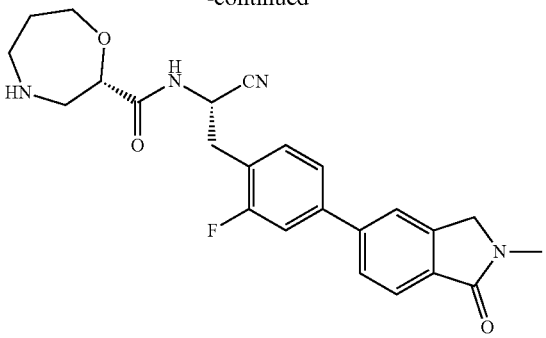

Compound 25

Step 1: tert-butyl (S)-(1-cyano-2-(2-fluoro-4-(2-methyl-1-oxoisoindolin-5-yl)phenyl)ethyl)carbamate (25B)

25A (0.27 g, 1.2 mmol), INT-2 (0.36 g, 0.92 mmol), [1,1'-bis(diphenylphosphino)ferrocene]palladium dichloride (71 mg, 0.1 mmol), and potassium carbonate (0.28 g, 2.0 mmol) were successively added to 1,4-dioxane (15 mL) and water (3 mL), and the system was subjected to nitrogen replacement three times and reacted at 100° C. for 2 hours. After the reaction was completed, the reaction solution was cooled to room temperature, water (50 mL) was added, and the resulting aqueous phase was extracted with ethyl acetate (50 mL×2). The combined organic phase was washed with saturated aqueous sodium chloride solution (100 mL), dried over anhydrous sodium sulfate, and filtered. The filtrate was concentrated under reduced pressure. The residue was separated by silica gel column chromatography (PE:EA=3:1-2:1) to obtain 25B as a brown solid (0.36 g, yield: 95%). LCMS m/z=410.1[M+1]$^+$.

Step 2: (S)-2-amino-3-(2-fluoro-4-(2-methyl-1-oxoisoindolin-5-yl)phenyl)propanenitrile (25C)

25B (0.36 g, 0.88 mmol) was dissolved in formic acid (6.0 mL) and upon completion of the addition, the mixture was reacted at 50° C. for 10 minutes. The reaction solution was concentrated to dryness. Ethyl acetate (60 mL) was added and then saturated aqueous sodium bicarbonate solution was added dropwise to adjust the pH to about 8. The organic layer was separated and the aqueous phase was extracted with ethyl acetate (60 mL×2). The combined organic phase was dried over anhydrous sodium sulfate, filtered and concentrated to obtain the title compound 25C (0.28 g, yield: 100%). LCMS m/z=310.1[M+1]$^+$.

Step 3: tert-butyl (S)-2-(((S)-1-cyano-2-(2-fluoro-4-(2-methyl-1-oxoisoindolin-5-yl)phenyl)ethyl)carbamoyl)-1,4-oxazepane-4-carboxylate (25D)

25C (0.28 g, 0.88 mmol) was dissolved in DMF (10 mL) and then INT-3 (0.25 g, 1.0 mmol), diisopropylethylamine (0.19 g, 1.5 mmol), and N,N,N',N'-tetramethyl-O-(7-azabenzotriazol-1-yl)uronium hexafluorophosphate (0.38 g, 1 mmol) were added. Upon completion of the addition, the mixture was reacted at room temperature for 1 hour. Saturated aqueous sodium chloride solution (30 mL) was added and the resulting mixture was extracted with ethyl acetate (60 mL×2). The organic phase was washed with saturated aqueous sodium chloride solution (60 mL), dried over anhydrous sodium sulfate, filtered and concentrated, and the residue was separated by silica gel column chromatography (PE:EA=2:1-1:2) to obtain the title compound 25D as a pale yellow solid (0.29 g, yield: 60%).

Step 4: (S)—N—((S)-1-cyano-2-(2-fluoro-4-(2-methyl-1-oxoisoindolin-5-yl)phenyl)ethyl)-1,4-oxazepane-2-carboxamide (Compound 25)

25D (0.29 g, 0.55 mmol) was dissolved in formic acid (6.0 mL) and the mixture was reacted at 50° C. for 10 minutes. The reaction solution was concentrated under reduced pressure and ethyl acetate (60 mL) was added. Then saturated aqueous sodium bicarbonate solution was added dropwise to adjust the pH to about 8. The organic layer was separated and the remaining aqueous layer was extracted with ethyl acetate (60 mL×5). The combined organic phase was dried over anhydrous sodium sulfate, filtered and concentrated, and the residue was separated and purified by silica gel column chromatography (dichloromethane:methanol (v/v)=10:1) to obtain compound 25 (0.15 g, yield: 64%).

$^1$H NMR (400 MHz, DMSO-d$_6$) δ 8.84 (d, 1H), 7.92 (s, 1H), 7.80 (dd, 1H), 7.73 (d, 1H), 7.64-7.55 (m, 2H), 7.48 (t, 1H), 5.07 (q, 1H), 4.51 (s, 2H), 4.16 (dd, 1H), 3.94-3.84 (m, 1H), 3.80-3.70 (m, 1H), 3.45-3.13 (m, 3H), 3.10 (s, 3H), 3.02-2.91 (m, 1H), 2.86-2.67 (m, 2H), 1.90-1.74 (m, 2H). LC-MS m/z=437.2 [M+1]$^+$

Example 26: (S)—N—((S)-1-cyano-2-(2-fluoro-4-(6-fluoro-3-methyl-2-oxo-2,3-dihydrobenzo[d]oxazol-5-yl)phenyl)ethyl)-1,4-oxazepane-2-carboxamide (Compound 26)

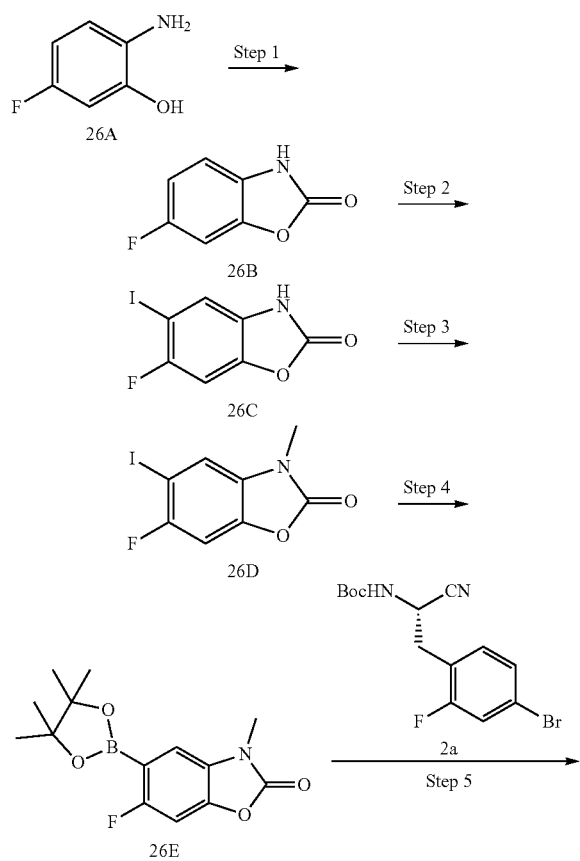

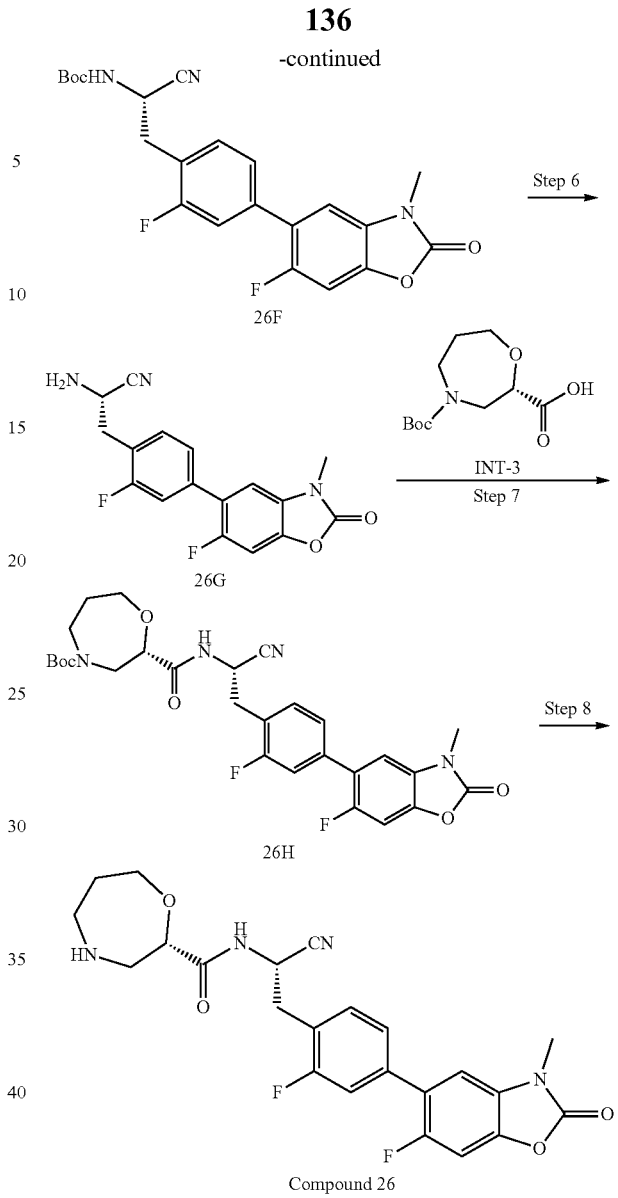

Compound 26

Step 1: 6-fluorobenzo[d]oxazol-2(3H)-one (26B)

26A (10 g, 78.67 mmol) was dissolved in anhydrous DMF (130 mL), a solution of N,N'-carbonyldiimidazole (15.31 g, 94.40 mmol) in DMF (100 mL) was added dropwise under ice bath, and after the addition, the mixture was reacted at 60° C. for 4 h. The reaction solution was cooled to room temperature and 600 mL of water was added. The resulting mixture was extracted with EA (100 mL×4). The organic layers were combined, back-flushed with saturated brine, dried over anhydrous sodium sulfate, and concentrated, and the residue was separated and purified by silica gel column chromatography (PE:EA (v/v)=3:1) to obtain the title compound 26B (11 g, 91%). LC-MS (ESI): m/z=154.1 [M+H]$^+$.

Step 2: 6-fluoro-5-iodobenzo[d]oxazol-2(3H)-one (26C)

26B (3 g, 19.59 mmol) was dissolved in sulfuric acid (40 mL) and N-iodosuccinimide (5.29 g, 23.51 mmol) was added in portions. The mixture was reacted at 40° C.

overnight. The reaction solution was cooled to room temperature, poured into 500 mL of water, and extracted with EA (50 mL×5). The organic layers were combined, back-flushed with saturated aqueous sodium bicarbonate solution (200 mL), dried over anhydrous sodium sulfate, and concentrated, and the residue was separated and purified by silica gel column chromatography (PE:EA (v/v)=4:1) to obtain the title compound 26C (1.1 g, 20%). LC-MS (ESI): m/z=280.0 [M+H]$^+$.

Step 3: 6-fluoro-5-iodo-3-methylbenzo[d]oxazol-2 (3H)-one (26D)

26C (1 g, 3.58 mmol) was dissolved in acetonitrile (40 mL), and potassium carbonate (0.59 g, 4.30 mmol) was added. The mixture was stirred at 40° C. for 30 min and transferred to room temperature. Iodomethane (1.02 g, 7.16 mmol) was added dropwise, and the resulting mixture was reacted at room temperature overnight. Insoluble matters were removed by filtration. The resulting mixture was extracted with EA (50 mL×3). The organic layers were combined, back-flushed with saturated brine, dried over anhydrous sodium sulfate, and concentrated, and the residue was separated and purified by silica gel column chromatography (PE:EA (v/v)=5:1) to obtain the title compound 26D (0.92 g, 88%). LC-MS (ESI): m/z=294.0 [M+H]$^+$.

Step 4: 6-fluoro-3-methyl-5-(4,4,5,5-tetramethyl-1,3,2-dioxaborolan-2-yl)benzo[d]oxazol-2(3H)-one (26E)

26D (0.92 g, 3.14 mmol), bis(pinacolato)diboron (0.96 g, 3.77 mmol), [1,1'-(diphenylphosphino)ferrocene]palladium dichloride (0.23 g, 0.31 mmol), and potassium acetate (0.92 g, 9.42 mmol) were dissolved in dioxane (40 mL), and the mixture was reacted at 100° C. under nitrogen protection for 5 h. The reaction solution was cooled to room temperature and 120 mL of water was added. The resulting mixture was extracted with EA (30 mL×3). The organic layers were combined, back-flushed with saturated brine, dried over anhydrous sodium sulfate, and concentrated, and the residue was separated and purified by silica gel column chromatography (PE:EA (v/v)=5:1) to obtain the title compound 26E (0.52 g, 56%).
$^1$H NMR (400 MHz, CDCl$_3$) δ 7.25 (d, J=4.5 Hz, 1H), 6.95 (d, J=8.2 Hz, 1H), 3.41 (s, 3H), 1.37 (s, 12H). LC-MS (ESI): m/z=294.1 [M+H]$^+$.

Step 5: tert-butyl (S)-(1-cyano-2-(2-fluoro-4-(6-fluoro-3-methyl-2-oxo-2,3-dihydrobenzo[d]oxazol-5-yl)phenyl)ethyl)carbamate (26F)

2a (0.62 g, 1.81 mmol), 26E (0.53 g, 1.81 mmol), [1,1'-(diphenylphosphino)ferrocene]palladium dichloride (0.13 g, 0.18 mmol), and potassium carbonate (0.75 g, 5.43 mmol) were dissolved in a mixed solvent of dioxane (27 mL) and water (3 mL), and the mixture was reacted at 90° C. under nitrogen protection for 5 h. The reaction solution was cooled to room temperature and 50 mL of water was added. The resulting mixture was extracted with ethyl acetate (20 mL×3). The organic layers were combined, successively washed with saturated sodium bicarbonate (20 mL) and saturated brine (20 mL), dried over anhydrous sodium sulfate, and concentrated, and the residue was separated and purified by silica gel column chromatography (PE:EA (v/v)=2:1) to obtain the title compound 26F (0.6 g, 77%). LC-MS (ESI): m/z=430.1 [M+H]$^+$.

Step 6: (S)-2-amino-3-(2-fluoro-4-(6-fluoro-3-methyl-2-oxo-2,3-dihydrobenzo[d]oxazol-5-yl)phenyl)propanenitrile (26G)

26F (0.6 g, 1.40 mmol) was dissolved in anhydrous formic acid (3 mL) and the mixture was reacted at 50° C. for 20 min. The reaction solution was cooled to room temperature and concentrated to remove most of the solvent. Saturated sodium bicarbonate solution (20 mL) was added to the residue and the resulting mixture was extracted with EA (10 mL×3). The organic layers were combined, dried over anhydrous sodium sulfate, and concentrated, and the residue was separated and purified by silica gel column chromatography (dichloromethane:methanol (v/v)=97:3) to obtain the title compound 26G (0.36 g, 78%). LC-MS (ESI): m/z=330.0 [M+H]$^+$.

Step 7: tert-butyl (S)-2-(((S)-1-cyano-2-(2-fluoro-4-(6-fluoro-3-methyl-2-oxo-2,3-dihydrobenzo[d]oxazol-5-yl)phenyl)ethyl)carbamoyl)-1,4-oxazepane-4-carboxylate (Compound 26H)

INT-3 (0.26 g, 1.06 mmol) was dissolved in DMF (5 mL) and then HATU (0.6 g, 1.59 mmol) and DIPEA (0.41 g, 3.18 mmol) were added under nitrogen protection. After the mixture was stirred at room temperature for 20 min, 26G (0.35 g, 1.06 mmol) was added. The resulting mixture was reacted at room temperature for 1 h. To the reaction solution, 30 mL of water was added. The resulting mixture was extracted with EA (15 mL×5). The organic layers were combined, dried over anhydrous sodium sulfate and concentrated. The residue was separated and purified by silica gel column chromatography (dichloromethane/methanol (v/v)=97:3) to obtain the title compound 26H (0.33 g, 56%). LC-MS (ESI): m/z=501.1 [M+H]$^+$.

Step 8: (S)—N—((S)-1-cyano-2-(2-fluoro-4-(6-fluoro-3-methyl-2-oxo-2,3-dihydrobenzo[d]oxazol-5-yl)phenyl)ethyl)-1,4-oxazepane-2-carboxamide (Compound 26)

26H (0.33 g, 0.59 mmol) was dissolved in anhydrous formic acid (3 mL) and the mixture was reacted at 50° C. for 1 h. The reaction solution was cooled to room temperature and concentrated to remove most of the solvent. Saturated sodium bicarbonate solution (25 mL) was added to the residue and the resulting mixture was extracted with EA multiple times until barely any product remained in the aqueous layer. The organic layers were combined, dried over anhydrous sodium sulfate, and concentrated, and the residue was separated and purified by silica gel column chromatography (dichloromethane:methanol (v/v)=10:1) to obtain compound 26 (120 mg, 44%).
$^1$H NMR (400 MHz, CD$_3$OD) δ 7.47-7.22 (m, 5H), 5.17 (dd, J=8.8, 6.8 Hz, 1H), 4.13 (dd, J=8.8, 3.6 Hz, 1H), 4.02-3.95 (m, 1H), 3.79 (m, 1H), 3.43 (s, 3H), 3.38-3.34 (m, 1H), 3.27-3.18 (m, 2H), 2.99-2.91 (m, 1H), 2.87-2.78 (m, 1H), 2.67 (dd, J=14.4, 8.6 Hz, 1H), 2.22-2.15 (m, 1H), 2.03 (m, 1H). LC-MS (ESI): m/z=457.1 [M+H]$^+$.

Example 27: (S)—N—((S)-1-cyano-2-(2-fluoro-4-(1-(oxetan-3-yl)-1,2,3,6-tetrahydropyridin-4-yl)phenyl)ethyl)-1,4-oxazepane-2-carboxamide

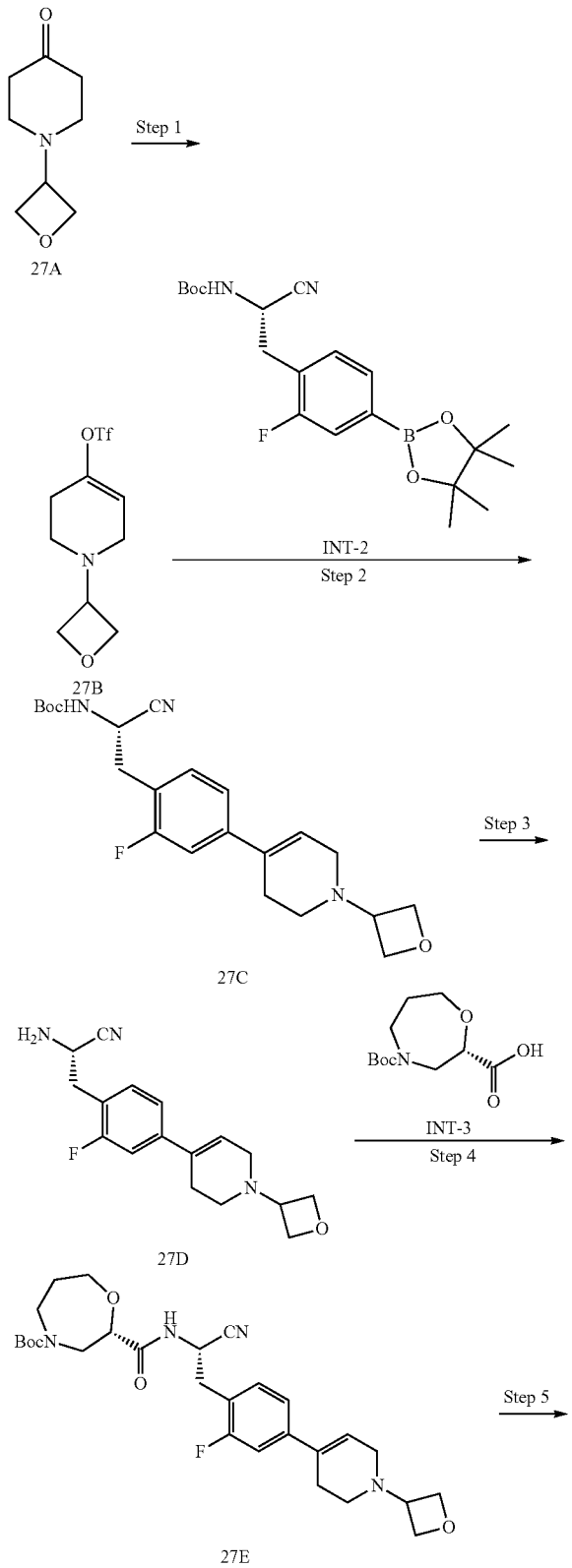

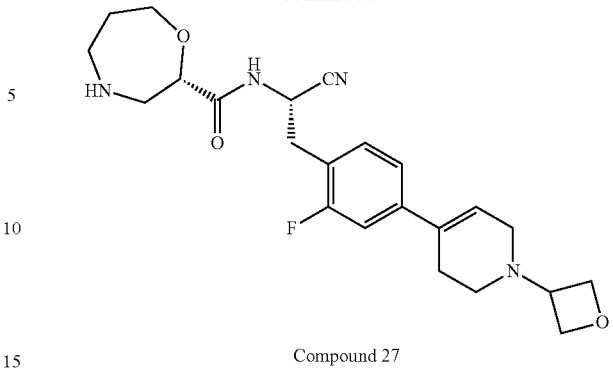

Compound 27

Step 1: 1-(oxetan-3-yl)-1,2,3,6-tetrahydropyridin-4-yl trifluoromethanesulfonate (27B)

At −78° C., under nitrogen protection, LDA (2.6 mL, 5.2 mmol) was slowly added dropwise to 27A (400 mg, 2.6 mmol, prepared with reference to WO 2016/172496 A1) in THF (4.0 mL). Stirring was continued for 30 minutes at this temperature and then a solution of N,N-bis(trifluoromethylsulfonyl)aniline (1.40 g, 3.9 mmol) in THF (2.0 mL) was added dropwise. The resulting mixture was allowed to naturally warm to room temperature and reacted for 1 hour. Water (5 mL) was added to quench the reaction, and the reaction solution was extracted with ethyl acetate (5 mL×3). The organic phases were combined, washed with water (5 mL×1) and saturated sodium chloride (5 mL×1), dried over anhydrous sodium sulfate, filtered and concentrated under reduced pressure, and the residue was subjected to column chromatography (DCM:MeOH=50:1-20:1) to obtain 27B as a pale yellow liquid (240 mg, 32.4%). LC-MS (ESI): m/z=288.1 [M+H]$^+$.

Step 2: tert-butyl-(S)-(1-cyano-2-(2-fluoro-4-(1-(oxetan-3-yl)-1,2,3,6-tetrahydropyridin-4-yl)phenyl)ethyl)carbamate (27C)

INT-2 (200 mg, 0.6 mmol), 27B (200 mg, 0.7 mmol), Pd(dppf)Cl$_2$ (44 mg, 0.06 mmol), and sodium carbonate (190 mg, 1.8 mmol) were added to a mixed solvent of 1,4-dioxane (5 mL) and water (1 mL) at room temperature, and the mixture was subjected to nitrogen replacement three times, warmed to 60° C., and reacted for 2 hours. The reaction solution was cooled to room temperature and subjected to rotary evaporation, and the residue was directly purified by column chromatography (DCM:MeOH=50:1-20:1) to obtain the title compound 27C as a yellow solid (180 mg, 64%). LC-MS (ESI): m/z=402.2 [M+H]$^+$.

Step 3: (S)-2-amino-3-(2-fluoro-4-(1-(oxetan-3-yl)-1,2,3,6-tetrahydropyridin-4-yl)phenyl)propanenitrile (27D)

27C (180 mg, 0.4 mmol) was added to anhydrous formic acid (3.0 mL) at room temperature and the mixture was warmed to 50° C. and reacted for 20 minutes. Most of formic acid was removed under reduced pressure, and saturated sodium bicarbonate was added to neutralize the solution to a basic pH. The resulting solution was extracted with dichloromethane (10 mL×4), washed with saturated sodium chloride (5 mL×1), dried over anhydrous sodium sulfate, filtered, and concentrated under reduced pressure to obtain the crude product of compound 27D as a yellow viscous substance (200 mg). LC-MS (ESI): m/z=302.2 [M+H]⁺.

Step 4: tert-butyl-(S)-2-(((S)-1-cyano-2-(2-fluoro-4-(1-(oxetan-3-yl)-1,2,3,6-tetrahydropyridin-4-yl) phenyl)ethyl)carbamoyl)-1,4-oxazepane-4-carboxylate (27E)

The crude product of 27D (200 mg), INT-3 (170 mg, 0.7 mmol), and DIPEA (180 mg, 1.4 mmol) were added to dichloromethane at room temperature, then HATU (270 mg, 0.7 mmol) was added, and stirring was continued at room temperature for 1 hour. The reaction solution was subjected to rotary evaporation and the residue was directly purified by column chromatography (DCM:MeOH=50:1-20:1) to obtain 27E as a yellow solid (200 mg, two-step yield: 94%). LC-MS (ESI): m/z=529.3 [M+H]⁺.

Step 5: (S)—N—((S)-1-cyano-2-(2-fluoro-4-(1-(oxetan-3-yl)-1,2,3,6-tetrahydropyridin-4-yl)phenyl) ethyl)-1,4-oxazepane-2-carboxamide (Compound 27)

27E (150 mg, 0.3 mmol) was added to anhydrous formic acid (3.0 mL) at room temperature and the mixture was warmed to 50° C. and reacted for 30 minutes. Most of formic acid was removed under reduced pressure, and saturated sodium bicarbonate was added to neutralize the solution to a basic pH. The resulting solution was extracted with dichloromethane (10 mL×4), washed with saturated sodium chloride (5 mL×1), dried over anhydrous sodium sulfate, filtered, and concentrated under reduced pressure to obtain compound 27 (40 mg, 33%). LC-MS (ESI): m/z=429.3 [M+H]⁺.

¹H NMR (400 MHz, CDCl₃) δ 7.27-7.21 (m, 2H), 7.18-7.15 (m, 1H), 7.12-7.08 (m, 1H), 6.12-6.10 (m, 1H), 5.16-5.10 (m, 1H), 4.74-4.68 (m, 4H), 4.18-4.15 (m, 1H), 4.05-3.99 (m, 1H), 3.81-3.75 (m, 1H), 3.68-3.63 (m, 1H), 3.42-3.37 (m, 1H), 3.22-3.14 (m, 2H), 3.09-3.07 (m, 2H), 3.01-2.92 (m, 3H), 2.61-2.56 (m, 4H), 1.95-1.92 (m, 3H).

Example 28: (S)—N—((S)-1-cyano-2-(2-fluoro-4-(7-methoxy-1-methyl-1H-indol-4-yl)phenyl)ethyl)-1,4-oxazepane-2-carboxamide (Compound 28)

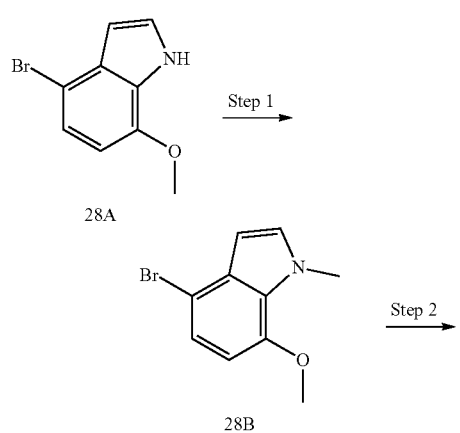

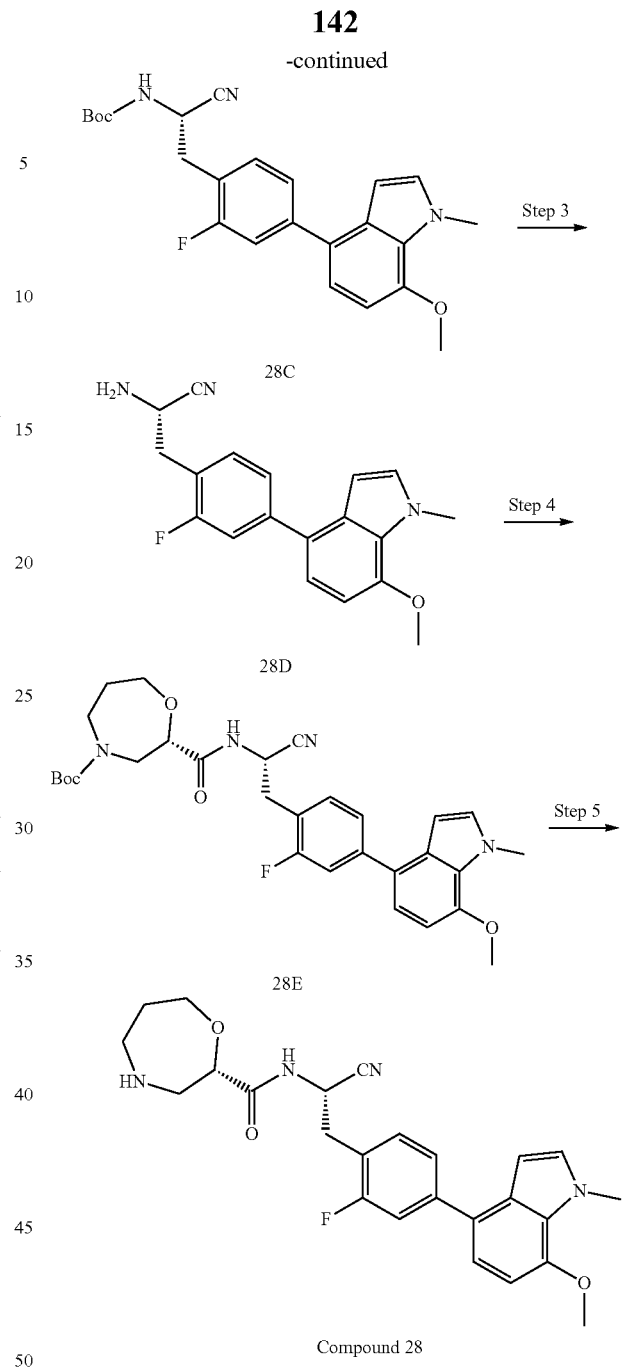

Step 1: 4-bromo-7-methoxy-1-methyl-1H-indole (28B)

28A (0.50 g, 2.21 mmol) was dissolved in acetonitrile (5 mL), cesium carbonate (1.44 g, 4.22 mmol) and iodomethane (0.47 g, 3.31 mmol) were added, and upon completion of the addition, the mixture was reacted at room temperature overnight. Water (25 mL) was added. The resulting mixture was extracted with ethyl acetate (30 mL×3). The combined organic phase was dried over anhydrous sodium sulfate, filtered and concentrated, and the residue was separated and purified by silica gel column chromatography (PE:EA (v/v)=4:1) to obtain the title compound 28B as a white solid (0.50 g, 94.23%). LC-MS (ESI): m/z=240.1 [M+H]⁺.

Step 2: tert-butyl (S)-(2-(4-(benzo[d]thiazol-2-yl)-2-fluorophenyl)-1-cyanoethyl)carbamate (28C)

28B (0.40 g, 1.02 mmol) was dissolved in 1,4-dioxane (10 mL) and water (0.4 mL), and then INT-2 (0.26 g, 1.22 mmol), [1,1'-bis(diphenylphosphino)ferrocene]palladium dichloride dichloromethane complex (0.17 g, 0.20 mmol), and potassium carbonate (0.28 g, 2.04 mmol) were added. Upon completion of the addition, the mixture was heated to 90° C. and reacted for 2 h under nitrogen protection. Then the reaction solution was reacted at room temperature overnight. The resulting reaction mixture was concentrated to dryness and saturated aqueous ammonium chloride solution (50 mL) was added. The resulting mixture was extracted with ethyl acetate (20 mL×3). The combined organic phase was dried over anhydrous sodium sulfate, filtered and concentrated, and the residue was separated and purified by silica gel column chromatography (PE:EA (v/v)=4:1) to obtain the title compound 28C as a pale yellow liquid (0.24 g, 59.20%). LC-MS (ESI): m/z=398.1 [M+H]$^+$.

Step 3: (S)-2-amino-3-(4-(benzo[d]thiazol-2-yl)-2-fluorophenyl)propanenitrile (28D)

28C (0.32 g, 0.81 mmol) was dissolved in formic acid (5 mL) and upon completion of the addition, the mixture was reacted at 30° C. for 3 h. Saturated aqueous sodium bicarbonate solution was added dropwise to adjust the pH to about 8, and the resulting mixture was extracted with ethyl acetate (25 mL×3). The combined organic phase was dried over anhydrous sodium sulfate, filtered and concentrated to obtain the title compound 28D as a colorless liquid (0.24 g, 99.65%), which was directly used in the next reaction. LC-MS (ESI): m/z=298.1 [M+H]$^+$.

Step 4: tert-butyl (S)-2-(((S)-2-(4-(benzo[d]thiazol-2-yl)-2-fluorophenyl)-1-cyanoethyl)carbamoyl)-1,4-oxazepane-4-carboxylate (28E)

28D (0.24 g, 0.81 mmol) was dissolved in dichloromethane (10 mL) and then INT-3 (0.26 g, 1.05 mmol), diisopropylethylamine (0.31 g, 2.43 mmol), and N,N,N',N'-tetramethyl-O-(7-azabenzotriazol-1-yl)uronium hexafluorophosphate (0.46 g, 1.22 mmol) were added. Upon completion of the addition, the mixture was reacted at room temperature overnight. Saturated aqueous sodium chloride solution (30 mL) was added and then the resulting mixture was extracted with ethyl acetate (25 mL). The organic phase was washed with saturated aqueous sodium chloride solution (25 mL×3), dried over anhydrous sodium sulfate, filtered and concentrated, and the residue was separated and purified by silica gel column chromatography (PE:EA (v/v)=4:1) to obtain the title compound 28E as a pale yellow solid (0.25 g, 58.83%). LC-MS (ESI): m/z=469.2 [M−57+H]$^+$.

Step 5: (S)—N—((S)-1-cyano-2-(2-fluoro-4-(7-methoxy-1-methyl-1H-indol-4-yl)phenyl)ethyl)-1,4-oxazepane-2-carboxamide (Compound 28)

28E (0.32 g, 0.59 mmol) was dissolved in formic acid (2.0 mL) and upon completion of the addition, the mixture was reacted at 35° C. for 4 h. The reaction solution was concentrated to dryness and ethyl acetate (25 mL) was added. Then saturated aqueous sodium bicarbonate solution was added dropwise to adjust the pH to about 8. The organic layer was separated and the remaining aqueous layer was extracted with ethyl acetate (25 mL×3). The combined organic phase was dried over anhydrous sodium sulfate, filtered and concentrated, and the residue was separated and purified by silica gel column chromatography (dichloromethane:methanol (v/v)=20:1) to obtain the title compound 28 (30 mg, 14.72%).

$^1$H NMR (400 MHz, CDCl$_3$) δ 7.49-7.28 (m, 3H), 7.04-6.88 (m, 2H), 6.67 (d, 1H), 6.54 (d, 1H), 5.32-5.04 (m, 1H), 4.12-4.05 (m, 4H), 4.01-3.89 (m, 4H), 3.75 (m, 1H), 3.26 (qd, 3H), 2.97-2.82 (m, 3H), 1.90-1.68 (m, 2H). LC-MS (ESI): m/z=451.2 [M+H]$^+$.

Example 29: (S)—N—((S)-1-cyano-2-(4'-cyano-3-fluoro-3'-(trifluoromethyl)-[1,1'-biphenyl]-4-yl)ethyl)-1,4-oxazepane-2-carboxamide (Compound 29)

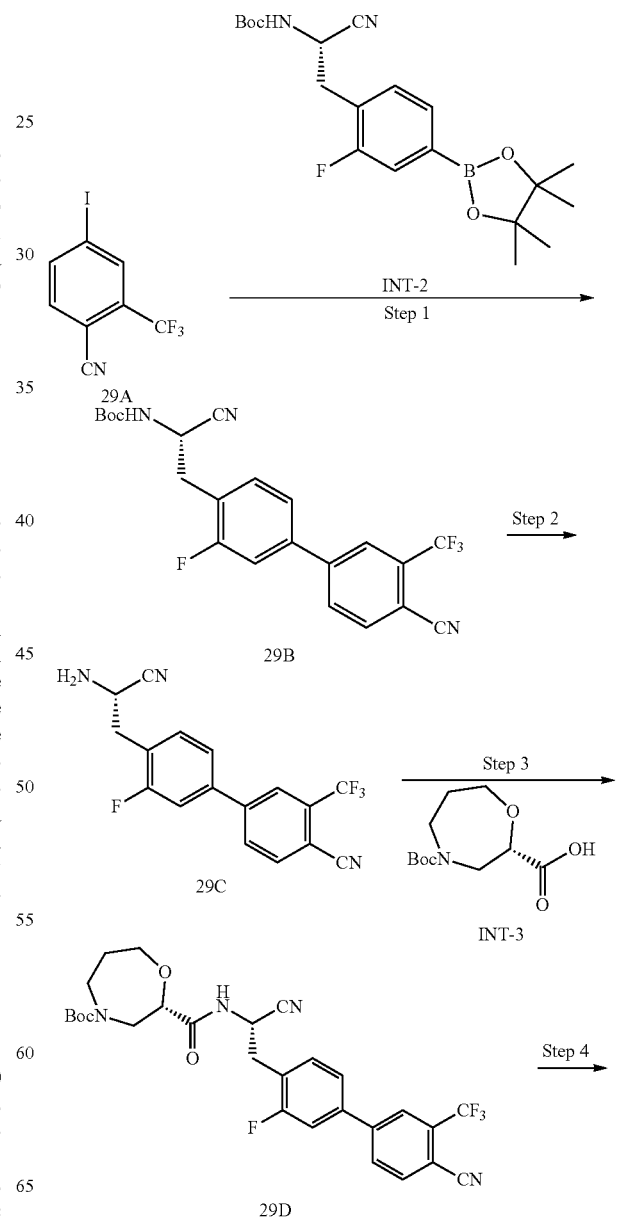

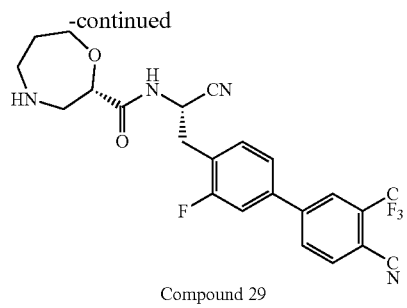

Compound 29

Step 1: tert-butyl (S)-(1-cyano-2-(4'-cyano-3-fluoro-3'-(trifluoromethyl)-[1,1'-biphenyl]-4-yl)ethyl)carbamate (29B)

29A (300.0 mg, 1.00 mmol), INT-2 (470.0 mg, 1.20 mmol), Pd(dppf)Cl$_2$ (160.0 mg, 0.20 mmol), and potassium carbonate (280.0 mg, 2.00 mmol) were added to a single-necked flask, and then 1,4-dioxane (10 mL) and water (0.4 mL) were added. The mixture was subjected to nitrogen replacement 3 times and then reacted at 95° C. for 4 hours. The reaction solution was cooled to room temperature and then concentrated, and the residue was separated and purified by silica gel column chromatography (PE:EA (v/v)=2:1) to obtain the title compound 29B as a white solid (230.0 mg, 53.1%). LC-MS (ESI): m/z=377.1 [M−57+H]$^+$.

Step 2: (S)-4'-(2-amino-2-cyanoethyl)-3'-fluoro-3-(trifluoromethyl)-[1,1'-biphenyl]-4-carbonitrile (29C)

29B (230.0 mg, 0.53 mmol) was dissolved in formic acid (5 mL) and the mixture was reacted at 35° C. for 4 h. The reaction system was adjusted to a basic pH with saturated potassium carbonate solution, extracted with ethyl acetate (30 mL×2), dried over anhydrous sodium sulfate, filtered and concentrated to obtain the title compound 29C as a pale yellow oil (180.0 mg, 100%), which was directly used in the next reaction. LC-MS (ESI): m/z=334.1 [M+H]$^+$.

Step 3: tert-butyl (S)-2-(((S)-1-cyano-2-(4'-cyano-3-fluoro-3'-(trifluoromethyl)-[1,1'-biphenyl]-4-yl)ethyl)carbamoyl)-1,4-oxazepane-4-carboxylate (29D)

29C (180 mg, 0.54 mmol) was dissolved in DMF (5 mL) and then INT-3 (160 mg, 0.65 mmol), HATU (250 mg, 0.65 mmol), and DIPEA (210 mg, 1.62 mmol) were added. Upon completion of the addition, the mixture was reacted at room temperature overnight. Water (20 mL) was added to the system. The resulting mixture was extracted with ethyl acetate (30 mL×2), dried over anhydrous sodium sulfate, filtered, and concentrated, and the residue was separated and purified by silica gel column chromatography (PE:EA (v/v)=2:1) to obtain the title compound 29D as a white solid (280 mg, 92.5%). LC-MS (ESI): m/z=505.2 [M−57+H]$^+$.

Step 4: (S)—N—((S)-1-cyano-2-(4'-cyano-3-fluoro-3'-(trifluoromethyl)-[1,1'-biphenyl]-4-yl)ethyl)-1,4-oxazepane-2-carboxamide (Compound 29)

29D (280 mg, 0.50 mmol) was dissolved in formic acid (5 mL) and the mixture was reacted at 35° C. for 4 h. The reaction system was adjusted to a basic pH with saturated potassium carbonate solution, extracted with ethyl acetate (30 mL×2), dried over anhydrous sodium sulfate, filtered and concentrated, and the residue was separated and purified by silica gel column chromatography (dichloromethane:methanol (v/v)=30:1) to obtain the title compound 29 (100.0 mg, 43.4%).

$^1$H NMR (400 MHz, CDCl$_3$) δ 7.96-7.92 (m, 2H), 7.85 (dd, 1H), 7.49 (t, 1H), 7.40 (dd, 1H), 7.35 (dd, 1H), 5.23-5.17 (m, 1H), 4.09 (q, 1H), 4.05-4.00 (m, 1H), 3.80-3.74 (m, 1H), 3.30 (dd, 1H), 3.29-3.20 (m, 2H), 2.98-2.86 (m, 3H), 1.93-1.80 (m, 2H), 1.61-1.50 (m, 2H). LC-MS (ESI): m/z=461.2 [M+H]$^+$.

Example 30: (S)—N—((S)-1-cyano-2-(2-fluoro-4-(3-oxoisoindolin-5-yl)phenyl)ethyl)-1,4-oxazepane-2-carboxamide (Compound 30)

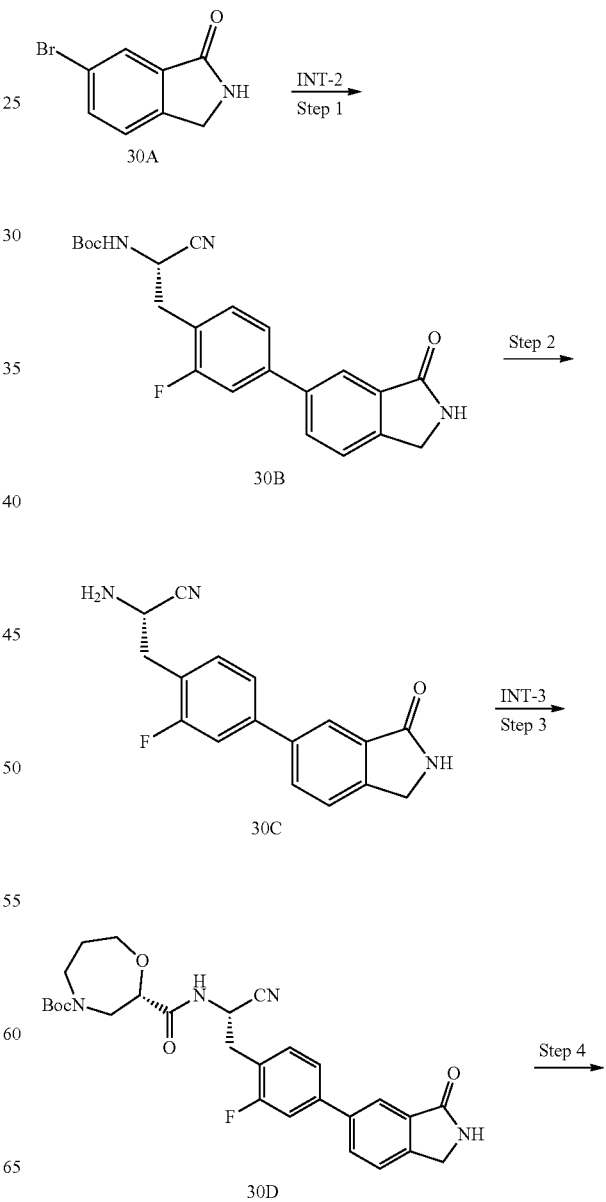

147

-continued

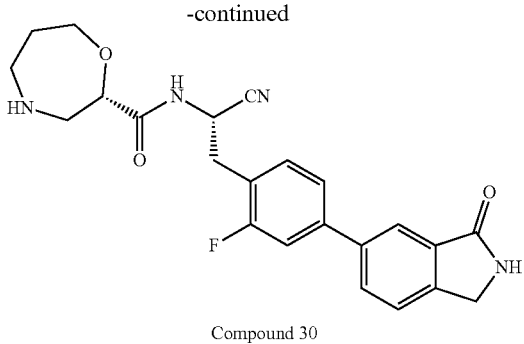

Compound 30

Step 1: tert-butyl (S)-(1-cyano-2-(2-fluoro-4-(3-oxoisoindolin-5-yl)phenyl)ethyl)carbamate (30B)

30A (0.20 g, 0.95 mmol), INT-2 (0.31 g, 0.79 mmol), [1,1'-bis(diphenylphosphino)ferrocene]palladium dichloride (0.12 g, 0.16 mmol), and potassium carbonate (0.22 g, 1.58 mmol) were successively added to 1,4-dioxane (20 mL) and water (4 mL), and the system was subjected to nitrogen replacement three times and reacted at 100° C. for 2.5 hours. After the reaction was completed, the reaction solution was cooled to room temperature, water (40 mL) was added, and the resulting aqueous phase was extracted with ethyl acetate (60 mL×3). The combined organic phase was washed with saturated aqueous sodium chloride solution (100 mL), dried over anhydrous sodium sulfate, and filtered. The filtrate was concentrated under reduced pressure. The residue was separated by silica gel column chromatography (PE:EA (v/v)=3:1-2:1) to obtain 30B (0.26 g, yield: 83%). LCMS m/z=396.1 [M+H]+.

Step 2: (S)-2-amino-3-(2-fluoro-4-(3-oxoisoindolin-5-yl)phenyl)propanenitrile (30C)

30B (0.26 g, 0.66 mmol) was dissolved in formic acid (5.0 mL) and upon completion of the addition, the mixture was reacted at 50° C. for 10 minutes. The reaction solution was concentrated to dryness. Ethyl acetate (60 mL) was added and then saturated aqueous sodium bicarbonate solution was added dropwise to adjust the pH to about 8. The organic layer was separated and the aqueous phase was extracted with ethyl acetate (60 mL×3). The combined organic phase was dried over anhydrous sodium sulfate, filtered and concentrated to obtain the title compound 30C (0.15 g, yield: 77%). LCMS m/z=296.1[M+H]+.

Step 3: tert-butyl (S)-2-(((S)-1-cyano-2-(2-fluoro-4-(3-oxoisoindolin-5-yl)phenyl)ethyl)carbamoyl)-1,4-oxazepane-4-carboxylate (30D)

30C (0.15 g, 0.51 mmol) was dissolved in N,N'-dimethylformamide (10 mL) and then INT-3 (0.13 g, 0.51 mmol), triethylamine (0.1 g, 1 mmol), and N,N,N',N'-tetramethyl-O-(7-azabenzotriazol-1-yl)uronium hexafluorophosphate (0.23 g, 0.61 mmol) were added. Upon completion of the addition, the mixture was reacted at room temperature for 1 hour. Saturated aqueous sodium chloride solution (30 mL) was added and the resulting mixture was extracted with ethyl acetate (60 mL×3). The organic phase was washed with saturated aqueous sodium chloride solution (60 mL), dried over anhydrous sodium sulfate, filtered and concentrated, and the residue was separated by silica gel column chromatography (PE:EA (v/v)=2:1-1:5) to obtain the title compound 30D (0.14 g, yield: 53%).

Step 4: (S)—N—((S)-1-cyano-2-(2-fluoro-4-(3-oxoisoindolin-5-yl)phenyl)ethyl)-1,4-oxazepane-2-carboxamide (Compound 30)

30D (0.14 g, 0.27 mmol) was dissolved in formic acid (6.0 mL) and the mixture was reacted at 50° C. for 10 minutes. The reaction solution was concentrated under reduced pressure and ethyl acetate (60 mL) was added. Then saturated aqueous sodium bicarbonate solution was added dropwise to adjust the pH to about 8. The organic layer was separated and the remaining aqueous layer was extracted with dichloromethane (60 mL×5). The combined organic phase was dried over anhydrous sodium sulfate, filtered and concentrated, and the residue was separated and purified by silica gel column chromatography (dichloromethane:methanol (v/v)=4:1) to obtain compound 30 (48 mg, yield: 42%).

1H NMR (400 MHz, DMSO-d6) δ 8.93 (d, 1H), 8.62 (s, 1H), 7.98-7.92 (m, 2H), 7.71-7.55 (m, 3H), 7.47 (t, 1H), 5.06 (q, 1H), 4.42 (s, 2H), 4.27 (dd, 1H), 3.95-3.90 m, 1H), 3.80-3.72 (m, 1H), 3.28-3.15 (m, 3H), 3.12-3.02 (m, 1H), 2.95-2.87 (m, 1H), 2.81 (dd, 1H), 1.94-1.84 (m, 2H). LC-MS m/z=423.2 [M+H]+.

Example 31: (S)—N—((S)-1-cyano-2-(2-fluoro-4-(2-methyl-3-oxoisoindolin-5-yl)phenyl)ethyl)-1,4-oxazepane-2-carboxamide (Compound 31)

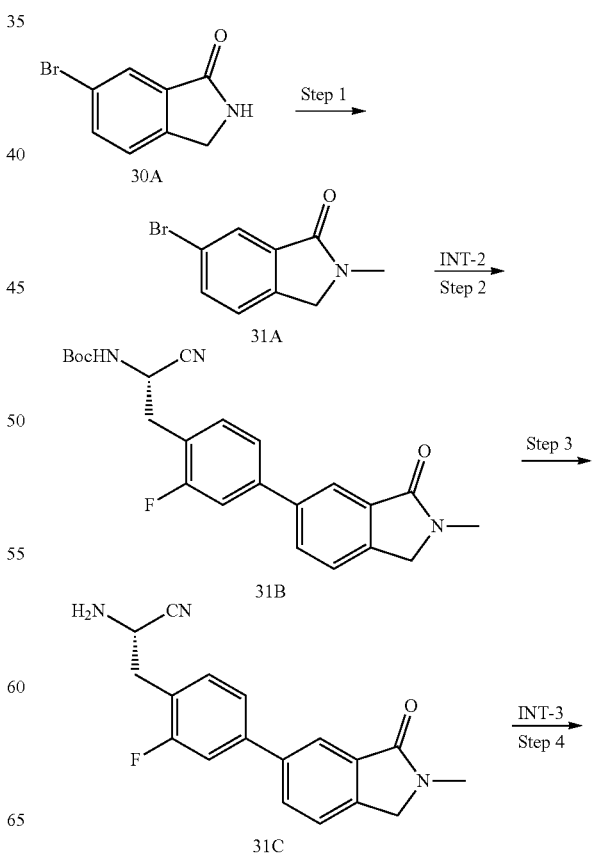

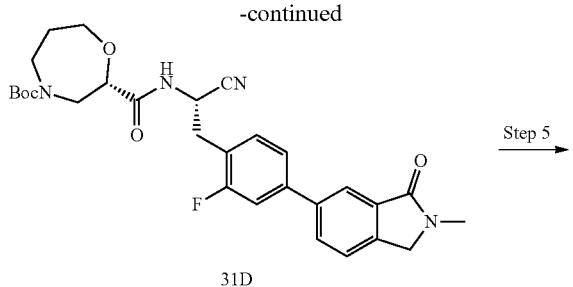

31D

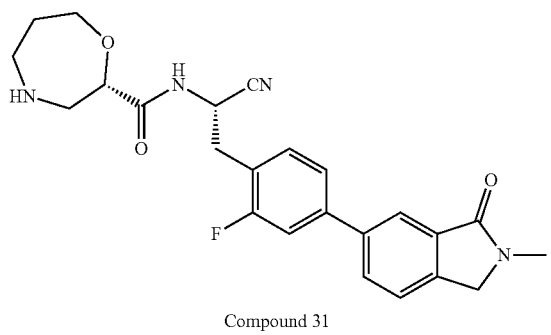

Compound 31

Step 1: 6-bromo-2-methylisoindolin-1-one (31A)

30A (0.49 g, 2.3 mmol) was dissolved in dry N,N-dimethylformamide (20 mL) and the mixture was cooled to 0° C. under nitrogen protection. Sodium hydride (0.14 g, 3.45 mmol, 60% wt) was added in portions. After the addition, the resulting mixture was reacted under such conditions for 20 minutes and then iodomethane (0.49 g, 3.45 mmol) was added dropwise to the system. After the addition, the mixture was reacted at room temperature for 30 minutes. Water (100 mL) was added to quench the reaction and the resulting mixture was extracted with ethyl acetate (100 mL×2). The organic phases were combined, washed with saturated brine (100 mL×1), dried over anhydrous sodium sulfate, and filtered, the filtrate was concentrated under reduced pressure, and the residue was separated by silica gel column chromatography (PE:EA=6:1) to obtain the target compound 31A (0.37 g, yield: 71%).
$^1$H NMR (400 MHz, CDCl$_3$) δ 7.97 (d, 1H), 7.64 (dd, 1H), 7.31 (d, 1H), 4.33 (s, 2H), 3.20 (s, 3H).

Step 2: tert-butyl (S)-(1-cyano-2-(2-fluoro-4-(2-methyl-3-oxoisoindolin-5-yl)phenyl)ethyl)carbamate (31B)

31A (0.18 g, 0.8 mmol), INT-2 (0.29 g, 0.74 mmol), [1,1'-bis(diphenylphosphino)ferrocene]palladium dichloride (0.11 g, 0.15 mmol), and potassium carbonate (0.2 g, 1.48 mmol) were successively added to 1,4-dioxane (20 mL) and water (4 mL), and the system was subjected to nitrogen replacement three times and reacted at 100° C. for 2 hours. After the reaction was completed, the reaction solution was cooled to room temperature, water (40 mL) was added, and the resulting aqueous phase was extracted with ethyl acetate (60 mL×3). The combined organic phase was washed with saturated aqueous sodium chloride solution (100 mL), dried over anhydrous sodium sulfate, and filtered. The filtrate was concentrated under reduced pressure. The residue was separated by silica gel column chromatography (PE:EA (v/v)=3:1-1:1) to obtain 31B (0.27 g, yield: 89%). LCMS m/z=432.1 [M+Na]$^+$.

Step 3: (S)-2-amino-3-(2-fluoro-4-(2-methyl-3-oxoisoindolin-5-yl)phenyl)propanenitrile (31C)

31B (0.27 g, 0.66 mmol) was dissolved in formic acid (6.0 mL) and upon completion of the addition, the mixture was reacted at 50° C. for 10 minutes. The reaction solution was concentrated to dryness. Ethyl acetate (60 mL) was added and then saturated aqueous sodium bicarbonate solution was added dropwise to adjust the pH to about 8. The organic layer was separated and the aqueous phase was extracted with ethyl acetate (60 mL×3). The combined organic phase was dried over anhydrous sodium sulfate, filtered and concentrated to obtain the title compound 31C (0.16 g, yield: 78%). LCMS m/z=310.2[M+H]$^+$.

Step 4: tert-butyl (S)-2-(((S)-1-cyano-2-(2-fluoro-4-(2-methyl-3-oxoisoindolin-5-yl)phenyl)ethyl)carbamoyl)-1,4-oxazepane-4-carboxylate (31D)

31C (0.16 g, 0.52 mmol) was dissolved in N,N'-dimethylformamide (10 mL) and then INT-3 (0.13 g, 0.52 mmol), triethylamine (0.1 g, 1 mmol), and N,N,N',N'-tetramethyl-O-(7-azabenzotriazol-1-yl)uronium hexafluorophosphate (0.24 g, 0.62 mmol) were added. Upon completion of the addition, the mixture was reacted at room temperature for 1 hour. Saturated aqueous sodium chloride solution (30 mL) was added and the resulting mixture was extracted with ethyl acetate (60 mL×3). The organic phase was washed with saturated aqueous sodium chloride solution (60 mL), dried over anhydrous sodium sulfate, filtered and concentrated, and the residue was separated by silica gel column chromatography (PE:EA (v/v)=2:1-1:3) to obtain the title compound 31D (0.21 g, yield: 75%). LCMS m/z=559.2[M+Na]$^+$.

Step 5: (S)—N—((S)-1-cyano-2-(2-fluoro-4-(2-methyl-3-oxoisoindolin-5-yl)phenyl)ethyl)-1,4-oxazepane-2-carboxamide (Compound 31)

31D (0.21 g, 0.39 mmol) was dissolved in formic acid (6.0 mL) and the mixture was reacted at 50° C. for 10 minutes. The reaction solution was concentrated under reduced pressure and ethyl acetate (60 mL) was added. Then saturated aqueous sodium bicarbonate solution was added dropwise to adjust the pH to about 8. The organic layer was separated and the remaining aqueous layer was extracted with dichloromethane (60 mL×5). The combined organic phase was dried over anhydrous sodium sulfate, filtered and concentrated, and the residue was separated and purified by silica gel column chromatography (dichloromethane:methanol (v/v)=10:1) to obtain compound 31 (100 mg, yield: 59%).
$^1$H NMR (400 MHz, DMSO-d$_6$) δ 8.85 (d, 1H), 7.94-7.90 (m, 2H), 7.68 (d, 1H), 7.65-7.56 (m, 2H), 7.46 (t, 1H), 5.11-5.01 (m, 1H), 4.51 (s, 2H), 4.18 (dd, 1H), 3.94-3.84 (m, 1H), 3.79-3.70 (m, 1H), 3.26-3.14 (m, 3H), 3.10 (s, 3H), 3.02-2.92 (m, 1H), 2.87-2.69 (m, 2H), 1.90-1.77 m, 2H). LC-MS m/z=437.2 [M+H]$^+$.

Example 32: (2S)—N-(1-cyano-2-(3-fluoro-5-(3-methyl-2-oxo-2,3-dihydrobenzo[d]oxazol-5-yl)thiophen-2-yl)ethyl)-1,4-oxazepane-2-carboxamide (Compound 32)

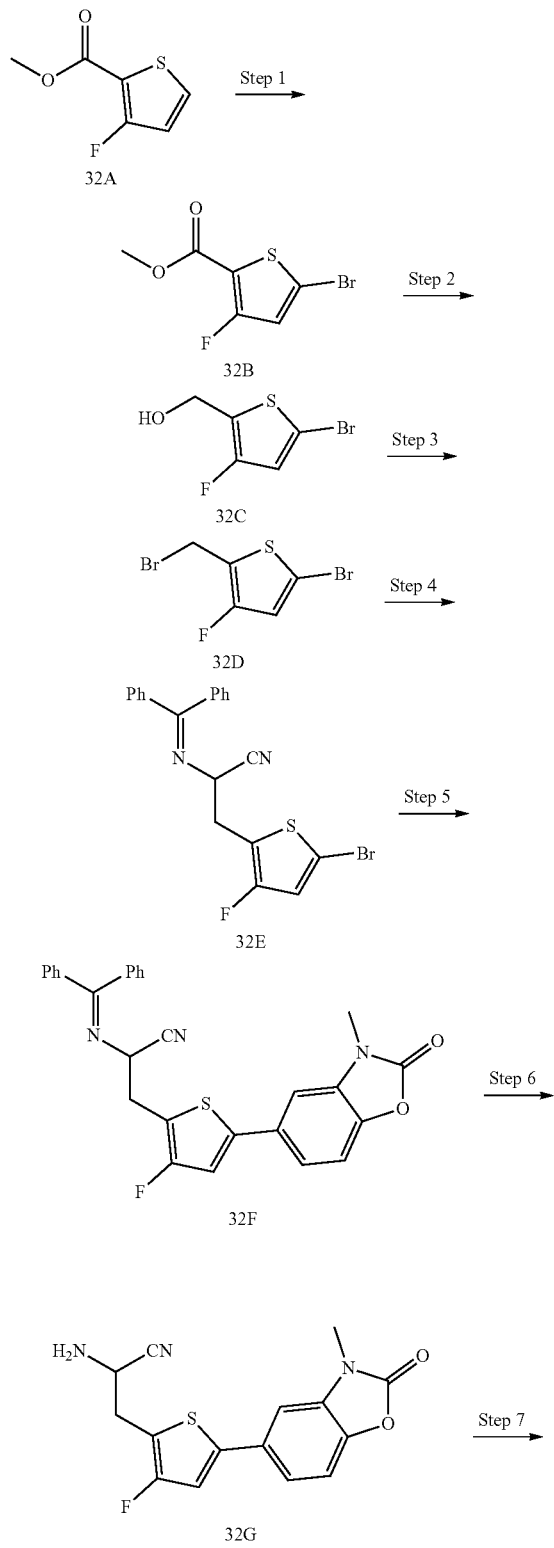

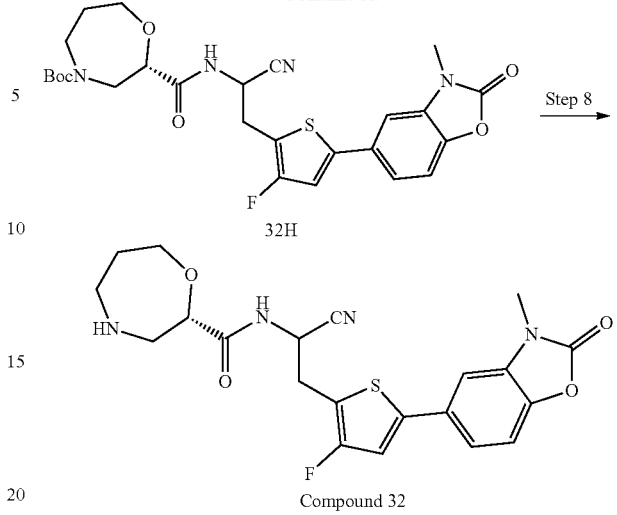

Step 1: methyl 5-bromo-3-fluorothiophene-2-carboxylate (32B)

At room temperature, 32A (15 g, 93.7 mmol) was dissolved in chloroform (200 mL), bromine (120 g, 750 mmol) was added, and the mixture was heated to 80° C. and reacted for 3 hours. The reaction solution was poured into saturated sodium thiosulfate solution (500 mL), the organic phase was concentrated to dryness, and the residue was separated and purified by preparative chromatography to obtain the title compound 32B (10 g, yield: 45%).

Step 2: (5-bromo-3-fluorothiophen-2-yl)methanol (32C)

At room temperature, 32B (5 g, 20.9 mmol) was dissolved in dichloromethane (120 mL) and then diisobutylaluminum hydride (42 mL, 62.8 mmol) was added dropwise. The mixture was reacted at room temperature for 3 hours and water (100 mL) was added. The resulting mixture was filtered, and the organic phase was concentrated to dryness to obtain the title compound 32C (4 g, yield: 90%).

Step 3: 5-bromo-2-(bromomethyl)-3-fluorothiophene (32D)

At room temperature, 32C (4 g, 19.0 mmol) was dissolved in dichloromethane (60 mL), and carbon tetrabromide (7.5 g, 22.7 mmol) and triphenylphosphine (7.5 g, 28.4 mmol) were added. The mixture was reacted at room temperature for 2 hours, the reaction solution was concentrated to dryness, and the residue was directly purified by column chromatography (PE:EA (v:v)=20:1-10:1) to obtain the title compound 32D (4 g, yield: 77%).

Step 4: 3-(5-bromo-3-fluorothiophen-2-yl)-2-((diphenylmethylene)amino)propanenitrile (32E)

At room temperature, 32D (2 g, 7.3 mmol) was dissolved in dichloromethane (40 mL) and water (4 mL), sodium hydroxide (0.5 g, 13.1 mmol) and benzyltrimethylammonium chloride (140 mg, 0.73 mmol) were added, and the mixture was reacted at room temperature for 16 hours. The reaction solution was washed with water (50 mL×1), the organic phase was concentrated, and the residue was directly purified by column chromatography (PE:EA (v:v)=20:1-10:1) to obtain the title compound 32E (1.2 g, yield: 40%). LC-MS (ESI): m/z=413.1[M+H]$^+$.

Step 5: 2-((diphenylmethylene)amino)-3-(3-fluoro-5-(3-methyl-2-oxo-2,3-dihydrobenzo[d]oxazol-5-yl)thiophen-2-yl)propanenitrile (32F)

At room temperature, 32E (1.2 g, 2.9 mmol) was dissolved in dioxane (30 mL) and water (3 mL), and 1A (1 g, 3.5 mmol), potassium carbonate (1 g, 7.3 mmol), 2-dicyclohexylphosphino-2,4,6-triisopropylbiphenyl (0.28 g, 0.6 mmol), and palladium acetate (0.065 g, 0.29 mmol) were successively added. The mixture was reacted at 100° C. for 3 hours, and the reaction solution was directly stirred with silica gel for purification by column chromatography (PE:EA (v:v)=5:1-1:1), to obtain the title compound 32F (1.4 g, yield: 70%). LC-MS (ESI): m/z=482.1 [M+H]$^+$.

Step 6: 2-amino-3-(3-fluoro-5-(3-methyl-2-oxo-2,3-dihydrobenzo[d]oxazol-5-yl)thiophen-2-yl)propanenitrile (32G)

At room temperature, 32F (1.4 g, 2.9 mmol) was dissolved in tetrahydrofuran (20 mL), 1N hydrochloric acid (40 mL) was added, and the mixture was reacted at room temperature for 1 hour. The reaction solution was extracted with ethyl acetate (50 mL×1) to remove the impurities and then the aqueous phase was adjusted to the pH of 8-9 with potassium carbonate and extracted with ethyl acetate (50 mL×2) for the product. The organic phase was concentrated to obtain the title compound 32G (0.45 g, yield: 49%). LC-MS (ESI): m/z=318.1 [M+H]$^+$.

Step 7: (2S)-tert-butyl-2-((1-cyano-2-(3-fluoro-5-(3-methyl-2-oxo-2,3-dihydrobenzo[d]oxazol-5-yl)thiophen-2-yl)ethyl)carbamoyl)-1,4-oxazepane-4-carboxylate (32H)

At room temperature, 32G (0.45 g, 1.4 mmol) was dissolved in N,N-dimethylformamide (10 mL), N,N,N',N'-tetramethyl-O-(7-azabenzotriazol-1-yl)uronium hexafluorophosphate (0.6 g, 1.6 mmol), INT-3 (0.4 g, 1.7 mmol), and diisopropylethylamine (0.5 g, 3.6 mmol) were added, and the mixture was reacted at room temperature for 2 hours. The reaction solution was poured into water (200 mL) and then extracted with ethyl acetate (100 mL×2). The organic phase was concentrated to dryness to obtain the title compound 32H (0.4 g, yield: 52%). LC-MS (ESI): m/z=545.2 [M+H]$^+$ Step 8: (2S)—N-(1-cyano-2-(3-fluoro-5-(3-methyl-2-oxo-2,3-dihydrobenzo[d]oxazol-5-yl)thiophen-2-yl)ethyl)-1,4-oxazepane-2-carboxamide (Compound 32)

At room temperature, compound 32G (0.4 g, 0.73 mmol) was dissolved in acetonitrile (20 mL) and p-toluenesulfonic acid (0.5 g, 3.0 mmol) was added. The mixture was reacted at 50° C. for 1 hour, and the reaction solution was poured into saturated aqueous sodium bicarbonate solution (100 mL) and then extracted with ethyl acetate (100 mL×2). The organic phase was concentrated and the residue was purified by column chromatography (DCM:MeOH (v:v)=50:1-20:1) to obtain compound 32 (0.24 g, 70%).

$^1$H NMR (400 MHz, CDCl$_3$) δ 7.33-7.29 (s, 1H), 7.21-7.19 (m, 1H), 7.07-7.03 (m, 1H), 7.00 (s, 1H), 5.18-5.13 (m, 1H), 4.14-4.00 (m, 2H), 3.81-3.71 (m, 1H), 3.41 (s, 3H), 3.36-3.23 (m, 3H), 3.04-2.90 (m, 3H), 1.91-1.81 (m, 2H). LC-MS (ESI): m/z=445.1[M+H]$^+$.

Example 33 and Example 34: (S)—N—((S)-1-cyano-2-(5-(3-methyl-2-oxo-2,3-dihydrobenzo[d]oxazol-5-yl)pyridin-2-yl)ethyl)-1,4-oxazepane-2-carboxamide and (S)—N—((R)-1-cyano-2-(5-(3-methyl-2-oxo-2,3-dihydrobenzo[d]oxazol-5-yl)pyridin-2-yl)ethyl)-1,4-oxazepane-2-carboxamide (Compound 33 and Compound 34)

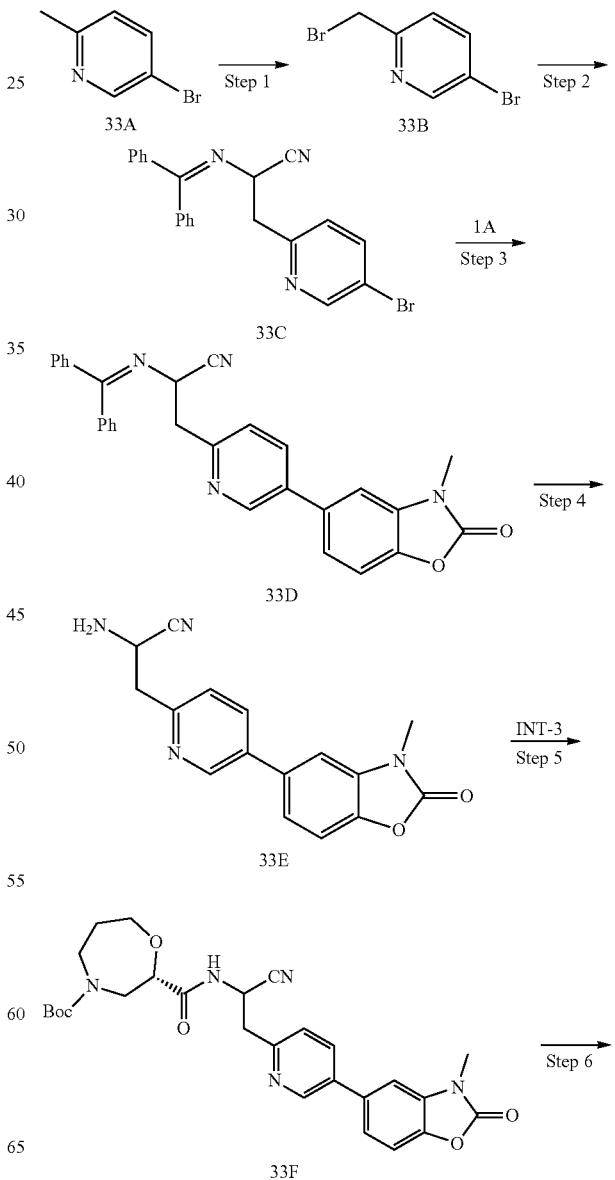

-continued

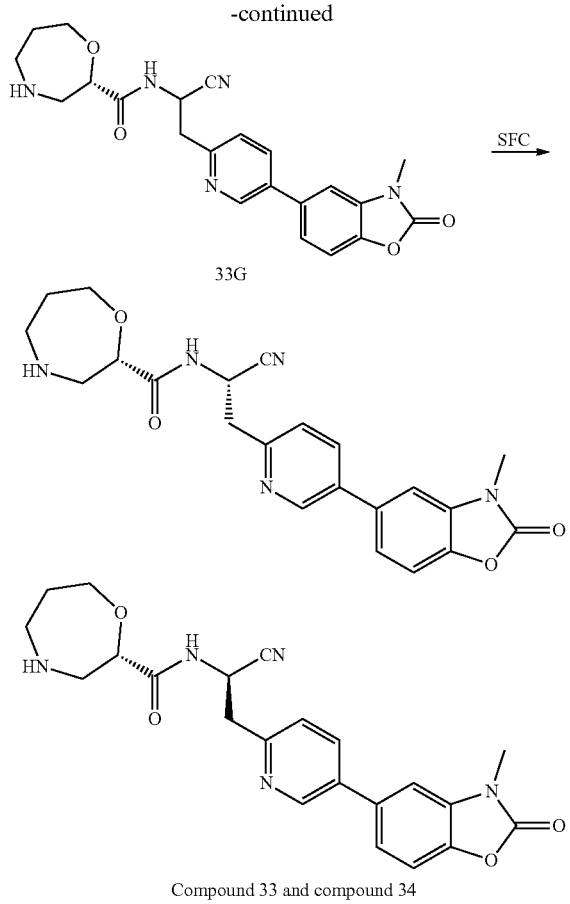

Compound 33 and compound 34

Step 1: 5-bromo-2-(bromomethyl)pyridine (33B)

2-methyl-5-bromopyridine 33A (5 g, 29.07 mmol) was dissolved in carbon tetrachloride (50 mL), N-bromosuccinimide (5.43 g, 30.52 mmol) and azodiisobutyronitrile (1.19 g, 7.27 mmol) were added, and the mixture was reacted at 90° C. for 2.5 h. The reaction solution was cooled to room temperature and concentrated, and the residue was separated and purified by silica gel column chromatography (PE:EA (v/v)=10:1) to obtain the title compound 33B (4.42 g, 61%). LC-MS (ESI): m/z=251.9 [M+H]$^+$.

Step 2: 3-(5-bromopyridin-2-yl)-2-((diphenylmethylene)amino)propanenitrile (33C)

33B (4.42 g, 17.54 mmol) and N-(diphenylmethylene) aminoacetonitrile (3.86 g, 17.54 mmol) were dissolved in dichloromethane (50 mL) and benzyltrimethylammonium chloride (0.33 g, 1.75 mmol) was added. An aqueous solution (5 mL) of sodium hydroxide (1.40 g, 35.08 mmol) was added under vigorous stirring and the mixture was reacted at room temperature overnight. Water (100 mL) was added. The resulting mixture was extracted with dichloromethane (30 mL×3). The organic layers were combined, dried over anhydrous sodium sulfate and concentrated. The residue was separated and purified by silica gel column chromatography (PE:EA (v/v)=10:1) to obtain the title compound 33C (5.20 g, 76%). LC-MS (ESI): m/z=390.0 [M+H]$^+$.

Step 3: 2-((diphenylmethylene)amino)-3-(5-(3-methyl-2-oxo-2,3-dihydrobenzo[d]oxazol-5-yl)pyridin-3-yl)propanenitrile (33D)

33C (1.73 g, 4.43 mmol), 1A (1.34 g, 4.87 mmol), [1,1'-(diphenylphosphino)ferrocene]palladium dichloride (0.33 g, 0.44 mmol), and potassium carbonate (1.22 g, 8.86 mmol) were dissolved in a mixed solvent of dioxane (50 mL) and water (5 mL), and the mixture was reacted at 90° C. under nitrogen protection for 5 h. The reaction solution was cooled to room temperature and 200 mL of water was added. The resulting mixture was extracted with ethyl acetate (50 mL×3). The organic layers were combined, successively washed with saturated sodium bicarbonate (50 mL) and saturated brine (50 mL), dried over anhydrous sodium sulfate, and concentrated, and the residue was separated and purified by silica gel column chromatography (PE:EA (v/v)=3:1) to obtain the title compound 33D (2.03 g, 68.92%). LC-MS (ESI): m/z=459.1 [M+H]$^+$.

Step 4: 2-amino-3-(5-(3-methyl-2-oxo-2,3-dihydrobenzo[d]oxazol-5-yl)pyridin-2-yl)propanenitrile (33E)

33D (1.02 g, 2.19 mmol) was dissolved in tetrahydrofuran (50 mL) and water (5 mL), 2.5 mL of 1 M HCl aqueous solution was added dropwise, and after the addition, the mixture was reacted at room temperature for 5 h. The reaction solution was extracted with ether (15 mL×3) and the resulting organic layer was discarded. The aqueous layer was adjusted to the pH of about 12 with 2 M NaOH aqueous solution and then extracted with DCM (20 mL×3). The organic layers were combined, dried over anhydrous sodium sulfate and concentrated to obtain the title compound 33E (crude product, 580 mg), which was directly used in the next reaction without further purification. LC-MS (ESI): m/z=295.0 [M+H]$^+$.

Step 5: tert-butyl (2S)-2-((1-cyano-2-(5-(3-methyl-2-oxo-2,3-dihydrobenzo[d]oxazol-5-yl)pyridin-2-yl) ethyl)carbamoyl)-1,4-oxazepane-4-carboxylate (33F)

33E (0.4 g, 1.36 mmol) was dissolved in dichloromethane (10 mL), DIPEA (0.34 mg, 2.64 mmol), HATU (0.55 mg, 1.45 mmol), and intermediate INT-3 (0.36 g, 1.5 mmol) were successively added, and the mixture was reacted at room temperature for 1 hour. After TLC detection showed complete reaction, water (20 mL) was poured into the reaction solution for layering. The organic phase was successively washed with water (20 mL) and saturated brine, dried over anhydrous sodium sulfate, and concentrated under reduced pressure to obtain a yellow oily crude product. The crude product was purified by flash column chromatography (DCM:MeOH (v/v)=96:4) to obtain 33F as a white solid (0.4 g, yield: 56.4%). LC-MS (ESI): m/z=522.2 [M+H]$^+$.

Step 6: (2S)—N-(1-cyano-2-(5-(3-methyl-2-oxo-2, 3-dihydrobenzo[d]oxazol-5-yl)pyridin-2-yl)ethyl)-1, 4-oxazepane-2-carboxamide (33G)

Compound 33F (0.3 g, 0.58 mmol) was dissolved in dichloromethane (10 mL) and TMSOTf (0.19 g, 0.87 mmol) was added. Under ice bath, 2,6-lutidine (0.12 g, 1.16 mmol) was added dropwise and after the dropwise addition, the mixture was warmed to room temperature and reacted for 1 h. The reaction solution was poured into 30 mL of saturated ammonium chloride solution and the resulting mixture was extracted with dichloromethane (20 mL×3). The organic phase was washed with saturated sodium chloride, dried over anhydrous sodium sulfate, and concentrated to obtain a pale yellow oily crude product, which was purified and separated by flash column chromatography (DCM:MeOH=95:5, v/v) to obtain compound 33G (0.14 g).

Compound 33G was subjected to SFC chiral preparative separation to obtain peak 1 (40 mg, ee %=100%, yield: 16.5%, retention time: 2.728 min, set to be compound 33) and peak 2 (50 mg, ee %=98.5%, yield: 20.6%, retention time: 3.987 min, set to be compound 34).

Purification conditions were as follows: (Instrument name: MG II preparative SFC (SFC-14); chromatographic column: ChiralPak AD, 250×30 mm I.D., 10 µm; mobile phase: phase A: $CO_2$; phase B: isopropanol (0.1% $NH_3 \cdot H_2O$); flow rate: 70 mL/min; column pressure: 100 bar; column temperature: 35° C.; absorption wavelength: 220 nm; and cycle time: about 7 min.).

Peak 1: LC-MS (ESI): m/z=422.2 [M+H]$^+$;

$^1$H NMR (400 MHz, DMSO-d$_6$) δ 8.79-8.78 (m, 1H), 8.50-8.48 (m, 1H), 7.88-7.85 (m, 1H), 7.37-7.31 (m, 3H), 7.14 (s, 1H), 5.37-5.35 (m, 1H), 4.28-4.25 (m, 1H), 4.12-4.08 (m, 1H), 3.85-3.69 (m, 1H), 3.52-3.51 (m, 1H), 3.47 (s, 3H), 3.37-3.35 (m, 2H), 3.13-3.05 (m, 2H), 2.02-2.01 (m, 2H), 1.26-1.20 (m, 2H).

Peak 2: LC-MS (ESI): m/z=422.2 [M+H]$^+$;

$^1$H NMR (400 MHz, DMSO-d$_6$) δ 8.79-8.78 (m, 1H), 8.50-8.48 (m, 1H), 7.88-7.85 (m, 1H), 7.37-7.31 (m, 3H), 7.14 (s, 1H), 5.39-5.34 (m, 1H), 4.28-4.25 (m, 1H), 4.15-4.09 (m, 1H), 3.85-3.71 (m, 1H), 3.52-3.51 (m, 1H), 3.47 (s, 3H), 3.37-3.34 (m, 2H), 3.14-3.04 (m, 2H), 2.02-2.01 (m, 2H), 1.26-1.20 (m, 2H).

Example 35 and Example 36: (S)—N—((S)-1-cyano-2-(4-fluoro-6-(3-methyl-2-oxo-2,3-dihydrobenzo[d]oxazol-5-yl)pyridin-3-yl)ethyl)-1,4-oxazepane-2-carboxamide and (S)—N—((R)-1-cyano-2-(4-fluoro-6-(3-methyl-2-oxo-2,3-dihydrobenzo[d]oxazol-5-yl)pyridin-3-yl)ethyl)-1,4-oxazepane-2-carboxamide (Compound 35 and Compound 36)

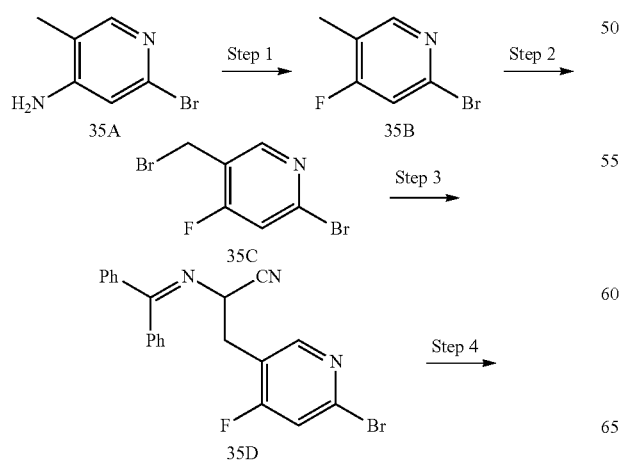

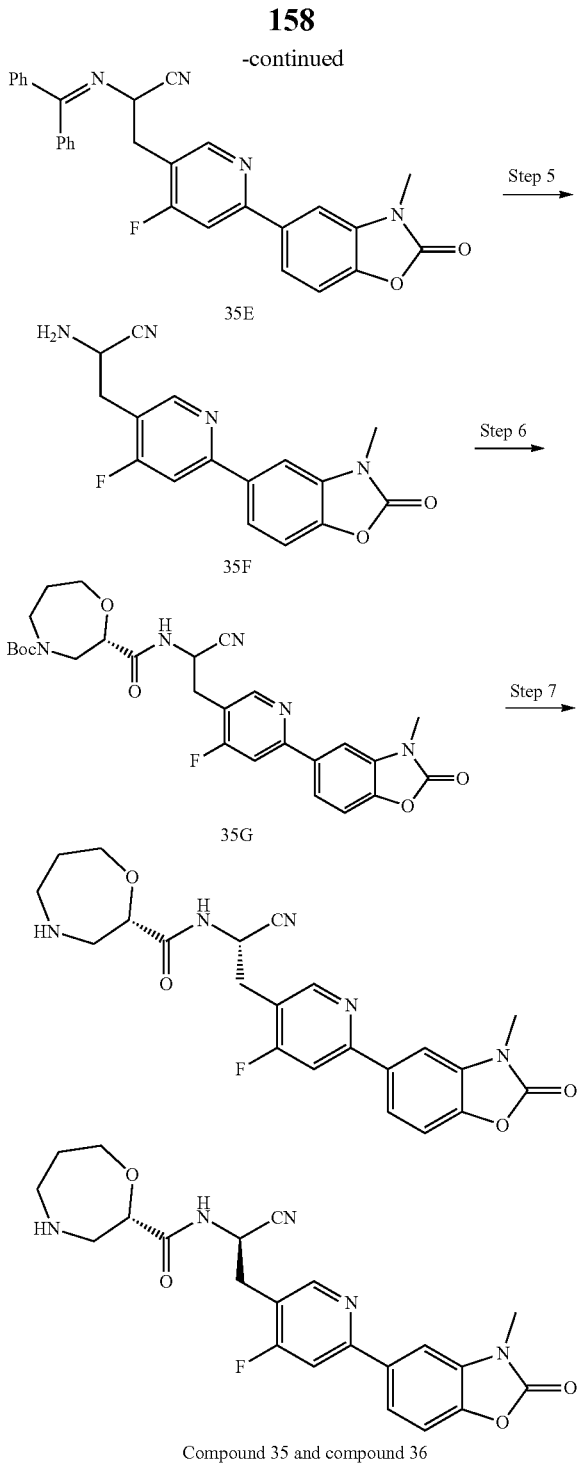

Step 1: 2-bromo-4-fluoro-5-methylpyridine (35B)

Compound 35A, i.e., 2-bromo-4-amino-5-methylpyridine (1.87 g, 10 mmol) was dissolved in pyridine hydrofluoride (20 mL), and sodium nitrite (0.83 g, 12 mmol) was added in portions at −10° C. After the addition, the mixture was naturally warmed to room temperature and reacted overnight. After the reaction was completed, water (100 mL) was added and the pH was adjusted to 8 with saturated sodium bicarbonate. The resulting mixture was extracted with ethyl acetate (100 mL×2), dried over anhydrous sodium sulfate and concentrated under reduced pressure, and the residue was separated by silica gel column chromatography (PE:EA=10:1, v/v) to obtain the target compound 35B (1.21 g, yield: 63.4%).

$^1$H NMR (400 MHz, CDCl$_3$) δ 8.20 (d, 1H), 7.19 (d, 1H), 2.23 (s, 3H). LC-MS m/z=190.0/192.0 [M+1]$^+$

Step 2: 2-bromo-5-(bromomethyl)-4-fluoropyridine (35C)

35B (2.84 g, 15.0 mmol) was dissolved in carbon tetrachloride (50 mL), N-bromosuccinimide (2.93 g, 16.5 mmol) and azodiisobutyronitrile (0.49 g, 3.0 mmol) were added, and the mixture was reacted at 90° C. for 4 h. The reaction solution was cooled to room temperature and concentrated, and the residue was separated and purified by silica gel column chromatography (petroleum ether:ethyl acetate (v/v)=10:1) to obtain the title compound 35C (2.45 g, 61%).

$^1$H NMR (400 MHz, CDCl$_3$) δ 8.40 (d, 1H), 7.28 (d, 1H), 4.43 (s, 2H).

Step 3: 3-(6-bromo-4-fluoropyridin-3-yl)-2-((diphenylmethylene)amino)propanenitrile (35D)

35C (2.4 g, 8.9 mmol) and N-(diphenylmethylene)aminoacetonitrile (1.96 g, 8.9 mmol) were dissolved in dichloromethane (40 mL) and benzyltrimethylammonium chloride (0.17 g, 0.89 mmol) was added. An aqueous solution (4 mL) of sodium hydroxide (1.07 g, 26.8 mmol) was added under vigorous stirring and the mixture was reacted at room temperature overnight. Water (100 mL) was added. The resulting mixture was extracted with dichloromethane (60 mL×3). The organic layers were combined, dried over anhydrous sodium sulfate and concentrated. The residue was separated and purified by silica gel column chromatography (PE:EA (v/v)=10:1) to obtain the title compound 35D (2.23 g, 61%). LC-MS (ESI): m/z=408.1 [M+H]$^+$.

Step 4: 2-((diphenylmethylene)amino)-3-(4-fluoro-6-(3-methyl-2-oxo-2,3-dihydrobenzo[d]oxazol-5-yl)pyridin-3-yl)propanenitrile (35E)

35D (1.3 g, 3.18 mmol), 1A (0.87 g, 3.18 mmol), [1,1'-(diphenylphosphino)ferrocene]palladium dichloride (0.35 g, 0.48 mmol), and potassium carbonate (0.88 g, 6.36 mmol) were dissolved in a mixed solvent of dioxane (30 mL) and water (5 mL), and the mixture was reacted at 90° C. under nitrogen protection for 5 h. The reaction solution was cooled to room temperature and 80 mL of water was added. The resulting mixture was extracted with ethyl acetate (60 mL×3). The organic layers were combined, successively washed with saturated sodium bicarbonate (50 mL) and saturated brine (50 mL), dried over anhydrous sodium sulfate, and concentrated, and the residue was separated and purified by silica gel column chromatography (PE:EA (v/v)=3:1) to obtain the title compound 35E (1.02 g, 67%). LC-MS (ESI): m/z=477.2 [M+H]$^+$.

Step 5: 2-amino-3-(4-fluoro-6-(3-methyl-2-oxo-2,3-dihydrobenzo[d]oxazol-5-yl)pyridin-3-yl)propanenitrile (35F)

35E (1.02 g, 2.14 mmol) was dissolved in tetrahydrofuran (25 mL) and water (5 mL), 5 mL of 1 M HCl aqueous solution was added dropwise, and after the addition, the mixture was reacted at room temperature for 5 h. The reaction solution was extracted with ether (40 mL) and the resulting organic layer was discarded. The aqueous layer was adjusted to the pH of about 12 with 2 M NaOH aqueous solution and then extracted with DCM (50 mL×3). The organic layers were combined, dried over anhydrous sodium sulfate and concentrated to obtain the title compound 35F (crude product, 0.64 g), which was directly used in the next reaction without further purification. LC-MS (ESI): m/z=313.1 [M+H]$^+$.

Step 6: (2S)—N-(1-cyano-2-(4-fluoro-6-(3-methyl-2-oxo-2,3-dihydrobenzo[d]oxazol-5-yl)pyridin-3-yl) ethyl)-1,4-oxazepane-2-carboxamide (35G)

35F (0.64 g, 2.05 mmol) was dissolved in dichloromethane (10 mL), intermediate INT-3 (0.5 g, 2.05 mmol), DIPEA (0.53 mg, 4.1 mmol), and HATU (0.94 mg, 2.46 mmol) were successively added, and the mixture was reacted at room temperature for 1 hour. After TLC detection showed complete reaction, water (20 mL) was poured into the reaction solution for layering. The organic phase was successively washed with water (20 mL) and saturated brine, dried over anhydrous sodium sulfate, and concentrated under reduced pressure to obtain a yellow oily crude product. The crude product was purified by flash column chromatography (DCM:MeOH (v/v)=20:1) to obtain 35G (0.98 g, yield: 88.6%). LC-MS (ESI): m/z=540.2 [M+H]$^+$.

Step 7: (S)—N—((S)-1-cyano-2-(4-fluoro-6-(3-methyl-2-oxo-2,3-dihydrobenzo[d]oxazol-5-yl)pyridin-3-yl) ethyl)-1,4-oxazepane-2-carboxamide and (S)—N—((R)-1-cyano-2-(4-fluoro-6-(3-methyl-2-oxo-2,3-dihydrobenzo[d]oxazol-5-yl)pyridin-3-yl) ethyl)-1,4-oxazepane-2-carboxamide (Compound 35 and Compound 36)

Compound 35G (0.98 g, 1.82 mmol) was dissolved in formic acid (10 mL) and the mixture was reacted at 50° C. for 10 min. The reaction solution was concentrated under reduced pressure. Dichloromethane (40 mL) and saturated sodium bicarbonate (40 mL) were added and the mixture was subjected to liquid-liquid separation. The aqueous phase was extracted with dichloromethane (50 mL×4) and the organic phases were combined, washed with saturated sodium chloride (40 mL), dried over anhydrous sodium sulfate, and concentrated to obtain the target compounds (0.76 g, yield: 95%). The target compounds were subjected to preparative SFC to obtain two isomers: peak 1 (retention time: 2.47 min, set to be compound 35) and peak 2 (retention time: 3.69 min, set to be compound 36).

Preparation conditions: Instrument: MG II preparative SFC (SFC-14). Column: ChiralPak AD, 250×30 mm I.D., 10 μm. Mobile phase: A: CO$_2$ and B: methanol (0.1% NH$_3$H$_2$O). Gradient: B 40%. Flow rate: 80 mL/min. Back pressure: 100 bar. Column temperature: 38° C. Wavelength: 220 nm. Cycle time: about 10 min. Sample preparation: the sample was dissolved in 15 ml of methanol/dichloromethane. Injection: 3.5 ml/injection.

Peak 1: LC-MS m/z=440.1 [M+1]$^+$.

$^1$H NMR (400 MHz, CDCl$_3$) δ 8.60 (d, 1H), 7.72 (d, 1H), 7.67 (dd, 1H), 7.47 (d, 1H), 7.32-7.26 (m, 2H), 5.28-5.17 (m, 1H), 4.12-3.99 (m, 2H), 3.81-3.73 (m, 1H), 3.48 (s, 3H), 3.34-3.16 (m, 3H), 3.01-2.80 (m, 3H), 1.97-1.75 (m, 2H).

Peak 2: LC-MS m/z=440.1 [M+1]$^+$.

$^1$H NMR (400 MHz, CDCl$_3$) δ 8.58 (d, 1H), 7.73 (d, 1H), 7.67 (dd, 1H), 7.48 (d, 1H), 7.32 (d, 1H), 7.28 (d, 1H), 5.17

(dt, 1H), 4.13-4.01 (m, 2H), 3.83-3.75 (m, 1H), 3.48 (s, 3H), 3.38 (dd, 1H), 3.33-3.19 (m, 2H), 3.07 (dd, 1H), 3.02-2.87 (m, 2H), 2.06-1.78 (m, 2H).

Example 37 and Example 38: (S)—N—((S)-1-cyano-2-(6-(3-methyl-2-oxo-2,3-dihydrobenzo[d]oxazol-5-yl)pyridin-3-yl)ethyl)-1,4-oxazepane-2-carboxamide and (S)—N—((R)-1-cyano-2-(6-(3-methyl-2-oxo-2,3-dihydrobenzo[d]oxazol-5-yl)pyridin-3-yl)ethyl)-1,4-oxazepane-2-carboxamide (Compound 37 and Compound 38)

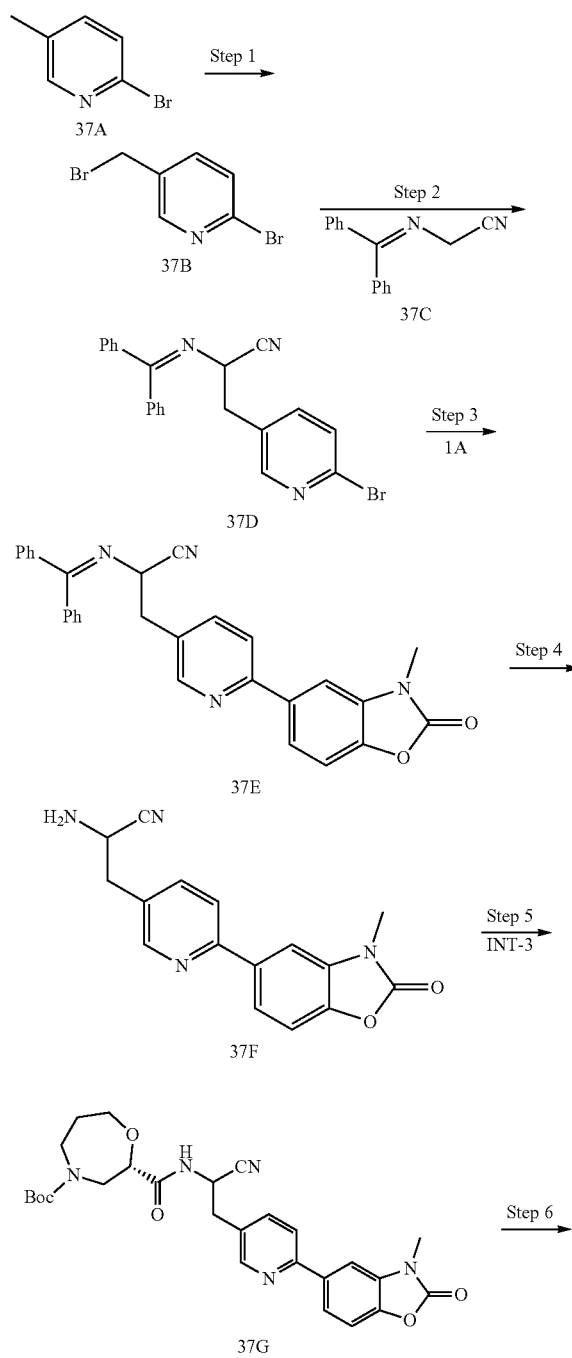

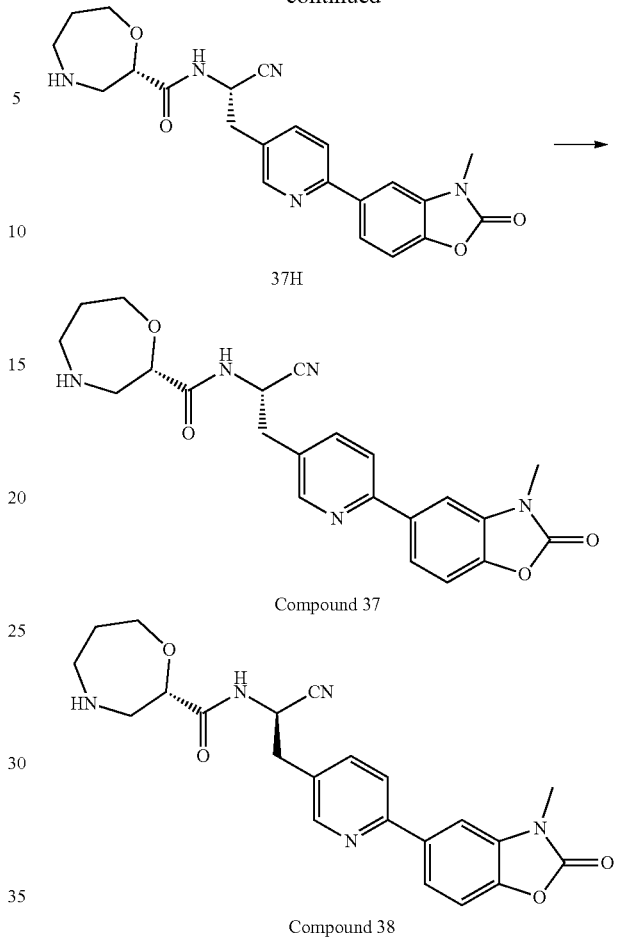

Step 1:2-bromo-5-(bromomethyl)pyridine (37B)

37A (5 g, 29.07 mmol) was dissolved in carbon tetrachloride (50 mL), N-bromosuccinimide (5.43 g, 30.52 mmol) and azodiisobutyronitrile (1.19 g, 7.27 mmol) were added, and the mixture was reacted at 90° C. for 2.5 h. The reaction solution was cooled to room temperature and concentrated, and the residue was separated and purified by silica gel column chromatography (PE:EA (v/v)=10:1) to obtain the title compound 37B (4.42 g, 61%). LC-MS (ESI): m/z=251.9 [M+H]$^+$.

Step 2: 3-(6-bromopyridin-3-yl)-2-((diphenylmethylene)amino)propanenitrile (37D)

37B (4.42 g, 17.54 mmol) and 37C (3.86 g, 17.54 mmol) were dissolved in dichloromethane (50 mL) and benzyltrimethylammonium chloride (0.33 g, 1.75 mmol) was added. An aqueous solution (5 mL) of sodium hydroxide (1.40 g, 35.08 mmol) was added under vigorous stirring and the mixture was reacted at room temperature overnight. Water (100 mL) was added. The resulting mixture was extracted with dichloromethane (30 mL×3). The organic layers were combined, dried over anhydrous sodium sulfate and concentrated. The residue was separated and purified by silica gel column chromatography (PE:EA (v/v)=10:1) to obtain the title compound 37D (5.20 g, 76%).

¹H NMR (400 MHz, CDCl₃) δ 8.16 (s, 1H), 7.64-7.57 (m, 2H), 7.50-7.32 (m, 8H), 6.96 (q, J=2.4 Hz, 2H), 4.40 (t, J=6.5 Hz, 1H), 3.17 (d, J=6.5 Hz, 2H). LC-MS (ESI): m/z=390.0 [M+H]⁺.

Step 3: 2-((diphenylmethylene)amino)-3-(6-(3-methyl-2-oxo-2,3-dihydrobenzo[d]oxazol-5-yl)pyridin-3-yl)propanenitrile (37E)

37D (1.5 g, 3.84 mmol), 1A (1.06 g, 3.84 mmol), [1,1'-(diphenylphosphino)ferrocene]palladium dichloride (0.28 g, 0.38 mmol), and potassium carbonate (1.59 g, 11.52 mmol) were dissolved in a mixed solvent of dioxane (50 mL) and water (5 mL), and the mixture was reacted at 90° C. under nitrogen protection for 5 h. The reaction solution was cooled to room temperature and 200 mL of water was added. The resulting mixture was extracted with ethyl acetate (50 mL×3). The organic layers were combined, successively washed with saturated sodium bicarbonate (50 mL) and saturated brine (50 mL), dried over anhydrous sodium sulfate, and concentrated, and the residue was separated and purified by silica gel column chromatography (PE:EA (v/v)=3:1) to obtain the title compound 37E (1.02 g, 57%). LC-MS (ESI): m/z=459.1 [M+H]⁺.

¹H NMR (400 MHz, CDCl₃) δ 8.48 (s, 1H), 7.74 (s, 1H), 7.69-7.61 (m, 5H), 7.49-7.42 (m, 4H), 7.36 (t, J=7.5 Hz, 2H), 7.28-7.24 (m, 1H), 6.98 (d, J=7.7 Hz, 2H), 4.50-4.42 (m, 1H), 3.47 (s, 3H), 3.29-3.24 (m, 2H).

Step 4: 2-amino-3-(6-(3-methyl-2-oxo-2,3-dihydrobenzo[d]oxazol-5-yl)pyridin-3-yl)propanenitrile (Compound 37F)

37E (1.02 g, 2.19 mmol) was dissolved in tetrahydrofuran (50 mL) and water (5 mL), 2.5 mL of 1 M HCl aqueous solution was added dropwise, and after the addition, the mixture was reacted at room temperature for 5 h. The reaction solution was extracted with ether (15 mL×3) and the resulting organic layer was discarded. The aqueous layer was adjusted to the pH of about 12 with 2 M NaOH aqueous solution and then extracted with DCM (20 mL×3). The organic layers were combined, dried over anhydrous sodium sulfate and concentrated to obtain the title compound 37F (crude product, 580 mg), which was directly used in the next reaction without further purification. LC-MS (ESI): m/z=295.1 [M+H]⁺.

Step 5: tert-butyl (2S)-2-((1-cyano-2-(6-(3-methyl-2-oxo-2,3-dihydrobenzo[d]oxazol-5-yl)pyridin-3-yl)ethyl)carbamoyl)-1,4-oxazepane-4-carboxylate (Compound 37G)

INT-3 (0.36 g, 1.22 mmol) was dissolved in DMF (5 mL) and then HATU (0.6 g, 1.59 mmol) and N,N-diisopropylethylamine (0.47 g, 3.66 mmol) were added under nitrogen protection. After the mixture was stirred at room temperature for 20 min, 37F (0.3 g, 1.22 mmol) was added. The resulting mixture was reacted at room temperature for 3 h. To the reaction solution, 30 mL of water was added. The resulting mixture was extracted with EA (15 mL×5). The organic layers were combined, dried over anhydrous sodium sulfate and concentrated. The residue was separated and purified by silica gel column chromatography (DCM:MeOH (v/v)=97:3) to obtain the title compound 37G (0.32 g, 51%). LC-MS (ESI): m/z=522.2 [M+H]⁺.

Step 6: (S)—N-(1-cyano-2-(6-(3-methyl-2-oxo-2,3-dihydrobenzo[d]oxazol-5-yl)pyridin-3-yl)ethyl)-1,4-oxazepane-2-carboxamide (Compound 37H)

37G (0.32 g, 0.61 mmol) was dissolved in anhydrous formic acid (3 mL) and the mixture was reacted at 50° C. for 1 h. The reaction solution was cooled to room temperature and concentrated to remove most of the solvent. Saturated sodium bicarbonate solution (25 mL) was added to the residue and the resulting mixture was extracted with EA multiple times until barely any product remained in the aqueous layer. The organic layers were combined, dried over anhydrous sodium sulfate, and concentrated, and the residue was separated and purified by silica gel column chromatography (DCM:MeOH (v/v)=10:1) to obtain compound 37H (140 mg, 55%).

Compound 37H was subjected to SFC chiral preparative separation to obtain peak 1 (63 mg, ee %=98.22%, yield: 24.8%, retention time: 2.120 min, set to be compound 37) and peak 2 (73 mg, ee %=100%, yield: 28.7%, retention time: 2.689 min, set to be compound 38).

Purification conditions were as follows: (Instrument name: MG II preparative SFC (SFC-14); chromatographic column: ChiralPak AD, 250×30 mm I.D., 10 μm; mobile phase: phase A: CO₂; phase B: methanol (0.1% NH₃·H₂O); flow rate: 80 mL/min; column pressure: 100 bar; column temperature: 35° C.; absorption wavelength: 220 nm; and cycle time: about 16.9 min).

Peak 1: LC-MS (ESI): m/z=422.3 [M+H]⁺.

¹H NMR (400 MHz, CD₃OD) δ 8.55 (s, 1H), 7.90-7.82 (m, 2H), 7.79 (m, 2H), 7.37-7.31 (m, 1H), 5.17 (dd, J=9.0, 6.8 Hz, 1H), 4.11 (dd, J=8.6, 3.6 Hz, 1H), 4.03-3.95 (m, 1H), 3.78 (m, 1H), 3.47 (s, 3H), 3.34 (m, 1H), 3.27-3.14 (m, 2H), 2.90 (m, 1H), 2.78 (m, 1H), 2.62 (dd, J=14.4, 8.6 Hz, 1H), 1.96-1.78 (m, 2H). Peak 2: LC-MS (ESI): m/z=422.3 [M+H]⁺.

¹H NMR (400 MHz, CD₃OD) δ 8.55 (s, 1H), 7.90-7.82 (m, 2H), 7.81-7.76 (m, 2H), 7.36-7.31 (m, 1H), 5.12 (dd, J=8.6, 6.8 Hz, 1H), 4.11 (dd, J=8.6, 3.6 Hz, 1H), 4.05 (m, 1H), 3.79 (m, 1H), 3.47 (s, 3H), 3.40-3.33 (m, 1H), 3.29-3.20 (m, 2H), 3.06-2.89 (m, 3H), 2.02-1.83 (m, 2H).

Example 39 and Example 40: (S)—N—((S)-1-cyano-2-(2-(3-methyl-2-oxo-2,3-dihydrobenzo[d]oxazol-5-yl)pyrimidin-5-yl)ethyl)-1,4-oxazepane-2-carboxamide and (S)—N—((R)-1-cyano-2-(2-(3-methyl-2-oxo-2,3-dihydrobenzo[d]oxazol-5-yl)pyrimidin-5-yl)ethyl)-1,4-oxazepane-2-carboxamide (Compound 39 and Compound 40)

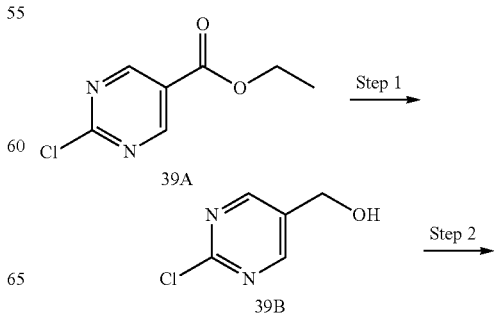

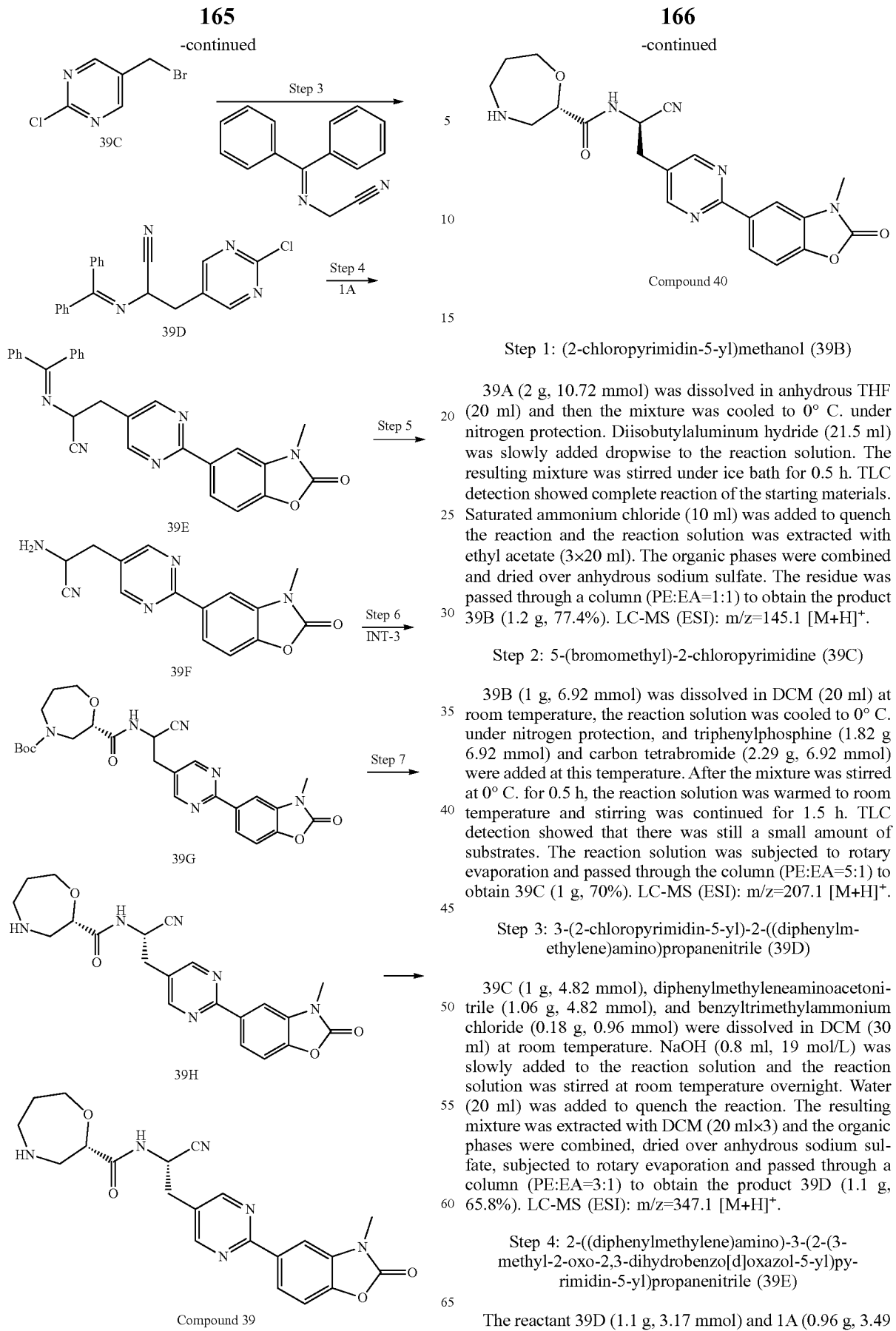

Step 1: (2-chloropyrimidin-5-yl)methanol (39B)

39A (2 g, 10.72 mmol) was dissolved in anhydrous THF (20 ml) and then the mixture was cooled to 0° C. under nitrogen protection. Diisobutylaluminum hydride (21.5 ml) was slowly added dropwise to the reaction solution. The resulting mixture was stirred under ice bath for 0.5 h. TLC detection showed complete reaction of the starting materials. Saturated ammonium chloride (10 ml) was added to quench the reaction and the reaction solution was extracted with ethyl acetate (3×20 ml). The organic phases were combined and dried over anhydrous sodium sulfate. The residue was passed through a column (PE:EA=1:1) to obtain the product 39B (1.2 g, 77.4%). LC-MS (ESI): m/z=145.1 [M+H]$^+$.

Step 2: 5-(bromomethyl)-2-chloropyrimidine (39C)

39B (1 g, 6.92 mmol) was dissolved in DCM (20 ml) at room temperature, the reaction solution was cooled to 0° C. under nitrogen protection, and triphenylphosphine (1.82 g 6.92 mmol) and carbon tetrabromide (2.29 g, 6.92 mmol) were added at this temperature. After the mixture was stirred at 0° C. for 0.5 h, the reaction solution was warmed to room temperature and stirring was continued for 1.5 h. TLC detection showed that there was still a small amount of substrates. The reaction solution was subjected to rotary evaporation and passed through the column (PE:EA=5:1) to obtain 39C (1 g, 70%). LC-MS (ESI): m/z=207.1 [M+H]$^+$.

Step 3: 3-(2-chloropyrimidin-5-yl)-2-((diphenylmethylene)amino)propanenitrile (39D)

39C (1 g, 4.82 mmol), diphenylmethyleneaminoacetonitrile (1.06 g, 4.82 mmol), and benzyltrimethylammonium chloride (0.18 g, 0.96 mmol) were dissolved in DCM (30 ml) at room temperature. NaOH (0.8 ml, 19 mol/L) was slowly added to the reaction solution and the reaction solution was stirred at room temperature overnight. Water (20 ml) was added to quench the reaction. The resulting mixture was extracted with DCM (20 ml×3) and the organic phases were combined, dried over anhydrous sodium sulfate, subjected to rotary evaporation and passed through a column (PE:EA=3:1) to obtain the product 39D (1.1 g, 65.8%). LC-MS (ESI): m/z=347.1 [M+H]$^+$.

Step 4: 2-((diphenylmethylene)amino)-3-(2-(3-methyl-2-oxo-2,3-dihydrobenzo[d]oxazol-5-yl)pyrimidin-5-yl)propanenitrile (39E)

The reactant 39D (1.1 g, 3.17 mmol) and 1A (0.96 g, 3.49 mmol) were dissolved in 1,4-dioxane (100 ml) and then potassium carbonate (1.31 g, 9.51 mmol) and Pd(dppf)Cl$_2$ (0.23 g, 0.32 mmol) were added. The mixture was under the protection of nitrogen replacement and reacted at 100° C. TLC and LC-MS showed that there was still a small amount of starting materials. The reaction solution was concentrated and subjected to rotary evaporation, then dissolved in DCM and filtered off with suction through celite, and the filtrate was subjected to rotary evaporation and passed through a column (EA/PE=0%-40%) to obtain a pale yellow solid 39E (1.1 g, 75.5%). LC-MS (ESI): m/z=460.2 [M+H]$^+$.

Step 5: 2-amino-3-(2-(3-methyl-2-oxo-2,3-dihydrobenzo[d]oxazol-5-yl)pyrimidin-5-yl)propanenitrile (39F)

Substrate 39E (1.1 g, 2.39 mmol) was dissolved in DCM (30 ml), 1 M HCl (7.2 ml) was added, and the mixture was stirred at room temperature for 3 h. TLC detection showed complete reaction of the starting materials. The solution was adjusted to the pH of 8-10 and then extracted with EA (20 ml×2), and the organic phase was dried over anhydrous sodium sulfate and subjected to rotary evaporation to obtain the product 39F (0.6 g, 85%). LC-MS (ESI): m/z=296.1 [M+H]$^+$.

Step 6: (2S)-tert-butyl 2-(1-cyano-2-(2-(3-methyl-2-oxo-2,3-dihydrobenzo[d]oxazol-5-yl)pyrimidin-5-yl)ethylcarbamoyl)-1,4-oxazepane-4-carboxylate (39G)

INT-3 (0.5 g, 2.03 mmol), HATU (0.85 g, 2.23 mmol), and DIPEA (0.7 ml) were dissolved in DCM (30 ml) at room temperature. After the mixture was stirred at room temperature for 10 min, 39F (0.6 g, 2.03 mmol) was added and the resulting mixture was stirred at room temperature for 1 h. TLC detection showed that the reaction was completed. Water (10 ml) was added to quench the reaction, and the reaction solution was extracted with dichloromethane (15 ml×2). The organic phases were combined, dried over anhydrous sodium sulfate and concentrated under reduced pressure, and the residue was purified by column chromatography (PE:EA=1:1) to obtain the product 39G (0.6 g, 56%). LC-MS (ESI): m/z=523.2 [M+H]$^+$.

Step 7: (2S)—N-(1-cyano-2-(2-(3-methyl-2-oxo-2,3-dihydrobenzo[d]oxazol-5-yl)pyrimidin-5-yl)ethyl)-1,4-oxazepane-2-carboxamide (39H)

39G (0.6 g, 1.15 mmol) was dissolved in anhydrous formic acid (20 ml) and after the mixture was stirred at room temperature for 2 h, TLC detection showed complete reaction of the substrate. Formic acid was removed by rotary evaporation at a low temperature, and saturated sodium bicarbonate solution was added to adjust the pH to 8-10. The resulting mixture was extracted with DCM (20 ml×2), dried over anhydrous sodium sulfate, subjected to rotary evaporation, and passed through a column (DCM:CH$_3$OH=10:1) to obtain the compound 39H (0.15 g, 31%). Compound 39H was subjected to SFC chiral preparative separation to obtain peak 1 (retention time: 1.528 min, set to be compound 39) and peak 2 (retention time: 2.387 min, set to be compound 40).

The resolution method was as follows: (Instrument name: MG II preparative SFC (SFC-14); chromatographic column: ChiralPak AD, 250×30 mm I.D., 10 μm; mobile phase: phase A: CO$_2$; phase B: isopropanol (0.1% NH3·H2O); flow rate: 80 mL/min; column pressure: 100 bar; column temperature: 35° C.; absorption wavelength: 220 nm; and cycle time: 3 min).

Peak 1: $^1$H NMR (400 MHz, DMSO-d$_6$) δ 8.79-8.78 (m, 1H), 8.38-8.35 (m, 1H), 7.43-7.38 (m, 3H), 6.48-6.46 (m, 1H), 5.03-4.99 (m, 1H), 4.05-4.02 (m, 1H), 3.90-3.84 (m, 1H), 3.76-3.70 (m, 1H), 3.50 (s, 3H), 3.25-3.09 (m, 4H), 2.86-2.80 (m, 1H), 2.70-2.58 (m, 2H), 1.80-1.71 (m, 2H).

Peak 2: $^1$H NMR (400 MHz, DMSO-d$_6$) δ 8.79-8.78 (m, 1H), 8.38-8.35 (m, 1H), 7.43-7.38 (m, 3H), 6.48-6.46 (m, 1H), 5.03-4.99 (m, 1H), 4.05-4.02 (m, 1H), 3.90-3.84 (m, 1H), 3.76-3.70 (m, 1H), 3.50 (s, 3H), 3.25-3.09 (m, 4H), 2.86-2.80 (m, 1H), 2.70-2.58 (m, 2H), 1.80-1.71 (m, 2H).

Examples 41 and 42: (S)—N—((S)-1-cyano-2-(6-(3-methyl-2-oxo-2,3-dihydrobenzo[d]oxazol-5-yl)pyridazin-3-yl)ethyl)-1,4-oxazepane-2-carboxamide and (S)—N—((R)-1-cyano-2-(6-(3-methyl-2-oxo-2,3-dihydrobenzo[d]oxazol-5-yl)pyridazin-3-yl)ethyl)-1,4-oxazepane-2-carboxamide (Compound 41 and Compound 42)

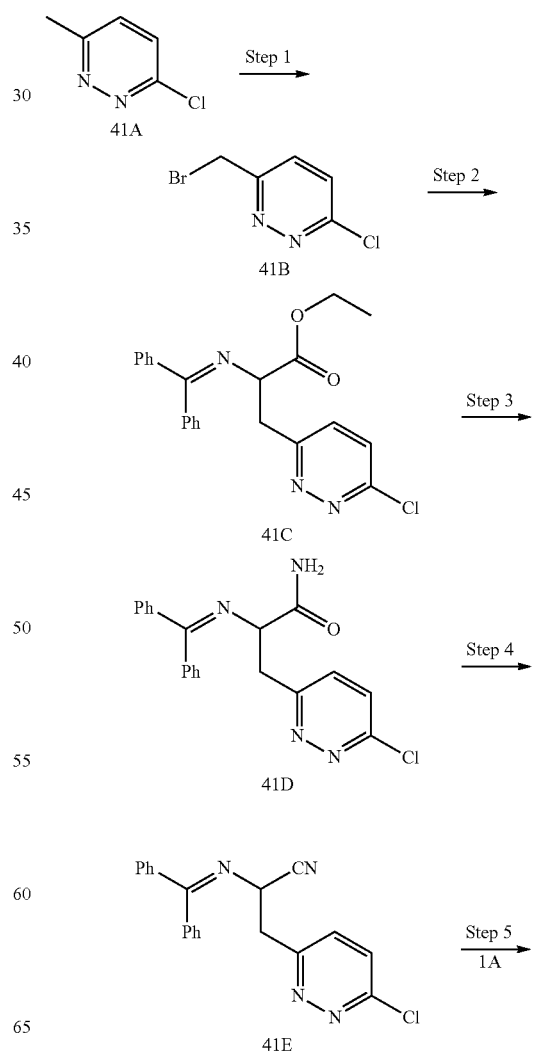

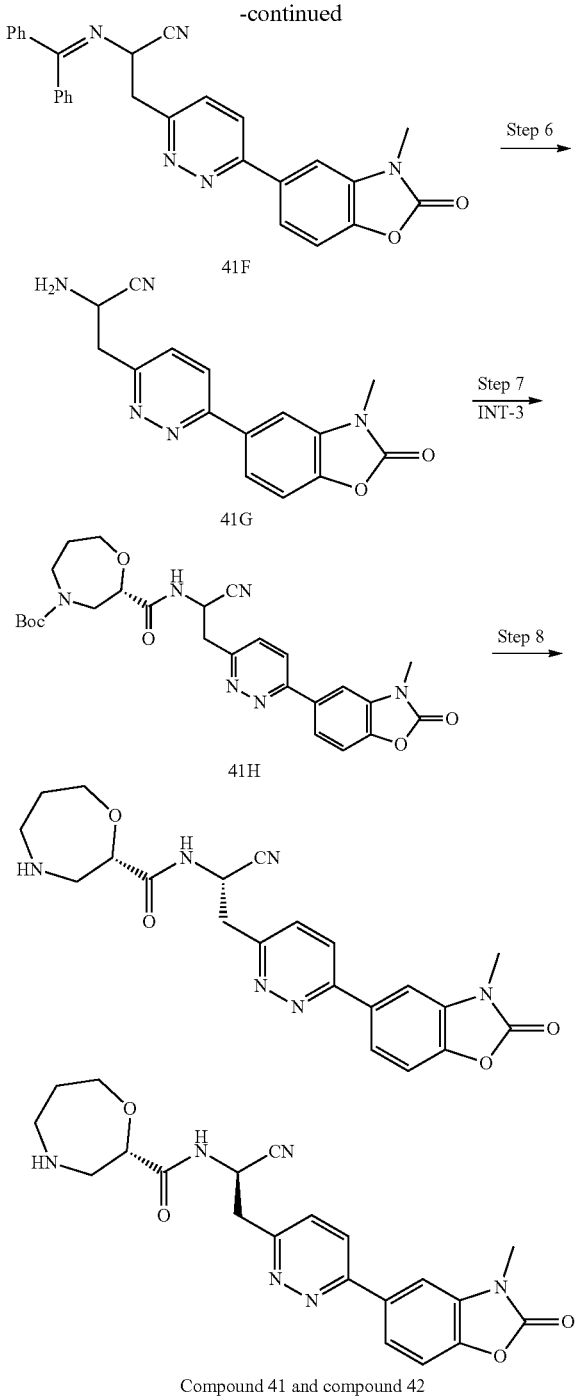

Compound 41 and compound 42

Step 1: 3-(bromomethyl)-6-chloropyridazine (41B)

3-(methyl)-6-chloropyridazine (12.8 g, 100 mmol) was dissolved in carbon tetrachloride (300 mL), N-bromosuccinimide (17.8 g, 100 mmol) and azodiisobutyronitrile (3.4 g, 20 mmol) were added, and the mixture was reacted at 70° C. overnight and filtered. The filtrate was concentrated and the residue was separated and purified by silica gel column chromatography (PE:EA (v/v)=1:10-1:5) to obtain the title compound 41B (4 g, yield: 20%). LCMS m/z=207.46 [M+1]$^+$ Step 2: ethyl 3-(6-chloropyridazin-3-yl)-2-((diphenylmethylene)amino)propanoate (41C)

Ethyl 2-((diphenylmethylene)amino)acetate (6.18 g, 23.14 mmol), tetrabutylammonium bromide (9.32 g, 28.92 mmol), and potassium hydroxide (3.25 g, 2.24 mmol) were dissolved in a mixed solvent of toluene (100 mL) and water (20 mL). 41B (4.0 g, 19.28 mmol) was added under ice bath and the mixture was naturally warmed to room temperature and reacted for 2 hours. Water (50 mL) was added and the resulting mixture was extracted with ethyl acetate (50 mL×3). The organic phase was washed with water (50 mL×3) three times, then dried over anhydrous sodium sulfate, and concentrated, and the residue was separated and purified by silica gel column chromatography (PE:EA (v/v)=1:10-1:5) to obtain the title compound 41C (3.4 g, yield: 45%). LCMS m/z=394.12 [M+1]$^+$ Step 3: 3-(6-chloropyridazin-3-yl)-2-((diphenylmethylene)amino)propanamide (41D)

41C (3.4 g, 8.7 mmol) was dissolved in an ammonia methanol solution (7 N, 50 mL) and the mixture was reacted at 80° C. overnight in a sealed tube (120 mL). After concentration, the reaction mixture was separated and purified by silica gel column chromatography (MeOH:DCM (v/v)=1:10) to obtain the title compound 41D (1.8 g, yield: 56%). LCMS m/z=365.11 [M+1]$^+$ Step 4: 3-(6-chloropyridazin-3-yl)-2-((diphenylmethylene)amino)propanenitrile (41E)

41D (1.8 g, 4.93 mmol) was dissolved in dichloromethane (30 mL), Burgess reagent (2.35 g, 9.86 mmol) was added, and the mixture was reacted at room temperature for 2 hours. After concentration, the reaction mixture was separated and purified by silica gel column chromatography (PE:EA (v/v)=1:5-5:5) to obtain the title compound 41E (1.4 g, yield: 82%). LCMS m/z=347.13 [M+1]$^+$ Step 5: 2-((diphenylmethylene)amino)-3-(6-(3-methyl-2-oxo-2,3-dihydrobenzo[d]oxazol-5-yl)pyridazin-3-yl)propanenitrile (41F)

41E (1.4 g, 4.04 mmol) was dissolved in dioxane (30 mL), and 1A (2.22 g, 8.08 mmol), potassium carbonate (1.67 g, 12.12 mmol), [1,1'-bis(diphenylphosphino)ferrocene]palladium dichloride (590 mg, 0.81 mmol) and then water (6 mL) were added. The mixture was reacted in a microwave reactor at 120° C. under nitrogen protection for 2 hours. After concentration, the reaction mixture was separated and purified by silica gel column chromatography (PE:EA (v/v)=1:5-1:1) to obtain the title compound 41F (800 mg, yield: 43%). LCMS m/z=460.17 [M+1]$^+$ Step 6: 2-amino-3-(6-(3-methyl-2-oxo-2,3-dihydrobenzo[d]oxazol-5-yl)pyridazin-3-yl)propanenitrile (41G)

41F (800 mg, 1.74 mmol) was dissolved in dioxane (20 mL), hydrochloric acid solution (0.5 N, 8 mL) was added, and the mixture was reacted at room temperature for 0.5 hours. The pH was adjusted to 7-8 with saturated aqueous sodium carbonate solution. The resulting mixture was extracted with dichloromethane (30 mL×3), and the organic phases were combined, washed with saturated brine (30 mL×1), dried over anhydrous sodium sulfate, and concentrated, and the residue was separated and purified by silica gel column chromatography (MeOH:DCM (v/v)=1:100-1:10) to obtain the title compound 41G (300 mg, yield: 58%). LCMS m/z=296.11 [M+1]$^+$ Step 7: tert-butyl (2S)-2-((1-cyano-2-(6-(3-methyl-2-oxo-2,3-dihydrobenzo[d]oxazol-5-yl)pyridazin-3-yl)ethyl)carbamoyl)-1,4-oxazepane-4-carboxylate (41H)

41G (300 mg, 1.02 mmol) was dissolved in DMF (20 mL) and then HATU (390 mg, 1.02 mmol), DIPEA (260 mg, 2.02 mmol), and INT-3 (250 mg, 1.02 mmol) were successively added. The mixture was reacted at room temperature for 12 hours. Water (30 mL) was added and the resulting mixture was extracted with ethyl acetate (30 mL×3). The organic phases were combined, washed with water (30 mL×2) and saturated brine (30 mL×1), dried over anhydrous sodium sulfate, and concentrated, and the residue was separated and purified by silica gel column chromatography (MeOH:DCM (v/v)=1:100-1:10) to obtain the title compound 41H (300 mg, yield: 56%). LCMS m/z=523.22 [M+1]$^+$ Step 8: (S)—N—((S)-1-cyano-2-(6-(3-methyl-2-oxo-2,3-dihydrobenzo[d]oxazol-5-yl)pyridazin-3-yl)ethyl)-1,4-oxazepane-2-carboxamide and (S)—N—((R)-1-cyano-2-(6-(3-methyl-2-oxo-2,3-dihydrobenzo[d]oxazol-5-yl)pyridazin-3-yl)ethyl)-1,4-oxazepane-2-carboxamide (Compound 41 and Compound 42)

41H (300 mg, 0.57 mmol) was dissolved in acetonitrile (20 mL), and p-toluenesulfonic acid (332 mg, 1.71 mmol) was added. The mixture was reacted at 30° C. for 3 hours, then adjusted to pH=7-8 with saturated aqueous sodium carbonate solution and extracted with dichloromethane (40 mL×3). The organic phases were combined, washed with saturated aqueous sodium chloride solution (50 mL), dried over anhydrous sodium sulfate and concentrated, and the residue was separated and purified by silica gel column chromatography (DCM:MeOH (v/v)=0.01:1-0.1:1) to obtain crude compounds.

150 mg of the crude compounds were taken and subjected to chiral preparative separation to obtain two optical isomers: peak 1 (retention time: 2.088 min, 30 mg, ee=99%, set to be compound 41) and peak 2 (retention time: 2.955 min, 30 mg, ee=99%, set to be compound 42). Resolution conditions: instrument: MG II preparative SFC (SFC-14); column: ChiralPak AD, 250×30 mm I.D.; mobile phase: A: CO2, and B: ethanol (0.05% NH$_3$H$_2$O); gradient: B 40%; flow rate: 70 mL/min; back pressure: 100 bar; column temperature: 38° C.; wavelength: 220 nm; cycle: 13 min; sample preparation: compound 1 was dissolved in methanol to achieve the concentration of 15 mg/ml; and injection: 1.0 ml/injection.

Peak 1: MS M/Z (ESI): m/z=423.17 [M+1]$^+$.

$^1$H NMR (400 MHz, DMSO-d$_6$) δ 8.73 (d, 1H), 8.27 (d, 1H), 8.08 (d, 1H), 8.00-7.90 (m, 1H), 7.78 (d, 1H), 7.50 (d, 1H), 5.41-5.32 (m, 1H), 4.02-3.84 (m, 2H), 3.78-3.49 (m, 3H), 3.44 (s, 3H), 3.18-3.07 (m, 1H), 2.90-2.53 (m, 4H), 1.82-1.63 (m, 2H).

Peak 2: MS M/Z (ESI): m/z=423.17 [M+1]$^+$.

$^1$H NMR (400 MHz, DMSO-d$_6$) δ 8.75 (d, 1H), 8.27 (d, 1H), 8.07 (d, 1H), 7.98-7.86 (m, 1H), 7.78 (d, 1H), 7.50 (d, 1H), 5.62-5.19 (m, 1H), 4.05-3.97 (m, 1H), 3.92-3.82 (m, 1H), 3.77-3.66 (m, 1H), 3.66-3.51 (m, 2H), 3.43 (s, 3H), 3.09-3.00 (m, 1H), 2.86-2.70 (m, 1H), 2.69-2.51 (m, 3H), 1.80-1.63 (m, 2H).

Example 43: N—((S)-1-cyano-2-(3-fluoro-4'-(pentafluoro-16-sulfanyl)-[1,1'-biphenyl]-4-yl)ethyl)-6-methoxy-1,4-oxazepane-2-carboxamide (Compound 43)

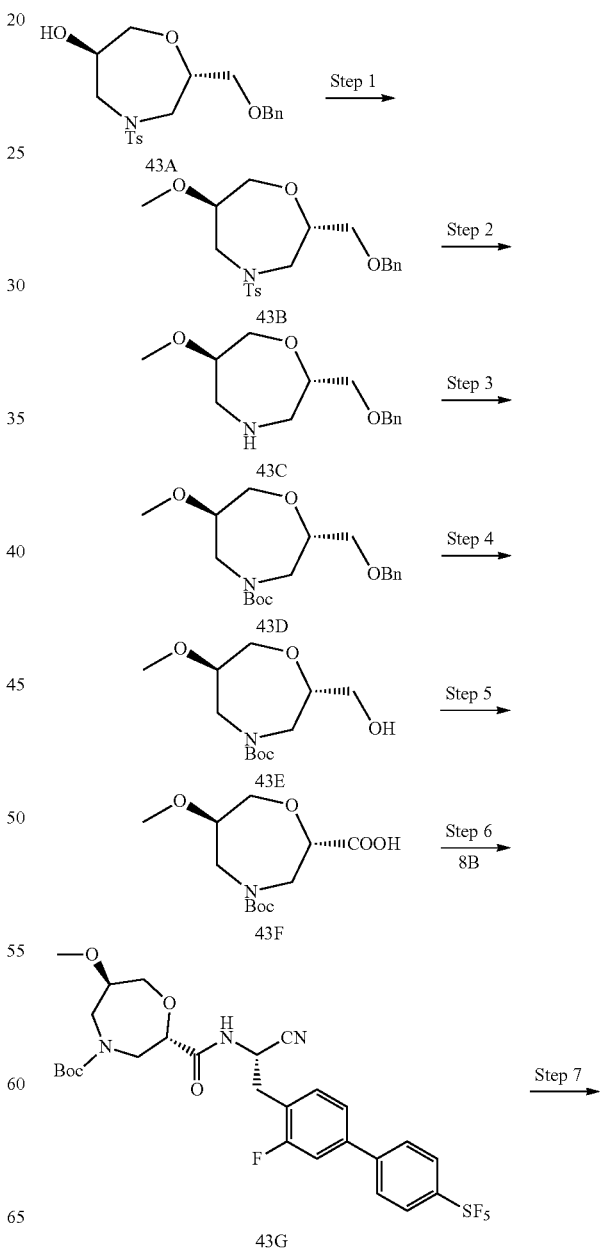

-continued

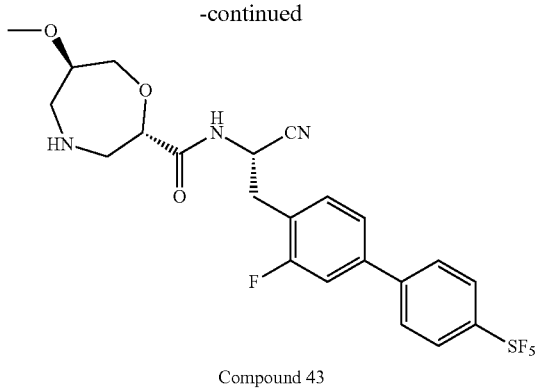

Compound 43

Step 1: (2S,6R)-2-((benzyloxy)methyl)-6-methoxy-4-tosyl-1,4-oxazepane (43B)

43A (0.5 g, 1.28 mmol, prepared with reference to the document: Eur. J. Org. Chem. 2007, 2107-2113 (DOI: 10.1002/ejoc.200700011) was dissolved in tetrahydrofuran (20 mL), sodium hydride (0.26 g, 6.4 mmol) was added at 0° C., and after the mixture was stirred for 30 min, iodomethane (0.91 g, 6.4 mmol) was added. After the resulting mixture was reacted at room temperature for 3 h, water (30 mL) was added at 0° C. Then the mixture was extracted with EA (20 mL×3), washed with saturated brine, dried over anhydrous sodium sulfate, and concentrated to obtain a colorless oil 43B (0.4 g, yield: 77%).

Step 2: (2S,6R)-2-((benzyloxy)methyl)-6-methoxy-1,4-oxazepane (43C)

43B (0.3 g, 0.74 mmol) was dissolved in methanol (10 mL), magnesium turnings (2.36 g, 97.08 mmol) were added, and after the mixture was subjected to ultrasonic treatment at 50° C. for 2 h, the mixture was reacted at room temperature for 16 h, then filtered and concentrated to obtain a white oil 43C (0.18 g, yield: 96%), which was directly used in the next step. LC-MS (ESI): m/z=252.3 $[M+1]^+$

Step 3: (2S,6R)-tert-butyl 2-((benzyloxy)methyl)-6-methoxy-1,4-oxazepane-4-carboxylate (43D)

43C (0.18 g, 0.72 mmol) was dissolved in DCM (10 mL), triethylamine (0.087 g, 0.85 mmol) and TBSCl (0.37 g, 1.71 mmol) were successively added, and after the mixture was reacted at room temperature under nitrogen protection for 2 hours, the reaction mixture was concentrated to dryness, and the residue was purified by column chromatography (PE:EA=10:1-4:1) to obtain a colorless oil 43D (0.12 g, yield: 47%).

Step 4: (2S,6R)-tert-butyl 2-(hydroxymethyl)-6-methoxy-1,4-oxazepane-4-carboxylate (43E) 43D (0.12 g, 0.34 mmol) was dissolved in methanol (10 mL), palladium on carbon (0.1 g, 10%) was added, and after the mixture was reacted under hydrogen atmosphere for 24 hours, the reaction mixture was filtered and then concentrated to dryness to obtain a colorless oil 43E (0.08 g, yield: 86%).

Step 5: (2S,6R)-4-(tert-butoxycarbonyl)-6-methoxy-1,4-oxazepane-2-carboxylic acid (43F) 43E (0.095 g, 0.3 mmol) was dissolved in acetone (7 mL), and saturated sodium bicarbonate (3 mL), sodium bromide (0.025 g, 0.24 mmol), and TEMPO (0.004 g, 0.024 mmol) were added. Then trichloroisocyanuric acid (0.25 g, 1.06 mmol) was added at 0° C. The mixture was reacted for 16 hours. Diluted hydrochloric acid was added to adjust the pH to 5-6 and water (30 mL) was added. The resulting mixture was extracted with dichloromethane (20 mL×3), and the organic phase was washed with water (30 mL) and saturated sodium chloride (30 mL), dried over anhydrous sodium sulfate, and concentrated to dryness to obtain a yellow oil 43F (0.046 g, yield: 44%).

Step 6: tert-butyl-2-(((S)-1-cyano-2-(3-fluoro-4'-(pentafluoro-16-sulfanyl)-[1,1'-biphenyl]-4-yl)ethyl)carbamoyl)-6-methoxy-1,4-oxazepane-4-carboxylate (43G)

Compound 8B (400 mg, 1.1 mmol), 43F (300 mg, 1.1 mmol), HATU (458 mg, 1.65 mmol), and DIEA (0.54 mL, 3.3 mmol) were mixed and dissolved in DMF, and the mixture was stirred at room temperature overnight. After the completion of the reaction detected by LCMS, water and EA were added for extraction, the organic phase was dried and concentrated, and the residue was separated by column chromatography (DCM:MeOH=10:1) to obtain the title compound 43G (512 mg, 75%). LC-MS (ESI): m/z=624.2 $[M+H]^+$.

Step 7: N—((S)-1-cyano-2-(3-fluoro-4'-(pentafluoro-16-sulfanyl)-[1,1'-biphenyl]-4-yl)ethyl)-6-methoxy-1,4-oxazepane-2-carboxamide (Compound 43)

Compound 43 (512 mg, 0.82 mmol) was dissolved in 40 mL of acetonitrile, p-toluenesulfonic acid (706 mg, 2.46 mmol) was added, and the mixture was heated to 40° C. and reacted for 2 hours. After the completion of the reaction detected by LCMS, the reaction solution was concentrated, EA and saturated aqueous sodium bicarbonate solution were added for extraction and liquid-liquid separation was carried out. The organic phase was dried and concentrated, and the residue was separated by column chromatography (DCM:MeOH=10:1) to obtain the title compound 43 (75 mg, 17%). LC-MS (ESI): m/z=524.2 $[M+H]^+$.
$^1$HNMR (400 MHz, DMSO-do): 8.74 (d, 1H), 7.92-8.00 (m, 4H), 7.48-7.66 (m, 3H), 5.03-5.09 (m, 1H), 3.97-4.01 (m, 2H), 3.56-3.59 (m, 1H), 3.28-3.30 (m, 1H), 3.24-3.25 (m, 6H), 2.78-2.89 (m, 3H), 1.91 (s, 1H).

Biological Test

1. In Vitro DPP1 Enzyme Activity Assay

Recombinant human DPP1 enzyme (R&D Systems, Cat. No. 1071-CY) at a final concentration of 100 μg/mL was mixed with recombinant human cathepsin L (R&D Systems, Cat. No. 952-CY) at a final concentration of 20 μg/mL were mixed and incubated at room temperature for 1 hour to activate the DPP1 enzyme. The activated DPP1 enzyme was diluted 100-fold, and 5 μL of compounds at different concentrations and 5 μL of the diluted DPP1 enzyme were added to a 384-well plate and incubated at room temperature for 30 minutes. After 10 μL of the substrate Gly-Arg-AMC (bachem, Cat. No. I-1215) at a concentration of 20 μM was added, incubation was continued at room temperature for 60 minutes, and the fluorescence intensity was detected with a microplate reader (excitation=380 nm and emission=460 nm). $IC_{50}$ values were calculated using the DosResp function of the Origin2019 software.

Test results: the compounds of the present invention showed inhibitory activity against the DPP1 receptor. The $IC_{50}$ values of the example compounds against the DPP1 receptor were in the range of less than 100 nM. The test results of some examples were shown in Table 1.

TABLE 1

| DPP1 inhibitory activity | |
|---|---|
| Compound No. | $IC_{50}$/nM |
| Compound 1 | 1.6 |
| Compound 10 | 6.7 |
| Compound 11 | 239 |
| Compound 12 | 21 |
| Compound 13 | 71 |
| Compound 14 | 12.9 |
| Compound 15 | 33 |
| Compound 17 | 7.4 |
| Compound 23 | 0.5 |
| Compound 29 | 4.9 |
| Compound 35 | 4.0 |
| Compound 43 | 0.3 |

Conclusion: the compounds of the present invention showed relatively high inhibitory activity against the DPP1 receptor.

2. Pharmacokinetic Experiment in Rats 1.1 Test animals: Male SD rats, about 220 g, 6-8 weeks old, 6 rats/compound. The rats were purchased from CHENGDU DOSSY EXPERIMENTAL ANIMALS CO., LTD.

1.2 Test design: On the day of the experiment, 6 SD rats were randomly grouped according to their body weight. The rats were fasted but given water for 12-14 h one day before the administration, and were fed 4 h after the administration.

TABLE 2

Administration information

| Group | No. of rats Male | Test compound | Dose of administration (mg/kg) | Administration concentration (mg/mL) | Administration volume (mL/kg) | Collected samples | Mode of administration |
|---|---|---|---|---|---|---|---|
| G1 | 3 | INS1007 | 1 | 0.2 | 5 | Plasma | Intravenously |
| G2 | 3 | Compound 1 | 1 | 0.2 | 5 | Plasma | |
| G3 | 3 | INS1007 | 3 | 0.3 | 10 | Plasma | Intragastrically |
| G4 | 3 | Compound 1 | 3 | 0.3 | 10 | Plasma | |

Vehicle for intravenous administration: 5% DMA+5% Solutol+90% Saline; Vehicle for intragastric administration: 0.5% MC; and control compound INS1007, namely compound 2 in patent WO 2015110826 A1, was prepared with reference to the method of the patent.

Before and after the administration, 0.1 ml of blood was taken from the orbit of the rats under isoflurane anesthesia and placed in an EDTAK2 centrifuge tube. The blood was centrifuged at 5000 rpm and 4° C. for 10 min to collect plasma. Blood sampling time point for the intravenous administration group: 0, 5, 15, 30 min, 1, 2, 4, 6, 8, and 24 h; and blood sampling time point for the intragastric administration group: 0, 5, 15, 30 min, 1, 2, 4, 6, 8, and 24 h. Before analysis and detection, all samples were stored at −80° C.

TABLE 3

Pharmacokinetic parameters of test compounds in plasma of rats

| Test compounds | Mode of administration | CL (mL/min/kg) | $Vd_{ss}$ (L/kg) | $AUC_{0-t}$ (hr*ng/mL) | F (%) |
|---|---|---|---|---|---|
| INS1007 | Intravenously | 2.08 | 0.738 | 8396 | — |
| Compound 1 | (1 mg/kg) | 1.66 | 0.753 | 9503 | — |
| INS1007 | Intragastrically | — | — | 22201 | 88.1 |
| Compound 1 | (3 mg/kg) | — | — | 31159 | >100 |

Conclusion: The compounds of the present invention have relatively good bioavailability and pharmacokinetic characteristics.

3. Toxicity Test in Rats Following 14-Day Repeated Oral Administration

According to their body weight, the SD rats were randomly divided into the following groups: vehicle control group (0.5% MC), INS1007 (30, 100, and 300 mg/kg) groups, and compound (30, 100, and 300 mg/kg) groups. For the administration groups, 16 rats were included in each group, and for the vehicle control group, 10 rats were included, with an equal number of male and female rats in each of the groups. The rats were orally gavaged with the drug or vehicle at the corresponding concentrations every day for 14 consecutive days, with a recovery period of 7 days. During the administration period, general symptoms were observed, and body weight and food intake were measured for each group. At the end of the administration period and at the end of the recovery period, hematology tests, serum biochemistry test and gross anatomy were performed on the rats in each group separately.

Conclusion: the compounds of the present invention are less toxic than INS1007 and thus are safer at the same dose.

What is claimed is:

1. A compound of formula (III), or a stereoisomer, a deuterated product, a solvate or a pharmaceutically acceptable salt thereof:

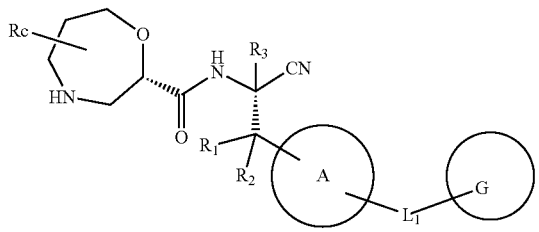

(III)

wherein Rc is H, =O, halogen, cyano, hydroxyl, $NH_2$, —COOH, $C_{1-4}$ alkyl, halo $C_{1-4}$ alkyl, hydroxy $C_{1-4}$ alkyl, $C_{1-4}$ alkoxy, $C_{1-6}$ alkoxyalkyl, or halo $C_{1-4}$ alkoxy;

$R_1$, $R_2$, and $R_3$ are each independently selected from H, deuterium, halogen, $C_{1-4}$ alkyl, and $C_{1-4}$ alkoxy, and the alkyl and alkoxy are optionally substituted with 1-3 groups selected from halogen, $C_{1-4}$ alkyl, cyano, hydroxyl, $NH_2$, and COOH;

optionally, $R_1$ and $R_2$ together with the carbon atom to which they are attached form $C_{3-6}$ cycloalkyl, and the cycloalkyl is optionally substituted with 1-3 groups selected from halogen, cyano, hydroxyl, $NH_2$, COOH, and $C_{1-4}$ alkyl;

$L_1$ is a bond;

ring G is a benzene ring, optionally substituted with 1-3 $R_G$ groups, or

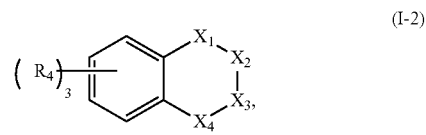

(I-2)

and $L_1$ is attached to the ring G by replacing any hydrogen atom on the ring atoms;

each $R_4$ is independently selected from H, halogen, $C_{1-4}$ alkyl, $C_{1-4}$ alkoxy, $C_{2-6}$ alkenyl, $C_{2-6}$ alkynyl, $C_{3-6}$ cycloalkyl, cyano, hydroxyl, and $NH_2$; the alkyl, alkenyl, alkynyl, and cycloalkyl in the case of $R_4$ are optionally substituted with 1-3 groups selected from deuterium and halogen, each $R_G$ is independently selected from deuterium, $SF_5$, halogen, cyano, hydroxyl, $NH_2$, $C_{1-4}$ alkyl, and the $R_G$ is optionally further substituted with 1-3 groups selected from deuterium and halogen;

$X_1$, $X_2$, $X_3$, and $X_4$ are each independently selected from a bond, $NR_5$, O, $CR_6R_7$, S, S(O), and $S(O)_2$, and at most one of $X_1$, $X_2$, $X_3$, and $X_4$ is a bond;

each $R_5$ is independently selected from H, $C_{1-4}$ alkyl, and $C_{3-6}$ cycloalkyl, wherein the alkyl and cycloalkyl are optionally substituted with 1-3 groups selected from deuterium, halogen, cyano, hydroxyl, $NH_2$, and COOH;

$R_6$ and $R_7$ are each independently selected from H, deuterium, halogen, $C_{1-4}$ alkyl, and $C_{1-4}$ alkoxy, wherein the alkyl and alkoxy are optionally substituted with 1-3 groups selected from deuterium, halogen, cyano, hydroxyl, $NH_2$, and COOH;

optionally, $R_6$ and $R_7$ form =O;

optionally, two $R_5$ on adjacent ring atoms, two $R_6$ on adjacent ring atoms, or $R_5$ and $R_6$ on adjacent ring atoms in $X_1$, $X_2$, $X_3$, and $X_4$ together with the atoms to which they are attached form a double bond;

provided that:

(1) A is

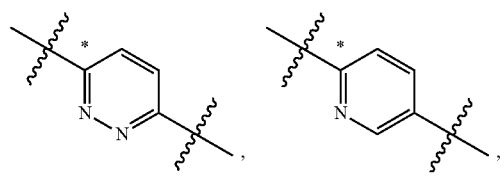

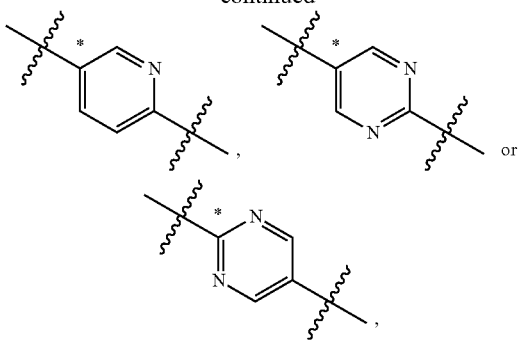

,   or

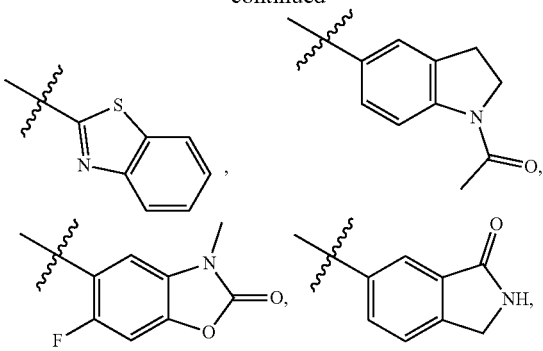

and ring A is optionally substituted with 1-3 $R_8$ groups;
each $R_8$ is independently selected from halogen, cyano, hydroxyl, $NH_2$, —COOH, $C_{1-4}$ alkyl, $C_{2-6}$ alkenyl, $C_{2-6}$ alkynyl, and $C_{3-6}$ cycloalkyl;
* indicates the end connected to the alkyl carbon atom;
or
(2) A is

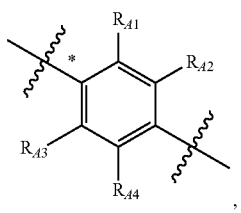

wherein * indicates the end connected to the alkyl carbon atom;
$R_{A1}$, $R_{A2}$, $R_{A3}$, and $R_{A4}$ are each independently $R_8$, and $R_{A1}$, $R_{A2}$, $R_{A3}$, and $R_{A4}$ are not H at the same time;
and each $R_8$ is independently selected from H, deuterium, halogen, $C_{1-4}$ alkyl, $C_{1-4}$ alkoxy, cyano, hydroxyl, $NH_2$, and COOH, wherein the alkyl and alkoxy are optionally substituted with 1-3 groups selected from deuterium, halogen, cyano, hydroxyl, $NH_2$, and COOH.

2. The compound, or the stereoisomer, deuterated product, solvate or pharmaceutically acceptable salt thereof according to claim 1, wherein
ring G is a benzene ring, or is selected from one of the following structures:

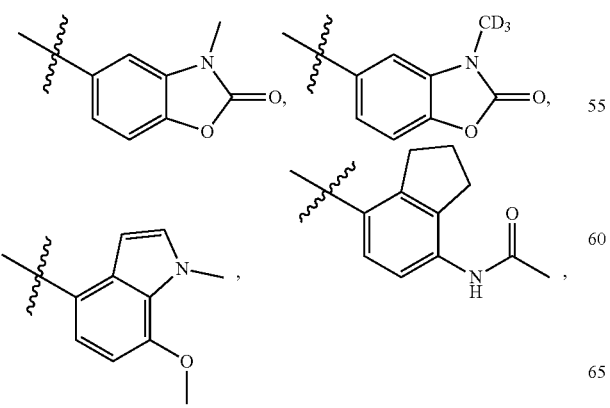

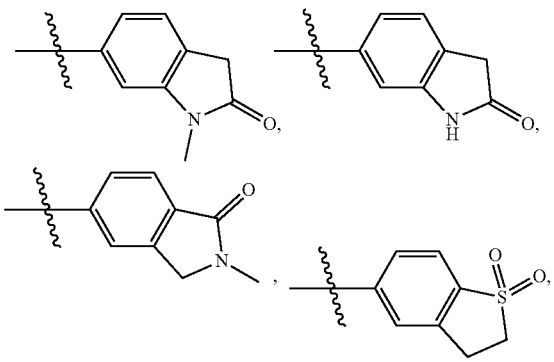

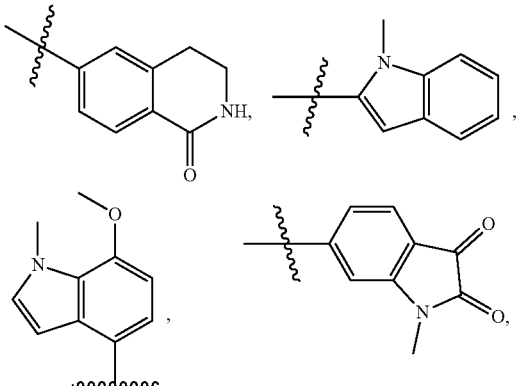

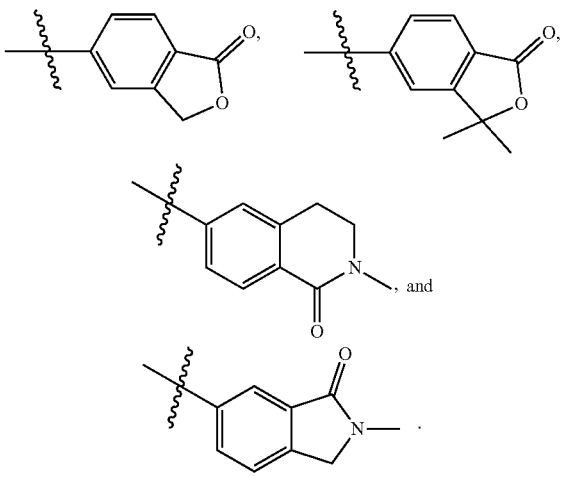

, and

.

each $R_G$ is independently selected from deuterium, $SF_5$, halogen, cyano, $C_{1-4}$ alkyl, $C_{1-4}$ alkoxy, $C_{3-6}$ cycloalkyl, —$NHC_{1-4}$ alkyl, —$N(C_{1-4}$ alkyl)2, —$COC_{1-4}$ alkyl, —$CONHC_{1-4}$ alkyl, —$CON(C_{1-4}$ alkyl)$_2$, —$NHCOC_{1-4}$ alkyl, and a 4-7-membered heterocycle containing 1-3 heteroatoms selected from N, S and O, provided that:

(1) A is

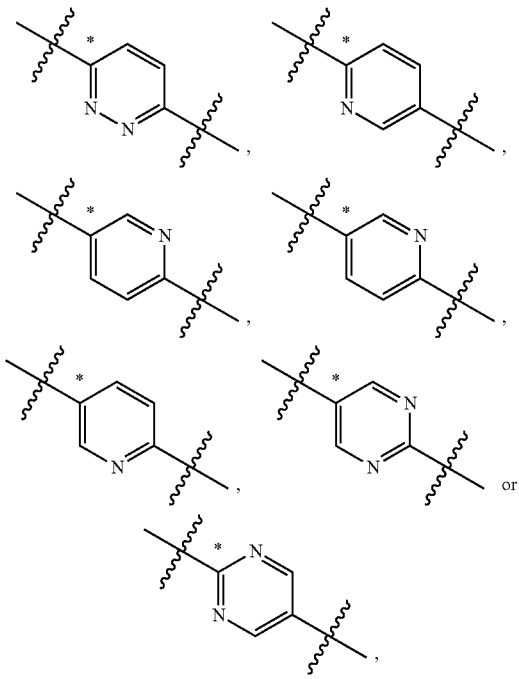

and ring A is optionally substituted with 1-3 $R_8$ groups;
each $R_8$ is independently selected from halogen, cyano, hydroxyl, $NH_2$, $C_{1-4}$ alkyl, and $C_{1-4}$ alkoxy;
* indicates the end connected to the alkyl carbon atom; or (2) A is

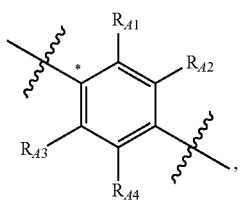

wherein * indicates the end connected to the alkyl carbon atom;
$R_{A1}$, $R_{A2}$, $R_{A3}$, and $R_{A4}$ are each independently $R_8$, and $R_{A1}$, $R_{A2}$, $R_{A3}$, and $R_{A4}$ are not H at the same time;
and each $R_8$ is independently selected from H, deuterium, halogen, $C_{1-4}$ alkyl, $C_{1-4}$ alkoxy, cyano, hydroxyl, $NH_2$, and COOH, wherein the alkyl and alkoxy are optionally substituted with 1-3 groups selected from deuterium, halogen, cyano, hydroxyl, $NH_2$, and COOH;
$R_1$, $R_2$, and $R_3$ are each independently selected from H and deuterium.

3. A compound, or the stereoisomer, deuterated product, solvate or pharmaceutically acceptable salt thereof, wherein the compound is selected from one of the following structures:

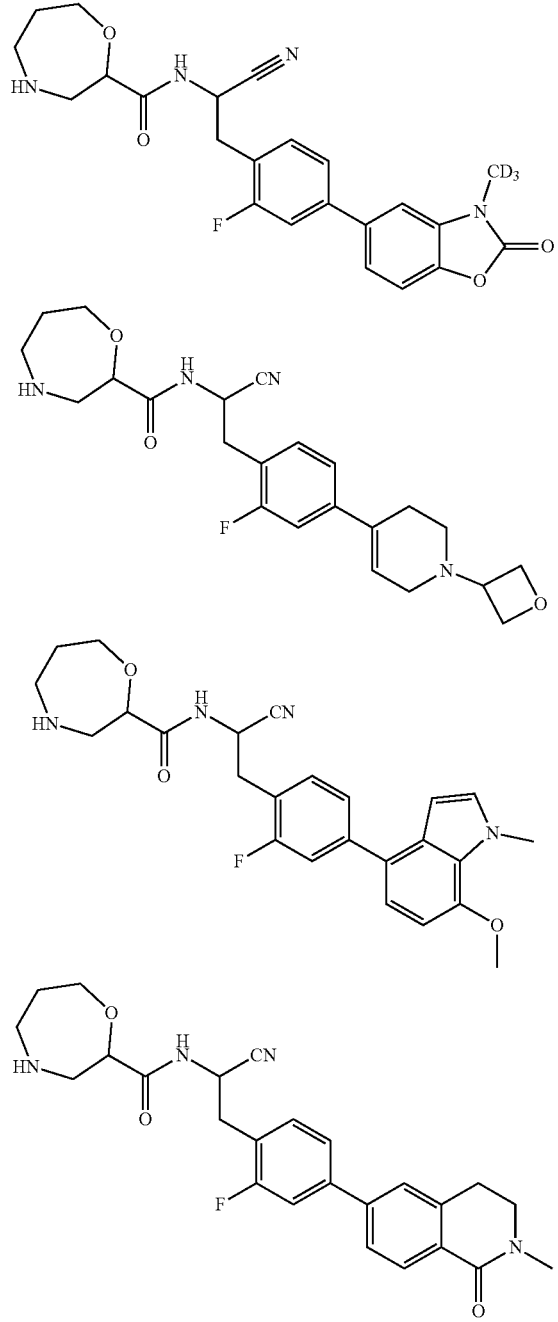

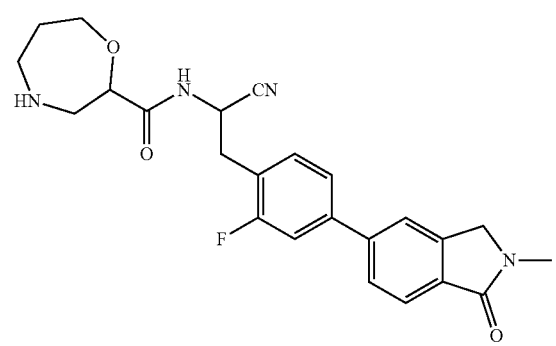

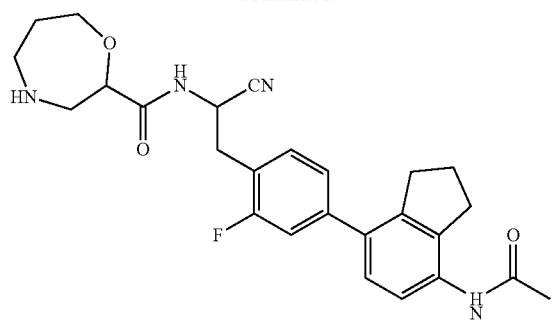
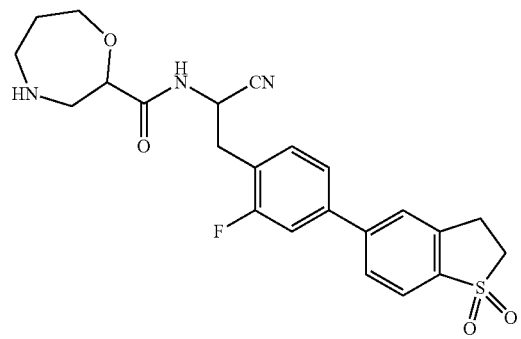
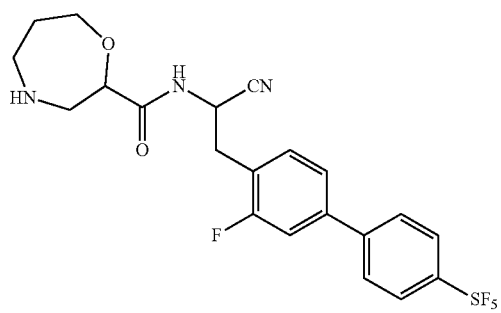
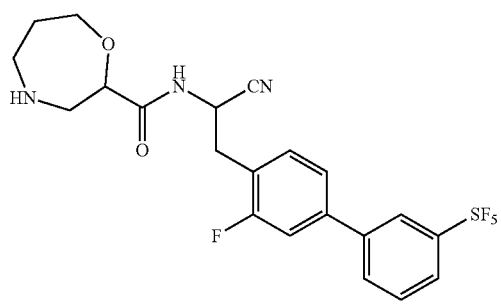
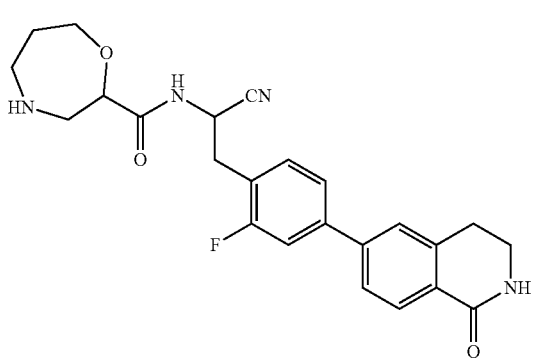
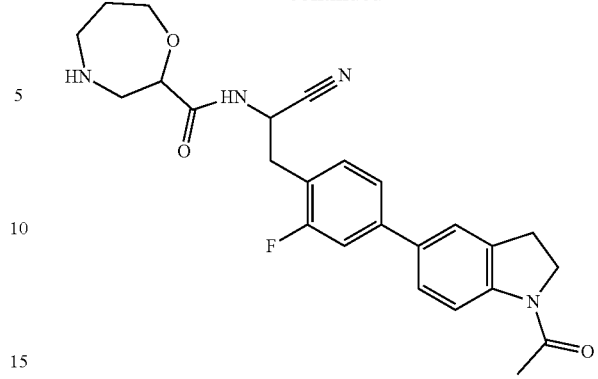
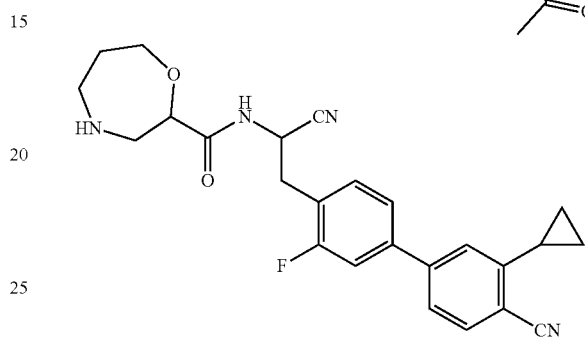
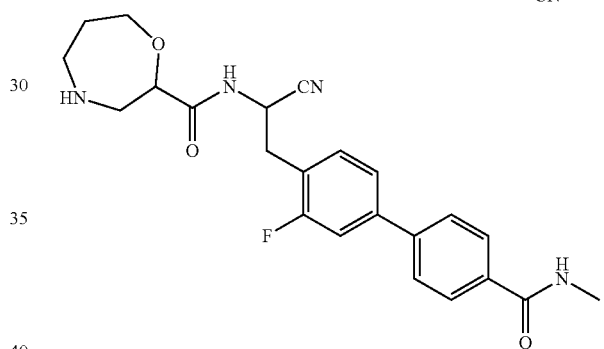
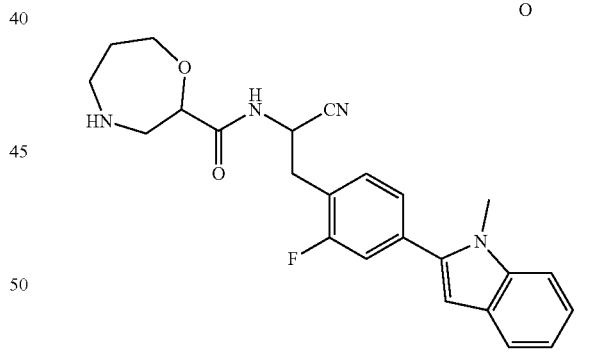
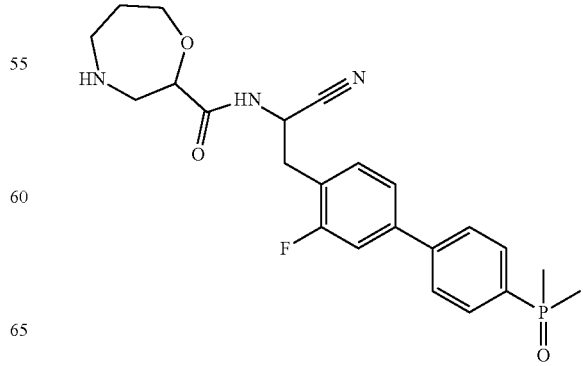

185
-continued
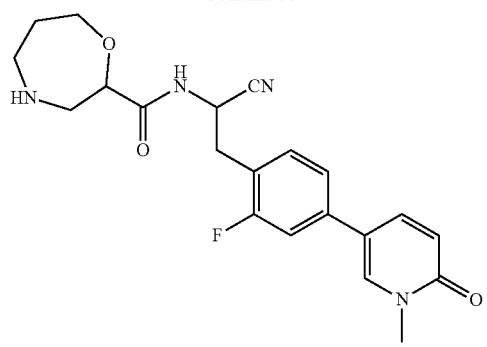
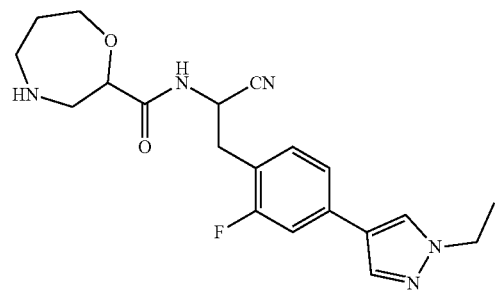
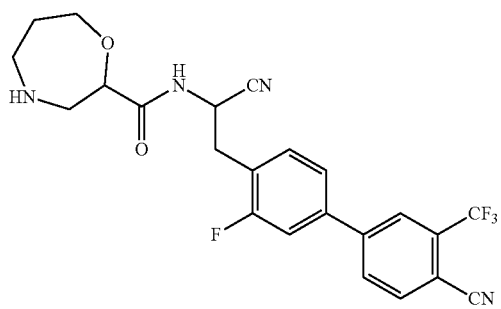
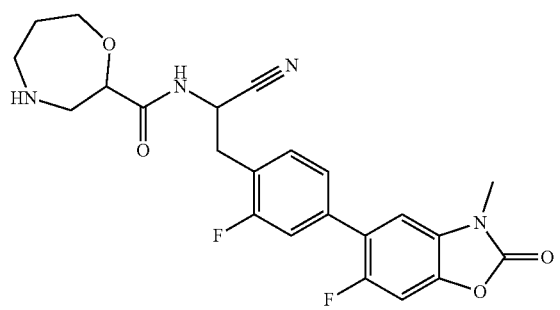
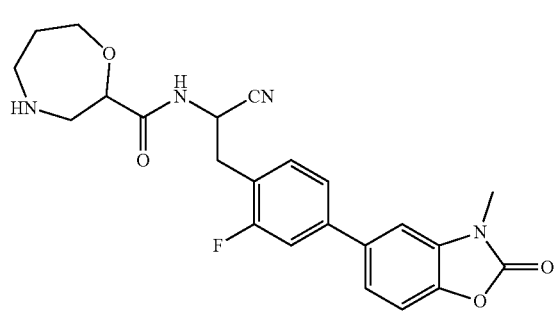
186
-continued
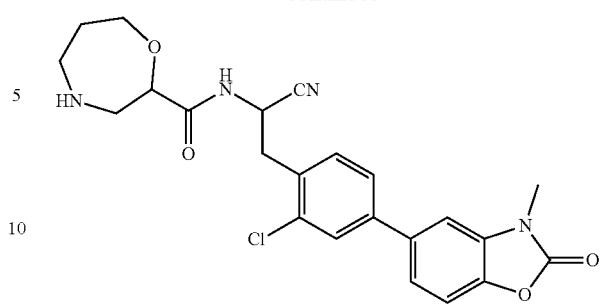
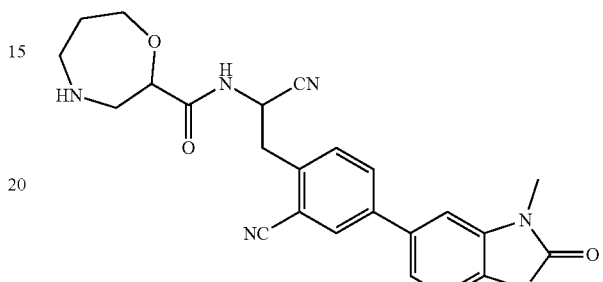
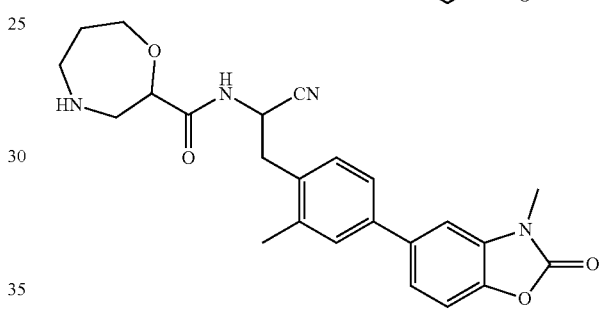
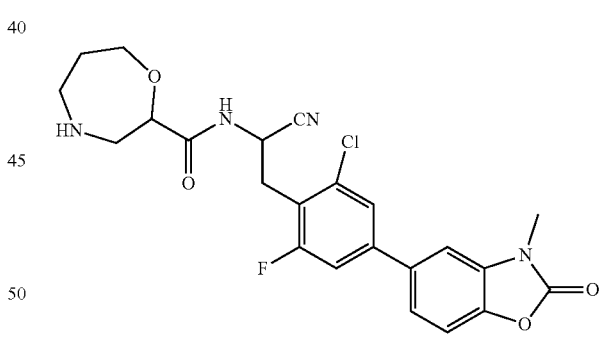
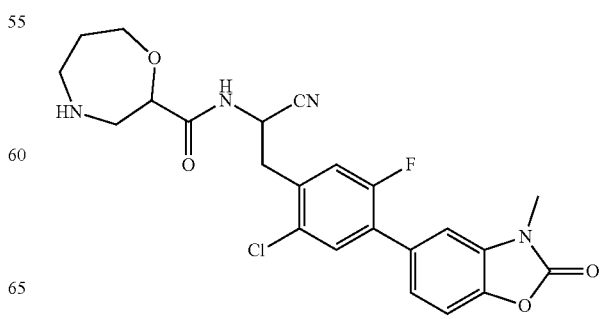

187
-continued
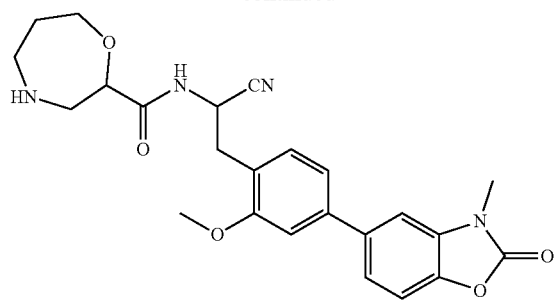
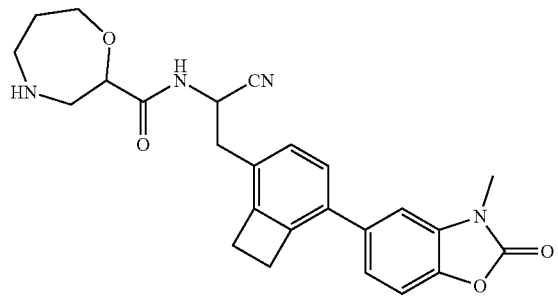
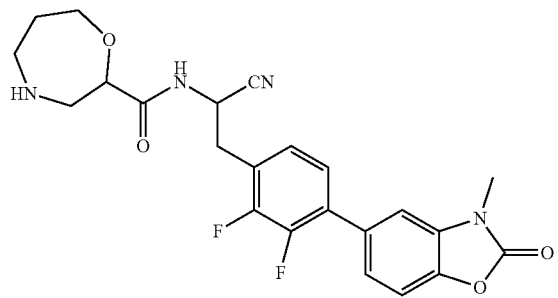
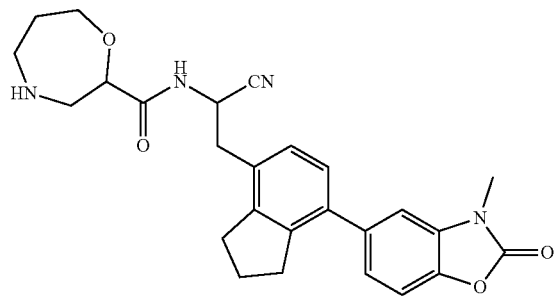
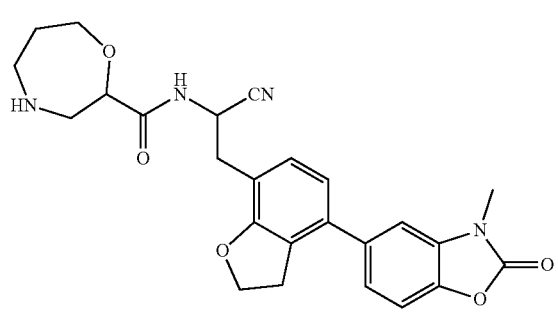
188
-continued
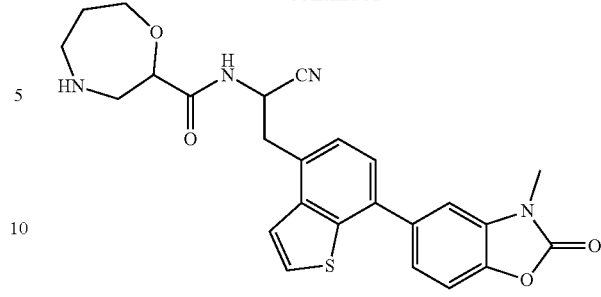
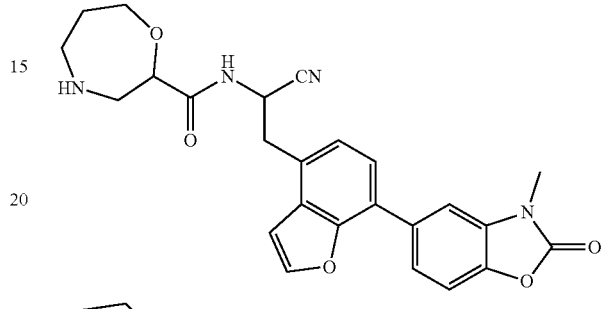
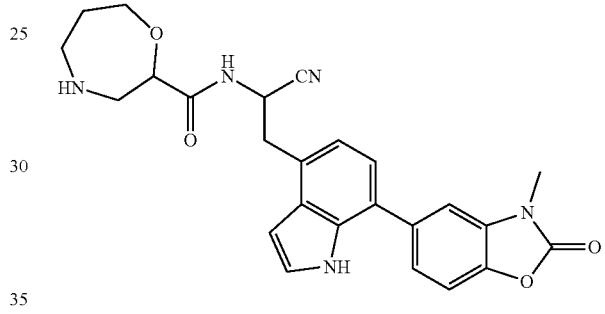
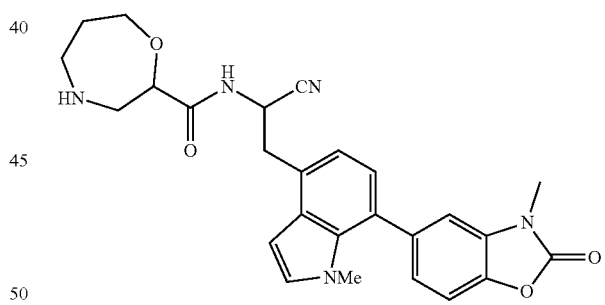
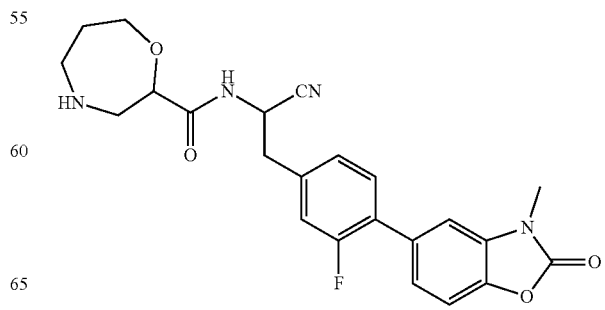

189
-continued
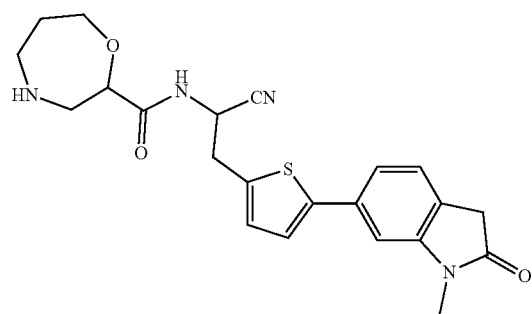
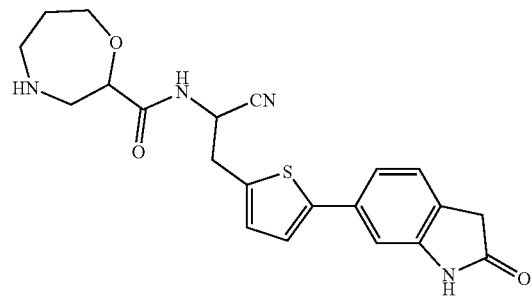
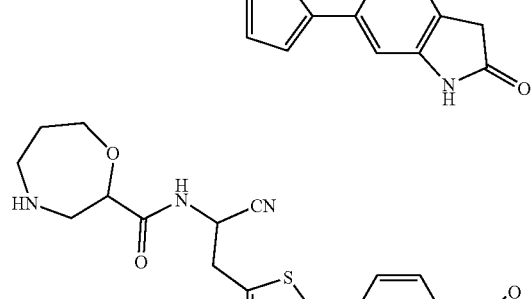
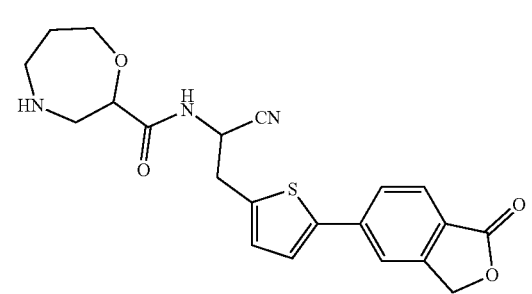
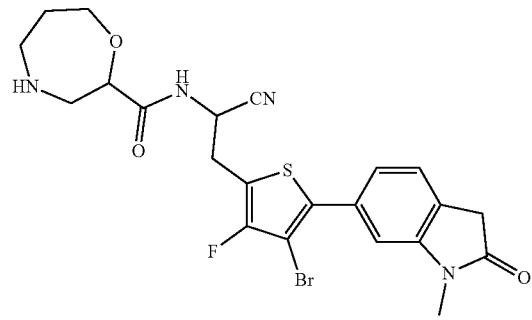
190
-continued
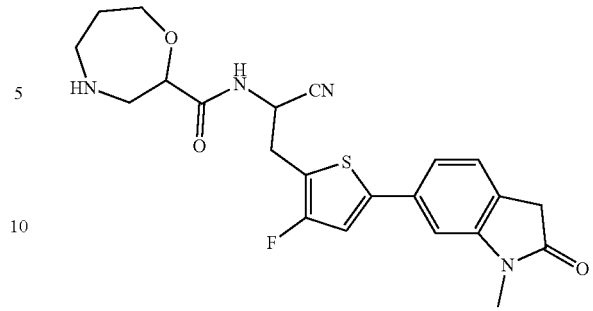
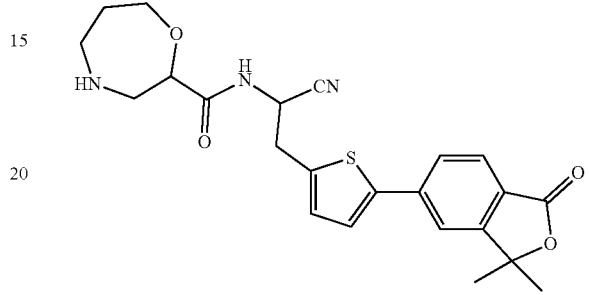
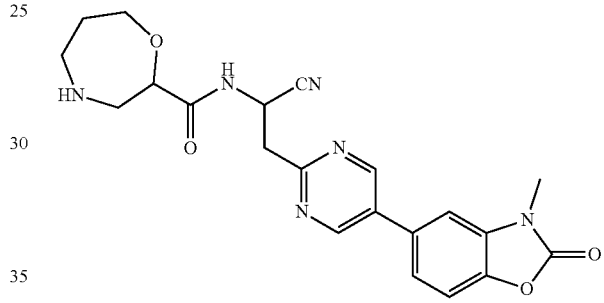
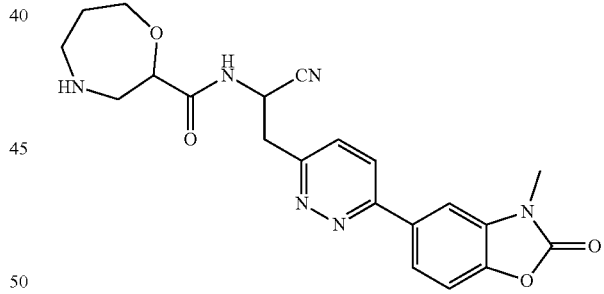
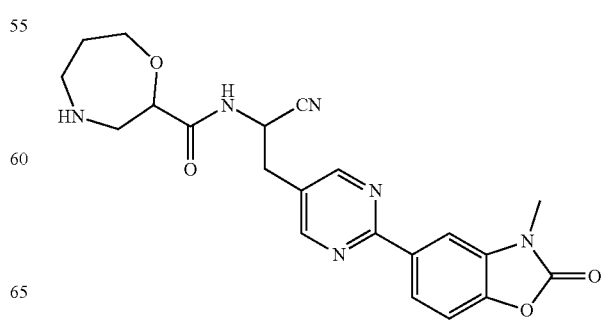

191
-continued
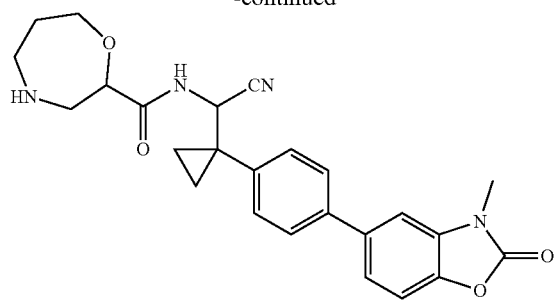
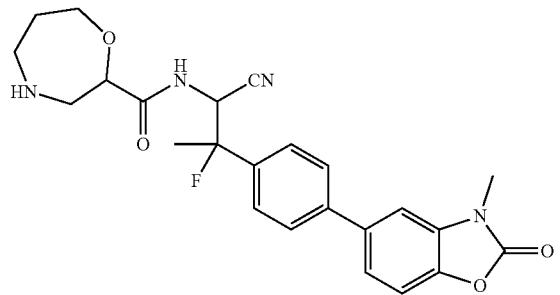
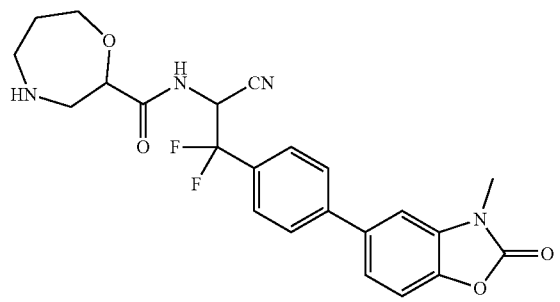
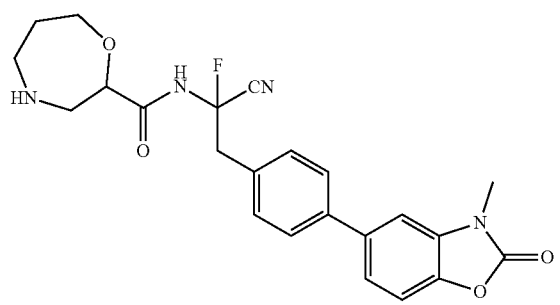
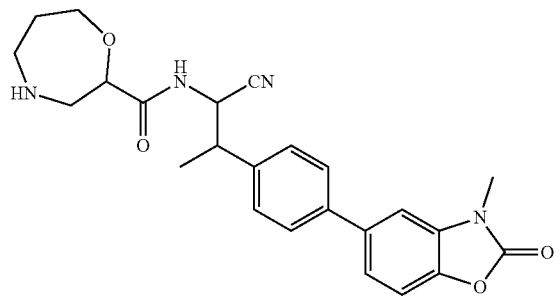
192
-continued
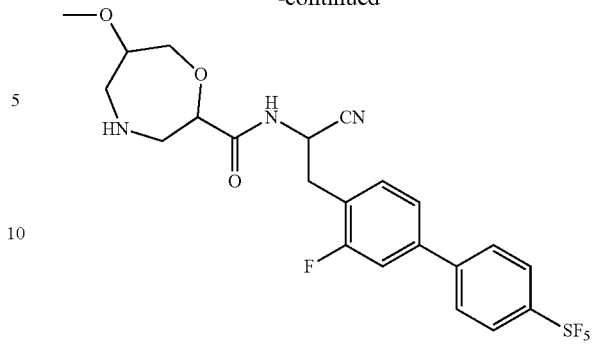
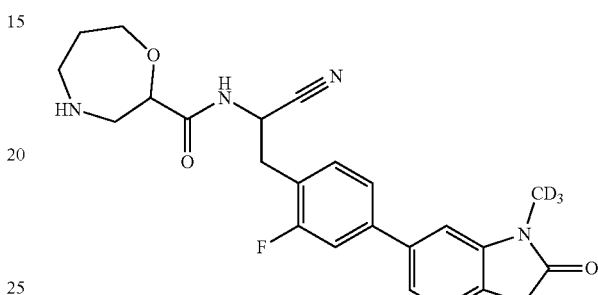
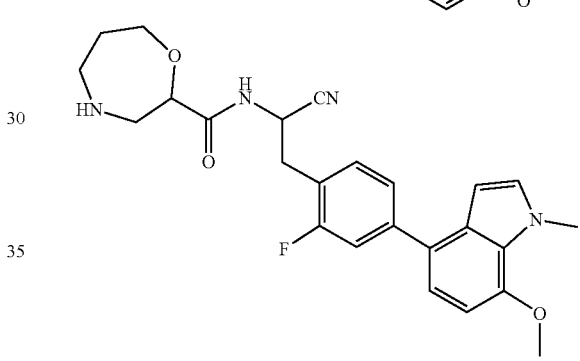
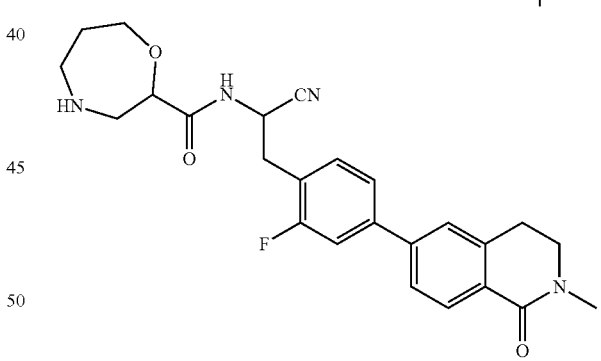
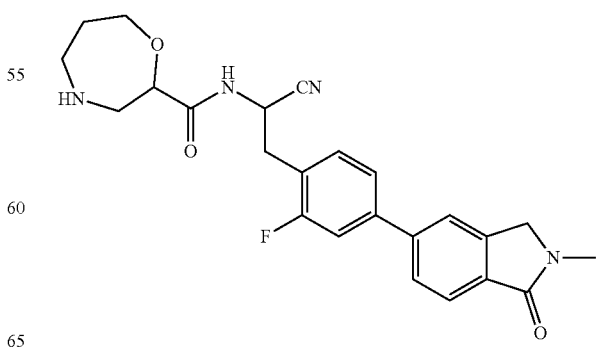

193
-continued
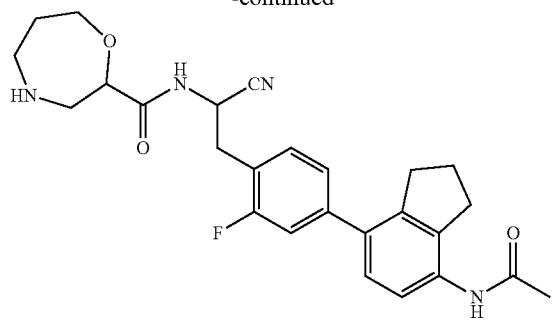
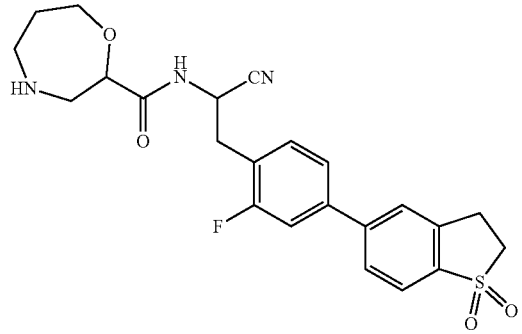
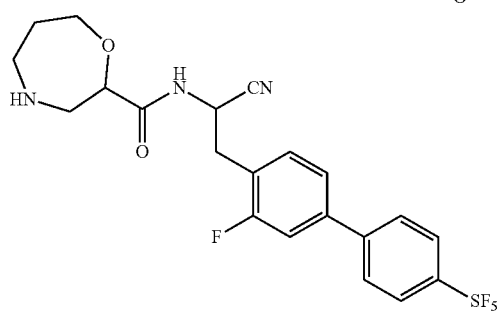
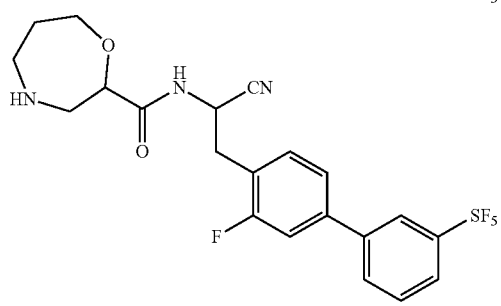
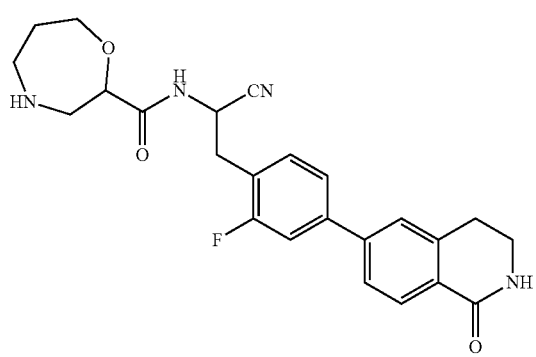
194
-continued
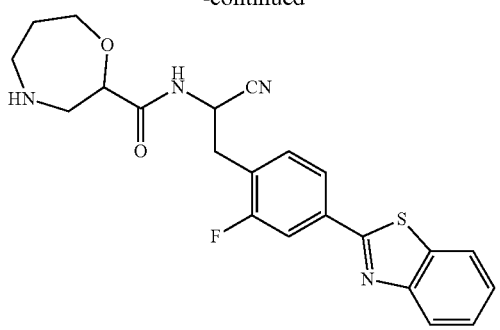
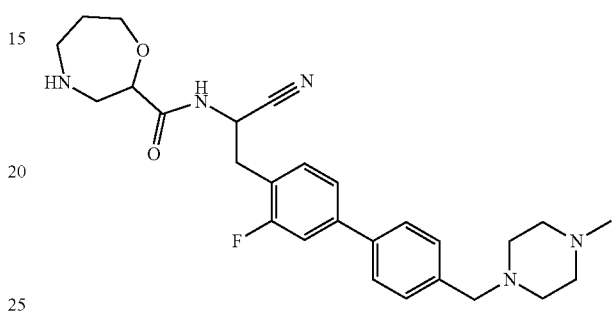
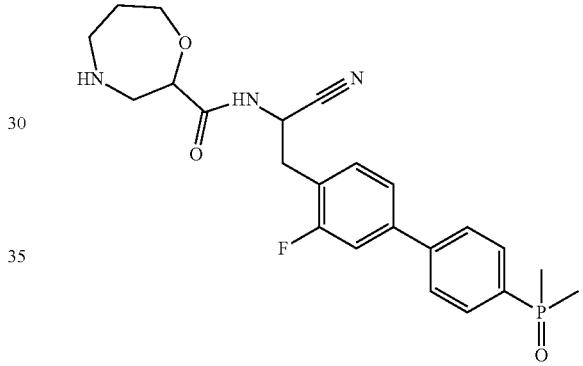
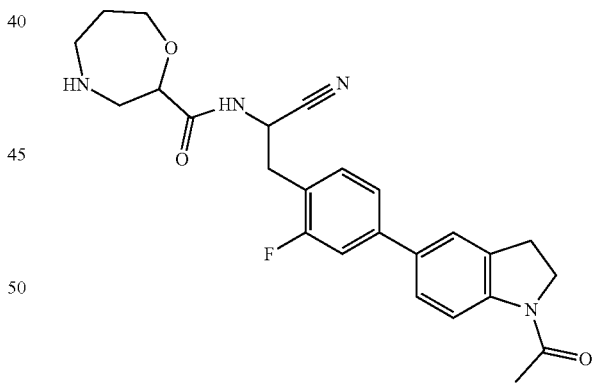
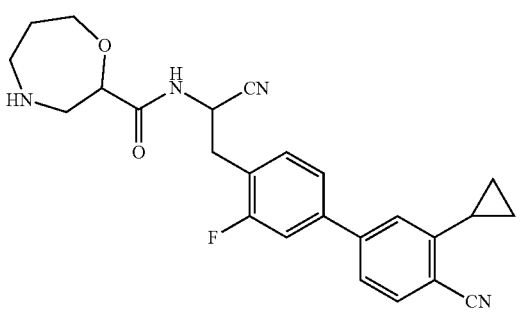

195
-continued
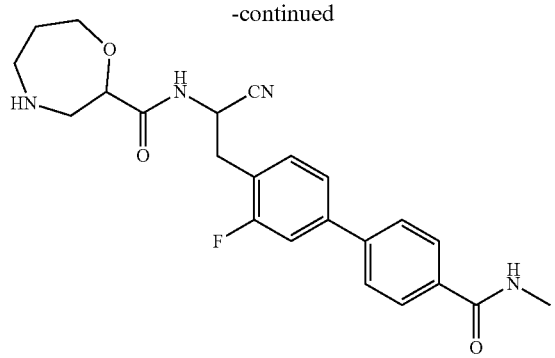
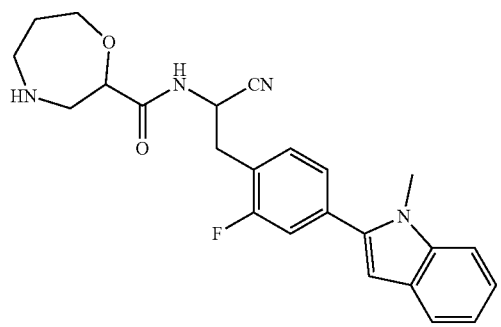
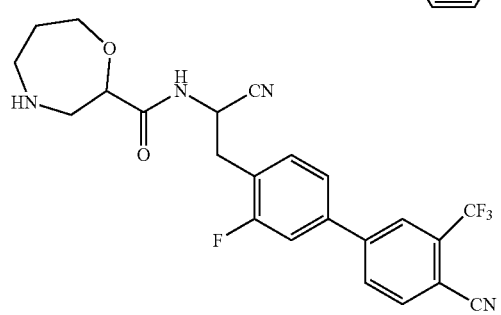
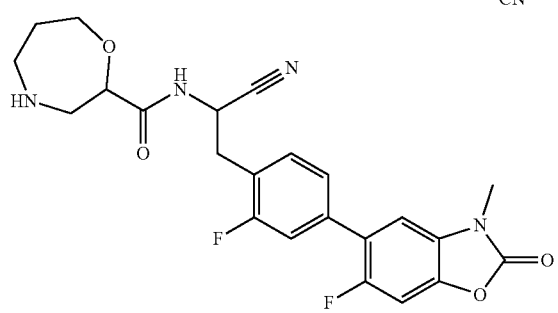
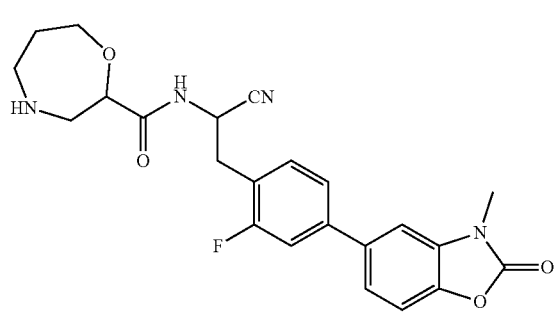
196
-continued
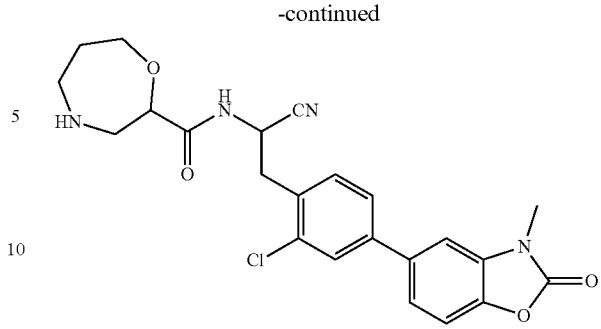
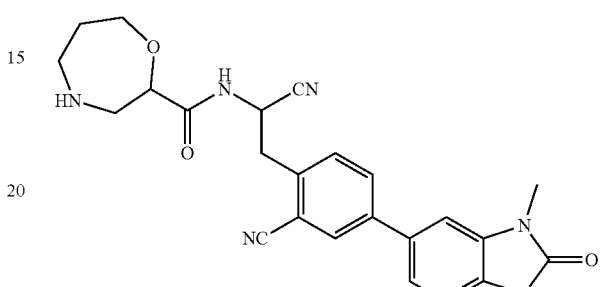
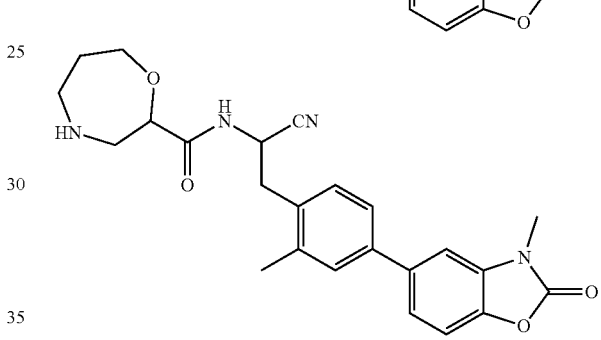
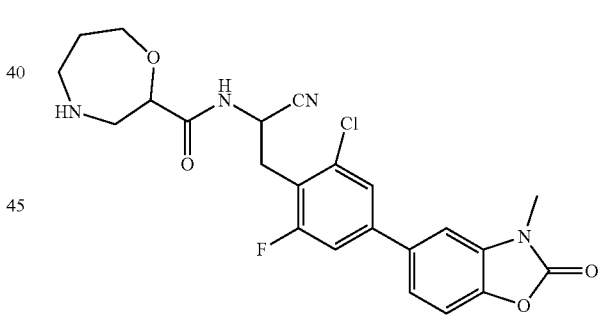
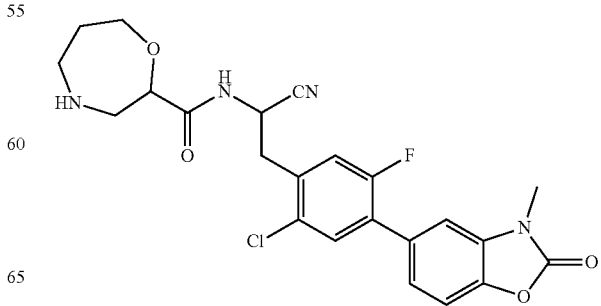

197
-continued
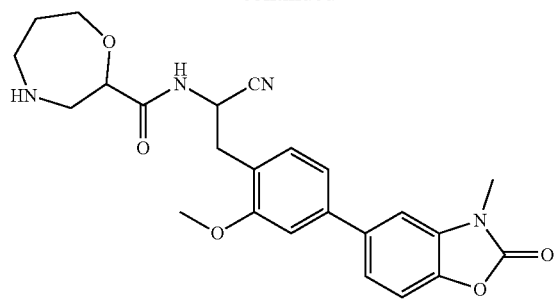
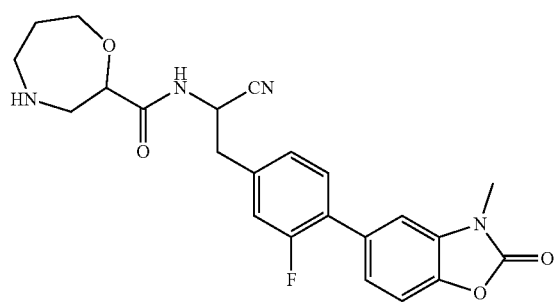
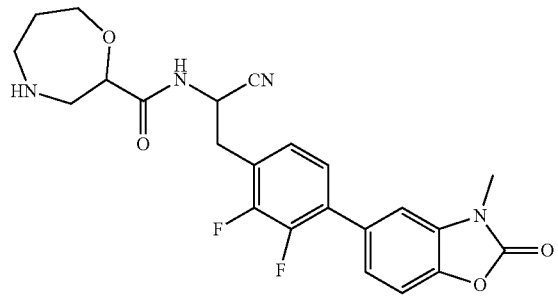
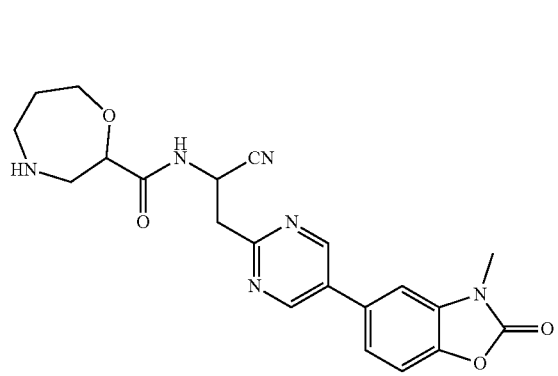
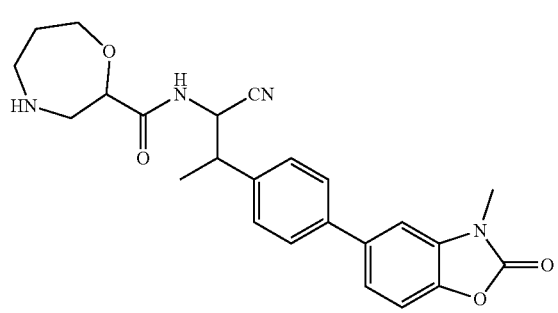
198
-continued
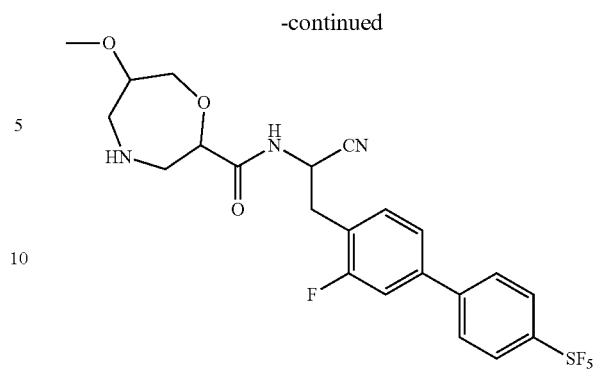
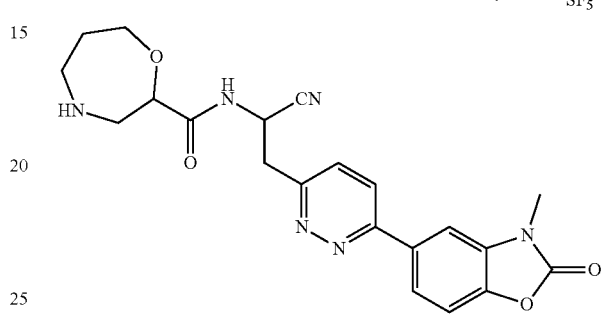
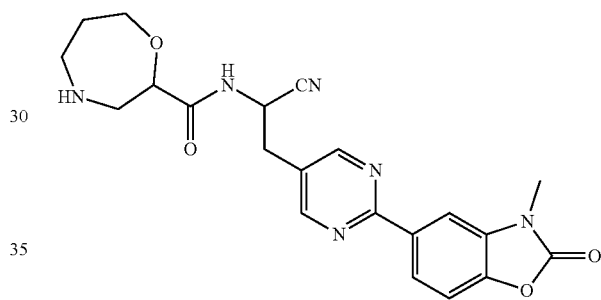
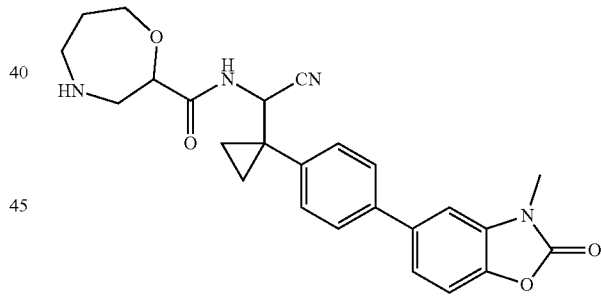
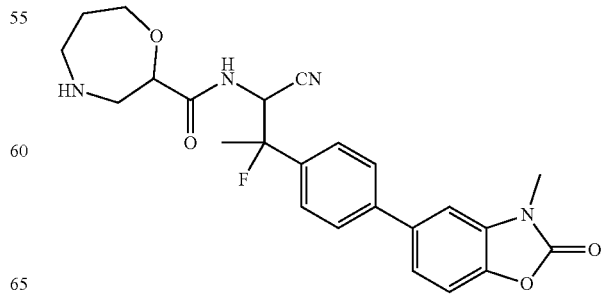

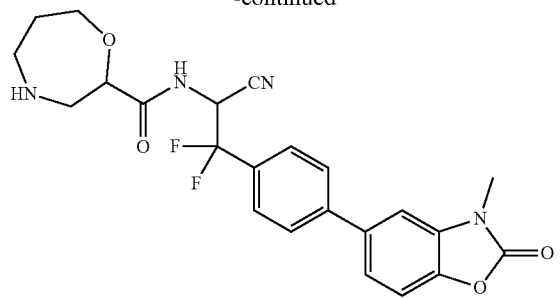
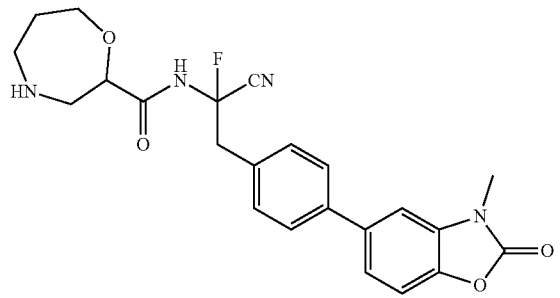
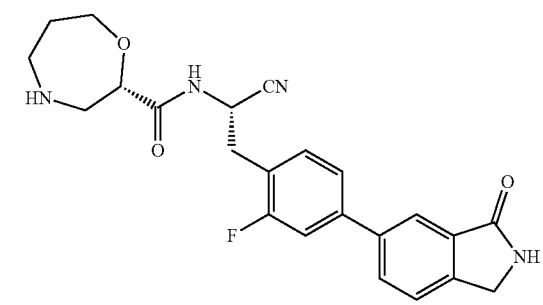
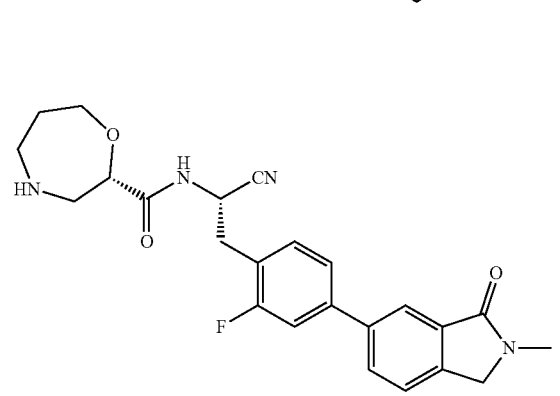
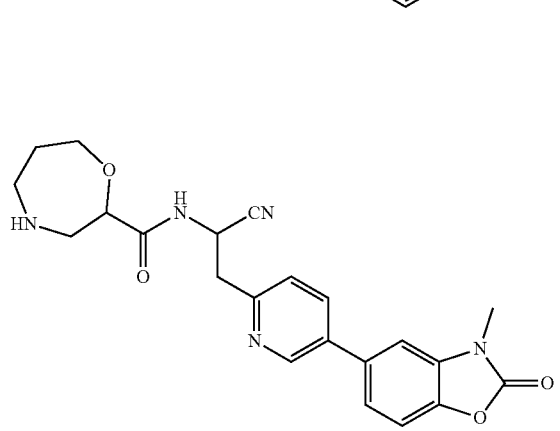
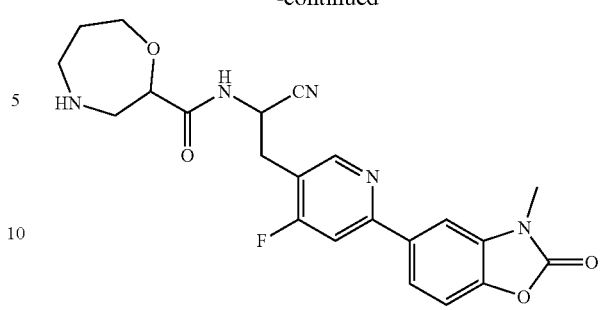
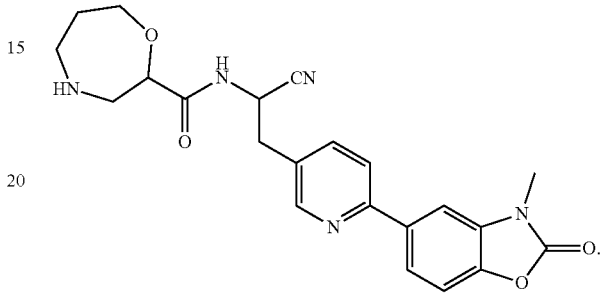
4. The compound, or the stereoisomer, deuterated product, solvate or pharmaceutically acceptable salt thereof according to claim 3, wherein the compound is selected from one of the following structures:
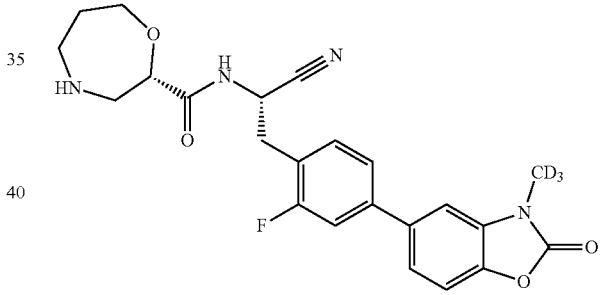
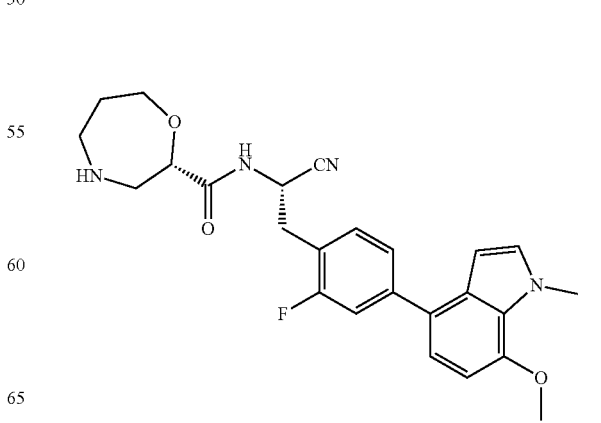

-continued
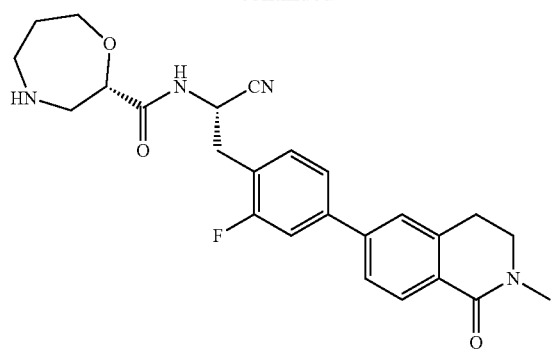
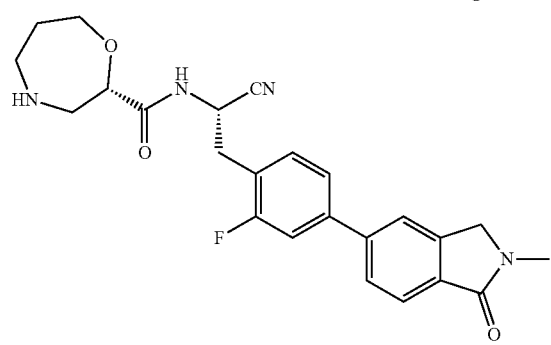
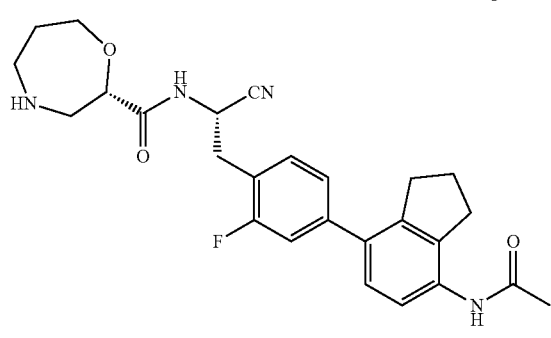
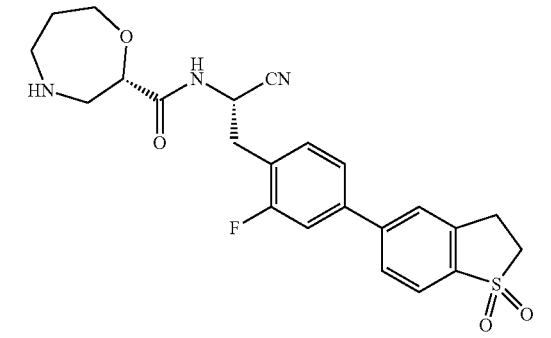
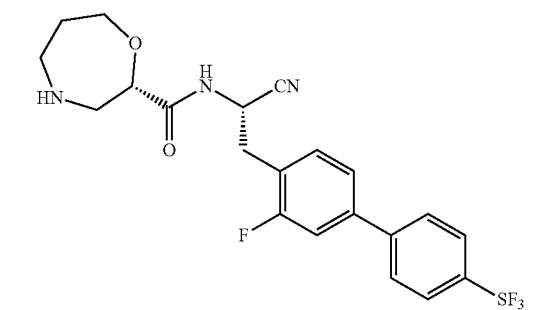
-continued
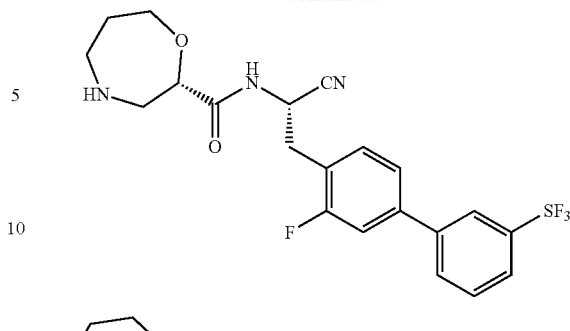
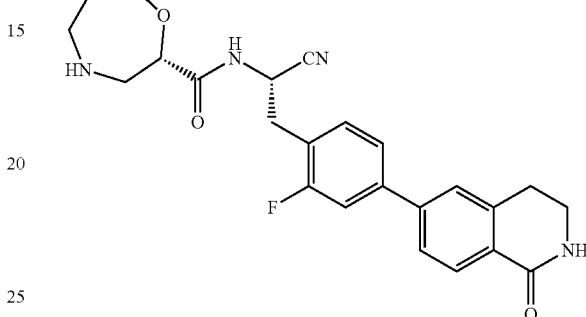
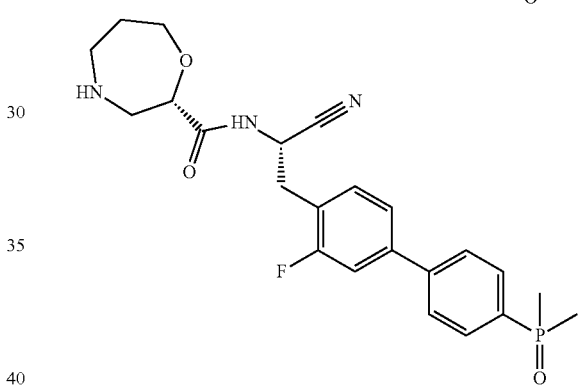
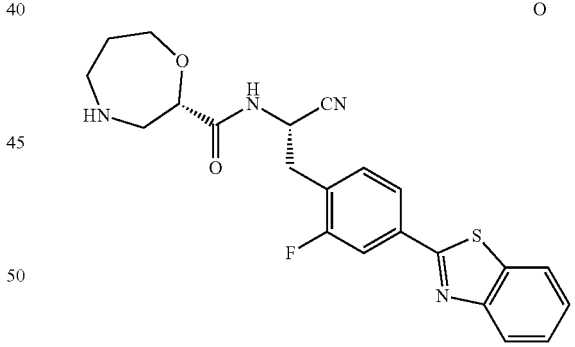
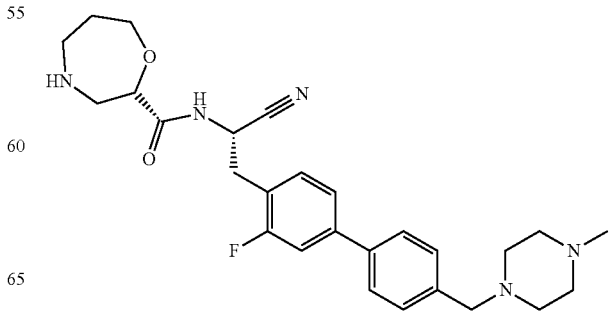

203
-continued
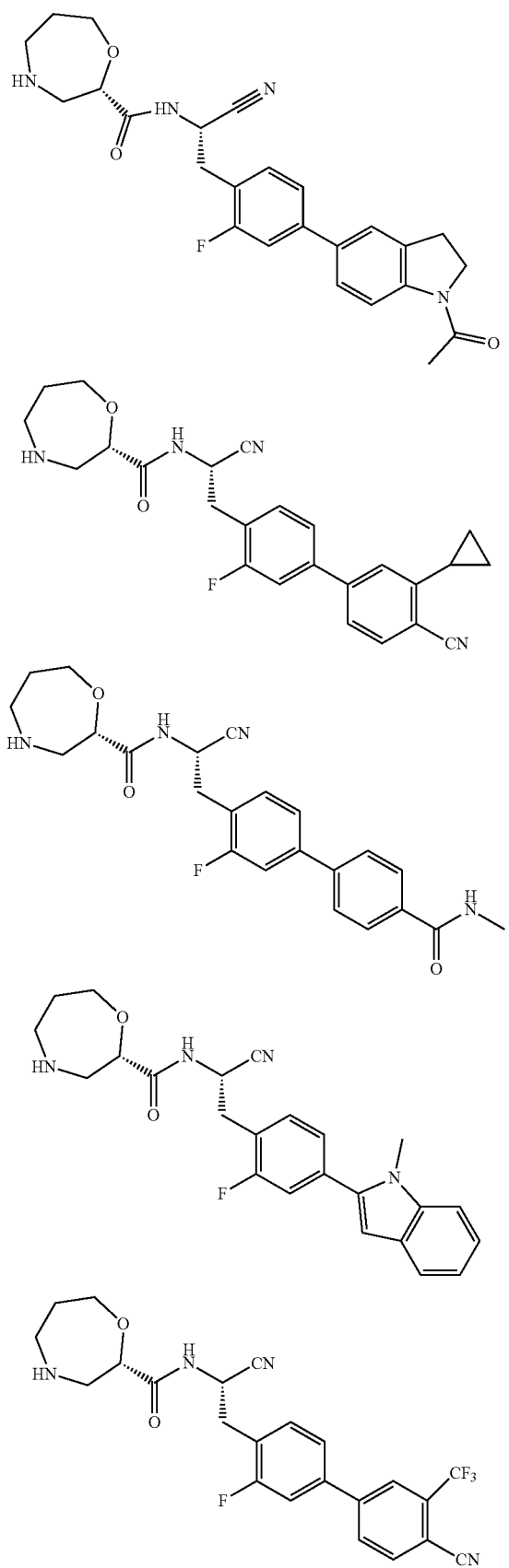
204
-continued
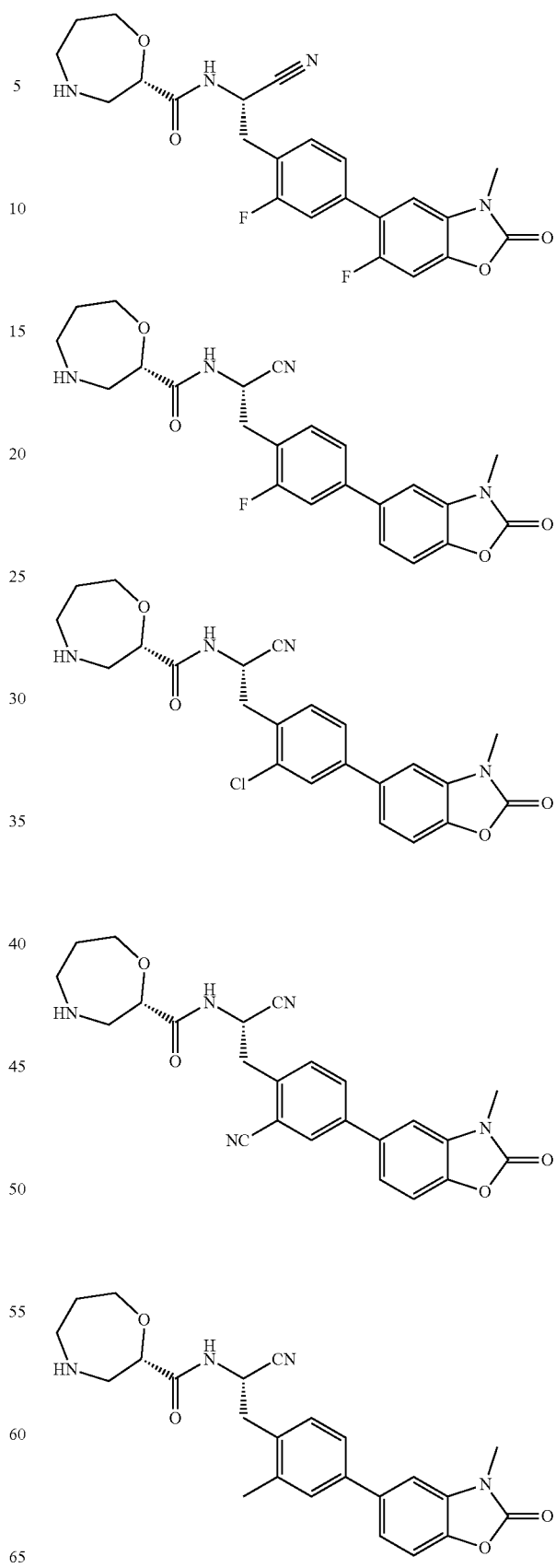

205
-continued
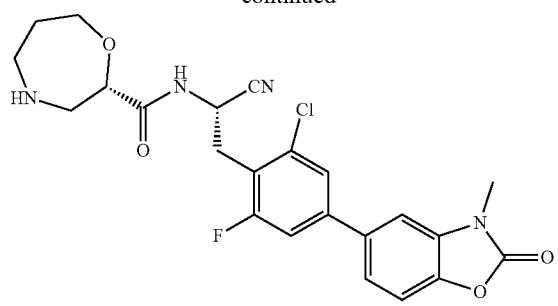
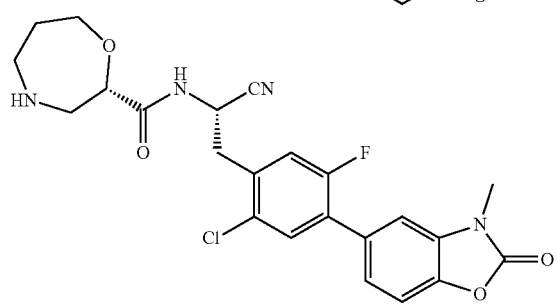
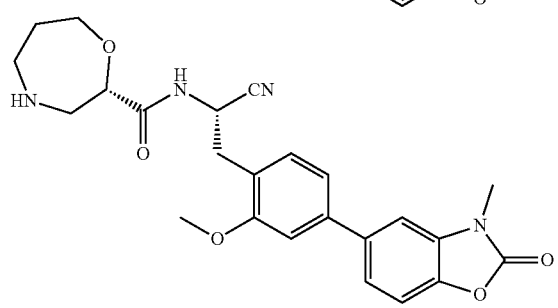
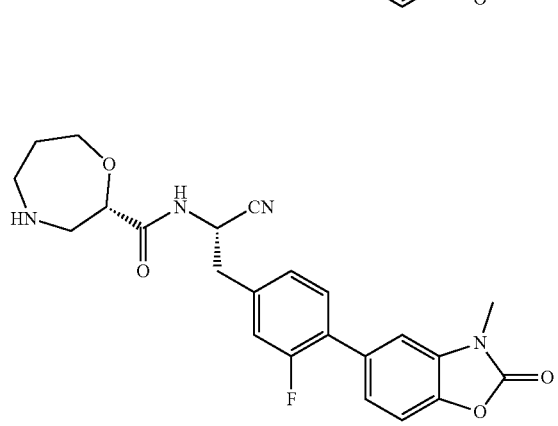
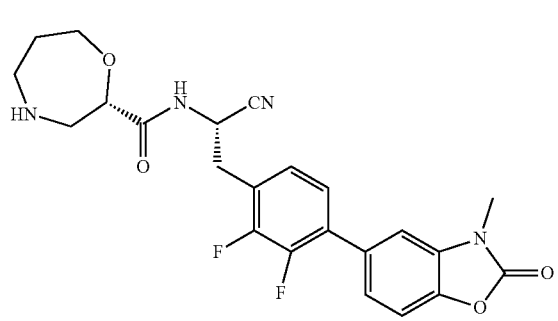
206
-continued
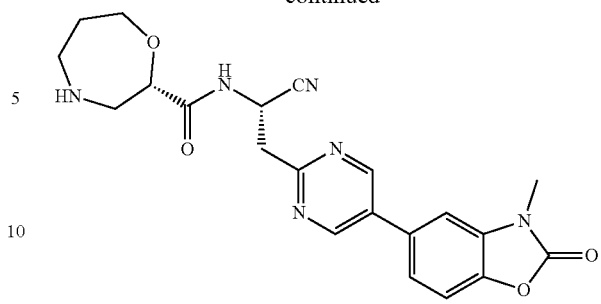
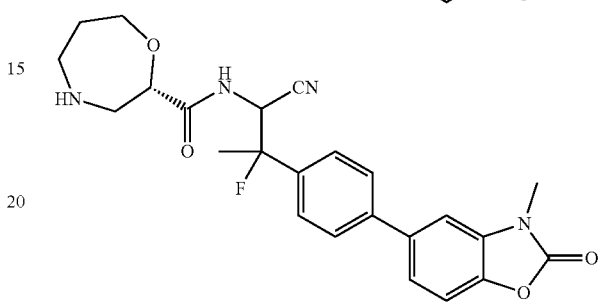
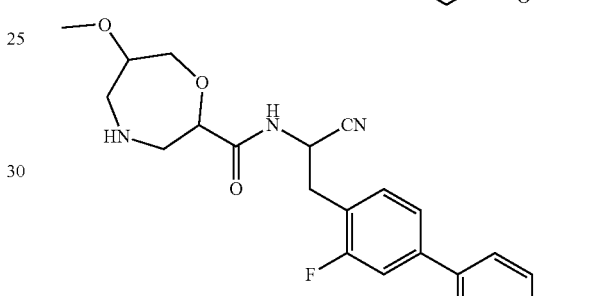
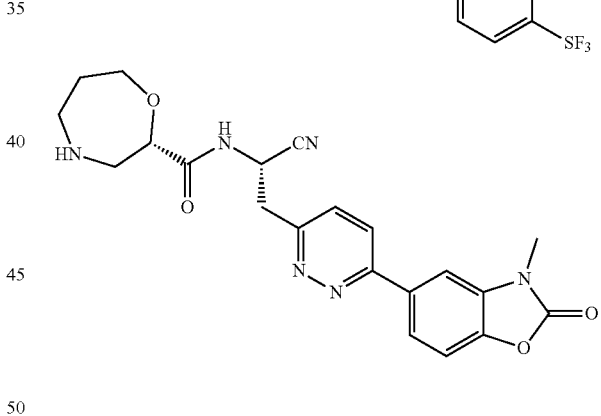
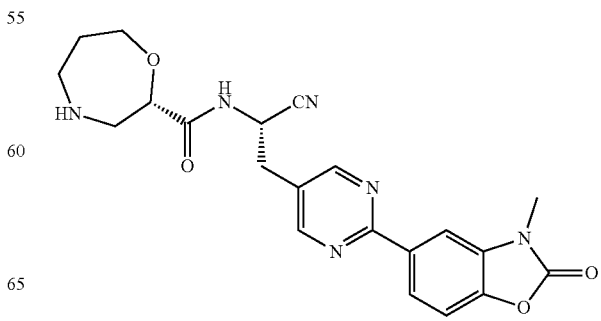

207
-continued
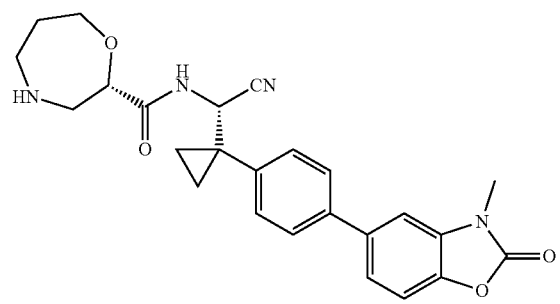
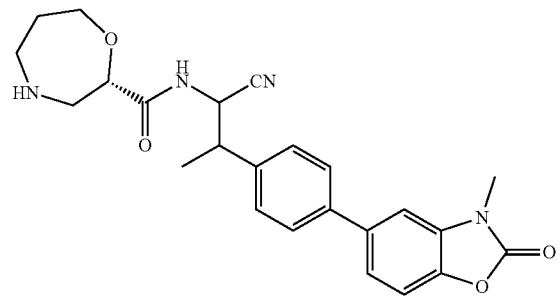
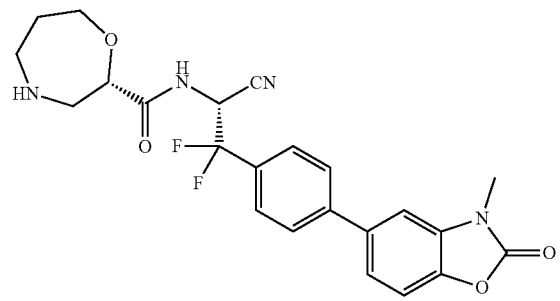
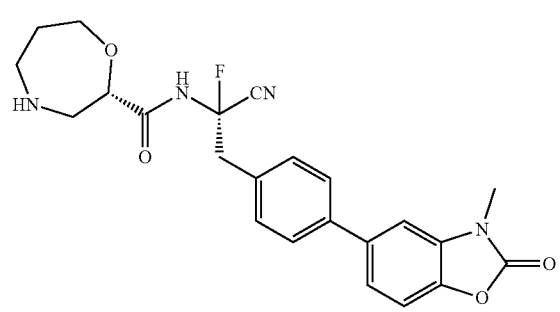
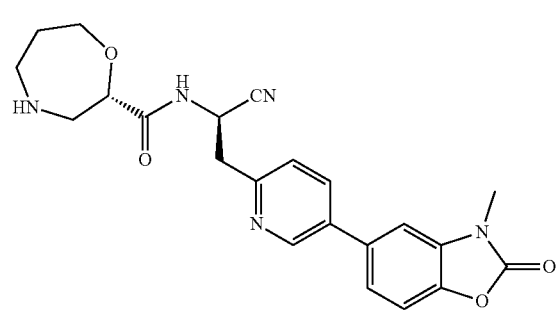
208
-continued
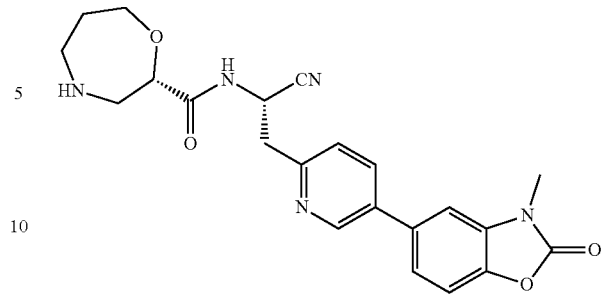
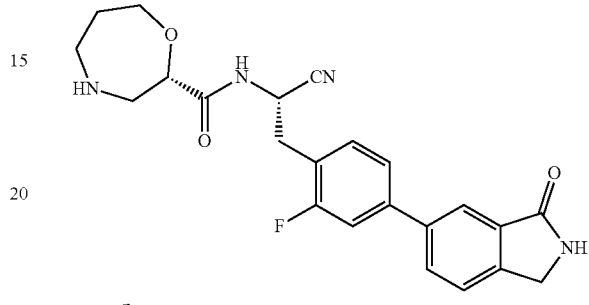
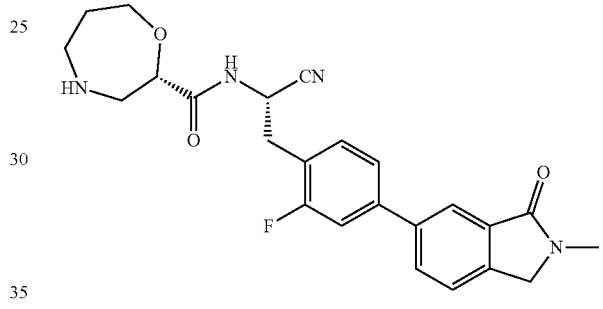
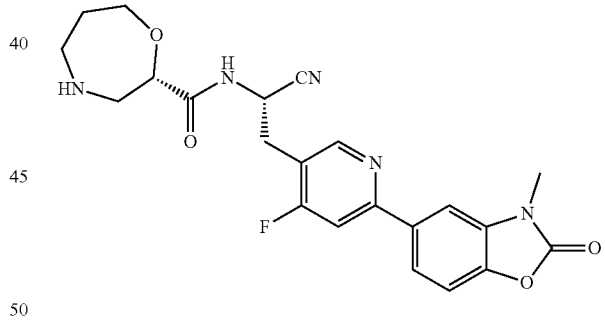
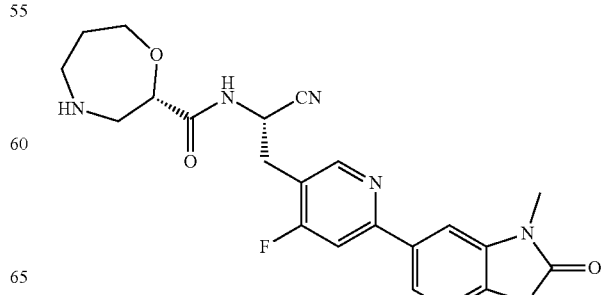

209
-continued

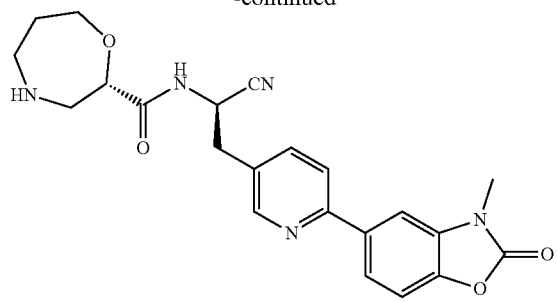

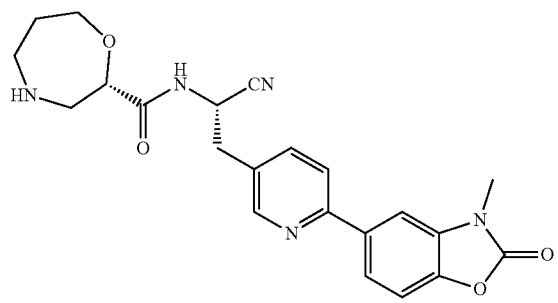

210
-continued

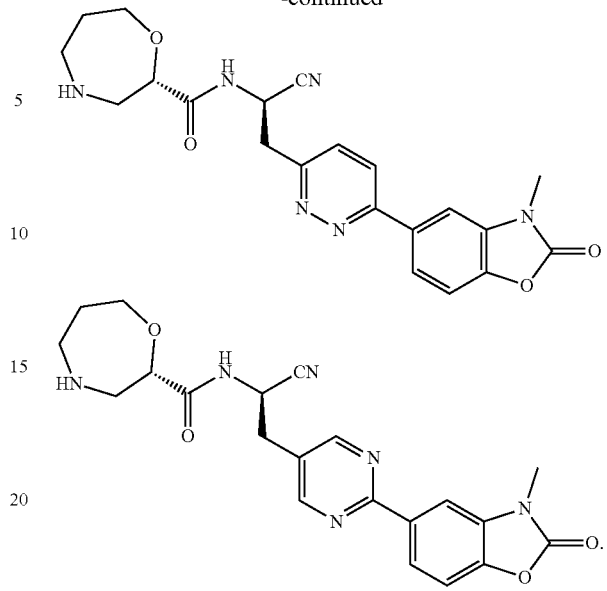

5. A pharmaceutical composition, comprising the compound, or the stereoisomer, deuterated product, solvate or pharmaceutically acceptable salt thereof according claim 1, and a pharmaceutically acceptable carrier and/or excipient.

6. A method of treating a disease mediated by dipeptidyl peptidase 1, comprising administering the compound, or the stereoisomer, deuterated product, solvate or pharmaceutically acceptable salt thereof according to claim 1, wherein the disease is selected from obstructive airway diseases, bronchiectasis, cystic fibrosis, asthma, emphysema, and chronic obstructive pulmonary diseases.

* * * * *